(12) United States Patent
Galagan et al.

(10) Patent No.: US 11,331,020 B2
(45) Date of Patent: May 17, 2022

(54) ENZYME-BASED ELECTROCHEMICAL NICOTINE BIOSENSOR

(71) Applicant: TRUSTEES OF BOSTON UNIVERSITY, Boston, MA (US)

(72) Inventors: James Galagan, Needham, MA (US); Mark W. Grinstaff, Brookline, MA (US); Uros Kuzmanovic, Brookline, MA (US); Mingfu Chen, Boston, MA (US); Margarita Alexandrovna Tararina, Bryn Mawr, PA (US); Karen Nazaretian Allen, Weston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 17/169,193

(22) Filed: Feb. 5, 2021

(65) Prior Publication Data
US 2021/0259585 A1   Aug. 26, 2021

Related U.S. Application Data

(60) Provisional application No. 62/971,012, filed on Feb. 6, 2020.

(51) Int. Cl.
*A61B 5/1486* (2006.01)
*A61B 5/00* (2006.01)
(Continued)

(52) U.S. Cl.
CPC ........ *A61B 5/1486* (2013.01); *A61B 5/14517* (2013.01); *A61B 5/4845* (2013.01);
(Continued)

(58) Field of Classification Search
None
See application file for complete search history.

(56) References Cited

U.S. PATENT DOCUMENTS

| 4,340,458 A | 7/1982 | Lerner et al. |
| 4,436,094 A | 3/1984 | Cerami |

(Continued)

FOREIGN PATENT DOCUMENTS

| CN | 102053161 A | 5/2011 |
| CN | 105136885 A | 12/2015 |

(Continued)

OTHER PUBLICATIONS

A. Chaubey, et al. "Mediated Biosensors", Biosensors and Bioelectronics, 17(6-7), p. 441-456, (Jun. 2002).*

(Continued)

*Primary Examiner* — J. Christopher Ball
*Assistant Examiner* — John C Ball
(74) *Attorney, Agent, or Firm* — Burns & Levinson LLP; Steven M. Mills

(57) ABSTRACT

Described herein is an amperometric biosensor, e.g., chronoamperometric biosensor for the measurement of the concentration of nicotine. Also disclosed herein is a wearable nicotine biosensor device and a biosensor that detects nicotine in smoke. The biosensor disclosed herein comprises a nicotine-catalyzing enzyme, such as NicA2 or mutant NicA2 enzymes. Also described herein are systems comprising said amperometric biosensor, e.g., chronoamperometric biosensor and methods of using said chronoamperometric biosensor.

25 Claims, 55 Drawing Sheets

Specification includes a Sequence Listing.

Mutations in Aromatic Cage can Improve Catalytic Activity

| Enzyme | $K_M$ | $k_{cat}$ (s⁻¹) | $K_d$ (µM) | $k_{red}$ (s⁻¹) | Oxidation $k_{obs}$ (s⁻¹) | $k_{cat}/K_m$ (M⁻¹ s⁻¹) | $k_{red}/K_d$ (M⁻¹ s⁻¹) |
|---|---|---|---|---|---|---|---|
| GOx | 33 – 110 mM | 1118.81 | | | | 2.20 x 10⁴ | |
| LOx | 0.94 mM | 280 | | | | 2.98 x 10⁵ | |
| NicA2 WT | 43.5 ± 4.7 nM | (6.64 ± 0.17) * 10⁻³ | 65.9 ± 10 | 186 ± 9.9 | 0.00137 | 5.35 x 10⁴ | 2.82 x 10⁶ |
| NicA2 (N462V) | | | 28.1 ± 4.6 | 0.353 ± 0.01 | 0.00170 | 1.29 x 10⁴ | 1.26 x 10⁴ |
| NicA2 (N462Y/W427Y) | | | 24.3 ± 3.3 | 0.103 ± 0.003 | 0.00626 | 1.58 x 10⁴ | 4.24 x 10³ |
| NicA2 (N462H) | | | 15.0 ± 2.5 | 20.3 ± 0.003 | 0.01028 | 1.98 x 10⁵ | 1.36 x 10⁶ |
| NicA2 (A107R) | 830 nM | 0.159 | | | | 1.9 x 10⁵ | |

(51) Int. Cl.
  *A61B 5/145* (2006.01)
  *G01N 33/487* (2006.01)
  *C12Q 1/26* (2006.01)
  *C12Q 1/00* (2006.01)
  *G01N 27/327* (2006.01)
  *A61B 10/00* (2006.01)

(52) U.S. Cl.
  CPC ............ *C12Q 1/004* (2013.01); *C12Q 1/005* (2013.01); *C12Q 1/26* (2013.01); *G01N 27/3272* (2013.01); *G01N 33/48714* (2013.01); *A61B 10/0064* (2013.01)

(56) References Cited

U.S. PATENT DOCUMENTS

| | | | |
|---|---|---|---|
| 4,633,878 | A | 1/1987 | Bombardieri |
| 4,911,794 | A | 3/1990 | Parce et al. |
| 5,387,327 | A | 2/1995 | Khan |
| 5,783,056 | A | 7/1998 | Hampp et al. |
| 6,241,863 | B1 | 6/2001 | Monbouquette |
| 6,605,200 | B1 | 8/2003 | Mao et al. |
| 6,736,777 | B2 | 5/2004 | Kim et al. |
| 7,341,846 | B2 | 3/2008 | Yamaoka et al. |
| 7,794,994 | B2 | 9/2010 | Cranley et al. |
| 9,034,262 | B2 | 5/2015 | Belbruno et al. |
| 9,228,988 | B2 | 1/2016 | Belbruno |
| 9,429,536 | B2 | 8/2016 | Belbruno et al. |
| 9,820,692 | B2 | 11/2017 | Wang et al. |
| 10,024,814 | B2 | 7/2018 | Belbruno |
| 10,182,795 | B2 | 1/2019 | Heikenfeld et al. |
| 10,415,050 | B2 | 9/2019 | Liedschulte et al. |
| 10,451,598 | B2 | 10/2019 | Belbruno et al. |
| 10,646,142 | B2 | 5/2020 | Heikenfeld et al. |
| 2003/0027239 | A1 | 2/2003 | Schaffar |
| 2005/0043515 | A1 | 2/2005 | Brown et al. |
| 2007/0136825 | A1 | 6/2007 | Frommer et al. |
| 2008/0057528 | A1 | 3/2008 | Sayre et al. |
| 2008/0160625 | A1 | 7/2008 | Palleschi et al. |
| 2009/0061451 | A1 | 3/2009 | Achim et al. |
| 2009/0099434 | A1 | 4/2009 | Liu et al. |
| 2010/0218270 | A1 | 8/2010 | Xu et al. |
| 2012/0181189 | A1 | 7/2012 | Merchant |
| 2013/0144131 | A1* | 6/2013 | Wang ............... A61B 5/021 600/301 |
| 2013/0172705 | A1 | 7/2013 | Petillo et al. |
| 2015/0132857 | A1 | 5/2015 | Belbruno et al. |
| 2015/0260674 | A1 | 9/2015 | Tsao |
| 2016/0370310 | A1 | 12/2016 | Belbruno et al. |
| 2018/0292341 | A1 | 10/2018 | Belbruno |
| 2019/0004005 | A1 | 1/2019 | Oja et al. |
| 2019/0153403 | A1 | 5/2019 | Xu et al. |
| 2020/0191740 | A1 | 6/2020 | Arduini et al. |

FOREIGN PATENT DOCUMENTS

| | | |
|---|---|---|
| CN | 110573868 A | 12/2019 |
| EP | 1845371 A1 | 10/2007 |
| EP | 1194585 B1 | 11/2008 |
| EP | 3735904 A1 | 11/2020 |
| WO | 2005/048834 A1 | 6/2005 |
| WO | 2006/091194 A1 | 8/2006 |
| WO | 2008/070274 A2 | 6/2008 |
| WO | 2009/064771 A2 | 5/2009 |
| WO | 2011/088180 A1 | 7/2011 |
| WO | 2012/034115 A1 | 3/2012 |
| WO | 2013/059534 A1 | 4/2013 |
| WO | 2017/210465 A1 | 12/2017 |
| WO | 2018/144879 A1 | 8/2018 |
| WO | 2018144879 A1 | 8/2018 |
| WO | 2018/202793 A2 | 11/2018 |
| WO | 2019/224628 A1 | 11/2019 |
| WO | 2019224628 A1 | 11/2019 |

OTHER PUBLICATIONS

K. Kivirand, et al. "Biosensors for Biogenic Amines: The Present State of the Art Mini-Review", Analytical Letters, 44(17), p. 2821-2833, (Nov. 2011).*
Application Note E-4 Subject: A Review of Techniques for Electrochemical Analysis, Princeton Applied Research, accessed on Jul. 6, 2021; 15 pages, http://ameteksi.com/-/media/ameteksi/download_links/documentations/library/princetonappliedresearch/application_note_e-4.pdf?la=en; available Jun. 22, 2017.*
Jing et al., "Determination of nicotine in tobacco products based on mussel-inspired reduced graphene oxide-supported gold nanoparticles." Scientific reports 6.1 (2016): 29230.
Jing et al., "Electrodeposition of Au nanoparticles on poly (diallyldimethylammonium chloride) functionalized reduced graphene oxide sheets for voltammetric determination of nicotine in tobacco products and anti-smoking pharmaceuticals." RSC advances 6.31 (2016): 26247-26253.
Kamra et al., "Implementation of molecularly imprinted polymer beads for surface enhanced Raman detection." Analytical chemistry 87.10 (2015): 5056-5061.
Kintses et al., "Picoliter cell lysate assays in microfluidic droplet compartments for directed enzyme evolution." Chemistry & biology 19.8 (2012): 1001-1009.
Ko et al., "Consumer sleep technologies: a review of the landscape." Journal of clinical sleep medicine 11.12 (2015): 1455-1461.
Lam et al., "Directed evolution of APEX2 for electron microscopy and proximity labeling." Nature methods 12.1 (2015): 51-54.
Li et al., "Electrochemical sensing of nicotine using screen-printed carbon electrodes modified with nitrogen-doped graphene sheets." Journal of Electroanalytical Chemistry 784 (2017): 77-84.
Lin et al., "Functional expression of horseradish peroxidase in *E. coli* by directed evolution." Biotechnology progress 15.3 (1999): 467-471.
Lindell et al., "Transdermally administered nicotine accumulates in gastric juice." European journal of clinical pharmacology 51.3 (1996): 315-318.
Liu et al., "Detection of secondhand cigarette smoke via nicotine using conductive polymer films." nicotine & tobacco research 15.9 (2013): 1511-1518.
Liu et al., "Nicotine-degrading microorganisms and their potential applications." Applied microbiology and biotechnology 99.9 (2015): 3775-3785.
Lo et al., "The use of nano-carbon as an alternative to multi-walled carbon nanotubes in modified electrodes for adsorptive stripping voltammetry." Sensors and Actuators B: Chemical 162.1 (2012): 361-368.
Lutz et al., "Protein engineering: past, present, and future." Protein Engineering: Methods and Protocols (2018): 1-12.
Marrazza "Aptamer sensors." Biosensors (Basel) 7.1 (2017): 5.
Martell et al., "Engineered ascorbate peroxidase as a genetically encoded reporter for electron microscopy." Nature biotechnology 30.11 (2012): 1143-1148.
McGinnis et al., "Actual causes of death in the United States." JAMA 270.18 (1993): 2207-2212.
Meier et al., "Hydrogen peroxide sensors for biomedical applications." Chemosensors 7.4 (2019): 64.
Mihasan et al., "An NAD(P)H-nicotine blue oxidoreductase is part of the nicotine regulon and may protect Arthrobacter nicotinovorans from oxidative stress during nicotine catabolism." Applied and environmental microbiology 73.8 (2007): 2479-2485.
Mitsubayashi et al., "Bioelectronic sniffer for nicotine using enzyme inhibition." Analytica chimica acta 573 (2006): 69-74.
Moyer et al., "Simultaneous analysis of nicotine, nicotine metabolites, and tobacco alkaloids in serum or urine by tandem mass spectrometry, with clinically relevant metabolic profiles." Clinical chemistry 48.9 (2002): 1460-1471.
Turner "Biosensors: then and now." Trends in biotechnology 31.3 (2013): 119-120.
Olczuk et al., "A history of continuous glucose monitors (CGMs) in self-monitoring of diabetes mellitus." Diabetes & Metabolic Syndrome: Clinical Research & Reviews 12.2 (2018): 181-187.

(56) References Cited

OTHER PUBLICATIONS

Ortiz et al., ""Automating Functional Enzyme Screening& Characterization"" Poster—International Workshop on Bio-Design Automation (IWBDA) conference in Berkeley, CA—Aug. 2018.
Peeters et al., "Heat-transfer-based detection of L-nicotine, histamine, and serotonin using molecularly imprinted polymers as biomimetic receptors." Analytical and bioanalytical chemistry 405.20 (2013): 6453-6460.
Popovic et al., "Activity screening of environmental metagenomic libraries reveals novel carboxylesterase families." Scientific reports 7.1 (2017): 44103.
Rezende et al., "Detection of hydrogen peroxide with fluorescent dyes." Antioxidants & redox signaling 29.6 (2018): 585-602.
Rice et al., "Nursing interventions for smoking cessation." Cochrane database of systematic reviews 12 (2017): CD001188.
Richter et al., "Characterization of functional states in nicotine-and cotinine-imprinted poly (4-vinylphenol) films by nanoindentation." Journal of applied polymer science 124.4 (2012): 2798-2806.
Roelofs et al., "Differential radial capillary action of ligand assay for high-throughput detection of protein-metabolite interactions." Proceedings of the National Academy of Sciences 108.37 (2011): 15528-15533.
Russell et al., "Relation of nicotine yield of cigarettes to blood nicotine concentrations in smokers." British Medical Journal 280. 6219 (1980): 972-976.
Sanders et al., "Devices for self-monitoring sedentary time or physical activity: A scoping review." Journal of Medical Internet Research 18.5 (2016): e90.
Shakleya et al., "Simultaneous and sensitive measurement of nicotine, cotinine, trans-3'-hydroxycotinine and norcotinine in human plasma by liquid chromatography-tandem mass spectrometry." Journal of Chromatography B 877.29 (2009): 3537-3542.
Shehata et al., "Nano-TiO2 modified carbon paste sensor for electrochemical nicotine detection using anionic surfactant." Biosensors and Bioelectronics 79 (2016): 589-592.
Shiwaku et al., "A printed organic circuit system for wearable amperometric electrochemical sensors." Scientific reports 8.1 (2018): 6368.
Sims et al., "Effects of thin-layer diffusion in the electrochemical detection of nicotine on basal plane pyrolytic graphite (BPPG) electrodes modified with layers of multi-walled carbon nanotubes (MWCNT-BPPG)." Sensors and Actuators B: Chemical, 2010. 144(1): 153-158.
Šmajs et al., "Construction of small genome BAC library for functional and genomic applications." Methods in Molecular Biology, vol. 255: Bacterial Artificial Chromosomes, vol. 1 :Library Construction, Physical Mapping, and Sequencing. Humana Press, 2004: 47-56.
Steinberg et al., "A wireless potentiostat for mobile chemical sensing and biosensing." Talanta 143 (2015): 178-183.
Švorc et al., "Boron-doped diamond electrochemical sensor for sensitive determination of nicotine in tobacco products and antismoking pharmaceuticals." Diamond and Related Materials 42 (2014): 1-7.
Tabassum et al., "Simultaneous tuning of electric field intensity and structural properties of ZnO: graphene nanostructures for FOSPR based nicotine sensor." Biosensors and Bioelectronics 91 (2017): 762-769.
Tan et al., "A study of a new TSM bio-mimetic sensor using a molecularly imprinted polymer coating and its application for the determination of nicotine in human serum and urine." Bioelectrochemistry 53.2 (2001): 141-148.
Tang et al., "A novel gene, encoding 6-hydroxy-3-succinoylpyridine hydroxylase, involved in nicotine degradation by Pseudomonas putida strain S16." Applied and environmental microbiology 74.5 (2008): 1567-1574.
Tang et al., "Genomic analysis of Pseudomonas putida: Genes in a genome island are crucial for nicotine degradation." Scientific reports 2.1 (2012): 377.
Tang et al., "Novel nicotine oxidoreductase-encoding gene involved in nicotine degradation by Pseudomonas putida strain S16." Applied and environmental microbiology 75.3 (2009): 772-778.
Tang et al., "Systematic unraveling of the unsolved pathway of nicotine degradation in Pseudomonas." PLoS Genetics 9.10 (2013): e1003923.
Tao et al., "Epidemiological perspectives of diabetes." Cell biochemistry and biophysics 73.1 (2015): 181-185.
Tararina et al., "Crystallography coupled with kinetic analysis provides mechanistic underpinnings of a nicotine-degrading enzyme." Biochemistry 57.26 (2018): 3741-3751.
Tararina et al., "Structural Analysis Provides Mechanistic Insight into Nicotine Oxidoreductase from Pseudomonas putida." Biochemistry 2016, 55 (48), 6595-6598.
Teepoo et al., "Electrospun chitosan-gelatin biopolymer composite nanofibers for horseradish peroxidase immobilization in a hydrogen peroxide biosensor." Biosensors 7.4 (2017): 47.
Thisted et al., "Optimization of a nicotine degrading enzyme for potential use in treatment of nicotine addiction." BMC biotechnology 19.1 (2019): 56.
Uchiyama et al., "Substrate-induced gene-expression screening of environmental metagenome libraries for isolation of catabolic genes." Nature biotechnology 23.1 (2005): 88-93.
Benowitz "Clinical pharmacology of inhaled drugs of abuse: implications in understanding nicotine dependence." NIDA Res Monogr 99 (1990): 12-29.
Van Der Helm et al., "The evolving interface between synthetic biology and functional metagenomics." Nature chemical biology 14.8 (2018): 752-759.
Vigneshvar et al., "Recent advances in biosensor technology for potential applications—an overview." Frontiers in bioengineering and biotechnology 4 (2016): 11.
Wackers et al., "Array formatting of the heat-transfer method (HTM) for the detection of small organic molecules by molecularly imprinted polymers." Sensors 14.6 (2014): 11016-11030.
Wadgave et al., "Nicotine replacement therapy: an overview." International journal of health sciences 10.3 (2016): 425-435.
Wallen et al. Accuracy of heart rate watches: Implications for weight management. PLoS One, 2016. 11 (5): p. e0154420.
Wang et al., "Accuracy of wrist-worn heart rate monitors." JAMA cardiology 2.1 (2017): 104-106.
Wang et al., "Low potential detection of nicotine at multiwalled carbon nanotube-alumina-coated silica nanocomposite". Electrochemistry Communications, 2009. 11(4): p. 733-735.
Woronoff et al., "Activity-Fed Translation (AFT) Assay: A New High-Throughput Screening Strategy for Enzymes in Droplets." Chembiochem 16.9 (2015): 1343-1349.
Wu et al., "A sensitive nicotine sensor based on molecularly imprinted electropolymer of o-aminophenol." Frontiers of Chemistry in China, 1.2 (2006): 183-187.
Xiao et al., "Electroanalysis of nicotine at an electroreduced carboxylated graphene modified glassy carbon electrode." Analytical methods 7.3 (2015): 1147-1153.
Xu et al., "Annual healthcare spending attributable to cigarette smoking: an update." American journal of preventive medicine 48.3 (2015): 326-333.
Xue et al., "A new strategy for smoking cessation: characterization of a bacterial enzyme for the degradation of nicotine." Journal of the American Chemical Society 137.32 (2015): 10136-10139.
Xue et al., "An enzymatic advance in nicotine cessation therapy." Chemical Communications 54.14 (2018): 1686-1689.
Yang et al., "Inhibition biosensor for determination of nicotine." Analytica chimica acta 509.2 (2004): 151-157.
Yu et al., "Complete genome sequence of the nicotine-degrading Pseudomonas putida strain S16." Journal of Bacteriology 193.19 (2011): 5541-5542.
Yu et al., "Molecular mechanism of nicotine degradation by a newly isolated strain, *Ochrobactrum* sp. strain SJY1." Applied and environmental microbiology 81.1 (2015): 272-281.
Zamojc et al., "Fluorescent probes used for detection of hydrogen peroxide under biological conditions." Critical reviews in analytical chemistry 46.3 (2016): 171-200.

(56) References Cited

OTHER PUBLICATIONS

World Health Organization "WHO report on the global tobacco epidemic 2017: Monitoring tobacco use and prevention policies." (2017): 1-135.
Balabanova et al., "Nicotine excretion by the apocrine and eccrine sweat in smokers and passive smokers." Der Hautarzt; Zeitschrift fur Dermatologie, Venerologie, und verwandte Gebiete 43.2 (1992): 73-76.
Alenus et al., "Detection of L-nicotine with dissipation mode quartz crystal microbalance using molecular imprinted polymers." Physica status solidi (a) 209.5 (2012): 905-910.
Alenus et al., "Molecularly imprinted polymers as synthetic receptors for the QCM-D-based detection of L-nicotine in diluted saliva and urine samples." Analytical and bioanalytical chemistry 405.20 (2013): 6479-6487.
Ang et al., "Study on different molecular weights of chitosan as an immobilization matrix for a glucose biosensor." PLoS One 8.8 (2013): e70597.
Antwi-Boampong et al., "A molecularly imprinted fluoral-p/polyaniline double layer sensor system for selective sensing of formaldehyde." IEEE Sensors Journal 14.5 (2014): 1490-1498.
Antwi-Boampong et al., "Detection of formaldehyde vapor using conductive polymer films." Sensors and Actuators B: Chemical 182 (2013): 300-306.
Arugula et al., "Novel trends in affinity biosensors: current challenges and perspectives." Measurement Science and Technology 25.3 (2014): 032001.
Bellin et al., "Integrated circuit-based electrochemical sensor for spatially resolved detection of redox-active metabolites in biofilms." Nature communications 5.1 (2014): 3256.
Benowitz "Cotinine as a biomarker of environmental tobacco smoke exposure." Epidemiologic reviews 18.2 (1996): 188-204.
Campanella et al., "Direct determination of nicotine in antismoking pharmaceutical products and in tobacco using an inhibition biosensor." Analytical letters 34.6 (2001): 855-866.
Carlson et al., "An automated, handheld biosensor for aflatoxin." Biosensors and Bioelectronics 14.10-11 (2000): 841-848.
Cennamo et al., "High selectivity and sensitivity sensor based on MIP and SPR in tapered plastic optical fibers for the detection of L-nicotine." Sensors and Actuators B: Chemical 191 (2014): 529-536.
Choi et al., "Toward a generalized and high-throughput enzyme screening system based on artificial genetic circuits." ACS synthetic biology 3.3 (2014): 163-171.
Croux et al., "Development of multichannel quartz crystal microbalances for MIP-based biosensing." Physica status solidi (a) 209.5 (2012): 892-899.
Daniel "Construction of environmental libraries for functional screening of enzyme activity." Directed Molecular Evolution of Proteins: or How to Improve Enzymes for Biocatalysis (2002): 63-78.
Debon et al., "Ultrahigh-throughput screening enables efficient single-round oxidase remodelling." Nature Catalysis 2.9 (2019): 740-747.
Diaz-Gonzalez et al., "Recent advances in electrochemical enzyme immunoassays." Electroanalysis: An International Journal Devoted to Fundamental and Practical Aspects of Electroanalysis 17.21 (2005): 1901-1918.
Dzyadavych et al., "Amperometric enzyme biosensors: Past, present and future." Irbm 29.2-3 (2008): 171-180.
Egorov et al., "Horseradish peroxidase isozyme C. A comparative study of native and recombinant enzyme produced by E. coli transformants." Annals of the New York Academy of Sciences 721 (1994): 73-81.
El-Amrawy et al., "Are currently available wearable devices for activity tracking and heart rate monitoring accurate, precise, and medically beneficial?." Healthcare informatics research 21.4 (2015): 315-320.
Etter et al., "Saliva cotinine levels in smokers and nonsmokers." American Journal of Epidemiology 151.3 (2000): 251-258.
Fei et al., "Screening small-molecule compound microarrays for protein ligands without fluorescence labeling with a high-throughput scanning microscope." Journal of biomedical optics 15.1 (2010): 016018.
Fekry et al., "A novel electrochemical nicotine sensor based on cerium nanoparticles with anionic surfactant." RSC Advances 5.64 (2015): 51662-51671.
Ferrer et al., "Metagenomics for mining new genetic resources of microbial communities." Journal of molecular microbiology and biotechnology 16 1-2 (2009): 109-123.
Ferrer et al., "Interplay of metagenomics and in vitro compartmentalization." Microbial biotechnology 2.1 (2009): 31-39.
Frenzel et al., "Expression of recombinant antibodies." Frontiers in immunology 4 (2013): 217.
Geerets et al., "Optimizing the thermal read-out technique for MIP-based biomimetic sensors: Towards nanomolar detection limits." Sensors 13.7 (2013): 9148-9159.
Goiffon et al., "A rapid bioluminescence assay for measuring myeloperoxidase activity in human plasma." Nature communications 6.1 (2015): 6271.
Goodarzi et al.."Evaluation of nicotine sensor based on copper nanoparticles and carbon nanotubes." Journal of Nanostructure in Chemistry 5.3 (2015): 237-242.
Grigorenko et al., "Recombinant horseradish peroxidase: Production and analytical applications." Biochemistry (Moscow) 80.4 (2015): 408-416.
Hammond et al., "A diffusion monitor to measure exposure to passive smoking." Environmental science & technology 21.5 (1987): 494-497.
Harrison et al., "Activity tracking: barriers, workarounds and customisation." Proceedings of the 2015 ACM International Joint Conference on Pervasive and Ubiquitous Computing. 2015.
Held "An introduction to reactive oxygen species." BioTek Instruments (2015): 1-21.
Hornsby et al., "A high through-put platform for recombinant antibodies to folded proteins." Molecular & Cellular Proteomics 14.10 (2015): 2833-2847.
Hosokowa et al., "Droplet-based microfluidics for high-throughput screening of a metagenomic library for isolation of microbial enzymes." Biosensors and Bioelectronics 67 (2015): 379-385.
Hosu et al., "Colorimetric multienzymatic smart sensors for hydrogen peroxide, glucose and catechol screening analysis." Talanta 204 (2019): 525-532.
International Search Report and Written Opinion dated Jul. 21, 2021 for International Application No. PCT/US21/016894.

\* cited by examiner

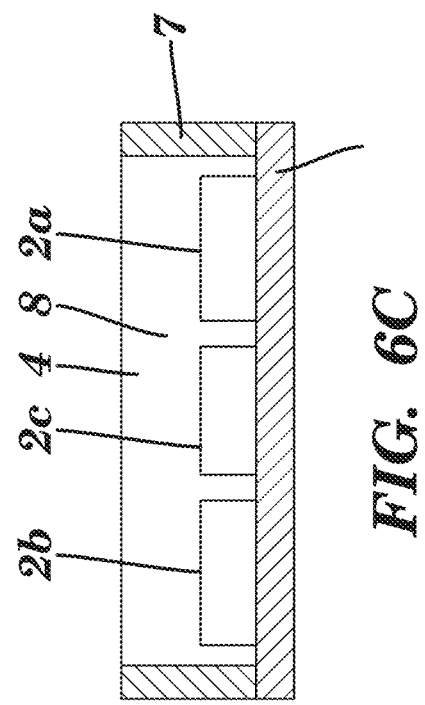
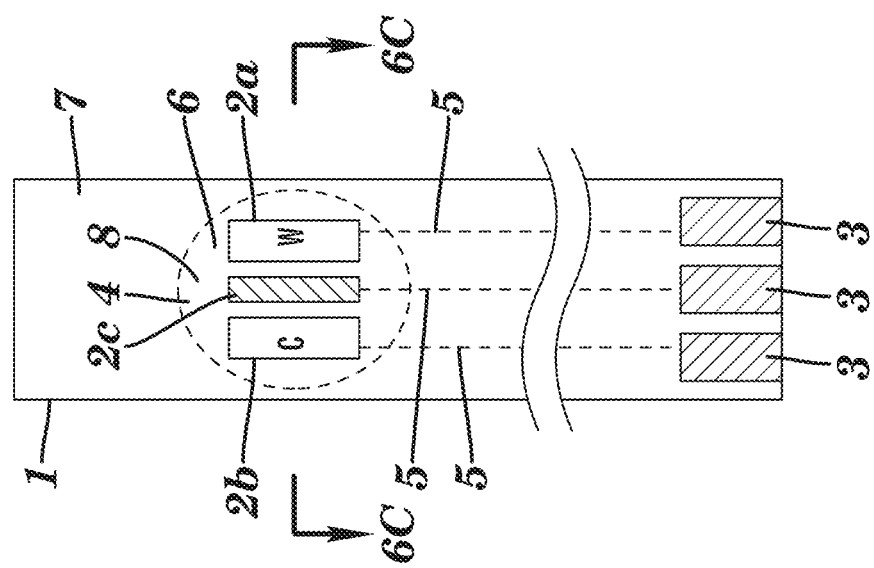
FIG. 6C
FIG. 6B

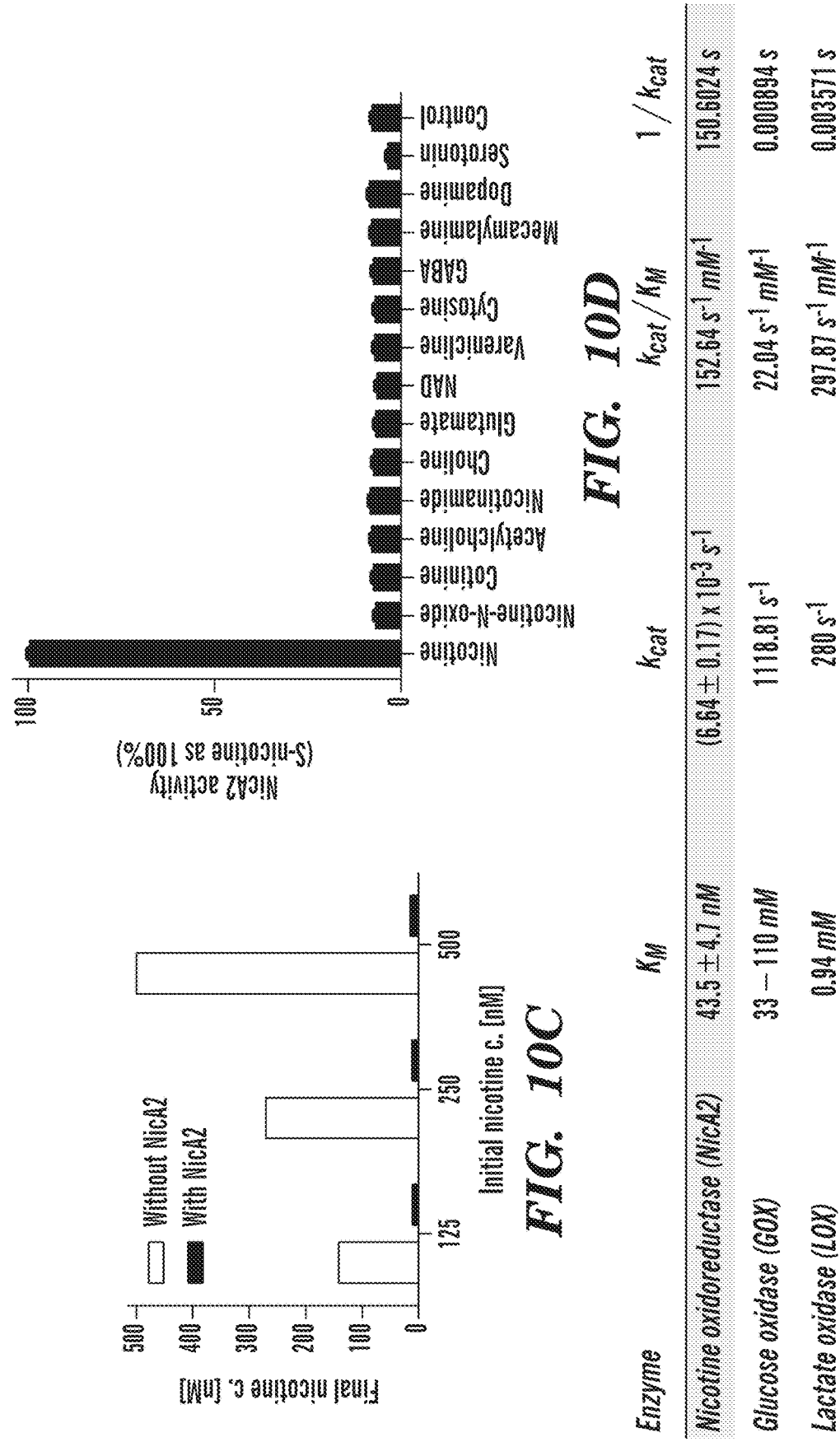

FIG. 11D Mutations in Aromatic Cage can Improve Catalytic Activity

| Enzyme | $K_M$ | $k_{cat}$ (s$^{-1}$) | $K_d$ (µM) | $k_{red}$ (s$^{-1}$) | Oxidation $k_{obs}$ (s$^{-1}$) | $k_{cat}/K_m$ (M$^{-1}$ s$^{-1}$) | $k_{red}/K_d$ (M$^{-1}$ s$^{-1}$) |
|---|---|---|---|---|---|---|---|
| GO$_X$ | 33 – 110 mM | 1118.81 | | | | $2.20 \times 10^4$ | |
| LO$_X$ | 0.94 mM | 280 | | | | $2.98 \times 10^5$ | |
| NicA2 WT | 43.5 ± 4.7 nM | (6.64 ± 0.17) * 10$^{-3}$ | 65.9 ± 10 | 186 ± 9.9 | 0.00137 | $5.35 \times 10^4$ | $2.82 \times 10^6$ |
| NicA2 (N462V) | | | 28.1 ± 4.6 | 0.353 ± 0.01 | 0.00170 | $1.29 \times 10^4$ | $1.26 \times 10^4$ |
| NicA2 (N462Y/W427Y) | | | 24.3 ± 3.3 | 0.103 ± 0.003 | 0.00626 | $1.58 \times 10^4$ | $4.24 \times 10^3$ |
| NicA2 (N462H) | | | 15.0 ± 2.5 | 20.3 ± 0.003 | 0.01028 | $1.98 \times 10^5$ | $1.36 \times 10^6$ |
| NicA2 (A107R) | 830 nM | 0.159 | | | | $1.9 \times 10^5$ | |

SEQUENCE LISTING

<160> NUMBER OF SEQ ID NOS: 7

<210> SEQ ID NO 1
<211> LENGTH: 1449
<212> TYPE: DNA
<213> ORGANISM: Pseudomonas putida

<400> SEQUENCE: 1

| | | | | | |
|---|---|---|---|---|---|
| atgagtgata | aaacaaaaac | aaatgaaggc | tttagccgca | ggtctttat | cggaagcgcg | 60 |
| gcagtcgtaa | cagcaggtgt | tgcgggattg | ggagctattg | atgcggcttc | ggctacgcaa | 120 |
| aaaacgaacc | gagcaagcac | cgtcaaaggt | ggcttcgatt | acgatgtggt | agtagttggt | 180 |
| ggagggtttg | ctggcgcgac | agccgcccgt | gaatgtggtt | tgcagggtta | tcgaacgctt | 240 |
| ttattggaag | cgaggtcccg | cctaggtggt | cgtacgttta | cctcgcgctt | tgcaggtcaa | 300 |
| gaaattgaat | ttggcggggc | atgggtgcac | tggctgcagc | cgcatgtttg | ggcagaaatg | 360 |
| cagcgttacg | gtctgggtgt | agtggaagat | ccacttacta | atttagataa | aaccttaatc | 420 |
| atgtataacg | acggaagcgt | cgaaagtatt | tcgcccgatg | aatttggcaa | aacattcga | 480 |
| atagcttttg | aaaagctttg | tcacgatgcc | tgggaagtat | ttcctcgtcc | gcatgagccg | 540 |
| atgtttactg | agcgcgctcg | ggaattggat | aaatcttctg | ttcttgatcg | catcaaaact | 600 |
| ttgggcttaa | gtcggctgca | acaggctcaa | atcaatagtt | acatggcctt | gtatgcaggt | 660 |
| gagacaactg | acaaatttgg | cctgcctggt | gtacttaagt | tgtttgcatg | cggcggttgg | 720 |
| aactatgacg | ccttcatgga | cactgaaact | cattatagaa | ttcaaggggg | cacgataggc | 780 |
| ctcattaatg | caatgttgac | cgatagcggt | gccgaggtcc | gcatgtctgt | gcccgtcact | 840 |
| gctgttgagc | aagtcaatgg | tggcgtcaaa | atcaagaccg | acgacgacga | aattattacc | 900 |
| gccggagtgg | tcgtaatgac | agttccactc | aatacgtata | acatatcgg | ttttacgcct | 960 |
| gcccttcta | aagtaaaaca | acgattcatc | aaagaggggc | agcttagcaa | aggtgctaag | 1020 |
| ctttatgttc | atgttaagca | gaatctcgga | cgggtttttg | cgtttgcgga | tgaacagcaa | 1080 |
| cctttaaact | gggtccagac | gcacgattac | agcgacgagt | tggggacaat | actgtcgatc | 1140 |
| accatcgctc | gcaaagaaac | aattgatgtg | aatgaccgag | atgctgtaac | tcgcgaagtt | 1200 |
| caaaaaatgt | ttccgggtgt | tgaggttctt | ggtacagcgg | cttacgactg | gacagctgat | 1260 |
| ccattttcct | tgggggcatg | gcggcttat | ggagtaggtc | aactaagtcg | tctcaaagat | 1320 |
| ctacaggcgg | ctgaaggacg | tatttttattt | gcaggagctg | aaaccagtaa | cggttggcac | 1380 |
| gcgaatatcg | atggtgctgt | tgaaagtgga | ctacgtgccg | gtagggaggt | taagcagctc | 1440 |
| ttaagctag | | | | | | 1449 |

<210> SEQ ID NO 2
<211> LENGTH: 482
<212> TYPE: PRT
<213> ORGANISM: Pseudomonas putida

<400> SEQUENCE: 2

Met Ser Asp Lys Thr Lys Thr Asn Glu Gly Phe Ser Arg Arg Ser Phe
1               5                   10                  15

Ile Gly Ser Ala Ala Val Val Thr Ala Gly Val Ala Gly Leu Gly Ala
            20                  25                  30

Ile Asp Ala Ala Ser Ala Thr Gln Lys Thr Asn Arg Ala Ser Thr Val
        35                  40                  45

Lys Gly Gly Phe Asp Tyr Asp Val Val Val Gly Gly Gly Phe Ala
    50                  55                  60

```
Gly Ala Thr Ala Ala Arg Glu Cys Gly Leu Gln Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
            100                 105                 110

Gln Pro His Val Trp Ala Glu Met Gln Arg Tyr Gly Leu Gly Val Val
        115                 120                 125

Glu Asp Pro Leu Thr Asn Leu Asp Lys Thr Leu Ile Met Tyr Asn Asp
    130                 135                 140

Gly Ser Val Glu Ser Ile Ser Pro Asp Glu Phe Gly Lys Asn Ile Arg
145                 150                 155                 160

Ile Ala Phe Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
            180                 185                 190

Ser Val Leu Asp Arg Ile Lys Thr Leu Gly Leu Ser Arg Leu Gln Gln
        195                 200                 205

Ala Gln Ile Asn Ser Tyr Met Ala Leu Tyr Ala Gly Glu Thr Thr Asp
    210                 215                 220

Lys Phe Gly Leu Pro Gly Val Leu Lys Leu Phe Ala Cys Gly Gly Trp
225                 230                 235                 240

Asn Tyr Asp Ala Phe Met Asp Thr Glu Thr His Tyr Arg Ile Gln Gly
                245                 250                 255

Gly Thr Ile Gly Leu Ile Asn Ala Met Leu Thr Asp Ser Gly Ala Glu
            260                 265                 270

Val Arg Met Ser Val Pro Val Thr Ala Val Glu Gln Val Asn Gly Gly
        275                 280                 285

Val Lys Ile Lys Thr Asp Asp Glu Ile Ile Thr Ala Gly Val Val
    290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser
                325                 330                 335

Lys Gly Ala Lys Leu Tyr Val His Val Lys Gln Asn Leu Gly Arg Val
            340                 345                 350

Phe Ala Phe Ala Asp Glu Gln Gln Pro Leu Asn Trp Val Gln Thr His
        355                 360                 365

Asp Tyr Ser Asp Glu Leu Gly Thr Ile Leu Ser Ile Thr Ile Ala Arg
    370                 375                 380

Lys Glu Thr Ile Asp Val Asn Asp Arg Asp Ala Val Thr Arg Glu Val
385                 390                 395                 400

Gln Lys Met Phe Pro Gly Val Glu Val Leu Gly Thr Ala Ala Tyr Asp
                405                 410                 415

Trp Thr Ala Asp Pro Phe Ser Leu Gly Ala Trp Ala Ala Tyr Gly Val
            420                 425                 430

Gly Gln Leu Ser Arg Leu Lys Asp Leu Gln Ala Ala Glu Gly Arg Ile
        435                 440                 445

Leu Phe Ala Gly Ala Glu Thr Ser Asn Gly Trp His Ala Asn Ile Asp
    450                 455                 460

Gly Ala Val Glu Ser Gly Leu Arg Ala Gly Arg Glu Val Lys Gln Leu
465                 470                 475                 480
```

Leu Ser

<210> SEQ ID NO 3
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ser Asp Lys Thr Lys Thr Asn Glu Gly Phe Ser Arg Arg Ser Phe
1               5                   10                  15

Ile Gly Ser Ala Ala Val Val Thr Ala Gly Val Ala Gly Leu Gly Ala
            20                  25                  30

Ile Asp Ala Ala Ser Ala Thr Gln Lys Thr Asn Arg Ala Ser Thr Val
        35                  40                  45

Lys Gly Gly Phe Asp Tyr Asp Val Val Val Gly Gly Gly Phe Ala
    50                  55                  60

Gly Ala Thr Ala Ala Arg Glu Cys Gly Leu Gln Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
            100                 105                 110

Gln Pro His Val Trp Ala Glu Met Gln Arg Tyr Gly Leu Gly Val Val
        115                 120                 125

Glu Asp Pro Leu Thr Asn Leu Asp Lys Thr Leu Ile Met Tyr Asn Asp
130                 135                 140

Gly Ser Val Glu Ser Ile Ser Pro Asp Glu Phe Gly Lys Asn Ile Arg
145                 150                 155                 160

Ile Ala Phe Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
            180                 185                 190

Ser Val Leu Asp Arg Ile Lys Thr Leu Gly Leu Ser Arg Leu Gln Gln
        195                 200                 205

Ala Gln Ile Asn Ser Tyr Met Ala Leu Tyr Ala Gly Glu Thr Thr Asp
210                 215                 220

Lys Phe Gly Leu Pro Gly Val Leu Lys Leu Phe Ala Cys Gly Gly Trp
225                 230                 235                 240

Asn Tyr Asp Ala Phe Met Asp Thr Glu Thr His Tyr Arg Ile Gln Gly
                245                 250                 255

Gly Thr Ile Gly Leu Ile Asn Ala Met Leu Thr Asp Ser Gly Ala Glu
            260                 265                 270

Val Arg Met Ser Val Pro Val Thr Ala Val Glu Gln Val Asn Gly Gly
        275                 280                 285

Val Lys Ile Lys Thr Asp Asp Glu Ile Ile Thr Ala Gly Val Val
290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser
                325                 330                 335

Lys Gly Ala Lys Leu Tyr Val His Val Lys Gln Asn Leu Gly Arg Val
            340                 345                 350

```
Phe Ala Phe Ala Asp Glu Gln Gln Pro Leu Asn Trp Val Gln Thr His
            355                 360                 365

Asp Tyr Ser Asp Glu Leu Gly Thr Ile Leu Ser Ile Thr Ile Ala Arg
    370                 375                 380

Lys Glu Thr Ile Asp Val Asn Asp Arg Asp Ala Val Thr Arg Glu Val
385                 390                 395                 400

Gln Lys Met Phe Pro Gly Val Glu Val Leu Gly Thr Ala Ala Tyr Asp
                405                 410                 415

Trp Thr Ala Asp Pro Phe Ser Leu Gly Ala Trp Ala Ala Tyr Gly Val
            420                 425                 430

Gly Gln Leu Ser Arg Leu Lys Asp Leu Gln Ala Ala Glu Gly Arg Ile
        435                 440                 445

Leu Phe Ala Gly Ala Glu Thr Ser Asn Gly Trp His Ala His Ile Asp
    450                 455                 460

Gly Ala Val Glu Ser Gly Leu Arg Ala Gly Arg Glu Val Lys Gln Leu
465                 470                 475                 480

Leu Ser Leu Glu His His His His His His
                485                 490

<210> SEQ ID NO 4
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ser Asp Lys Thr Lys Thr Asn Glu Gly Phe Ser Arg Arg Ser Phe
1               5                   10                  15

Ile Gly Ser Ala Ala Val Val Thr Ala Gly Val Ala Gly Leu Gly Ala
            20                  25                  30

Ile Asp Ala Ala Ser Ala Thr Gln Lys Thr Asn Arg Ala Ser Thr Val
        35                  40                  45

Lys Gly Gly Phe Asp Tyr Asp Val Val Val Gly Gly Gly Phe Ala
50                  55                  60

Gly Ala Thr Ala Ala Arg Glu Cys Gly Leu Gln Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
            100                 105                 110

Gln Pro His Val Trp Ala Glu Met Gln Arg Tyr Gly Leu Gly Val Val
        115                 120                 125

Glu Asp Pro Leu Thr Asn Leu Asp Lys Thr Leu Ile Met Tyr Asn Asp
    130                 135                 140

Gly Ser Val Glu Ser Ile Ser Pro Asp Glu Phe Gly Lys Asn Ile Arg
145                 150                 155                 160

Ile Ala Phe Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
            180                 185                 190

Ser Val Leu Asp Arg Ile Lys Thr Leu Gly Leu Ser Arg Leu Gln Gln
        195                 200                 205

Ala Gln Ile Asn Ser Tyr Met Ala Leu Tyr Ala Gly Glu Thr Thr Asp
    210                 215                 220
```

Lys Phe Gly Leu Pro Gly Val Leu Lys Leu Phe Ala Cys Gly Gly Trp
225                 230                 235                 240

Asn Tyr Asp Ala Phe Met Asp Thr Glu Thr His Tyr Arg Ile Gln Gly
            245                 250                 255

Gly Thr Ile Gly Leu Ile Asn Ala Met Leu Thr Asp Ser Gly Ala Glu
        260                 265                 270

Val Arg Met Ser Val Pro Val Thr Ala Val Glu Gln Val Asn Gly Gly
    275                 280                 285

Val Lys Ile Lys Thr Asp Asp Glu Ile Ile Thr Ala Gly Val Val
290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser
                325                 330                 335

Lys Gly Ala Lys Leu Tyr Val His Val Lys Gln Asn Leu Gly Arg Val
            340                 345                 350

Phe Ala Phe Ala Asp Glu Gln Gln Pro Leu Asn Trp Val Gln Thr His
        355                 360                 365

Asp Tyr Ser Asp Glu Leu Gly Thr Ile Leu Ser Ile Thr Ile Ala Arg
    370                 375                 380

Lys Glu Thr Ile Asp Val Asn Asp Arg Asp Ala Val Thr Arg Glu Val
385                 390                 395                 400

Gln Lys Met Phe Pro Gly Val Glu Val Leu Gly Thr Ala Ala Tyr Asp
                405                 410                 415

Trp Thr Ala Asp Pro Phe Ser Leu Gly Ala Tyr Ala Ala Tyr Gly Val
            420                 425                 430

Gly Gln Leu Ser Arg Leu Lys Asp Leu Gln Ala Ala Glu Gly Arg Ile
        435                 440                 445

Leu Phe Ala Gly Ala Glu Thr Ser Asn Gly Trp His Ala Tyr Ile Asp
    450                 455                 460

Gly Ala Val Glu Ser Gly Leu Arg Ala Gly Arg Glu Val Lys Gln Leu
465                 470                 475                 480

Leu Ser Leu Glu His His His His His His
                485                 490

<210> SEQ ID NO 5
<211> LENGTH: 1473
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgagtgata aacaaaaac aaatgaaggc tttagccgca ggtcttttat cggaagcgcg      60
gcagtcgtaa cagcaggtgt tgcgggattg ggagctattg atgcggcttc ggctacgcaa     120
aaaacgaacc gagcaagcac cgtcaaaggt ggcttcgatt acgatgtggt agtagttggt     180
ggagggtttg ctggcgcgac agccgcccgt gaatgtggtt tgcagggtta tcgaacgctt     240
ttattggaag cgaggtcccg cctaggtggt cgtacgttta cctcgcgctt tgcaggtcaa     300
gaaattgaat ttgcgggggc atgggtgcac tggctgcagc cgcatgtttg gcagaaatg     360 cagcgttacg gtctgggtgt agtggaagat ccacttacta atttagataa aaccttaatc    420
atgtataacg acggaagcgt cgaaagtatt tcgcccgatg aatttggcaa aaacattcga    480

```
atagcttttg aaaagctttg tcacgatgcc tgggaagtat ttcctcgtcc gcatgagccg    540
atgtttactg agcgcgctcg ggaattggat aaatcttctg ttcttgatcg catcaaaact    600
ttgggcttaa gtcggctgca acaggctcaa atcaatagtt acatggcctt gtatgcaggt    660
gagacaactg acaaatttgg cctgcctggt gtacttaagt tgtttgcatg cggcggttgg    720
aactatgacg ccttcatgga cactgaaact cattatagaa ttcaaggggg cacgataggc    780
ctcattaatg caatgttgac cgatagcggt gccgaggtcc gcatgtctgt gcccgtcact    840
gctgttgagc aagtcaatgg tggcgtcaaa atcaagaccg acgacgacga attattacc     900 gccggagtgg tcgtaatgac agttccactc aatacgtata acatatcgg ttttacgcct     960 gcccttt cta aaggtaaaca acgattcatc aaagaggggc agcttagcaa aggtgctaag   1020
ctttatgttc atgttaagca gaatctcgga cgggttttg cgtttgcgga tgaacagcaa    1080
cctttaaact gggtccagac gcacgattac agcgacgagt tggggacaat actgtcgatc   1140
accatcgctc gcaaagaaac aattgatgtg aatgaccgag atgctgtaac tcgcgaagtt   1200
caaaaaatgt ttccgggtgt tgaggttctt ggtacagcgg cttacgactg gacagctgat   1260 ccatttt cct tggggg catg ggc ggcttat ggagtaggtc aactaagtcg tctcaaagat   1320
ctacaggcgg ctgaaggacg tattttattt gcaggagctg aaaccagtaa cggttggcac   1380
gcgcatatcg atggtgctgt tgaaagtgga ctacgtgccg gtagggaggt taagcagctc   1440
ttaagcctag agcaccacca ccaccaccac tag                                1473
```

<210> SEQ ID NO 6
<211> LENGTH: 1473
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atgagtgata aacaaaaac aaatgaaggc tttagccgca ggtctttat cggaagcgcg      60 gcagtcgtaa cagcaggtgt tgcgggattg ggagctattg atgcggcttc ggctacgcaa    120
aaaacgaacc gagcaagcac cgtcaaaggt ggcttcgatt acgatgtggt agtagttggt    180
ggagggtttg ctggcgcgac agccgcccgt gaatgtggtt tgcagggtta tcgaacgctt    240
ttattggaag cgaggtcccg cctaggtggt cgtacgttta cctcgcgctt tgcaggtcaa    300
gaaattgaat ttggcggggc atgggtgcac tggctgcagc cgcatgtttg ggcagaaatg    360
cagcgttacg gtctgggtgt agtggaagat ccacttacta atttagataa aaccttaatc    420
atgtataacg acggaagcgt cgaaagtatt tcgcccgatg aatttggcaa aaacattcga    480
atagcttttg aaaagctttg tcacgatgcc tgggaagtat ttcctcgtcc gcatgagccg    540
atgtttactg agcgcgctcg ggaattggat aaatcttctg ttcttgatcg catcaaaact    600
ttgggcttaa gtcggctgca acaggctcaa atcaatagtt acatggcctt gtatgcaggt    660
gagacaactg acaaatttgg cctgcctggt gtacttaagt tgtttgcatg cggcggttgg    720
aactatgacg ccttcatgga cactgaaact cattatagaa ttcaaggggg cacgataggc    780
ctcattaatg caatgttgac cgatagcggt gccgaggtcc gcatgtctgt gcccgtcact    840
gctgttgagc aagtcaatgg tggcgtcaaa atcaagaccg acgacgacga attattacc     900 gccggagtgg tcgtaatgac agttccactc aatacgtata acatatcgg ttttacgcct     960 gcccttt cta aaggtaaaca acgattcatc aaagaggggc agcttagcaa aggtgctaag   1020
```

```
ctttatgttc atgttaagca gaatctcgga cgggttttg cgtttgcgga tgaacagcaa    1080
cctttaaact gggtccagac gcacgattac agcgacgagt tggggacaat actgtcgatc    1140
accatcgctc gcaaagaaac aattgatgtg aatgaccgag atgctgtaac tcgcgaagtt    1200 caaaaatgt ttccgggtgt tgaggttctt ggtacagcgg cttacgactg gacagctgat    1260 ccatttcct tggggcata cgcggcttat ggagtaggtc aactaagtcg tctcaaagat    1320
ctacaggcgg ctgaaggacg tatttattt gcaggagctg aaaccagtaa cggttggcac    1380
gcgtacatcg atggtgctgt tgaaagtgga ctacgtgccg gtagggaggt taagcagctc    1440
ttaagcctag agcaccacca ccaccaccac tag                                 1473
```

<210> SEQ ID NO 7
<211> LENGTH: 305
<212> TYPE: PRT
<213> ORGANISM: Escherichia coli

<400> SEQUENCE: 7

```
Met Asn Ile Arg Asp Leu Glu Tyr Leu Val Ala Leu Ala Glu His Arg
1               5                   10                  15

His Phe Arg Arg Ala Ala Asp Ser Cys His Val Ser Gln Pro Thr Leu
            20                  25                  30

Ser Gly Gln Ile Arg Lys Leu Glu Asp Glu Leu Gly Val Met Leu Leu
        35                  40                  45

Glu Arg Thr Ser Arg Lys Val Leu Phe Thr Gln Ala Gly Met Leu Leu
    50                  55                  60

Val Asp Gln Ala Arg Thr Val Leu Arg Glu Val Lys Val Leu Lys Glu
65                  70                  75                  80

Met Ala Ser Gln Gln Gly Glu Thr Met Ser Gly Pro Leu His Ile Gly
                85                  90                  95

Leu Ile Pro Thr Val Gly Pro Tyr Leu Leu Pro His Ile Ile Pro Met
            100                 105                 110

Leu His Gln Thr Phe Pro Lys Leu Glu Met Tyr Leu His Glu Ala Gln
        115                 120                 125

Thr His Gln Leu Leu Ala Gln Leu Asp Ser Gly Lys Leu Asp Cys Val
    130                 135                 140

Ile Leu Ala Leu Val Lys Glu Ser Glu Ala Phe Ile Glu Val Pro Leu
145                 150                 155                 160

Phe Asp Glu Pro Met Leu Leu Ala Ile Tyr Glu Asp His Pro Trp Ala
                165                 170                 175

Asn Arg Glu Cys Val Pro Met Ala Asp Leu Ala Gly Glu Lys Leu Leu
            180                 185                 190

Met Leu Glu Asp Gly His Cys Leu Arg Asp Gln Ala Met Gly Phe Cys
        195                 200                 205

Phe Glu Ala Gly Ala Asp Glu Asp Thr His Phe Arg Ala Thr Ser Leu
    210                 215                 220

Glu Thr Leu Arg Asn Met Val Ala Ala Gly Ser Gly Ile Thr Leu Leu
225                 230                 235                 240

Pro Ala Leu Ala Val Pro Pro Glu Arg Lys Arg Asp Gly Val Val Tyr
                245                 250                 255

Leu Pro Cys Ile Lys Pro Glu Pro Arg Arg Thr Ile Gly Leu Val Tyr
            260                 265                 270
```

```
Arg Pro Gly Ser Pro Leu Arg Ser Arg Tyr Glu Gln Leu Ala Glu Ala
        275                 280                 285

Ile Arg Ala Arg Met Asp Gly His Phe Asp Lys Val Leu Lys Gln Ala
    290                 295                 300

Val
305
```

ENZYME-BASED ELECTROCHEMICAL NICOTINE BIOSENSOR

CROSS-REFERENCE TO RELATED APPLICATION

This application claims benefit under 35 U.S.C. § 119(e) of U.S. Provisional Application Nos. 62/971,012 filed Feb. 6, 2020, the contents of each of which are incorporated herein by reference in their entirety.

GOVERNMENT SUPPORT

This invention was made with Government Support under Contract No. W911NF-16-C-0044 awarded by the Army Research Office and Contract No. 1522074 awarded by the National Science Foundation. The Government has certain rights in the invention.

SEQUENCE LISTING

The instant application contains a Sequence Listing which has been submitted electronically in ASCII format and is hereby incorporated by reference in its entirety. Said ASCII copy, created on Mar. 11, 2021, is named 701586-093890USPT_SL.txt and is 22,004 bytes in size.

TECHNICAL FIELD

The technology described herein relates to enzyme-based electrochemical nicotine biosensors.

BACKGROUND

The advent of rapid, facile sensing is changing daily life and empowering clinical decision making. The Fitbit™ and Apple Watch™ for monitoring pH, hydration, temperature, heart rate, oxygen, etc., and glucose sensors for managing type 2 diabetes are prime examples. However, enzymatic electrochemical based sensors are few in number and limited in analyte scope (e.g., glucose, fructose, lactate, glutamate, lysine, ethanol), despite the fact that the glucose sensor was developed/discovered approximately 50 years ago. Given the interest in sensing varied analytes for applications in medicine, health/nutrition, agriculture, and environmental management, there is need to develop new sensor designs and diagnostic technologies both for single use detection and for continuous monitoring.

Nicotine is one such analyte of interest, is present in tobacco products, and is one of the most heavily used addictive stimulants. Cigarette smoking accounts for 90 percent of lung cancer cases, causes about 80% of all deaths from chronic obstructive pulmonary disease, and increases the risk of stroke, vascular disease, and a heart attack in the U.S. It is the leading preventable cause of disease, disability, and death. Overcoming nicotine dependence is arduous as nicotine provides pleasing physical and mood-altering effects and withdrawal systems include irritability, anxiety, hunger, and craving for tobacco products. Outcomes for addiction treatment are best when tailored to the individual patient, however this is not easily accomplished. There is a need to identify those patients which are fast or slow nicotine metabolizers to determine treatment dosing and scheduling. Furthermore, there is a need to provide continuous monitoring of nicotine in conjunction with counseling and holistic approaches for altering behavior represent. Such needs represent paradigms in care where actionable intelligence and decisions are guided by biology.

The most accurate methods for currently measuring nicotine require sample collection followed by mass spectroscopy analysis. However, these methods are not practical for portable or point-of-need applications. Additionally, most nicotine detecting kits use antibodies to give a positive or negative result with a certain cutoff (e.g. NicAlert™, NicoTests™, and One Step™). Additionally, these kits lack a continuous measurement and cannot specify how much nicotine is present in a solution, nor do such kits allow for communication of the information with a physician or one's phone or computer. Although current nicotine detection kits are fairly cheap, the cost effectiveness of one-time use does not compare to continuous monitoring, reliability or detection of the levels of nicotine. If quantitative levels of nicotine are to be measured, expensive and time consuming analytical techniques such as gas or liquid chromatography-mass spectrometry (GCMS or LCMS) are required, however, these are neither accessible to a majority of users or adaptable to point of care (POC) detection.

Accordingly, there is a need for a point-of-care biosensor device for specifically detecting the levels of nicotine at physiological ranges in fluid samples, which enables real-time and continuous detection, and can be easily and inexpensively manufactured.

SUMMARY

The technology described herein relates to an amperometric biosensor, e.g., a chronoamperometric biosensor for the measurement of nicotine. In order to design a chronoamperometric sensor for nicotine, a nicotine sensing element, also referred to herein as a nicotine biorecognition element, was identified from a bacterial source. In some embodiments, the nicotine biosensor disclosed herein is a wearable nicotine biosensor. Bacteria have evolved over 3 billion years to detect and respond to virtually all classes of stimuli or chemicals relevant to their surroundings. For example, *Pseudomonas putida* S16, a bacteria present in the soil of tobacco fields, grows on nicotine as its sole carbon source. Since *P. putida* S16 metabolizes nicotine into fumaric acid through the pyrrolidine pathway, identification and utilization of a pathway monoamine oxidase (MAO) can provide such a sensing element. In the presence of the substrate, the MAO produces hydrogen peroxide for chronoamperometric measurement. Described herein is a point-of-care (POC) nicotine detection device with sensitivity and specificity for clinical use as well as quantification of nicotine from samples.

The inventors have discovered that nicotine can be converted to N-methly-myosamine by the enzyme NicA2, and that NicA2 is an oxidoreductase. Accordingly, the inventors have developed a nicotine biosensor comprising the nicotine-catalyzing redox enzymes, for example, NicA2.

In all aspects of the technology described herein is a nicotine biosensor, comprising on its surface, a nicotine-catalyzing enzyme, where the nicotine-catalyzing enzyme is electronically coupled to a redox mediator (referred to herein as a "Med" or an "electronically active mediator"), so that when the nicotine-catalyzing enzyme catalyzes the analyte nicotine, it transfers electrons (i.e., causes a redox reaction) to a redox mediator/electronically active mediator, were the redox mediator/electronically active mediator then transfers electrons, either directly (or indirectly, as discussed herein with the use of Intermediate Redox Enzymes) to a suitable electron detection method, for example, to an electrode to produce a current, or to an electronically excitable product which can be detected by fluorescence or colorimetric methods.

Accordingly, in one aspect, described herein is an amperometric biosensor comprising: (a) an electrode comprising a surface; (b) an electronically active mediator deposited on the surface of the electrode; and (c) a plurality of nicotine-catalyzing enzymes, e.g., NicA2 enzymes or mutant NicA2 enzymes deposited on the surface of the electrode, wherein the nicotine-catalyzing enzyme is an oxidase that catalyzes nicotine to produce hydrogen peroxide ($H_2O_2$).

The advantage of the nicotine biosensor described herein is that produces a signal or response that is: (1) specific to nicotine, (2) occurs in real-time, (3) is continuous, and (4) does not cross-react to cotinine, the common human metabolite of nicotine. Moreover, the nicotine biosensor described herein can also be easily and inexpensively manufactured, and manufactured at scale using well established methods. In some embodiments, the readout of the biosensor described herein requires simple, inexpensive, and miniaturizable electronics.

Described herein is an enzyme-based electrochemical nicotine biosensor that can specifically and continuously detect nicotine in real-time and at concentrations appropriate for a range of commercial and health applications. The underlying sensing part is a nicotine degrading enzyme, for example, NicA2 and mutant NicA2 enzymes, which function similar to glucose oxidase found in commercially available continuously monitoring glucose biosensors. Thus, the NicA2 enzyme can be used as a biorecognition element and combined with known biosensor components for the generation of a small scale, portable biosensor, that can be a point-of-care (POC) monitor that can measure nicotine levels in the environment, e.g., in air or from fluids, e.g., bodily fluids.

Importantly, the inventors optimized multiple parameters of the NicA2 biosensor disclosed herein to achieve a biosensor that enabled real-time measurements of nicotine, was sensitive to physiological levels of nicotine in sweat and other samples obtained from a smoker, and enabled repeated detection of nicotine in a variety of different samples. In particular, the surface of the electrode on which NicA2 or NicA2 mutant is located was carefully optimized to comprise low- and medium molecular weight (MW) chitosan in 0.5% acetic acid, the surface area and size of the electrode was increased, and surprisingly, the inventors also discovered that optimal results were achieved using only two electrodes (e.g., see FIG. 16). Accordingly, the NicA2 biosensor disclosed herein are very different from glucose oxidase biosensors, as shown in the Examples.

In addition, the inventors assessed a variety of different NicA2 mutants as disclosed herein, and discovered that one mutant, NicA2(N462H) has the highest oxidation activity and is suitable for use as a biorecognition element in a nicotine biosensor (see, e.g., FIG. 11D).

Accordingly, as demonstrated herein, the inventors have optimized a nicotine biosensor that is capable of capable of detecting nicotine concentrations in the range expected in the sweat and urine of smokers and also those exposed to second-hand smoke. This is a significant development from the art, as there is currently no commercial available real-time nicotine biosensor which can measure nicotine from bodily fluids continuously. In some embodiments, the nicotine biosensor as described herein, can detect the presence of nicotine in second hand smoke from as little as one cigarette. Accordingly, the nicotine biosensor as described herein can be used in any application and/or sample where the accurate, specific, and rapid sensing of nicotine is useful.

In some embodiments, the NicA2 enzyme-based nicotine biosensor can detect the presence of nicotine both in solution and aerosolized in the air. In some embodiments, the nicotine biosensor described herein can detect a range of 0.4 uM-100 µM in solution, for example as determined by using artificial sweat with nicotine added. Accordingly, the NicA2 biosensor disclosed herein can detect nicotine within a wide range of nicotine concentrations that are present in active smoker's sweat, gastric juice, urine, saliva, as well as detecting the high end of nicotine concentrations in an active smoker's blood. The NicA2 biosensor disclosed herein can also detect nicotine within the range of nicotine in the human sweat of a passive smoker (i.e. a person exposed to second-hand smoke). Accordingly, the nicotine NicA2 biosensor described herein can be used to test nicotine levels from sweat, urine, and saliva of smokers and non-smokers as well as those exposed to second-hand smoke.

Accordingly, in one aspect described herein is a biosensor, e.g., an amperometric biosensor, for the measurement of the concentration of nicotine comprising: (a) an electrode comprising a surface; (b) an electronically active mediator deposited on the surface of the electrode; and (c) a plurality of NicA2 enzymes, or mutant NicA2 enzymes deposited on the surface of the electrode, wherein the NicA2 or NicA2 mutant enzyme catalyze nicotine to produce hydrogen peroxide ($H_2O_2$).

Another aspect of the technology described herein is a wearable nicotine biosensor device, for example, an exemplary wearable NicA2(N462H) biosensor device is shown in FIGS. 29A-29B herein. In some embodiments, a wearable NicA2 device comprises two parts, an electroconductive part comprising a housing with a removable lid, and within the housing an electric control circuit to control the screen printed electrode (SPE), a battery, and PDMS layer housing a paper channel to wick a subject's sweat from their skin into the SPE. Magnets or other means can be used to attach the removable lid to the housing. The housing is positioned above or adjacent to a two electrode-screen printed electrode (SPE), where at least one electrode has a NicA2 enzyme deposited on, where the NicA2 serves as the nicotine biorecognition element, and where the SPE is in fluid communication via the paper channel to a wicking apparatus, where the wicking apparatus contacts the skin of the wearer (i.e., the subject) and wicks sweat from the surface of a subject's skin. Accordingly, FIG. 29B shows an exemplary wearable nicotine electrochemical biosensor device that comprises a housing portion of the biosensor and underneath or adjacent to the housing is the placement of a 2-electrode SPE where one electrode is deposited with NicA2(N462H), and where the SPE is in fluid communication with a sweat sample. In particular, the SPE is in fluid communication via a paper channel with a wicking paper, where the wicking paper wicks sweat from the skin surface of a subject, and 1) the sweat is wicked onto the SPE by the paper channel, and then, 2) sweat is drawn towards the sink by capillary action and passed onto of the 2-electrode sensor comprising the NicA2 (N462H) biorecognition element, and 3) sweat is collected at the sink after measurement. The inventors demonstrate that such a wearable NicA2 biosensor has high sensitivity and can repeatedly measure nicotine in numerous samples, and has a sensitivity to be able to detect nicotine within a 2-50 µM and 50-1000 µM range.

In another aspect, described herein is use of an amperometric biosensor of as described herein, a system as described herein, or a method as described herein, in any one of: (a) detecting a person smoking or using a nicotine containing device in a restricted area; (b) reducing nicotine intake in a subject; (c) reducing cigarette smoking or use of a nicotine containing device by a subject; (d) monitoring exposure of a subject to second-hand or environmental cigarette smoke; or (e) monitoring nicotine levels in a subject.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

FIG. 2A is a schematic showing the Amplex® UltraRed mechanism. Nicotine is oxidized into n-methyl-myosmine and $H_2O_2$ with presence of NicA2 and $O_2$. Horseradish peroxidase (HRP) then reduces Amplex® UltraRed in the presence of $H_2O_2$ into resorufin, which is fluorescent. FIG. 2B-2C show that the signal is analyte dependent when keeping NicA2 concentrations constant; FIG. 2B shows nicotine concentrations from 0.390625 uM to 50 uM, and FIG. 2C shows nicotine concentrations from 0.078125 uM to 10 uM. FIG. 2D shows that the signal is not enzyme limited when varying NicA2 concentrations; however, the catalytic rate is concentration dependent. FIG. 2D shows NicA2 concentrations from 0.078125 uM to 10 uM. FIG. 2E compares resorufin fluorescence from nicotine to fluorescence from $H_2O_2$, which directly confirms a 1:1 production of $H_2O_2$ from nicotine by NicA2. RFU: relative fluorescent units.

FIG. 3A shows a dose response to various concentrations of nicotine. FIG. 3B shows a calibration curve. A chronoamperometric assay with 200 μM nicotine is shown in the inset. FIG. 3C shows a specificity study. A mixture of common interferents were prepared in PBS (see e.g., Table 4). Addition of 30 μL 200 μM nicotine solution to 30 μL mixture was performed at a predefined time point, and current was recorded over time. Similar experiments were performed to evaluate the selectivity of the sensor to cotinine. FIG. 3D shows NicA2 dependence of the biosensor. Myosmine, an inhibitor of NicA2, was added in the middle of a chronoamperometric experiment. There was minimal response from myosmine alone or nicotine addition after NicA2 was inhibited by myosmine. FIG. 3E shows signal with various combinations of nicotine, myosmine, glucose, NicA2, and glucose.

FIG. 6A-6C shows a schematic of an electron flow mechanism for the NicA2 biosensor. FIG. 6A shows an exemplary embodiment of the NicA2 nicotine biosensor which can be comprised composed of a carbon three-electrode screen printed electrode (SPE) with a Ag/AgCl reference electrode. Before deposition of enzyme onto the SPE, Prussian Blue (PB) mediator is electrodeposited onto the SPE. Once the mediator is electrodeposited, NicA2 is deposited onto the SPE working electrode (WE) with chitosan, a natural polymer. When analyte is added onto the three electrodes of the SPE the circuit is completed between them, and a current response can be measured when a constant potential is applied by a potentiostat. The presence of the nicotine in the solution causes the creation of a diffusion layer and a gradient between regions of high and low analyte concentrations. This gradient creates flux governed by Fick's Law and drives the movement of analyte to the working electrode. In another exemplary embodiment, the NicA2 biosensor comprises a two-electrode SPE, as shown in FIG. 16 or FIG. 12A-12B. FIGS. 6B and 6C shows exemplary representations of a NicA2 amperometric biosensor, e.g., chronoamperometric biosensor for the measurement of nicotine.

FIG. 10A-10E shows that NicA2 oxidase enzyme is specific and has a high affinity for nicotine over several days. Furthermore, NicA2 is a hardy oxidase, with a specific high affinity for nicotine, but it is slow. FIG. 10A shows NicA2 is active between 37-90° C. FIG. 10B is a graph showing NicA2 is active for as long as 25 days. FIG. 10C is a graph showing degradation of nicotine by NicA2 between 125 nM-500 nM. FIG. 10D shows NicA2 activity with a range of analytes, demonstrating that NicA2 has specific affinity for nicotine. FIG. 10E shows a table of the kinetic parameters ($K_M$, $K_{cat}$, $K_{cat}/K_M$ and $1/k_{cat}$) of NicA2 versus other oxidases, glucose oxidase and lactose oxidases used as biorecognition elements in biosensors. The $K_M$ is (substrate concentration at which ½ maximum enzymatic reaction rate is achieved by): (i) substrate's binding affinity, and (ii) rate of enzyme-substrate complex turned into product ($k_{cat}$).

FIG. 11A-11D shows exemplary mutations in the NicA2 protein improve activity. FIG. 11A is a schematic showing conserved aromatic cage at the active site of NicA2. FIG. 1B shows potential amino acids of NicA2 around the active site for modification. FIG. 11C shows increased activity of the NicA2 mutant N462H, as compared to the other NicA2 mutants N462Y/W427Y and wild type NicA2. FIG. 1D is a table showing increased oxidative activity of NicA2 mutant N462H compared to WT and other NicA2 mutants N462V, B462Y/W427Y, A107R. Kd: ligand concentration where ½ of proteins have ligand bound. Kd: ligand concentration where ½ of proteins have ligand bound. Mutants for NicA2, in particular N462H have improved $k_{obs}$ (how fast oxygen is entering) and $k_{red}$ rates (how fast FAD is reduced) and $K_d$ (ligand binds more tightly).

FIG. 12A shows a nicotine biosensor comprising NicA2 that comprises three electrodes has significant drift overtime (200 μM nicotine was used). FIG. 12B shows a nicotine biosensor comprising NicA2 as the biorecognition element with two electrodes and a shortened CE circuit showed less drift and less noise with at least two samples of nicotine (200 μM nicotine was used each time).

FIG. 13A shows low molecular weight chitosan had no difference to medium molecular weight chitosan with 0.5% acetic acid in a chronoamperometric experiment with three additions of the same concentration of nicotine. FIG. 13B shows no difference in current with 2% acetic acid between low and medium MW chitosan when glucose oxidase is the biorecognition element, but there was no current when NicA2 was the biorecognition element, demonstrating that the surface of the electrode with NicA2 needs careful optimization and was not the same as glucose oxidase, and that NicA2 is not as durable or robust as glucose oxidase.

FIG. 14A shows effect of FAD with the glucose oxidase biosensor, showing FAD does not improve the enzyme's activity. FIG. 14B shows effect of FAD with glucose and FAD showing that the FAD co-factor does not improve the current in a biosensor comprising a glucose oxidase enzyme.

FIG. 15A shows current is preserved only with the configuration of electrode-Prussian-Blue (PB)-Chitosan in 0.5% acetic acid-NicA2. The top surface of nafion (e.g., 5% or 1%) did not preserve current, nor did chitosan in 2% acetic acid. FIG. 15B shows that, in contrast to an electrode with NicA2, an electrode with glucose oxidase as the biorecognition element, Nafion did preserve current as well as chitosan in 2% acetic acid. FIG. 15C shows increasing the surface area of the electrode comprising NicA2 on the surface was significant in increasing the current.

FIG. 17A-B were performed with the N462H mutant, FIG. 17C-E were performed with the N462Y/W427Y mutant, and FIG. 17F was performed with WT NicA2. FIG. 17A shows the NicA2 biosensor can detect nicotine between the range of 0.48 M-1000 M, demonstrating it is sensitive for the detection of smoker nicotine levels. FIG. 17B shows detection of nicotine levels sufficient to detect nicotine in smoker urine, smoker sweat, smoker interstitial fluid (ISF), and smoker saliva. FIG. 17C shows the NicA2 biosensor detects nicotine only and does not detect Cotinine, a byproduct of nicotine metabolism. FIG. 17D is a graph showing detection in nicotine in saliva vs. saliva only, showing no interferent signal from saliva. FIG. 17E shows the NicA2 biosensor is active and functional over the range of pH levels from pH4.5-8.0, which spans the pH range of smoker urine, smoker sweat, smoker ISF, and smoker saliva. FIG. 17F shows a graph of current (nA) of the NicA2 biosensor after multiple days stored at different temperatures, showing the biosensor is stable at 37° C. for as many as 7 days, demonstrating suitability for use as a wearable nicotine biosensor (from left to right for each time point: room temperature, 37° C., 4° C.). FIG. 17G shows detection of nicotine from urine. FIG. 17H shows the detection of nicotine in 3 saliva samples from a chewing tobacco user using the NicA2 biosensor (labeled "electrochemistry") is comparable to the detection of nicotine using Mass spectrometry (labelled "LTQ").

FIG. 18A shows addition of nicotine on 8 separate occasions at ranges of 0 nmol, 0.25 nmol, 1 nmol, 5 nmol amounts, and can be repeatedly detected with NicA2 WT on a 3-electrode biosensor. FIG. 18B shows total charge v. nicotine on a 3 electrode biosensor, showing the measured nicotine was similar to the expected nicotine levels. FIG. 18C shows the total charge vs. nicotine on a 3 electrode biosensor showing a linear trend for nicotine concentrations added over time.

FIG. 19A shows addition of nicotine on 10 separate occasions at ranges with the amounts 0 nmol, 0.625 nmol, 1.25 nmol, 2.75 nmol, 1.625 nmol, 3.5 nmol, 0.9375 nmol, 2 nmol and 4.25 nmol of Nicotine, and demonstrates that nicotine can be repeatedly detected in increasing and decreasing amounts using NicA2 (N462H) on a 3-electrode biosensor. FIG. 19B shows addition of nicotine on 10 separate occasions at the same amount to FIG. 19A, and demonstrates that nicotine can be repeatedly detected in increasing and decreasing amounts using NicA2(N462H) on a 2-electrode biosensor. Notably, optimization of the biosensor with NicA2(N462H) on a 2-electrode biosensor (FIG. 19B) eliminated the drift that occurred using the 3 electrode biosensor (FIG. 19A). FIG. 19C shows detection of nicotine in decreasing amounts can be repeatedly detected using NicA2(N462H) on a 2-electrode biosensor, demonstrating that nicotine can be detected using the NicA2(N462H) 2 electrode biosensor as low as 1.25 nmol.

FIG. 20A shows total charge vs. nicotine concentration on a 3 electrode system where $R^2=0.7676$. FIG. 20B shows total charge vs. nicotine concentration on a 2 electrode system where $R^2=0.9531$, demonstrating no drift in the current with increasing nicotine addition in the 2 electrode system. FIG. 20C shows the linear dose response of the total charge vs. nicotine concentration on a 2 electrode system of the final concentration between 10-50 μM, showing that evaporation causes a difference in the charge calculated with the final nicotine concentration. FIG. 20D shows the linear dose response of the total charge vs. nicotine concentration on a 2 electrode system of the amount of nicotine added between 50-1000 M, showing a very tight linear correlation $R^2=0.9916$ and reliable calibration of the NicA2 biosensor.

FIG. 21A shows the current measured on addition of artificial urine with specific amounts of nicotine (0 nmol, 0.5625 nmol, 1.25 nmol and 2 nmol) and in blind samples (BS1, BS2, BS3). FIG. 21B shows the measured charge vs. the expected charge on a 2 electrode system.

FIG. 22A shows the linear dose response of the total charge vs. nicotine concentration on a 2 electrode system of the final concentration between 0.5 nmol-1 nmol nicotine. FIG. 22B shows the measured nicotine levels in artificial urine samples was the same as the expected nicotine levels.

FIG. 23A shows the current measured on addition of non-smoker urine spiked with specific amounts of nicotine (0 nmol, 0.5625 nmol, 1.25 nmol and 2 nmol) and in blind samples (BS1, BS2, BS3). FIG. 23B shows the linear dose response of the total charge vs. nicotine concentration on a 2 electrode system of the final concentration between 0.5 nmol-2 nmol nicotine, and shows the measured nicotine levels in non-smoker urine samples were the same as the expected nicotine levels.

FIG. 24A shows the current measured on addition of artificial sweat samples spiked with specific amounts of nicotine (0 nmol, 0.5625 nmol, 1.25 nmol and 2 nmol) and in blind samples (BS1, BS2, BS3). FIG. 24B shows the linear dose response of the total charge vs. nicotine concentration on a 2 electrode system of the final concentration between 0.5 nmol-2 nmol nicotine, and shows the measured nicotine levels in the artificial sweat samples was over-predicted but by the same concentration and following the same trend as the actual nicotine levels.

FIG. 26 shows the linear dose response of the total charge vs. nicotine concentration on a 2 electrode system of the final concentration between 0.5 nmol-2 nmol nicotine, and shows the measured nicotine levels in the artificial saliva samples was the same as the expected nicotine levels.

FIG. 29A is a schematic illustrating the main components of an exemplary NicA2 biosensor device, comprising a housing with a removable lid, and within the housing an electric control circuit to control the SPE, a battery, and PDMS layer housing a paper channel to wick sweat from a subject into the SPE. Magnets or other means can be used to attach the removable lid to the housing. The housing is positioned above the SPE comprising the NicA2 biorecognition element, which is in contact with a wicking apparatus for wicking sweat from the surface of a subject's skin. FIG. 29B is a schematic illustrating the principal of operation, showing the housing portion of the biosensor of FIG. 29A and underneath the housing the placement of a 2-electrode SPE comprising the NicA2(N462H) biorecognition element which is in fluid communication with a sweat sample. In particular, the SPE is in contact with a paper channel that wicks sweat from the skin surface of a subject, and 1) the sweat is wicked onto the SPE by the paper channel, and then, 2) sweat is drawn towards the sink by capillary action and passed onto of the 2-electrode sensor comprising the NicA2 (N462H) biorecognition element, and 3) sweat is collected at the sink after measurement. FIG. 29C is a photograph of an exemplary wearable nicotine biosensor device (left), showing the biosensor device is able to quantitatively detect, in a continuous, reproducible and real-time manner nicotine in sweat within the range of 1 µM-1000 µM. FIG. 29D shows the sensitivity of the wearable NicA2 biosensor device can detect nicotine within a 2 µM-50 µM and 50 µM-1000 µM range.

FIG. 29E shows results of the nicotine biosensor exposed to 1 cigarette smoked in a 1 ft×0.5 ft box. On the left is paper containing horseradish peroxide (HRP) and Amplex UltraRed (AUR). On the right is horseradish peroxide (HRP) and Amplex UltraRed (AUR) and WT-NicA2 imaged after 20 mins in the smoke filled box.

DETAILED DESCRIPTION

Figure 1:
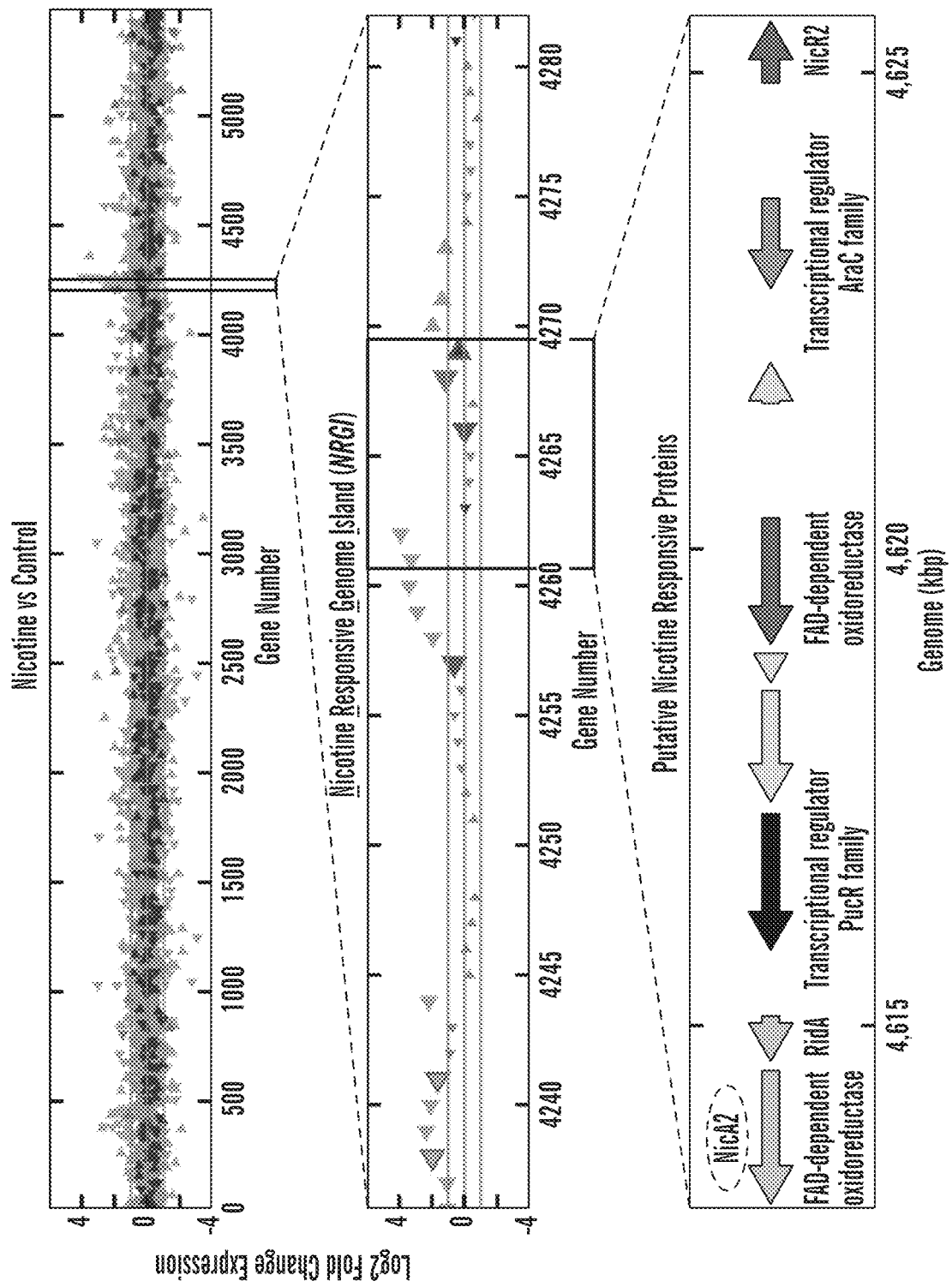
FIG. 1 is a series of graphs showing that RNA-Seq correctly identified the reported nic2 nicotine degrading genome cluster in *Pseudomonas putida* S16. In the nic2 cluster, the nicotine oxidoreductase enzyme (NicA2) is the highest differentially expressing enzyme which was then used in the nicotine biosensor described herein.

The technology described herein relates to a amperometric biosensor, e.g., chronoamperometric biosensor for the measurement of nicotine. In order to design a chronoamperometric sensor for nicotine, a nicotine sensing element was identified from a bacterial source. Bacteria have evolved over 3 billion years to detect and respond to virtually all classes of stimuli or chemicals relevant to their surroundings. For example, *Pseudomonas putida* S16, a bacteria present in the soil of tobacco fields, grows on nicotine as its sole carbon source. Since *P. putida* S16 metabolizes nicotine into fumaric acid through the pyrrolidine pathway, identification and utilization of a pathway monoamine oxidase (MAO) can provide such a sensing element. In the presence of the substrate, the MAO produces hydrogen peroxide for chronoamperometric measurement. Described herein is a prototype point-of-care (POC) detection device based on the MAO with sensitivity and specificity for clinical use as well as quantification of nicotine from samples. Accordingly, in one aspect, described herein is a amperometric biosensor, e.g., chronoamperometric biosensor comprising: (a) an electrode comprising a surface; (b) an electronically active mediator deposited on the surface of the electrode; and (c) a plurality of nicotine-catalyzing enzyme deposited on the surface of the electrode, wherein the nicotine-catalyzing enzyme is an oxidase that catalyzes nicotine to produce hydrogen peroxide ($H_2O_2$).

I. Elements of a Nicotine Biosensor Device

Label-free sensing of small molecule analytes such as nicotine is of critical importance to biomedical research, point of care diagnostics, and environmental sensing, among other applications. Connected devices that monitor human biology or the environment in real-time represent the next frontier in biosensors. Monitoring nicotine is of significant interest to subjects exposed to tobacco or cigarette smoke. However, the real-time monitoring of analytes such as nicotine is challenging from a biology, chemistry, and engineering perspective, with glucose detection being the one notable success. Using natural sensing elements from microbial species, e.g. native biomolecules that have evolved sensor and modulator capabilities, provides the opportunity to utilize a detection platform that is distinct from the typical antibody- or aptamer-based strategies for nicotine detection. Described herein is an amperometric, e.g., a chronoamperometric biosensor for the measurement of nicotine in a sample.

A biosensor is a device comprising a biological sensor element (also referred to as a biorecognition element or biological component) that typically produces electronic signals that are proportional to the concentration of a particular substance to be determined. As used herein the term "amperometric" refers to the measurement of current of an electrode, and "chronoamperometric" refers to the measurement of current of an electrode as a function of time.

Biosensors, e.g., nanobiosensors are a type of analytical device that use biological molecules to monitor biorecognition events and interactions. Generally, a biosensor comprises a biological component, a redox-mediator alongside nanoelectrodes; the various components can be equated with the electronic elements of a sensor because the components transduce the signal generated at the source (bioelement) to the detector (electrode). In general, a biological component of a biosensor can be a protein (e.g., enzyme or antibody), nucleic acid (DNA or RNA) or even entire cells.

The use of enzymes as bioactive interfaces is well known in the art, and such interfaces are used in analytical methods of detecting electronic transduction of enzyme-substrate reactions. Direct electrical activation of enzymes such as redox enzymes permits stimulation of bioelectrocatalyzed oxidation or reduction of enzyme substrates. Rapid transfer of electrons between an electrode and a given redox enzyme results in current generation corresponding to the rate of turnover of the electron exchange between the substrate and biocatalyst. In other words, the transduced current of the system correlates with enzyme substrate concentration. Electrical contacting of redox proteins in a biosensor and the electrode support contained therein may be mediated by direct electron transfer with electrode surfaces. Redox enzymes lacking direct electrical communication with electrodes may achieve electrical contact by mediated electron transfer via redox mediators that serve as active charge carriers.

For non-limiting examples of biosensors, see e.g., U.S. Pat. Nos. 6,241,863, 6,736,777, 7,794,994; US patent publications US 2003/0027239, US 2009/0099434, US 2009/0061451, US 2012/0181189, US 2019/0004005; PCT publications WO 2013/059534, WO 2005/048834; European patent 1194585; Vigneshvar et al. Front Bioeng Biotechnol. 2016, 4:11; Turner, Chem Soc Rev. 2013 Apr. 21, 42(8): 3184-96; Hosu et al., Talanta Volume 204, 1 Nov. 2019, Pages 525-532; the contents of each of which, including but not limited to biosensors and methods and systems comprising them, are incorporated herein by reference in their entireties.

In all aspects of the technology described herein is a nicotine biosensor, comprising on its surface, a nicotine-catalyzing enzyme, where the nicotine-catalyzing enzyme is electronically coupled to a redox mediator (referred to herein as a "Med" or an "electronically active mediator"), so that when the nicotine-catalyzing enzyme binds to, and catalyzes the analyte nicotine, it transfers electrons (i.e., causes a redox reaction) to a redox mediator/electronically active mediator, were redox mediator/electronically active mediator then transfers electrons, either directly (or indirectly, as discussed herein with the use of Readout enzyme) to a suitable electron detection method, for example, to an electrode thereby producing a current, or to an electronically excitable product.

Without wishing to be limited to theory, in catalyzing nicotine to a product, the nicotine-catalyzing enzyme causes a redox event which is coupled to a redox mediator which acts as a conductor of electrons to the detector, typically an electrode, thereby relaying the detection of the nicotine analyte. In some embodiments, the amount of electrons produced, and detected by the electron detector is corresponds to the amount of the analyte, in this instance, the amount of nicotine. In some embodiments, the biosensor is set up to allow multiple redox events, e.g., 2, or 3 redox events. In some embodiments, a redox event occurs between the transfer of electrons from the nicotine to the redox mediator/electronically active mediator when nicotine is catalyzed to N-methyl-mysoamine (step 1), and a second redox event occurs the when the reduced redox mediator returns to the oxidized form, thereby transferring electrons to the electron detector, typically an electrode (step 2). In another embodiment, a redox event occurs between the transfer of electrons from the nicotine to a redox mediator/electronically active mediator when nicotine is catalyzed to N-methyl-mysoamine and $H_2O_2$ (step 1), where the redox mediator/electronically active mediator can only accept the electrons in the presence of an intermediate redox enzyme (IRE) and $H_2O_2$, and a second redox event occurs the when the reduced redox mediator produces a signal (step 2).

A. Nicotine Degrading Enzymes for Use in Nicotine Biosensors

Herein, the technology relates to a nicotine biosensor device comprising a nicotine detecting or nicotine catalyzing redox-enzyme. Redox-enzymes in general are responsible for the binding and recognition of the special target analyte, whether a small molecule or a large protein partner. The binding of the redox-enzyme to the target analyte is the basis for signal generation and a physical element, such a detectable signal is generated, and can an electrode, captures the signal as the output. Thus, coupling the redox-enzyme with a mediator, translates information from the binding of the target analyte and redox-enzyme into a chemical or physical output with a defined sensitivity. The information that is detected can be chemical, energetic, such as detection of light, and/or signal detection and transduction.

In all aspects of the technology described herein, the redox enzyme in the biosensor is a nicotine detecting- or nicotine catalyzing-redox enzyme that catalyzes or detects the analyte nicotine or a nicotine derivative, for example, but not limited to, neonicotinoids. The nicotine detecting or nicotine-catalyzing redox enzyme detects each optical active nicotine variant, including the optically active, two enantiomeric forms. The naturally occurring form of nicotine is levorotatory with a specific rotation of $[\alpha]D=-166.4°$ ((−)-nicotine). The dextrorotatory form, (+)-nicotine is physiologically less active than (−)-nicotine. (−)-nicotine is more toxic than (+)-nicotine. The salts of (+)-nicotine are usually dextrorotatory; this conversion between levorotatory and dextrorotatory upon protonation is common among alkaloids. The hydrochloride and sulfate salts become optically inactive if heated in a closed vessel above 180° C. Anabasine is a structural isomer of nicotine, as both compounds have the molecular formula C10H14N2.

A "redox enzyme" or "oxidoreductases" are used interchangeably herein and refer to an enzyme that catalyzes a reaction with one or more enzyme substrate(s), resulting in generation or utilization of electrons. Redox enzymes are proteins that catalyze electron transfer by reduction or oxidation of substrates within the redox network. The oxidoreductases (redox) enzyme reaction and the electrode coupling method has become attractive to develop biosensors. In particular, for a range of substrates, i.e., glucose (i.e., glucose oxidase and glucose dehydrogenase reaction, respectively), electrochemical detection of reduced coenzyme nicotinamide adenine dinucleotide (NADH) or hydrogen peroxide has been used in galvanometer biosensors.

A redox reaction is a chemical reaction in which the oxidation states of atoms are changed. Any such reaction involves both a reduction process and a complementary oxidation process, two key concepts involved with electron transfer processes. Redox reactions include all chemical reactions in which atoms have their oxidation state changed; in general, redox reactions involve the transfer of electrons between chemical species.

Aspects of the biosensor described herein rely on catalyzing an electrochemical reaction (redox) of the redox-enzyme biosensor in the presence of a target analyte (i.e., substrate; e.g., nicotine). In use, an analyte specific to the redox-enzyme biosensor is catalyzed, changing electron flow through the biosensor. In one non-limiting embodiment, the redox-enzyme biosensor (or a functional portion thereof) catalyzes a redox event in the presence of a target analyte (i.e., where the analyte is a substrate of the redox enzyme). The redox event can be coupled to a redox-mediator (referred to herein as a "Med") which acts as a conductor of electrons to permit detection of the redox event between the target analyte (e.g., nicotine) and the redox-enzyme (e.g., nicotine-catalyzing or -detecting redox enzyme). In some embodiments, the redox event between the target analyte (e.g., nicotine) and the redox-enzyme (e.g., nicotine-catalyzing or -detecting redox enzyme) can be coupled to an intermediate redox enzyme (IRE), that acts as a conductor of electrons between the first redox event (between and the redox-enzyme (e.g., nicotine-catalyzing or -detecting redox enzyme) and the redox-mediator (Med). In some embodiments, the redox-mediator can be linked to an electrode, nano-electrode or nanobioneedle, which all act as conductors of electrons to permit detection of any signal changes in the redox-enzyme biosensor.

In some embodiments, the redox-mediator generates a signal detectable by optical methods, such as, without limitation, fluorescence, surface plasmon resonance, or piezoelectric methods.

i. NicA2 Enzymes

In some embodiments of any of the aspects, the redox enzyme is a nicotine catalyzing or nicotine-detecting enzyme. One aspect described herein relates to an amperometric biosensor comprising a nicotine-catalyzing or nicotine detecting enzyme. In all aspects herein, the nicotine-catalyzing enzyme or a nicotine-detecting enzyme is a redox enzyme. In some embodiments, the nicotine-catalyzing enzyme or a nicotine-detecting enzyme is an oxidase enzyme. Accordingly, in one aspect described herein is a amperometric biosensor, e.g., chronoamperometric biosensor comprising a nicotine-catalyzing enzyme. In some embodiments of any of the aspects, the biosensor described herein comprises a plurality of nicotine-catalyzing enzyme deposited on the surface of the electrode. In some embodiments of any of the aspects, the nicotine-catalyzing enzyme is an oxidase that catalyzes nicotine to produce hydrogen peroxide ($H_2O_2$).

In some embodiments of any of the aspects, the nicotine-catalyzing enzyme is *Pseudomonas putida* NicA2.

In some embodiments of any of the aspects, the biosensor described herein comprises a nicotine-catalyzing enzyme encoded by any of SEQ ID NO: 1, SEQ ID NO: 5 or SEQ ID NO: 6 or a nucleic acid sequence that is at least 70%, at least 80%, at least 90%, at least 91%, at least 92%, at least 93%, at least 94%, at least 95%, at least 96%, at least 97%, at least 98%, at least 99%, or at least 99.5% identical to the sequence of SEQ ID NO: 1, SEQ ID NO: 5 or SEQ ID NO: 6 that maintains the same function (e.g., nicotine degradation).

SEQ ID NO: 1 Wild Type NicA2 from *Pseudomonas putida* S16, complete genome GenBank: CP002870.1 complement (REGION: 4613081-4614529), G-43961 (MetaCyc); PPS_4081; F8G0P2 (UniProt) 1449 bp.

(SEQ ID NO: 1)
ATGAGTGATAAAACAAAAACAAATGAAGGCTTTAGCCGCAGGTCTTTTA

TCGGAAGCGCGGCAGTCGTAACAGCAGGTGTTGCGGGATTGGGAGCTAT

TGATGCGGCTTCGGCTACGCAAAAAACGAACCGAGCAAGCACCGTCAAA

GGTGGCTTCGATTACGATGTGGTAGTAGTTGGTGGAGGGTTTGCTGGCG

CGACAGCCGCCCGTGAATGTGGTTTGCAGGGTTATCGAACGCTTTTATT

GGAAGCGAGGTCCCGCCTAGGTGGTCGTACGTTTACCTCGCGCTTTGCA

GGTCAAGAAATTGAATTTGGCGGGGCATGGGTGCACTGGCTGCAGCCGC

ATGTTTGGGCAGAAATGCAGCGTTACGGTCTGGGTGTAGTGGAAGATCC

ACTTACTAATTTAGATAAAACCTTAATCATGTATAACGACGGAAGCGTC

GAAAGTATTTCGCCCGATGAATTTGGCAAAAACATTCGAATAGCTTTTG

AAAAGCTTTGTCACGATGCCTGGGAAGTATTTCCTCGTCCGCATGAGCC

GATGTTTACTGAGCGCGCTCGGGAATTGGATAAATCTTCTGTTCTTGAT

CGCATCAAAACTTTGGGCTTAAGTCGGCTGCAACAGGCTCAAATCAATA

GTTACATGGCCTTGTATGCAGGTGAGACAACTGACAAATTTGGCCTGCC

TGGTGTACTTAAGTTGTTTGCATGCGGCGGTTGGAACTATGACGCCTTC

ATGGACACTGAAACTCATTATAGAATTCAAGGGGGCACGATAGGCCTCA

TTAATGCAATGTTGACCGATAGCGGTGCCGAGGTCCGCATGTCTGTGCC

CGTCACTGCTGTTGAGCAAGTCAATGGTGGCGTCAAAATCAAGACCGAC

GACGACGAAATTATTACCGCCGGAGTGGTCGTAATGACAGTTCCACTCA

ATACGTATAAACATATCGGTTTTACGCCTGCCCTTTCTAAAGGTAAACA

ACGATTCATCAAAGAGGGGCAGCTTAGCAAAGGTGCTAAGCTTTATGTT

CATGTTAAGCAGAATCTCGGACGGGTTTTTGCGTTTGCGGATGAACAGC

AACCTTTAAACTGGGTCCAGACGCACGATTACAGCGACGAGTTGGGGAC

AATACTGTCGATCACCATCGCTCGCAAAGAAACAATTGATGTGAATGAC

CGAGATGCTGTAACTCGCGAAGTTCAAAAAATGTTTCCGGGTGTTGAGG

TTCTTGGTACAGCGGCTTACGACTGGACAGCTGATCCATTTTCCTTGGG

GGCATGGGCGGCTTATGGAGTAGGTCAACTAAGTCGTCTCAAAGATCTA

CAGGCGGCTGAAGGACGTATTTTATTTGCAGGAGCTGAAACCAGTAACG

GTTGGCACGCGAATATCGATGGTGCTGTTGAAAGTGGACTACGTGCCGG

TAGGGAGGTTAAGCAGCTCTTAAGCTAG

In some embodiments of any of the aspects, the amino acid sequence of the nicotine-catalyzing enzyme comprises SEQ ID NO: 2, SEQ ID NO: 3 or SEQ ID NO: 4 or an amino acid sequence that is at least 70%, at least 80%, at least 90%, at least 91%, at least 92%, at least 93%, at least 94%, at least 95%, at least 96%, at least 97%, at least 98%, at least 99%, or at least 99.5% identical to the sequence of SEQ ID NO: 2 that maintains the same function of SEQ ID NO: 2, SEQ ID NO: 3 or SEQ ID NO: 4 (e.g., nicotine degradation).

```
NicA2(WT) + Pseudomonas putida S16], see e.g.,
GenBank: AEJ14620.1, 482 aa.
                                      SEQ ID NO: 2
                                     (SEQ ID NO: 2)
MSDKTKTNEGFSRRSFIGSAAVVTAGVAGLGAIDAASATQKTNRASTVK

GGFDYDVVVVGGGFAGATAARECGLQGYRTLLLEARSRLGGRTFTSRFA

GQEIEFGGAWVHWLQPHVWAEMQRYGLGVVEDPLTNLDKTLIMYNDGSV

ESISPDEFGKNIRIAFEKLCHDAWEVFPRPHEPMFTERARELDKSSVLD

RIKTLGLSRLQQAQINSYMALYAGETTDKFGLPGVLKLFACGGWNYDAF

MDTETHYRIQGGTIGLINAMLTDSGAEVRMSVPVTAVEQVNGGVKIKTD

DDEIITAGVVVMTVPLNTYKHIGFTPALSKGKQRFIKEGQLSKGAKLYV

HVKQNLGRVFAFADEQQPLNWVQTHDYSDELGTILSITIARKETIDVND

RDAVTREVQKMFPGVEVLGTAAYDWTADPFSLGAWAAYGVGQLSRLKDL

QAAEGRILFAGAETSNGWHANIDGAVESGLRAGREVKQLLS (aa NicA2 (N462H) (which is encoded by SEQ ID
NO: 5)
                                      SEQ ID NO: 3
MSDKTKTNEGFSRRSFIGSAAVVTAGVAGLGAIDAASATQKTNRASTVK

GGFDYDVVVVGGGFAGATAARECGLQGYRTLLLEARSRLGGRTFTSRFA

GQEIEFGGAWVHWLQPHVWAEMQRYGLGVVEDPLTNLDKTLIMYNDGSV

ESISPDEFGKNIRIAFEKLCHDAWEVFPRPHEPMFTERARELDKSSVLD

RIKTLGLSRLQQAQINSYMALYAGETTDKFGLPGVLKLFACGGWNYDAF

MDTETHYRIQGGTIGLINAMLTDSGAEVRMSVPVTAVEQVNGGVKIKTD

DDEIITAGVVVMTVPLNTYKHIGFTPALSKGKQRFIKEGQLSKGAKLYV

HVKQNLGRVFAFADEQQPLNWVQTHDYSDELGTILSITIARKETIDVND

RDAVTREVQKMFPGVEVLGTAAYDWTADPFSLGAWAAYGVGQLSRLKDL

QAAEGRILFAGAETSNGWHAHIDGAVESGLRAGREVKQLLSLEHHHHHH (aaNicA2 (N462Y/W427Y) (which is encoded by SEQ
ID NO: 6)
                                      SEQ ID NO: 4
MSDKTKTNEGFSRRSFIGSAAVVTAGVAGLGAIDAASATQKTNRASTVK

GGFDYDVVVVGGGFAGATAARECGLQGYRTLLLEARSRLGGRTFTSRFA

GQEIEFGGAWVHWLQPHVWAEMQRYGLGVVEDPLTNLDKTLIMYNDGSV

ESISPDEFGKNIRIAFEKLCHDAWEVFPRPHEPMFTERARELDKSSVLD

RIKTLGLSRLQQAQINSYMALYAGETTDKFGLPGVLKLFACGGWNYDAF

MDTETHYRIQGGTIGLINAMLTDSGAEVRMSVPVTAVEQVNGGVKIKTD

DDEIITAGVVVMTVPLNTYKHIGFTPALSKGKQRFIKEGQLSKGAKLYV

HVKQNLGRVFAFADEQQPLNWVQTHDYSDELGTILSITIARKETIDVND

RDAVTREVQKMFPGVEVLGTAAYDWTADPFSLGAYAAYGVGQLSRLKDL

QAAEGRILFAGAETSNGWHAYIDGAVESGLRAGREVKQLLSLEHHHHHH
```

In some embodiments, the NicA2 enzyme does not the N-terminal domain. In some embodiments, the NicA2 enzyme does not the C-terminal domain. In some embodiments, the NicA2 enzyme does not comprise amino acids 1-50 of SEQ ID NO: 2, which are predicted to be disordered, play a role in localization, and not be critical to the enzyme's properties. In some embodiments, the NicA2 enzyme comprises residues 51-482 of SEQ ID NO: 2, or a sequence that is at least 70%, at least 80%, at least 90%, at least 91%, at least 92%, at least 93%, at least 94%, at least 95%, at least 96%, at least 97%, at least 98%, at least 99%, or at least 99.5% identical to residues 51-482 of SEQ ID NO: 2 that maintains the same function (e.g., nicotine degradation). See e.g., Xue et al., Chem Commun 2018 Feb. 13; 54(14): 1686-1689, the content of which is incorporated herein by reference in its entirety.

In some embodiments, the NicA2 enzyme comprises a substitution in at least one residue involved in the active site (e.g., L217, Y218, Q427, W427, N462/W427, N462, E249, W108, T250, W364, T318); see e.g., Tararina et al. Biochemistry. 2018 Jul. 3; 57(26): 3741-3751, the content of which is incorporated herein by reference in its entirety.

In some embodiments, the NicA2 enzyme is a mutant NicA2 enzyme comprising at least one mutation selected from any of: N462V, N462Y/W427Y, N462H, A107R of SEQ ID NO: 2, or an amino acid comprising at least 85%, or at least 90% or at least 95% sequence identity to SEQ ID NO: 2 and comprising at least one mutation selected from N462V, N462Y/W427Y, N462H, A 107R.

In some embodiments, the NicA2 enzyme in the biosensor is a mutant NicA2(N462H) enzyme comprising an enzyme comprising amino acids of SEQ ID NO: 2 where amino acid Asn (asparagine or N) at position 462 is changed to histidine (His or H), or a conservative amino acid of histidine, e.g., glutamine (Q or Gln) or threonine (T or Thr). In some embodiments, the NicA2 enzyme is a mutant NicA2(N462H) enzyme or a protein comprising at least 85% sequence identity to SEQ ID NO: 2 or SEQ ID NO: 3, and where amino acid 462 is changed from asparagine to a histidine (H) residue or a conservative amino acid of histidine (H), (e.g., any of Gln, Arg, Tyr, Glu).

In some embodiments, the NicA2 enzyme is a mutant NicA2(N462Y/W427Y) enzyme or a protein comprising at least 85% sequence identity to SEQ ID NO: 2 or SEQ ID NO: 4 and where amino acid 462 is changed from asparagine (N) to a valine (V) residue or a conservative amino acid of valine (V) (e.g., any of Ile, Leu, Met, Ala, Thr), and amino acid residue 427 is changed from tryptophan (W) to tyrosine (Y), or a conservative amino acids of tyrosine (Y) (e.g., any of His, Phe, Trp).

In some embodiments, the NicA2 enzyme comprises a mutation that enhances catalytic activity of the enzyme. In some embodiments, the NicA2 enzyme for use in the nicotine biosensors described herein comprises at least one mutation selected from: Δ50; Δ50R91Δ; R91Q; Δ50R91Q; Δ50R91F; Δ50R91G; Δ50R91T; Δ50R91L; Δ50R91S; F104R; F104K; F104I; F104L; F104S; F104 T; G106S; G106Δ; Δ107R; Δ50Δ107R; Δ107K; Δ107T; Δ107G; Δ107H; Δ107P; Δ50L217Q; Δ50L217G; Δ50L217E; E249 W; E249D; T250G; Δ50T250L; Δ50K340P; F355H; F355K; F355C; Δ50Q366K; Δ50Q366E; Q366K; Δ50Q366V; Δ50Q366L; Δ50T381P; Δ50T381I; Δ50T381V; Δ50T381Q; Δ50T381N; Δ50T381L; Δ50T381M; Δ426Q; Δ426 W; Δ50W427S; Δ50W427E; Δ50W427Q; Δ50W427M; Δ50N462L; Δ50N462Y; Δ50N462S; N462Y; Δ50N462F; Δ50N462G; Δ50N462E; Δ50N462Δ; 463 Δ50I463F; Δ50I463Y; or any two or more thereof at different positions; see e.g., Thisted et al., Optimization of a nicotine degrading enzyme for potential use in treatment of nicotine addiction, BMC Biotechnology (2019) 19:56, the content of which is incorporated herein by reference in its entirety.

Further non-limiting examples of mutations that enhance catalytic activity of the NicA2 enzyme are provided herein. In some embodiments, the NicA2 enzyme comprises a mutation of N462. In some embodiments, the NicA2 enzyme comprises a N462H mutation. In some embodiments, the NicA2 enzyme comprises a N462Y mutation. In some embodiments, the NicA2 enzyme comprises a N462V mutation. In some embodiments, the NicA2 enzyme comprises a mutation of W427. In some embodiments, the NicA2 enzyme comprises a W427Y mutation. In some embodiments, the NicA2 enzyme comprises a mutation of W427 and N462. In some embodiments, the NicA2 enzyme comprises a double mutation of W427Y and N462Y. In some embodiments, the NicA2 enzyme comprises a mutation of A107. In some embodiments, the NicA2 enzyme comprises a A107R mutation.

In some embodiments, directed evolution of the NicA2 enzyme can be done to improve selectivity, catalytic rates (kcat/Km), and substrate affinity (Km). In alternative embodiments, alternative nicotine-catalyzing enzymes can be used, or nicotine-catalyzing redox enzymes from other that have similar or enzymatic properties to NicA2.

In some embodiments, the NicA2 enzyme is a modified NicA2 variant enzyme, for example, as disclosed in US applications US201762454331 and US 201762535507 and in International Application WO2018144879, each of which are incorporated herein in their entirety. Such modified NicA2 enzymes have increased nicotine-degrading activity as compared to wild-type NicA2 enzymes. In some embodiments, the NicA2 enzyme for use in the nicotine biosensors described herein is selected from any of SEQ ID NO: 1, SEQ ID NO: 5, SEQ ID NO: 6, SEQ ID NO: 7, SEQ ID NO: 8, and SEQ ID NO: 135; SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 129; SEQ ID NO: 17, SEQ ID NO: 18, SEQ ID NO: 19, SEQ ID NO: 20, SEQ ID NO: 136, SEQ ID NO: 26, SEQ ID NO: 27, SEQ ID NO: 28, SEQ ID NO: 29, SEQ ID NO: 30, SEQ ID NO: 31, SEQ ID NO: 130; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 131; SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 132, SEQ ID NO: 133; SEQ ID NO: 46, SEQ ID NO: 47, SEQ ID NO: 48, SEQ ID NO: 49, SEQ ID NO: 50; SEQ ID NO: 51, SEQ ID NO: 52, SEQ ID NO: 53, SEQ ID NO: 54, SEQ ID NO: 55, SEQ ID NO: 56; SEQ ID NO: 124, SEQ ID NO: 125, SEQ ID NO: 126, SEQ ID NO: 134, SEQ ID NO: 142, SEQ ID NO: 143; SEQ ID NO: 124, SEQ ID NO: 125, SEQ ID NO: 126, SEQ ID NO: 134, SEQ ID NO: 142, SEQ ID NO: 143; SEQ ID NO: 62, SEQ ID NO: 63, SEQ ID NO: 137, SEQ ID NO: 138; and SEQ ID NO: 140 as disclosed in International Application WO2018144879, which is incorporated herein in its entirety by reference.

In some embodiments, a NicA2 variant used in the nicotine biosensor as described herein exhibits increased nicotine-degrading activity relative to the wild-type NicA2 enzyme. In some embodiments, a variant of the wild-type NicA2 sequence comprises at least one substitution F104L, G106S, A107H, A107P, 107R, A107K, A107T, F355C, F355V, W427Q, W427E, W427S, W427M, W427H, W427L, W427R, R91A, R91Q, R91F, R91G, R91T, R91L, R91 S, R91N, T250G, T250L, T250R, T250V, T250P, K340P, K340I, K340V, K340D, K340E, Q366K, Q366E, Q366V, Q366L, Q366I, Q366Y, T381P, T381I, T381V, T381Q, T381N, T381L, T381M, N462L, N462Y, N462S, N462F, N462G, N462E, N462A, N462M, I463F, I463Y, I463A, I463V, I463L, L217Q, L217G, L217E, L217I, L217C, or L217S, T250V/T381V in reference to SEQ ID NO: 2, or any two or more thereof at different positions. In some embodiments, the variant sequence comprises an amino acid sequence selected from any one of SEQ ID NOs: 5-56 as disclosed in International Application WO2018144879, which is incorporated herein in its entirety by reference. In some embodiments, the nicotine-degrading activity of the variant is at least 200%, at least 300%, or at least 400% of the nicotine-degrading activity of the wild-type NicA2 enzyme. In some embodiments, the variant sequence comprises at least one, at least two, or at least three substitution(s) at amino acid positions 91, 104, 106, 107, 217, 250, 340, 355, 366, 381, 427, 462, or 463 of SEQ ID NO: 1 as disclosed in International Application WO2018144879, which is incorporated herein in its entirety by reference. In some embodiments, the variant may have a deletion of 1-52 amino acids at the N-terminus of the peptide. For example, a variant derived from SEQ ID NO: 1 as disclosed in International Application WO2018144879, may comprise a deletion of 5, 10, 15, 20, 25, 30, 35, 40, 45, 50, 51, or 52 amino acids from the N-terminus of the peptide. In some embodiments, the variant additionally or alternatively may have a deletion of 1 or more amino acids from the C-terminus of the peptide, such as a deletion of the C-terminal residue.

ii. Other Nicotine Detecting Enzymes

Other nicotine-detecting or nicotine catalyzing redox enzymes are encompassed for use in the nicotine biosensor described herein, for example, one can readily use a nicotine N-demethyl enzyme, which catalyzes N-demethylation of nicotine to nornicotine can be used in place of NicA2 and a different electrochemical mediator, and is disclosed in U.S. patent Ser. No. 10/415,050, which is incorporated in its entirety by reference. Other nicotine demethylase (NDM) enzymes can be used, e.g., as disclosed in US application US20100/218270, which is incorporated in its entirety by reference. (Similarly, NicA2 can be replaced with nicotinamidemethy enzyme polypeptide (CYP82E10), which is involved in the metabolism of nicotine to the nicotine at the root of a tobacco plant and is disclosed in WO2011/088180, which is incorporated in its entirety by reference. Nicotinic demethylase belongs to the group of cytochrome P450 monooxygenase (CYP). Other nicotinic demethylase genes, including CYP82E4 and CYP82E5, which are involved in the conversion of nicotine to nornicotine can be used, and are described in WO2006091194, WO2008070274, and WO2009064771, WO 2011088180 A1, and are incorporated herein in their entirety by reference.

In some embodiments, a nicotine-detecting or nicotine catalyzing redox enzyme useful in the nicotine biosensor is Nicotine Blue oxidoreductase. Nicotine blue oxidoreductase (EC 1.1.1.328, nboR (gene)) is an enzyme with systematic name 3,3'-bipyridine-2,2',5,5',6,6'-hexol:NADP+11-oxidoreductase. This enzyme catalyzes the following chemical reaction: 3,3'-bipyridine-2,2',5,5',6,6'-hexol+NAD(P)+⇌ (E)-2,2',5,5'-tetrahydroxy-6H,6'H-[3,3'-bipyridinylidene]-6,6'-dione+NAD(P)H+H+. This enzyme is extracted from bacterium *Arthrobacter nicotinovorans*. (Mihasan M, et al., Applied and Environmental Microbiology. 2017; 73 (8): 2479-85.)

In some embodiments of any of the aspects, the nicotine-catalyzing enzyme is immobilized on an electrode of the biosensor. In some embodiments of any of the aspects, the nicotine-catalyzing enzyme is immobilized on an electrode of the biosensor electrode with a polymer.

In a preferred embodiment, the nicotine-catalyzing enzyme is immobilized on the electrode with chitosan. Chitosan was selected as a matrix for immobilization of the enzyme because of its biocompatibility, non-toxicity, high mechanical strength and excellent membrane forming ability. Chitosan can be divided into three categories, namely low molecular weight (e.g., 50 kDa-190 kDa), medium molecular weight (e.g., 190 kDa-310 kDa), and high molecular weight (e.g., 310 kDa-375 kDa). Chitosan of higher molecular weight possesses longer molecular chains with the availability of more hydroxyl groups. There is also a higher possibility that there are more amino groups, although the number of amino groups is determined by the degree of deacetylation. These amino groups are responsible for crosslinking. In some embodiments of any of the aspects, higher molecular weight chitosan (e.g., medium molecular weight compared to low molecular weight chitosan) can improve enzyme retention activity and loading, and thus function as a suitable matrix for enzyme immobilization. Using this chitosan membrane as a biosensor can provide a better performance in terms of sensitivity and stability. In some embodiments of any of the aspects, a amperometric biosensor, e.g., chronoamperometric biosensor can comprise chitosan of different molecular weights as a matrix for enzyme immobilization using a variety of adsorption and crosslinking techniques. See e.g., Ang et al., Study on Different Molecular Weights of Chitosan as an Immobilization Matrix for a Glucose Biosensor, PLoS One. 2013 Aug. 5, 8(8):e70597; Teepoo et al., Electrospun Chitosan-Gelatin Biopolymer Composite Nanofibers for Horseradish Peroxidase Immobilization in a Hydrogen Peroxide Biosensor, Biosensors (Basel). 2017 Oct. 15; 7(4). pii: E47. In some embodiments of any of the aspects, the nicotine-catalyzing enzyme is immobilized on the working electrode of the biosensor as described further herein.

In some embodiments of any of the aspects, the nicotine-catalyzing enzyme is immobilized on the electrode surface using crosslinking of a redox polymer. Generally, an aqueous mixture containing the enzymes, the redox polymer, and crosslinking agent in an aqueous solution are applied on an electrode and dried or allowed to dry to form a sensing film or coating on the electrode surface. See e.g., US patent publication US 2012/0181189.

In some embodiments of any of the aspects, the nicotine-catalyzing enzyme is immobilized on the electrode surface on a self-assembled monolayer (SAM) comprising chemisorbed alkanethiols. In this embodiment, a gold electrode is preferred as the transducer in the sensor system since thiols chemisorb to gold to give a strong, stably bound layer. Other chemical groups suitable for adsorption to a metal surface include sulfates, sulfonates, phosphates, and selenides. In some embodiments, thiol chemisorption on gold yielding thiolate is preferred, due to the relative stability of the metal-sulfur bond. See e.g., U.S. Pat. No. 6,241,863, the content of which is incorporated by reference herein it its entirety.

B. Detection of a Signal from NicA2 Catalysis of Nicotine.

In some embodiments, an exemplary nicotine biosensor disclosed herein comprises NicA2 oxidase or other nicotine biosensing redox enzyme. In one embodiment, the nicotine biosensor can operate with the following reaction steps shown in the reaction scheme 1 below:

NE(ox)+Nicotine(red)→Product(ox)+NE(red)

NE(red)+O2→NE(ox)+H2O2

H2O2+Med(red)→2H2O+Med(ox)

Med(ox)+2e-→Med(red) [signal]

where: NE(ox) is oxidized form of the nicotine enzyme (NE), e.g., NicA2 oxidase, NE(red)—reduced form of the nicotine enzyme (NE), e.g., NicA2 oxidase, Med(ox)—oxidized from of redox mediator, Med(red)—reduced form of redox mediator.

In step 1, the nicotine enzyme (NE), e.g., NicA2 oxidizes nicotine to produce a product and the NE itself is reduced. In step 2, the reduced form of the nicotine enzyme (NE), e.g., NicA2 oxidase reacts with oxygen in order to produce hydrogen peroxide. In step 3, hydrogen peroxide is oxidized into water while the oxidized form of the redox mediator Med(ox) is reduced to Med(red). In step 4, in the presence of an electric potential, the Med(red) is oxidized to regenerate Med(ox) and a measurable detectable signal is produced in the form of electrons. In some embodiments, the electrons are a detectable signal which can be measured as a current (amperometrically).

A general reaction scheme 1 for detection of nicotine using a nicotine enzyme (NE), e.g., NicA2 oxidase through electrochemical methods ($2^{nd}$ generation) can also be represented as shown in reaction scheme 2 as follows:

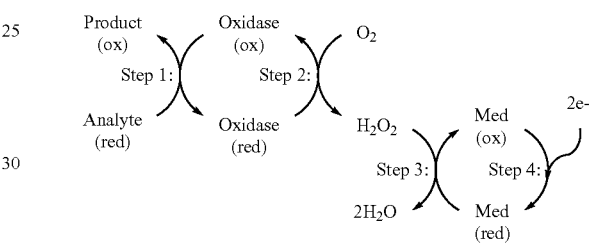

In some embodiments, nicotine can be identified through electrochemical methods ($1^{st}$ generation) via detection with the nicotine enzyme (NE), e.g., NicA2 oxidase as shown in reaction scheme 3 as follows:

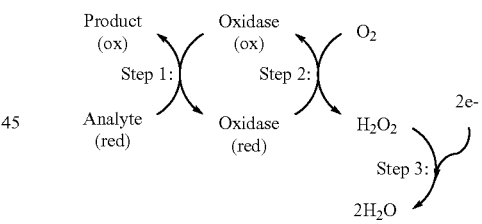

In some embodiments, nicotine can be identified through electrochemical methods ($3^{rd}$ generation) using the nicotine enzyme (NE), e.g., NicA2 oxidase as shown in reaction scheme 3 as follows:

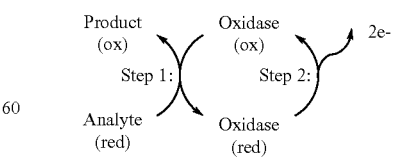

In some embodiments, nicotine can be identified through electrochemical methods ($2^{nd}$ generation) using the nicotine NAD(P)-dependent dehydrogenase enzyme as shown in reaction scheme 4 as follows:

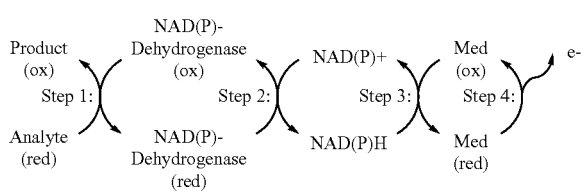

In some embodiments, nicotine can be identified through electrochemical methods (3$^{rd}$ generation) using the nicotine NAD(P)-dependent dehydrogenase enzyme as shown in reaction scheme 5 as follows:

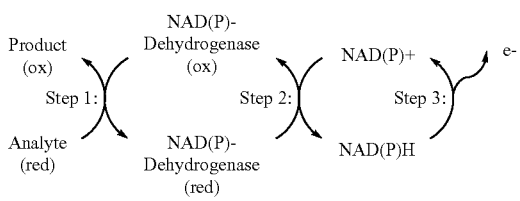

In some embodiments, nicotine can be identified through electrochemical methods (2$^{nd}$ generation) using the nicotine NAD(P)-independent dehydrogenase enzyme as shown in reaction scheme 6 as follows:

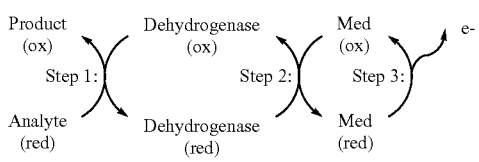

In some embodiments, nicotine can be identified through electrochemical methods (3$^{rd}$ generation) using the nicotine NAD(P)-independent dehydrogenase enzyme as shown in reaction scheme 7 as follows:

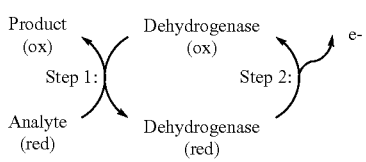

(i) Redox Mediators

In some embodiments, the nicotine-catalyzing enzyme is not capable of transferring electrons to a redox mediator/electrically active mediator directly. That is, a detectable signal is not produced when the nicotine-catalyzing enzyme interacts with nicotine. Accordingly, in some embodiments, nicotine is detected by a nicotine-catalyzing enzyme that is capable of interacting directly with nicotine, but cannot exchange electrons with a redox mediator. Such an embodiment is useful where some redox-enzymes cannot exchange electrons directly with an electrode because their redox active sites are buried deep within the enzyme protein structure. Therefore, in order to transfer electrons between the redox active site of the enzyme and produce a detectable signal, a redox mediator (Med) also known as an "electron transfer agent" or an "electronically active mediator" is used. In some embodiments, the analyte-specific enzyme is cross-linked to the electron transfer agent. In some embodiments of any of the aspects, the amperometric biosensor, e.g., chronoamperometric biosensor described herein comprises an electronically active mediator deposited on the surface of the electrode.

In some embodiments, redox mediators are electroreducible and electrooxidizable ions or molecules having redox potentials (voltages) that are a few hundred millivolts above or below the redox potential (voltage) of the standard calomel electrode. In some embodiments, the redox mediators are not more reducing than about −150 mV and not more oxidizing than about +400 mV versus a standard calomel electrode. Examples of suitable redox mediators are disclosed, for example, in Mao et al. (U.S. Pat. No. 6,605,200) the entire content of which is herein incorporated by reference.

Accordingly, the biosensor disclosed herein comprises redox mediators (Med) that serve as electron carriers, or electron signal mediators. That is, they are multi-electron transfer mediators that function as electrochemically detectable signal mediators to produce a detectable signal when transfer of electrons occurs. Preferably a redox-mediator as disclosed herein is linearly or exponentially amplified by magnifying electrochemical signal output via recycling the enzyme substrates.

In some embodiments of any of the aspects, the electronically active mediator (Med) can be reduced from an reduced form (Med$_{red}$) to a oxidative form (Med$_{ox}$), wherein the Med$_{ox}$ produces a detectable signal. n some embodiments of any of the aspects, the detectable signal is produced when nicotine is catalyzed by the nicotine-catalyzing enzyme and transfers at least one electron from Med$_{red}$ to hydrogen peroxide (H$_2$O$_2$), resulting in its oxidation to Med$_{ox}$. In some embodiments of any of the aspects, the electronically active mediator Med$_{ox}$ is reduced by the electrode, producing a detectable signal due to the flow of electrons. In some embodiments, the redox-mediator is catalyzed to produce a detectable signal that is electrochemical or colorimetric. In some embodiments, the redox-mediator produces an optical readout comprising fluorescence, bioluminescence, or luminescence.

A redox-mediator can be any of the natural or synthetic mediators commonly used in biosensors known to date, and is preferably selected from the group consisting of cytochromes, quinones, aminophenols, electron-acceptor aromatic compounds (e.g., TTF=tetratiafulvalene and NMP=N-methylphenazine), electron-donor aromatic compounds (e.g., TCNQ=tetrakyano-p-quinodimethane), organic conductive salts (e.g., TTF.TCNQ=tetratiafulvalene-7,7,8,8-tetrakyano-p-quinodimethane and NMP.TCNQ=N-methylphenylene-7,7,8,8-tetracyano-p-quinodimethane), organic dyes, metallocenes, organometallic complexes of osmium, ruthenium and duct, inorganic iron complexes. In some embodiments, redox mediators are ferricyanide ferrocene, 1,1-dimethyl-ferrocene, hexacyanoferrate or hexacyanoferrate.

In some embodiments, the redox mediator is AUR as disclosed herein. Natural and artificial mediators are shown in Table 1.

TABLE 1

| Natural mediators | Artificial mediators |
| --- | --- |
| Cytochrome a3 | Ferricyanide (hexacyanoferrate III) |
| Cytochrome c3 | 2,6-dichlorophenol |

TABLE 1-continued

| Natural mediators | Artificial mediators |
| --- | --- |
| Cytochrome b | Indophenol |
| Ubiquitone | Ferrocene |
| Vitamin K2 | Phenazine |
| Rubredoxin | Methosulphate |
| Flavoproteins | Methylene blue |
| FAD-FADH$_2$ | Phtalocyannine |
| FMN-FNH$_2$ | Phenosafranine |
| NAD+-NADH | Benzyl violet |
| NADP+-NADPH | Methyl violet |
| PQQ-PQQH$_2$ | Ferredoxin |
|  | Prussian Blue |
|  | Nile blue |
|  | Meldola's Blue |
|  | NQSA |
|  | Potassium hexacyanoferrate |
|  | Potassium ferricyanide |
|  | Potassium ferrocyanide |
|  | PMS |
|  | Dichlorophenolindophenol |
|  | p-benzoquinone |
|  | o-phenylenediamine |
|  | 3,4-dihydroxybenzaldehyde |
|  | Potassium hexacyanoferrate (II) |
|  | Tetracyanoquinodimethane |
|  | Cobalt (II) phtalocyanine |

In some embodiments, the redox-mediator is a ferricyanide compound (i.e., Prussian blue). Prussian blue is a dark blue pigment produced by oxidation of ferrous ferrocyanide salts. It has the chemical formula $Fe^{III}{}_4[Fe^{II}(CN)_6]_3$. The IUPAC name of Prussian Blue is iron(II,III) hexacyanoferrate(II,III), but it can also be referred to as Berlin blue, ferric ferrocyanide, ferric hexacyanoferrate, iron(III) ferrocyanide, iron(III) hexacyanoferrate(II), or Parisian blue. Prussian blue nanoparticles (PB NPs) exhibit an intrinsic peroxidase-like catalytic activity towards the hydrogen peroxide ($H_2O_2$)-mediated oxidation of classical peroxidase substrate 2,2'-azino-bis(3-ethylbenzothiazoline-6-sulfonic acid) diammonium salt to produce a colored product. See e.g., PCT publication WO 1990/012487A2, which is incorporated herein by reference in its entirety. In some embodiments, the electronically active mediator comprises a ferricyanide compound which is reducible in the presence of an electron from hydrogen peroxide ($H_2O_2$) to produce a ferrocyanide compound. In some embodiments, the electronically active mediator comprises iron(II,III) hexacyanoferrate(II,III) (Prussian blue).

(ii) Optical or Fluorescence Detection of Nicotine Using a Readout Enzyme

In some embodiments, the reaction between the nicotine-catalyzing enzyme and nicotine is coupled to one or more additional enzymes, herein referred to an intermediate redox enzyme (e.g., IRE) to form a multi-enzyme system for detection of the redox reaction between nicotine and the nicotine-catalyzing enzyme. In some embodiments of any of the aspects, the oxidase redox-enzyme of the amperometric biosensor, e.g., chronoamperometric biosensor described herein can be coupled to an intermediate redox-enzyme (IRE), for example, a peroxidase enzyme, as disclosed herein.

In some embodiments, the Med(red) can catalyze a redox reaction with a readout enzyme (ReadE) to convert a readout substrate (ReadS) into a readout product (ReadP), where the ReadP produces a detectable signal which can be measured optically, e.g., by fluorescence or other luminescence methods.

In some embodiments, a nicotine biosensor described herein can also comprise an intermediate redox-enzyme. For example, the Med(ox) is reduced to Med(red) in the presence of hydrogen peroxide and a peroxidase enzyme, thereby avoiding issues of auto-oxidation of the Med(red) and increasing the accuracy of measurement of analyte concentration.

In some embodiments, the nicotine biosensor comprising, e.g., NicA2 oxidase, can comprise use of a readout enzyme (ReadE), also referred to as an intermediate redox-enzyme (IRE), for example, a peroxidase enzyme, where the basic chemical and electrochemical transformation are shown with reference to an oxidase biosensor system in the following reaction scheme 3 below:

Nicotine(red)+NicA2(ox)→Product(ox)+NicA2(red)

NicA2(red)+O2→NicA2(ox)+H$_2$O$_2$ (Catalyzed by the MRE)

H$_2$O$_2$+ReadS(red)→2H$_2$O+ReadP(ox) (Catalyzed by the ReadE)

In step 1, the oxidase NicA2 oxidizes the target nicotine analyte to produce a product and the NicA2 enzyme itself becomes reduced. In step 2, the reduced form of NicA2 reacts with oxygen to produce hydrogen peroxide and the oxidized form of NicA2. In step 3, the hydrogen peroxide, in the presence of the readout enzyme (ReadE), oxidizes the readout substrate (ReadS) to form the readout product (ReadP) which is itself a readable signal. In some embodiments, the ReadP is a signal which can be measured optically or by luminescence techniques such as by fluorescence or chemiluminescence, and the measurement can be correlated to the concentration of nicotine.

A general reaction scheme for detecting nicotine using the NicA2 biosensor comprising a readout enzyme (ReadE), such as a peroxidase can also be represented as shown in reaction scheme 8 as follows:

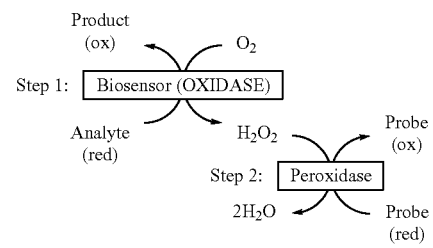

In some embodiments, the conversion of Med(red) back to Med(ox) can produce a signal which can be measured as a current or amperometrically, and the measurement can be correlated to the concentration of the analyte.

In some embodiments, the readout enzyme (ReadE) (also referred to as "intermediate redox-enzyme (IRE)") is a peroxidase enzyme, for example, but not limited to, APEX2 which, in the presence of hydrogen peroxidase, catalyzes the conversion of the readout substrate (ReadS) AMPLEX® UltraRed (AUR) to the readout product (ReadP) Resorufin, which produces a detectable signal. An exemplary reaction scheme for identification of an oxidase MRE using APEX2 as a peroxidase as a readout enzyme can be represented as shown in reaction scheme 9 as follows:

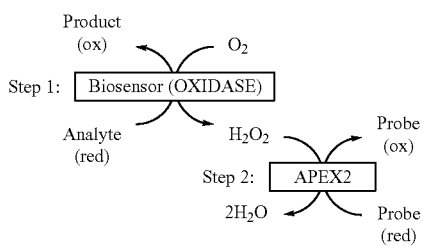

While the NicA2 biosensor is exemplified using components and electrochemical reactions schemes using NicA2 as the nicotine oxidase, other nicotine sensing enzymes are encompassed for use herein.

In some embodiments, nicotine can be identified through non-electrochemical methods using the nicotine NAD(P)-dependent dehydrogenase enzyme as shown in reaction scheme 10 as follows:

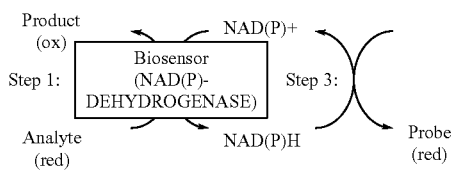

In some embodiments, nicotine can be identified through non-electrochemical methods using the nicotine NAD(P)-independent dehydrogenase enzyme as shown in reaction scheme 11 as follows:

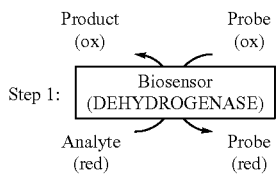

In some embodiments, the intermediate redox enzyme (IRE) is a peroxidase enzyme, for example, but not limited to, APEX2, and the redox mediator (Med) is Amplex® UltraRed (AUR) that in the presence of hydrogen peroxidase and the peroxidase enzyme APEX2, is converted to Resorufin which produces a detectable signal.

In some embodiments, the technology encompasses alternative or modified Readout substrates (also referred to herein as intermediate redox enzymes (IREs)), for example, such as modifying the APEX2 enzyme to have improved enzyme kinetics or to use alternative peroxidase enzymes, or HRP derivatives. Additionally, in some embodiments, the redox-mediator, such as AUR, can be replaced with other $H_2O_2$ responsive probes known in the art, for example, but not limited to PY1, PO1, Amplex® Red, homovanillic acid (HVA), luminol, OPD, DCFH, ABST, K iodide, or ABTS. In some embodiments, other redox enzymes can be used, for example, the peroxidase IRE APEX2 can be substituted for another enzyme, or peroxidase enzyme which is sensitive to other enzyme products. In some embodiments, transcription factors (TFs) can be used to respond to the produced $H_2O_2$. In some embodiments, OxyR, a TF responsive to $H_2O_2$, can be used to regulate and induce GFP expression downstream of an OxyR binding site. In some embodiments, the redox-responsive probe (RRP) is catalyzed to produce a detectable signal that is fluorescence, or bioluminescence, luminescence or produce an optical readout or detectable signal.

By way of an illustrative example only, in some embodiments, the intermediate redox enzyme (IRE) is a peroxidase enzyme, such as, but not limited to, ascorbate peroxidase (APEX2), and the redox-mediator (Med) is, but not limited to, Amplex® UltraRed (AUR), which produces a fluorescent product only in the presence of hydrogen peroxide ($H_2O_2$) and the peroxidase enzyme as the IRE. In this illustrative example, the nicotine biosensor comprising an oxidase nicotine-catalyzing enzyme which degrades nicotine will produce a fluorescent signal, because the oxidase will produce $H_2O_2$, which is used as a substrate, along with AUR, for the peroxidase enzyme, APEX2 to produce a fluorescent product.

APEX2 is an engineered ascorbate peroxidase enzyme that functions both as an electron microscopy tag, and as a promiscuous labeling enzyme for live-cell proteomics. In some embodiments, APEX2 can be used as an IRE to catalyze the generation of a fluorescent product from Amplex® UltraRed (AUR) only in the presence of hydrogen peroxide ($H_2O_2$). In some embodiments, the assay, methods and composition as disclosed herein can also use modified version of the APEX2 enzyme, e.g., a modified APEX2 enzyme with improved enzyme kinetics or catalyzes a different HRP derivative (e.g., catalyzes a different substrate to AUR).

In some embodiments, the technology encompasses alternative or modified intermediate redox enzymes (IREs), for example, such as modifying the APEX2 enzyme to have improved enzyme kinetics or to use alternative peroxidase enzymes, or HRP derivatives. Additionally, in some embodiments, the redox-mediator, such as AUR, can be replaced with other $H_2O_2$ responsive probes known in the art, for example, but not limited to PY1, PO1, Amplex® Red, homovanillic acid (HVA), luminol, OPD, DCFH, ABST, K iodide, or ABTS. In some embodiments, other redox enzymes can be used, for example, the peroxidase IRE APEX2 can be substituted for another enzyme, or peroxidase enzyme which is sensitive to other enzyme products. In some embodiments, transcription factors (TFs) can be used to respond to the produced $H_2O_2$. In some embodiments, OxyR, a TF responsive to $H_2O_2$, can be used to regulate and induce GFP expression downstream of an OxyR binding site. In some embodiments, the redox-responsive probe (RRP) is catalyzed to produce a detectable signal that is fluorescence, or bioluminescence, luminescence or produce an optical readout or detectable signal.

In some embodiments of any of the aspects, the one or more fluorescence probes to detect $H_2O_2$ is 10-Acetyl-3,7-dihydroxyphenoxazine (N-Acetyl-3,7-dihydroxyphenoxazine or ADHP) (Amplex® Red). 10-Acetyl-3,7-dihydroxyphenoxazine is highly specific and stable. The substrate itself is nearly colorless and nonfluorescent until it is oxidized by $H_2O_2$ (reacting in a 1:1 stoichiometry) in the presence of horseradish peroxidase (HRP) to become the highly red fluorescent resorufin.

The structure of 10-Acetyl-3,7-dihydroxyphenoxazine (N-Acetyl-3,7-dihydroxyphenoxazine is as follows:

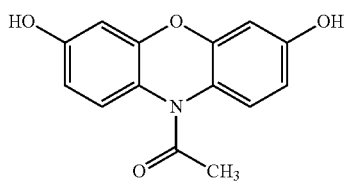 [SMILES: CC(=O)N1c2ccc(O)cc2Oc2cc(O)ccc21]

Additionally, in some embodiments, the redox-mediator, such as AUR, can be replaced with other $H_2O_2$ responsive probes known in the art, for example, but not limited to PY1, PO1, Amplex® Red, homovanillic acid (HVA), luminol, OPD, DCFH, ABST, K iodide, or ABTS.

In some embodiments, other redox enzymes can be used as intermediate redox enzymes, for example, the peroxidase IRE APEX2 can be substituted for another enzyme, or peroxidase enzyme which is sensitive to other enzyme products.

Other intermediate redox enzymes (IRE) are encompassed for use in this assay system can be selected from a nicotinamide adenine dinucleotide (NAD)-dependent dehydrogenase, a flavin adenine dinucleotide (FAD)-dependent oxidase, or a flavin mononucleotide (FMN)-dependent oxidase. For example, in some embodiments, the IRE of this system is selected from 11β-hydroxysteroid dehydrogenase type 2 (11β-HSD-2), glucose oxidase, NAD-glucose dehydrogenase, FAD-glucose dehydrogenase, lactate oxidase, NAD-lactate dehydrogenase, NAD-alcohol dehydrogenase, pyruvate oxidase, NAD-glutamate dehydrogenase, and xanthine oxidase.

In some embodiments, transcription factors (TFs) can be used as an alternative to an IRE, and coupled to the candidate redox-enzyme to respond to the produced $H_2O_2$. In some embodiments, the transcription factor coupled to detect the interaction of the target analyte and the redox-enzyme is OxyR, which is a transcription factor responsive to $H_2O_2$, and in some embodiments, be used to regulate and induce gene expression, such as GFP expression, downstream of an OxyR binding site.

Accordingly, in some embodiments, transcription factors (TFs) can be used to respond to the $H_2O_2$ produced by the nicotine-catalyzing enzyme. In some embodiments, OxyR, a TF responsive to $H_2O_2$, can be used to regulate and induce GFP expression downstream of an OxyR binding site. OxyR encodes a transcription factor that senses $H_2O_2$ and is activated through the formation of an intramolecular disulfide bond. OxyR activates the expression of a regulon of hydrogen peroxide-inducible genes including but not limited to katG, gor, ahpC, ahpF, oxyS, dps, fur and grxA. OxyR expression is negatively autoregulated by binding to a 43 bp region upstream of its own coding sequence. OxyR is inactivated by reduction of its essential disulfide bond by the product of GrxA, itself positively regulated by OxyR. The following sequence of OxyR is provided: OxyR amino acid-encoding polynucleotide sequence, e.g. P0ACQ4-1 (SEQ ID NO: 7):

```
(OxyR)
                                    SEQ ID NO: 7
MNIRDLEYLVALAEHRHFRRAADSCHVSQPTLSGQIRKLEDELGVMLLE

RTSRKVLFTQAGMLLVDQARTVLREVKVLKEMASQQGETMSGPLHIGLI

PTVGPYLLPHIIPMLHQTFPKLEMYLHEAQTHQLLAQLDSGKLDCVILA
```

-continued
```
LVKESEAFIEVPLFDEPMLLAIYEDHPWANRECVPMADLAGEKLLMLED

GHCLRDQAMGFCFEAGADEDTHFRATSLETLRNMVAAGSGITLLPALAV

PPERKRDGVVYLPCIKPEPRRTIGLVYRPGSPLRSRYEQLAEAIRARMD

GHFDKVLKQAV
```

C. Electrode(s)

Figure 12A:
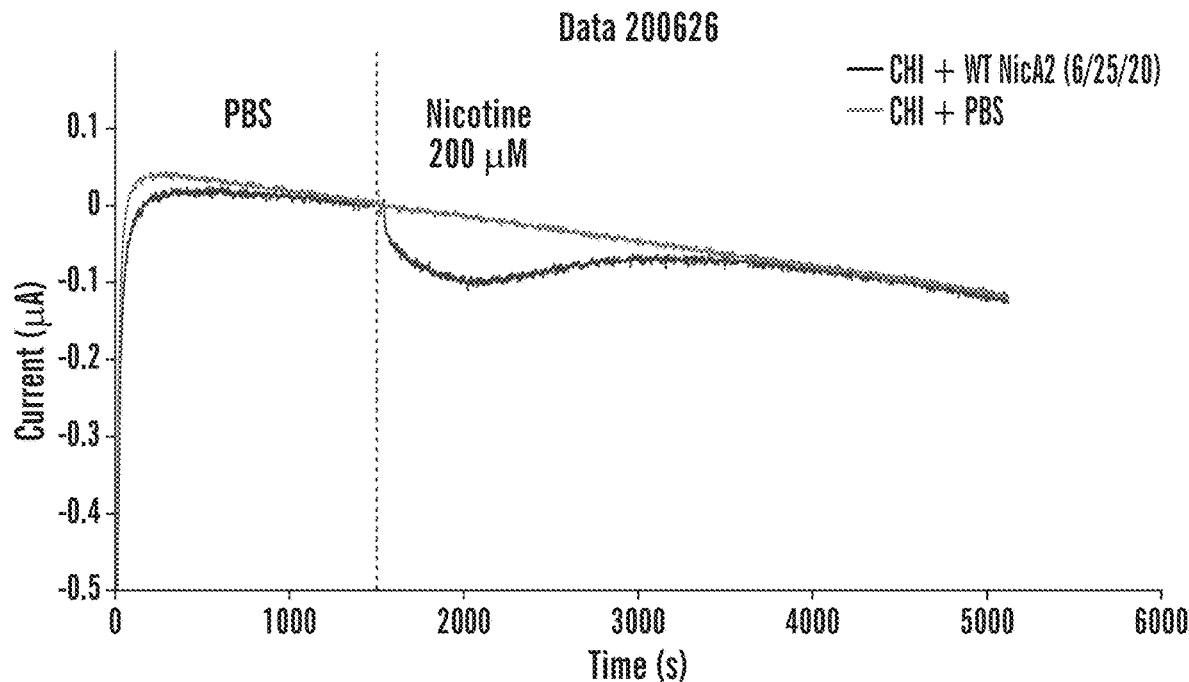
FIG. 12A-12B show the NicA2 biosensor with three and two electrodes.

As disclosed herein in the Examples, the inventors discovered that careful optimization of the surface of the electrode was necessary for a functional nicotine biosensor comprising NicA2 enzyme. In particular, the inventors optimized multiple parameters of the electrode of the NicA2 biosensor disclosed herein to achieve a nicotine biosensor that enabled real-time measurements of nicotine, was sensitive to physiological levels of nicotine in sweat and other samples obtained from a smoker, and enabled repeated detection of nicotine in a variety of different samples. In particular, the surface of the electrode on which NicA2 or NicA2 mutant is located was carefully optimized to comprise low- and medium molecular weight (MW) chitosan in 0.5% acetic acid, the surface area and size of the electrode was increased, and surprisingly, the inventors also discovered that optimal results were achieved using only two electrodes (e.g., see FIG. 16 and FIG. 12A-12B). Accordingly, the NicA2 biosensor disclosed herein are very different from glucose oxidase biosensors, as shown in the Examples.

In some embodiments of any of the aspects, the amperometric biosensor, e.g., chronoamperometric biosensor as described comprises at least one electrode. In some embodiments, the nicotine biosensor comprises two electrodes. In some embodiments, the nicotine biosensor consists of, or consists essentially of two electrodes, a working electrode and a reference electrode, where the working electrode has a NicA2 enzyme deposited on it. In some embodiments, the nicotine biosensor does not comprise a third electrode. In some embodiments, the nicotine biosensor disclosed herein does not comprise a counter electrode. In some embodiments of any of the aspects, the working electrode comprises a surface, for example to which NicA2 or a NicA2 mutant enzymes and optionally, a Readout enzyme can be immobilized as described herein.

In some embodiments of any of the aspects, the electrode is metallic. In some embodiments of any of the aspects, the metallic electrode is gold, silver, platinum, or palladium. In some embodiments of any of the aspects, the electrode is non-metallic. In some embodiments of any of the aspects, the non-metallic electrode comprises carbon (e.g., glassy carbon).

In some embodiments of any of the aspects, the amperometric biosensor, e.g., chronoamperometric biosensor comprises one electrode referred to herein as a "working electrode." The working electrode is the electrode in an electrochemical system on which the reaction of interest is occurring. Accordingly, herein the nicotine biosensor disclosed herein comprises a working electrode comprising NicA2 enzyme or mutant NicA2 enzyme (e.g., NicA2 (N462H)) deposited on the working electrode. Typically, the working electrode is often used in conjunction with a counter electrode and a reference electrode in a three electrode system. However, in specific embodiments of the nicotine biosensor disclosed herein, the working electrode is used in conjunction with a reference electrode but not the counter electrode. In some embodiments of any of the aspects, the working electrode is coated with the redox mediator (e.g., Prussian blue). In some embodiments of any of the aspects, the redox enzyme (e.g., the nicotine degrading enzyme or NicA2 or NicA2(N462H) enzyme)) is immobilized to the surface of the working electrode with a polymer.

In some embodiments of any of the aspects, the amperometric nicotine biosensor, e.g., chronoamperometric biosensor disclosed herein further comprises an auxiliary electrode. As used herein, the term "counter electrode" (also referred to as the "auxiliary electrode") is an electrode used in an electrode electrochemical cell for voltammetric analysis or other reactions in which an electric current is expected to flow.

In some embodiments of any of the aspects, the amperometric nicotine biosensor, e.g., chronoamperometric nicotine biosensor can optionally comprise a reference electrode. As used herein, the term "reference electrode" is an electrode which has a stable and well-known electrode potential. The high stability of the electrode potential is usually reached by employing a redox system with constant (buffered or saturated) concentrations of each participant of the redox reaction. The counter (or auxiliary) electrode is distinct from the reference electrode, which establishes the electrical potential against which other potentials may be measured, and the working electrode, at which the analyte detection (e.g., nicotine detection) by NicA2 or a NicA2 mutant enzyme takes place.

In some embodiments, the nicotine biosensor disclosed herein is a two-electrode system (e.g., working and reference electrodes), where either a known current or potential is applied between the working and reference electrodes and the other variable may be measured. The counter electrode functions as a cathode whenever the working electrode is operating as an anode and vice versa. In some embodiments, the counter electrode often has a surface area much larger than that of the working electrode to ensure that the half-reaction occurring at the counter electrode can occur fast enough so as not to limit the process at the working electrode.

As disclosed herein in the Examples, the inventors that the size of the working electrode influence the current produced from the NicA2 biosensor. Accordingly, in some embodiments, the working electrode has an area of >4π mm$^2$. In some embodiments, the size of the working electrode is in the range of 5-8 π mm$^2$, or 8-10π mm$^2$, or 10-12π mm$^2$, or 12-15π mm$^2$, or greater than 15π mm$^2$. In some embodiments, the shape of the working electrode is circular, and in some embodiments the shape is oval. In some embodiments, the reference electrode is a geometric shape which wraps or circles around the working electrode.

When a three electrode cell (e.g., working, counter, and reference electrodes) is used to perform electroanalytical chemistry, the auxiliary electrode, along with the working electrode, provides a circuit over which current is either applied or measured. Here, the potential of the counter electrode is usually not measured and is adjusted so as to balance the reaction occurring at the working electrode. This configuration allows the potential of the working electrode to be measured against a known reference electrode without compromising the stability of that reference electrode by passing current over it.

In some embodiments of any of the aspects, the amperometric nicotine biosensor, e.g., chronoamperometric biosensor comprises, or consist essentially of, a working electrode and a reference electrode. In some embodiments of any of the aspects, the biosensor can comprise a multi-electrode configuration including a working electrode, a counter electrode, and a reference electrode. In one example, the nicotine-catalyzing enzyme (e.g., NicA2 or a NicA2 mutant enzyme as disclosed herein) and optionally, readout enzyme or redox mediator are immobilized on the working electrode. The working electrode can be, for example, carbon, glassy carbon, metal, metal oxides or a mixture of carbon and metal or metal oxides. In one example, the working electrode is a glassy carbon electrode. The reference electrode can be, for example, a saturated calomel reference electrode (SCE), Ag/AgCl, or saturated $Hg_2Cl_2$. In some embodiments, the counter or reference electrode can be, for example, a metal such as gold, silver, platinum or stainless steel, such as a metal wire counter or reference electrode. In some embodiments, the working and/or the reference electrodes, and optionally the counter electrode are screen printed electrodes (SPE).

The biosensor electrodes, such as active electrodes, can be formed by coating a fine metal wire with a formulation (e.g., comprising the nicotine-catalyzing enzyme, e.g., NicA2 or a NicA2 mutant enzyme, redox mediator, and polymer such as chitosan) and drying the coating in place on the wire. For example, a fine platinum wire can be coated with the enzyme-formulation and the coating dried in place. The coated wire can be arranged in a syringe or other suitable flow cell or channel device that can be placed, for example, in-line or into the flow of an analyte stream to be monitored for nicotine concentration.

Platinum, silver, carbon, and Ag/AgCl ink also can be used in screen-printing methods, or photolithographically patterned metal vapor deposition methods, to form film sensors for the fabrication of miniaturized, planar, solid state electrodes. These electrodes can be used in electrode strips, biochips, and other miniaturized sensor configurations. The biosensor can be, for example, a screen-printed (e.g., a screen printed electrode (or SPE)) or photolithographically patterned three-electrode transducer with a carbon or platinum working electrode. In some embodiments, the biosensor can be screen-printed or ink-jet printed as disclosed in WO2019/224628, which is incorporated herein in its entirety by reference. As a non-limiting example, in some embodiments of any of the aspects, the working electrode comprises a Prussian blue screen-printed electrode. See e.g., US patent publication 2008/0160625, PCT publications WO2017210465, WO2018202793A2 Chinese patent publications CN110573868, CN102053161, CN105136885; the contents of each of which are incorporated herein by reference in their entireties. Other transducer configurations also can be used.

Figure 6A:
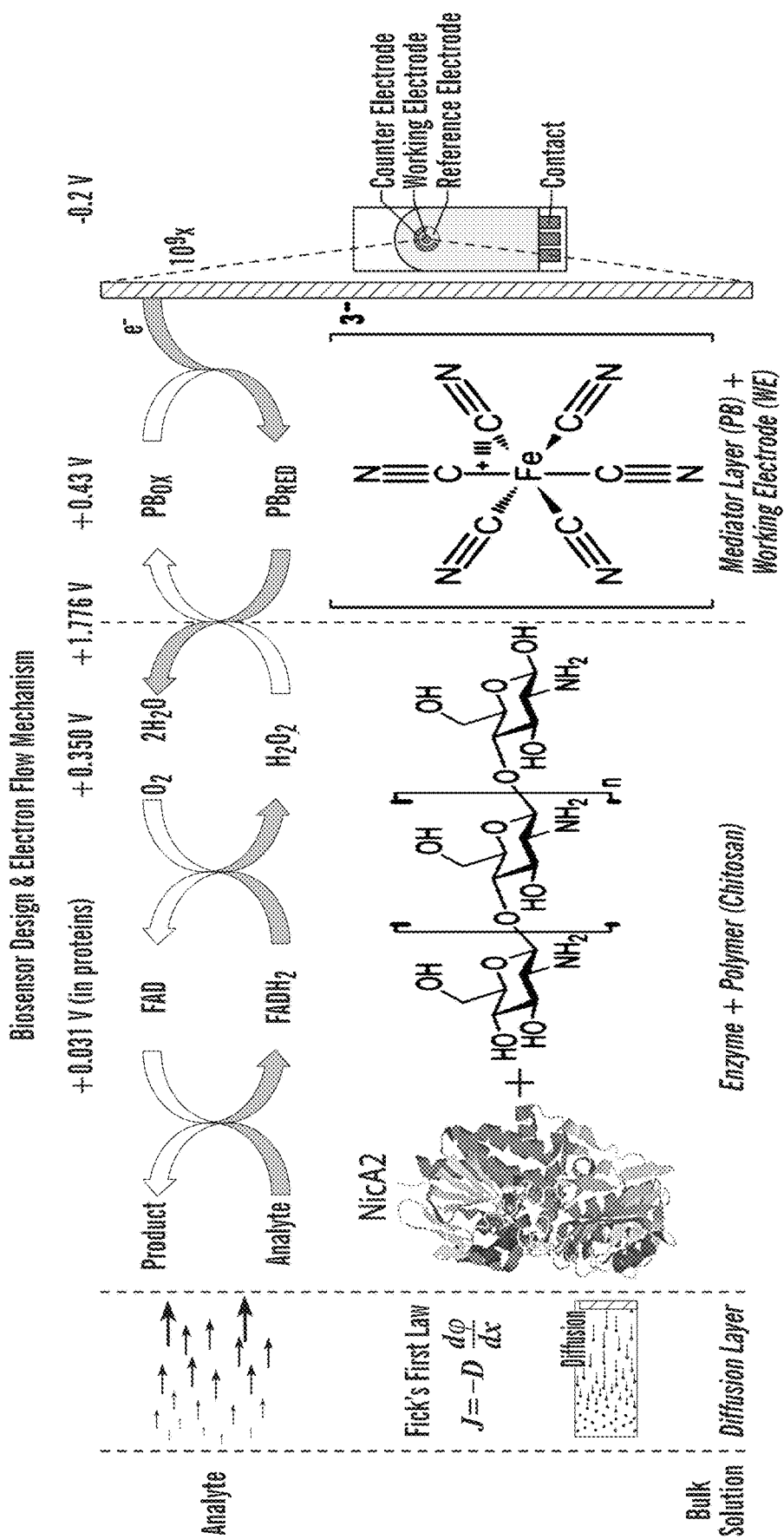
Figure 7:
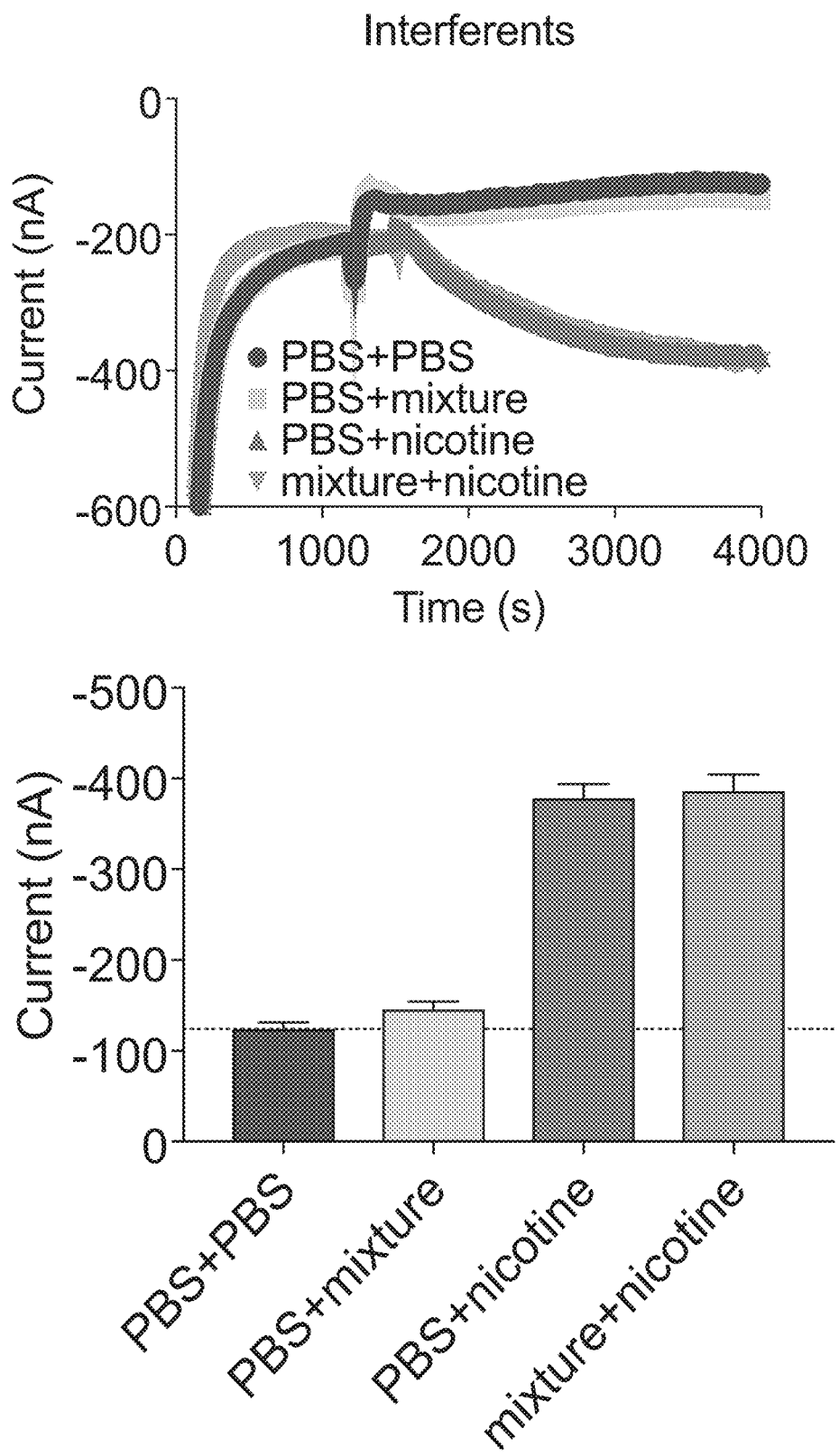
FIG. 7 is a series of graphs showing the effects of common interferents (e.g., cotinine and myosmine) on the nicotine biosensor, showing that NicA2 is specific for nicotine only.
Figure 7:
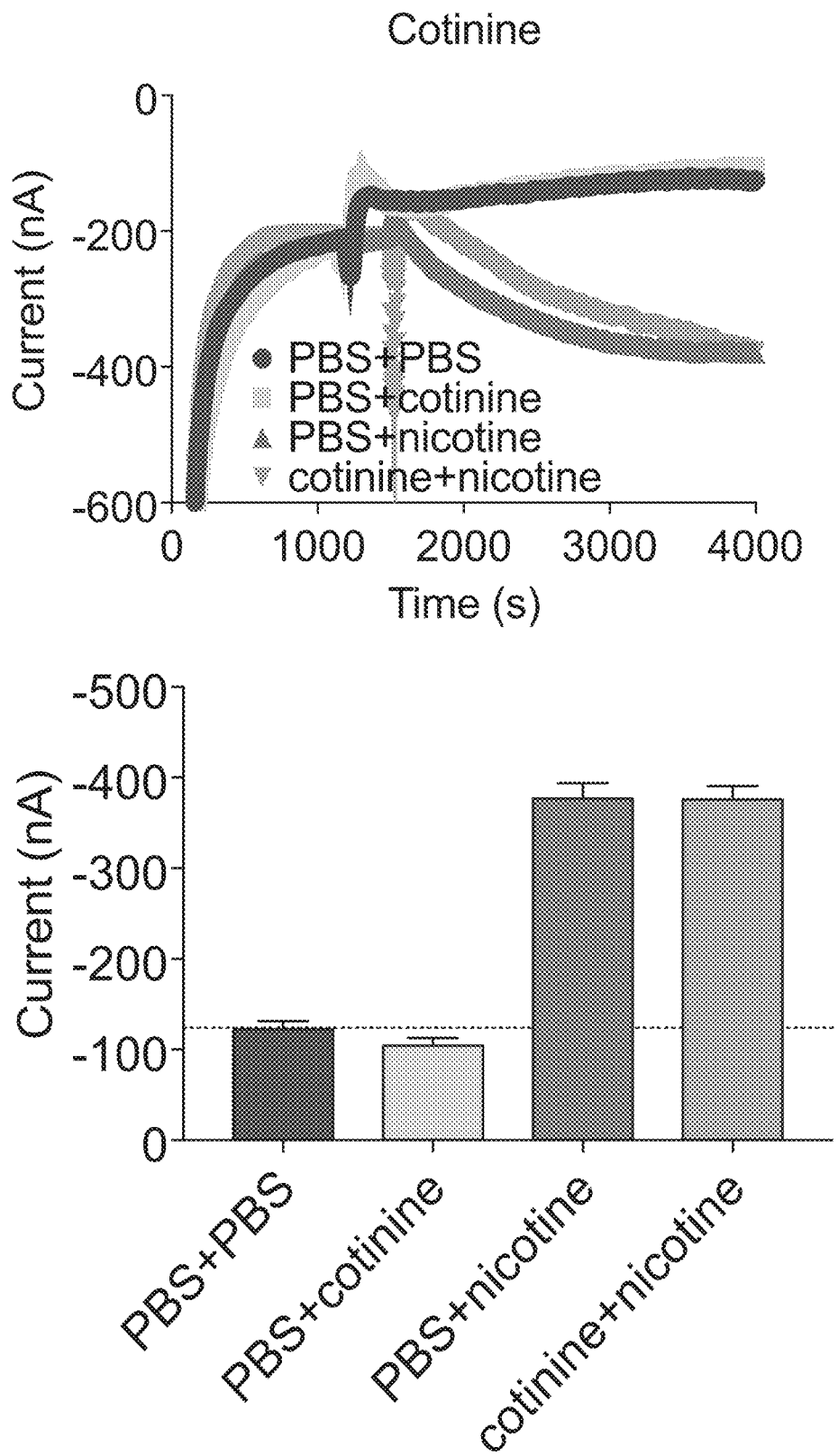
Figure 7:
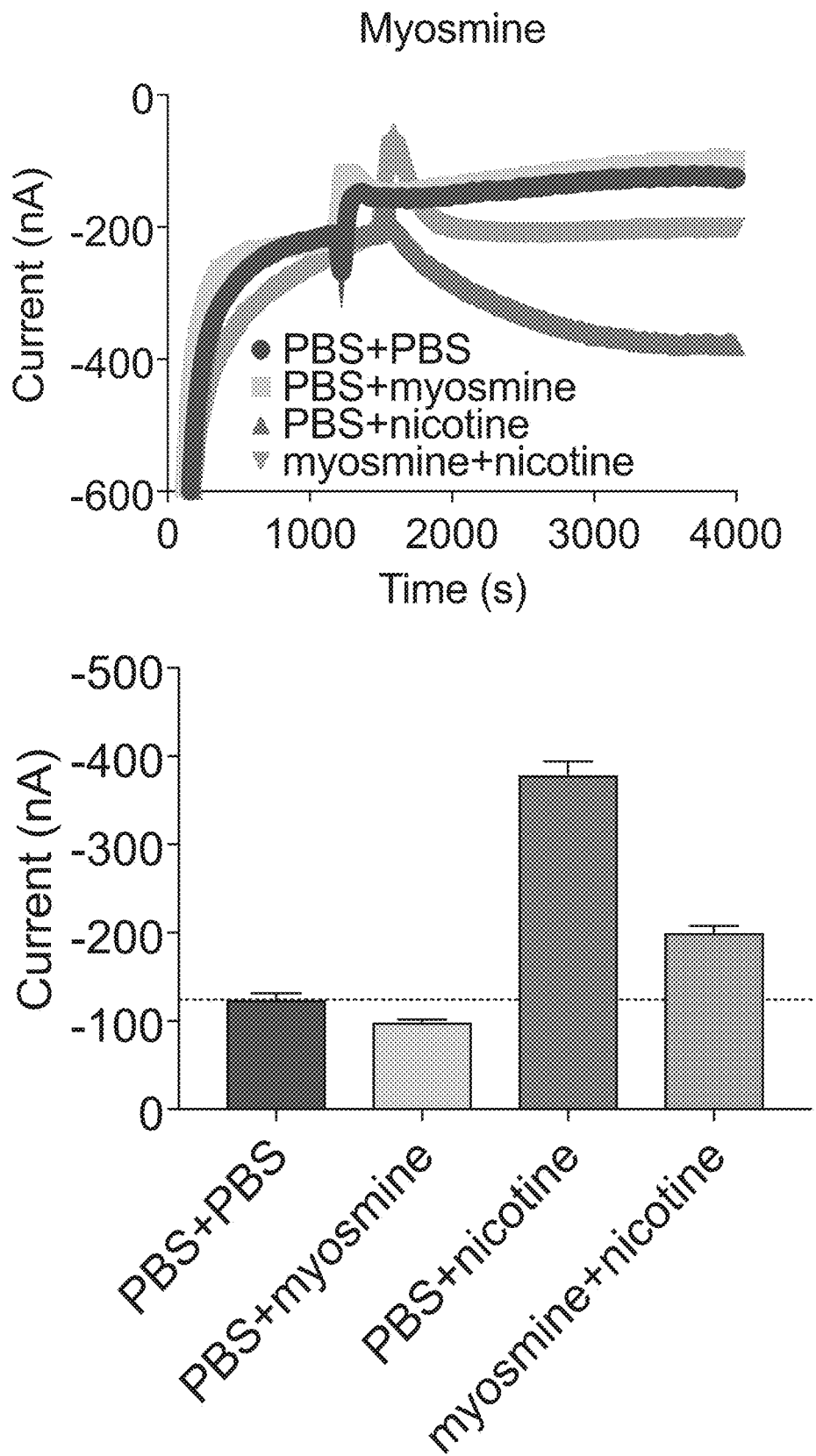
Figure 8:
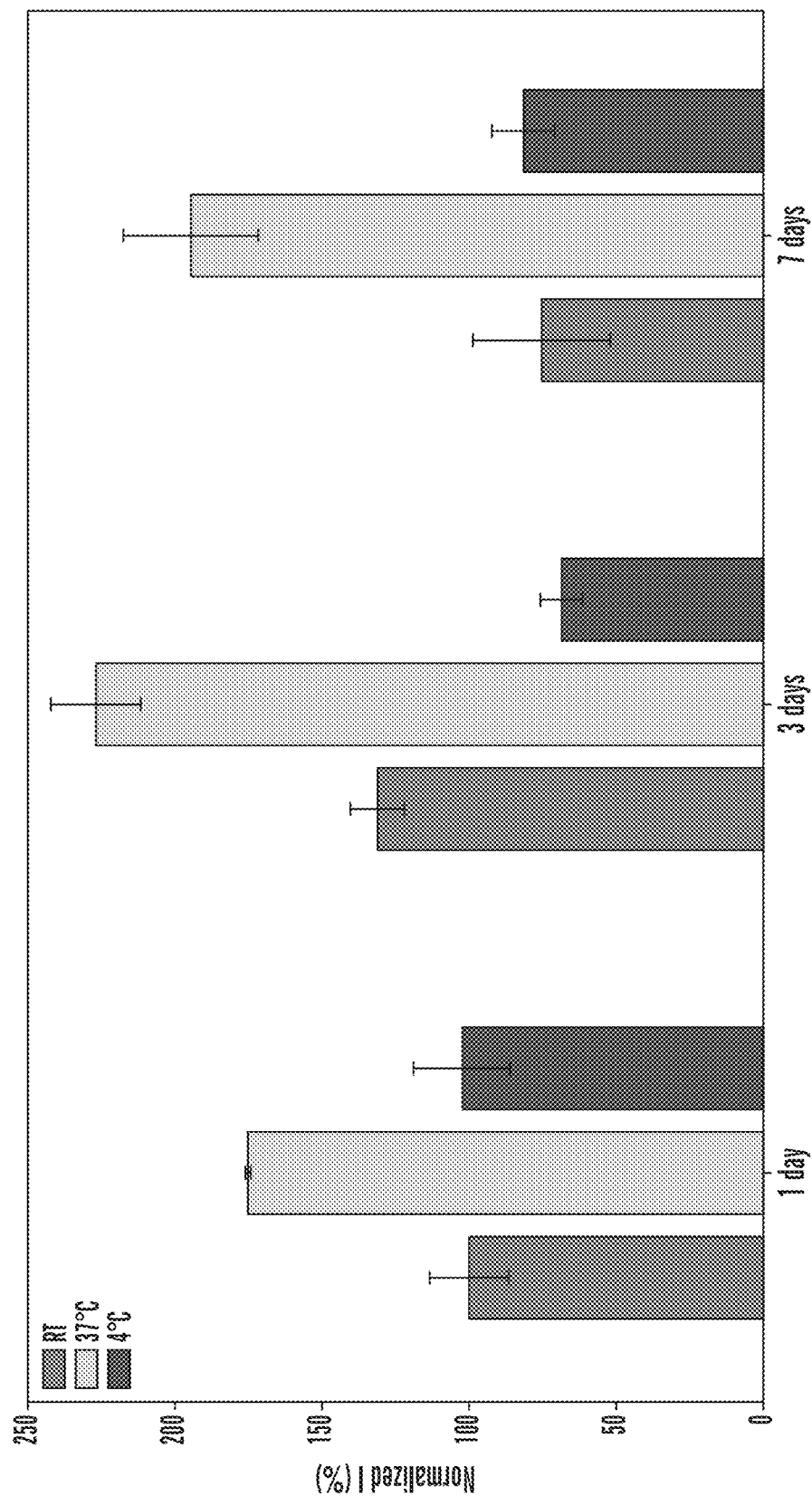
FIG. 8 is a series of bar graphs showing that the sensitivity of the nicotine biosensor improves when stored at 37° C.
Figure 9:
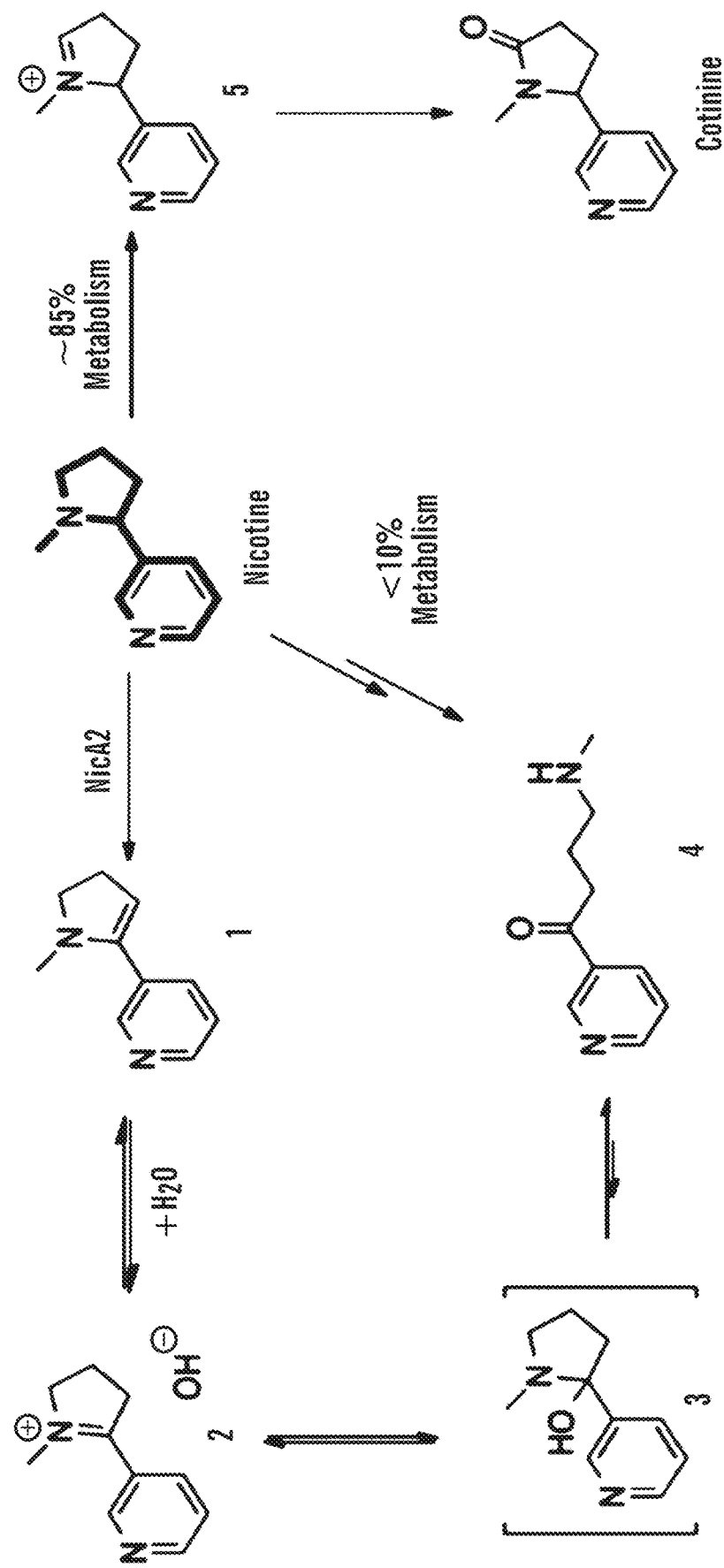
FIG. 9 is a schematic showing an abbreviated nicotine degradation pathway in mammals (cotinine pathway) and in bacteria and mammals (aminoketone 4 pathway); see e.g., Xue et al. 2015, J Am Chem Soc 137(32) 10136-9, showing metabolism of nicotine to its common Cotinine metabolite byproduct.

Referring to FIG. 6B, in one example, an amperometric nicotine biosensor for use herein has the configuration of an electrode test strip 1 having an electrode support layer 6, a redox-enzyme and redox-mediator coated-working electrode 2 *a* disposed on the support layer 6, and a counter electrode 2 *b* and reference electrode 2 *c* spaced from the working electrode 2 *a* and disposed on the support. A covering layer 7 defines an aperture 4 that opens into a recessed space or well 8 having walls defined by layer 7 and a bottom defined by layer 6. As shown, the electrodes 2 *a*, 2 *b*, and 2 *c* are situated in well 8. The electrodes are left exposed in well 8, such that sample fluid can be received in well 8 to contact the electrodes. The working electrode 2 *a* comprises a coating of the redox-enzyme and redox-mediator composition immobilized to a conductive electrode material, such as referenced herein. The counter electrode 2 *b* is a conductive electrode material without the coating of the redox-enzyme and redox-mediator composition. The electrode support 6, typically an elongated strip of electrical insulating polymeric material, e.g., PVC, polycarbonate or polyester, supports two or more printed tracks of electrically conducting carbon ink 5. The conducting inks 5 are hidden in the view of FIG. 6B, and are represented by hatched lines. These printed tracks define the positions of the working, counter, and reference electrodes, and of the electrical contacts 3 that are operable to be inserted into an appropriate measurement device (not shown; e.g., a potentiostat). The covering layer 7 also can be an electrical insulating polymeric material. The insulating layers 6 and 7 can be, for example, hydrophobic insulating polymeric material. FIG. 6C further shows the electrodes as positioned in the well 8, where they can be contacted and covered by fluid sample during measurements. In addition to the arrangement shown, the working, counter, and reference electrodes can be arranged in other configurations relative to each other within recess well 8. The working, reference and counter electrodes can be spaced, for example, from about 0.25 mm to about 0.5 mm, and the working, counter, and reference electrodes can have a width, for example, of about 0.5 mm to 1.5 mm, and a length, for example, of from about 1.5 mm to about 2.5 mm, or other dimensions.

In some embodiments of any of the aspects, the amperometric nicotine biosensor, e.g., chronoamperometric biosensor comprises an electrochemical sensor strip. In some embodiments of any of the aspects, the electrochemical sensor strip comprises: an insulation substrate; a first conduction film mounted on the insulation substrate and having a first and a second ends; and an insulation layer mounted on the first conduction film to cover the first end, wherein the second end serves as a signal output terminal, the first end has a first conduction section exposed between the insulation layer and the insulation substrate, and the first conduction section serves as a working surface of an electrode (i.e., working electrode) of the electrochemical sensor strip. See e.g., European patent publication 1845371, the content of which is incorporated herein by reference in its entirety.

In still another aspect of the present invention, the biosensor electrode is contained within a miniaturized device to further facilitate sample quantification. This amperometric microbiosensor comprises several components. First, a metal wire with a working end to be further electroplated with a noble metal serves as the working electrode. This biosensing electrode forms the working electrode about which an encasement is then drawn. The working electrode within the encasement is further drawn to a tip of about 1-20 µm in diameter. A Ag/AgCl wire is then inserted into the encasement wherein the Ag/AgCl wire serves both as a reference and counter electrode. Finally, an electrolyte filler is inserted into the encasement to complete the microbiosensor.

D. Detection of signals from Redox Mediators

The technology described herein relates to a biosensor useful for the accurate, reliable and sensitive measurement of nicotine in the environmental, industrial, or clinical setting.

The redox-enzyme biosensor generates an electrochemically or non-electrochemically detectable product or by-product directly, or alternatively, the enzyme system can also include at least one further component, such as an intermediate redox enzyme (IRE) as disclosed herein. In some embodiments, the further component may be: one or more additional enzyme(s) forming an enzymatic pathway utilizing the product or by-product of the initial redox-enzyme reaction to thereby generate a photometrically or electrochemically detectable product or by-product; or at least one signal mediator; or both the additional enzyme(s) and the signal mediator(s). The signal mediator(s) may be selected from, for example: indicators, such as a pH-change indicators; electron transfer mediators; photometric mediators, and other components.

In some embodiments in an electrochemical embodiment of the assay, the redox-enzyme system utilizes an electrochemically detectable cofactor, such as NADH, or generates a by-product, such as $H_2O_2$, during the course of the enzymatic reaction with nicotine.

For illustrative purposes only, the oxidase enzyme can be conjugated to an electroactive molecule and the analyte probe is attached or on the surface of a conducting surface of a semiconductor device, such that when the oxidase enzyme is bound to nicotine, the electroconductive molecule conjugated to the oxidase enzyme and nicotine are in close proximity to allow electron transfer, and the flow of electrons to the semiconductor device which is detected by an increase in current on the surface.

In another embodiment, electrochemical impedance spectroscopy can be used to measure the resistance of the system by using redox markers.

Other methods to modify the oxidase enzyme and analyte probes for electrochemical detection of the analyte and generating electroconductive biosensors for use herein are described in Electrochemical methods—Fundamentals and applications, 2Ed., Allen Bard and Larry Faulkner, and Electrochemistry for biomedical researchers, Richie L C Chen, World Scientific Press, each of which are incorporated herein in their entirety by reference.

In some embodiments of any of the aspects, detection of nicotine is not limited to electrochemical means, and the redox-enzyme system disclosed herein may employ different detection methods, e.g., UV, fluorescence, or other suitable methods of detecting the target analyte and redox-enzyme interactions.

Non-electrochemical detection of redox-mediators (Med) involves, for example, any calorimetric or photometric detection mode known in the art (for example, any colorimetric, spectrometric, spectrophotometric, luminescence-based, chemiluminescence-based, or fluorescence-based detection method.)

A fluorescence detection device has the following minimum requirements: it must be light-tight to eliminate stray light from its surroundings, its fluorophores must be stored in the dark to prevent photobleaching (that is increase shelf life), and its optics must be at a 90° angle. A diode emitting the desired excitation wavelength can function as the light source, and a PMT can function as the detector. These need not be elaborate since both the excitation and emission λmax of the fluor are known, and these are the only wavelengths required. The same redox-enzyme and redox-mediator used in an enzyme electrochemical device can be used in a fluorescence device. A portable fluorescence detector for aflatoxin has been described in the literature (M A Carlson et al., An automated handheld biosensor for aflatoxin, Biosens. Bioelectr. 14:841 (2000)), so a precedent for a portable fluorescence detector exists.

Both direct and indirect fluorescence allows the detection of nicotine and redox-enzyme interactions, via the redox-mediator. The $H_2O_2$-generating systems can use $H_2O_2$ and an additional fluor. In these systems, $H_2O_2$ production causes an increase in fluorescence intensity that is proportional to the nicotine concentration.

Indirect fluorescence of NADH can be detected using the dye rhodamine 123. In some embodiments, non-radiative energy transfer (also called fluorescence resonance energy transfer, FRET) occurs between the excited states of NADH and rhodamine 123. FRET is a well-known technique for determining the proximity of two species, i.e. FRET is utilized as a "molecular yardstick" both in vitro and in vivo. In this context of the target analyte and redox-enzyme interactions, a donor fluorophore, e.g., NADH, transfers its excited state energies to the acceptor fluorophore, rhodamine 123. (R P Haugland, Handbook of Fluorescent Probes and Research Products, 2002 (9th ed.; Molecular Probes, Inc.; Eugene, Oreg.); K Van Dyke et al., eds. Luminescence Biotechnology. Instruments and Applications, 2002 (CRC Press; Boca Raton, Fla.) and references contained therein). The NADH-rhodamine 123 FRET method has been successfully employed in other enzymatic assays (M H Gschwend et al., Optical detection of mitochondria) NADH content in intact human myotubes, Cell. Mol. Biol. 47:OL95 (2001); H. Schneckenberger et al., Time-gated microscopic imaging and spectroscopy in medical diagnosis and photobiology, Opt. Eng. 33:2600 (1994)). Bioluminescence resonance energy transfer, or BRET, may also be used in conjunction with a nicotine-specific enzyme system according to the present invention. In BRET, the donor fluorophore is replaced by a luciferase. Bioluminescence from luciferase in the presence of a substrate excites the acceptor fluorophore. BRET has also been applied in vitro and in vivo (K Van Dyke et al., 2002).

ATP can be derivatized with a fluorophore for indirect fluorescence. Several commercially available dyes include BODIPY ATP and trinitrophenyl ATP (Haugland, 2002). These analogs change their fluorescence intensity or become fluorescent when bound to an enzyme's ATP binding site.

Indirect fluorescence detection of $H_2O_2$ has also been reported (Carr & Bowers, 1980). These methods utilize dyes that reduce the peroxide to $H_2O$ and are themselves oxidized. Homovanillic acid (4-hydroxy-3-phenylacetic acid) and p-hydroxyphenylacetic acid are among the most commonly used in clinical chemistry (Can and Bowers, 1980). A commercially available kit uses the dye Amplex® Red for fluorescence detection of $H_2O_2$ (Haugland, 2002).

Any fluorescent dyes and fluorescence-detectable enzyme substrate or cofactor analogs can be used in a fluorescence device to detect nicotine and redox-enzyme interactions.

In one embodiment, fluorescent molecule detection can be achieved using a number of detection systems. The choice of a proper detection system for a particular application is well within the abilities of one skilled in the art. Exemplary optical detection system capable of detecting the fluorescence means include, but are not limited to, detection by unaided eye, Fluorescence activated cell sorting (FACS), light microscopy using the eye or an optical sensor as the detector, confocal microscopy, laser scanning confocal microscopy, imaging using quantum dot color, fluorescence spectrum or other quantum dot property and wide-field imaging with a 2 D CCD camera and a high numerical aperture microscope objective. An exemplary laser based microscope system capable of detecting and spectrally resolving the fluorescence from single semiconductor nanocrystals is known in the art.

In some embodiments, the optical detection system may or may not comprise at least one source of excitatory light, such as at least one laser. A source of excitatory light is not needed to detect objects which luminesce independently of light absorption, such as can be generated via bioluminescence or chemiluminescence, for example. In some embodiments, an optical detection system useful herein to measure fluorescence may comprise a light detector detecting light emitted from the object. The light detector is capable of at least partially absorbing light incident thereon and generating output signals in response to the light. The light detector may comprise a control circuit for controlling the operation of the light detector. The control circuit may comprise a circuit of signal amplifier, A/D convertor, integrator, comparator, logic circuit, readout circuit, memory, microprocessor, clock, and/or address.

In some embodiments, the detecting apparatus may comprise a computer for processing output signals from the light detector and generating a determination result. The detecting apparatus may further comprise a blind sheet with a pinhole. The apparatus may further comprise an excitation light source. The object may absorb light emitted from the excitation light source and then emit another light to be detected by the detecting apparatus. The light emitted from the object may have different wavelength than the light emitted from the excitation light source.

In some embodiments, the detection device, e.g., optical sensor or semiconductive device allows point of care testing (POCT), that is, the subject can perform all the relevant step in analyte (e.g., nicotine) detection, including obtaining the sample, applying the sample to the biosensor, placement in the reader device (e.g., optical sensor or semiconductive device), which will transmit the results to a mobile device (e.g., a mobile phone or smartphone, ipad, tablet, smartwatch), or other interface, e.g., cloud to be accessed by the subjects clinical practitioner.

Chemiluminescence (CL) and electrogenerated chemiluminescence (ECL) (collectively referred to herein as "(E)CL") are widely used in medical diagnostics and analytical chemistry (C Dodeigne et al., Chemiluminescence as a diagnostic tool: A review, Talanta 2000, 51:415; K A Fahnrich et al., Recent applications of electrogenerated chemiluminescence in chemical analysis, Talanta 2001, 54:531). Enzyme-based (E)CL systems are sensitive and specific, and many CL systems are used with enzyme cycling to detect $H_2O_2$ (Dodeigne et al., 2000). (E)CL can detect picomolar (pM; 10-12M) concentrations of analyte over a wide linear range (Dodeigne et al., 2000; Fahnrich et al., 2001). An (E)CL device can be constructed in accordance with the following principles. Since the reaction itself emits light, an (E)CL device does not need a light source. A photomultiplier tube (PMT) can function as the detector; (E)CL is visible to the unaided, dark-adapted eye. A battery can be the power source for ECL. ECL requires electrodes and a source of applied potential. Like a fluorescence detection device, (E)CL devices need to be light tight and their reagents need to be protected from light until use. Also like fluorescence, (E)CL requires derivatized reagents or additional enzymes and reagents to detect nicotine. (E)CL devices can be used with disposable strips (B D Leca et al., Screen-printed electrodes as disposable or reusable optical devices for luminol electrochemiluminescence, Sens. Actuat. B. 2001, 74: 190) and can be miniaturized (Y Lv et al., Chemiluminescence biosensor chip based on a microreactor using carrier airflow for determination of uric acid in human serum, Analyst 2002, 127:1176).

An optical electrode (or optrode) can be fabricated using for detection of the target analyte and redox-enzyme interactions according to the present invention. For example, an optrode such as that used in a glucose optrode that uses ECL, may be employed (see C H Wang et al., Co-immobilization of polymeric luminol, iron(II) tris(5-aminophenanthroline) and glucose oxidase at an electrode surface, and its application as a glucose optrode, Analyst 2002, 127:1507)).

The most common CL systems involve the detection of $H_2O_2$ or another reactive oxygen species (Carr & Bowers, 1980; Haugland, 2002; Dodeigne et al., 2000; K Van Dyke et al., 2002) and references contained therein). The classic system is luminol-peroxidase. In basic solution, $H_2O_2$ oxidizes luminol to an excited amino-phthalate ion; the excited amino-phthalate ion emits a 425-nm photon to return to its ground state. When used in medical diagnostics, this reaction is catalyzed with horseradish peroxidase (HRP) (Carr & Bowers, 1980; Dodeigne et al., 2000). Thus any enzyme system that produces $H_2O_2$ or requires a cofactor that can react with additional reagents to form $H_2O_2$ can be used in a CL device. The $H_2O_2$-generating systems described herein can use luminol-HRP directly for nicotine detection. These enzyme cycling schemes increase the light emission over time because the substrates are continuously recycled (Dodeigne et al., 2000). While luminol itself is frequently used in CL, its improved analogs can also be used in a CL-based detector according to the present invention, in place of luminol, in order to increase the sensitivity. Examples of such analogs are those described in Carr & Bowers, 1980; and Dodeigne et al., 2000.

NADH detection using CL is a common technique (Dodeigne et al., 2000). For example, in the presence of 1-methoxy-5-methylphenazinium methylsulfate, NADH reduces $O_2$ to $H_2O_2$ which generates light using the luminol-peroxidase system (Dodeigne et al., 2000). For a nicotine monitor, the $O_2$ in ambient air is sufficient to detect nicotine using this system. NADH also reacts with oxidized methylene blue to form $H_2O_2$ that reacts with luminol (Carr and Bowers, 1980). NADH can also act as a CL quencher. The fluorescence intensity of the substrate ALPDO is decreased in the presence of NADH and HRP (Van Dyke et al., 2002). NADH also can be used with Ru(bpy)3 2+ for ECL (E S Jin et al., An electrogenerated chemiluminescence imaging fiber electrode chemical. sensor for NADH, Electroanal. 2001, 13(15):1287). Rhodamine B isothiocyanate can also be used for ECL detection of $H_2O_2$(Fahnrich et al., 2001). ECL also offers another advantage in that, by use of a properly poised electrode, the electroactive species can be regenerated at the electrode surface. Regeneration both conserves reagents and allows durable and/or "reagentless" sensors. All these systems can be used in a (E)CL device interfaced to a nicotine-specific enzyme system according to the present invention.

CL is widely used to quantitate ATP simply and sensitively (Carr & Bowers, 1980). The enzyme luciferase catalyzes the reaction of ATP and luciferin to produce excited-state oxyluciferin, which returns to its ground state with the emission of a 562-nm photon (Carr & Bowers, 1980; Haugland, 2002). The quantum yield for this reaction is very high; 10-14 mol ATP can be detected. A kit for this reaction is commercially available (Haugland, 2002). Because luciferase is the enzyme that causes fireflies to "glow," this reaction is referred to as bioluminescence. Both native and recombinant luciferase are commercially available, and several groups have reported using bioluminescence ATP assays to quantify biological analytes (P Willemsen et al., Use of specific bioluminescence cell lines for the detection of steroid hormone [ant]agonists in meat producing animals, Anal. Chim. Acta 2002, 473:119; S J Dexter et al., Development of a bioluminescent ATP assay to quantify mammalian and bacterial cell number from a mixed population, Biomat. 2003, 24:nb27). In addition to the luminol-HRP system, $H_2O_2$ can also be detected using peroxyoxalic acid derivatives (Dodeigne et al., 2000). $H_2O_2$ can also be detected with CL non-enzymatically with ferricyanide as the catalyst (Dodeigne et al., 2000). In these (E)CL systems, detection of the target analyte and redox-enzyme interactions as described herein either produce $H_2O_2$ or require cofactors that can be utilized to form $H_2O_2$.

Optical biosensors use photometric detection (that is, absorbance, fluorescence) of substrates consumed or products formed by the reaction catalyzed by the enzyme system incorporated into the sensor. The target analyte and redox-enzyme reactions as described may be monitored by several photometric methods-namely by measuring NAD(P)H absorbance at 340 nm for the pyridine nucleotide-dependent enzymes or absorbance of the quinoneimine dye for the $H_2O_2$ forming enzyme systems. For the later, addition of a peroxidase allows detection of $H_2O_2$ by catalyzing the reduction of $H_2O_2$ with concomitant oxidation of a dye compound that upon oxidation absorbs at a specified wavelength. Peroxidase enzymes (for example, commercially available horseradish peroxidase) typically have broad substrate specificities so several different electron donor compounds may be used. NAD(P)H consumption may also be measured by fluorescence detection (excitation at 350 nm and emission at 450 nm).

Calorimetry may be employed as a detection means to detect the target analyte and redox-enzyme interactions according to the present invention. Chemical reactions are typically either exo- or endothermic; that is, they release or absorb heat as they occur. Calorimeters detect and measure this heat by measuring a change in the temperature of the reaction medium (K Ramanathan & B Danielsson, Principles and applications of thermal biosensors, Biosens Bioelectr. 16:417 (2001); B Danielsson, Enzyme Thermistor Devices. In Biosensor Principles and Applications. Vol. 15, pp. 83-105 (L J Blum & P R Coulet, eds.; Bioprocess Technology Series, volume 15; Marcel Dekker, Inc: New York, 1991, pp. 83-105, and references contained therein). Thus, the action of the target analyte (e.g., nicotine) and redox-enzyme interactions may be monitored calorimetrically. Calorimeters have been designed that are sensitive enough to detect protein conformational changes, and calorimetry has been used to study many enzymatic reactions in detail (M. J. Todd & J Gomez, Enzyme kinetics determined using calorimetry: a general assay for enzyme activity? Anal. Biochem. 2001, 296:179 (2001)).

The major advantage of calorimetry is the lack of derivatization required for analysis (Danielsson, 1991). Since most reactions involve heat exchange, and this heat is detected, no chromophores, fluorophores, luminophores, "mediators," or other modifications of the analyte are required. Reagents and analytes can be used "as is." This allows the analysis of both reactions that lack a chromophore or fluorophore and/or would be difficult or impossible to derivatize or couple to the generation of an electroactive species.

Miniaturized or chip-based thermosensors have been reported in the literature (Ramanathan & Danielsson, 200:1; B Xie & B Danielsson, Development of a thermal micro-biosensor fabricated on a silicon chip. Sens. Actuat. B 6:127 (1992); P Bataillard et al., An integrated silicon thermopile as biosensor for the thermal monitoring of glucose, urea, and penicillin. Biosen. Bioelect. 8:89 (1993)). These devices range from radically arranged thermopiles on freestanding membranes to groups of thermopiles constructed on silicon/glass microchannels. These devices have been used to detect specific, single enzymatic reactions (Danielsson, 1991; Xie & Danielsson, 1992; Bataillard et al., 1993). Moreover, two groups have reported thermosensors for glucose (B Xie et al., Fast determination of whole blood glucose with a calorimetric micro-biosensor, Sens. Actuat. B 15-16:141 (1993); M J Muehlbauer et al., Model for a thermoelectric enzyme glucose sensor, Anal. Chem. 61:77 (1989); B C Towe & E J Guilbeau, Designing Medical Devices, 1998.

II. Nicotine Biosensor Devices

In one aspect, described herein is a system comprising a nicotine amperometric biosensor, e.g., in some instances, a chronoamperometric nicotine biosensor as described herein and a potentiostat. A potentiostat is the electronic hardware required to control a three electrode cell and run most electroanalytical experiments. The system functions by maintaining the potential of the working electrode at a constant level with respect to the reference electrode by adjusting the current at an auxiliary electrode. A potentiostat is a control and measuring device; as such it can be referred to as a power supply unit, a processing unit, and/or a display unit. A potentiostat comprises an electric circuit which controls the potential across the cell by sensing changes in its resistance, varying accordingly the current supplied to the system: a higher resistance will result in a decreased current, while a lower resistance will result in an increased current.

In some embodiments of any of the aspects, the potentiostat allows for chronoamperometry, an electrochemical technique in which the potential of the working electrode is stepped and the resulting current from faradaic processes occurring at the electrode (caused by the potential step) is monitored as a function of time. In some embodiments of any of the aspects, the potentiostat measures the current of the chronoamperometric biosensor. In some embodiments of any of the aspects, the current readings are output onto a display (e.g., a display unit of the potentiostat or a separate display module).

Figure 5:
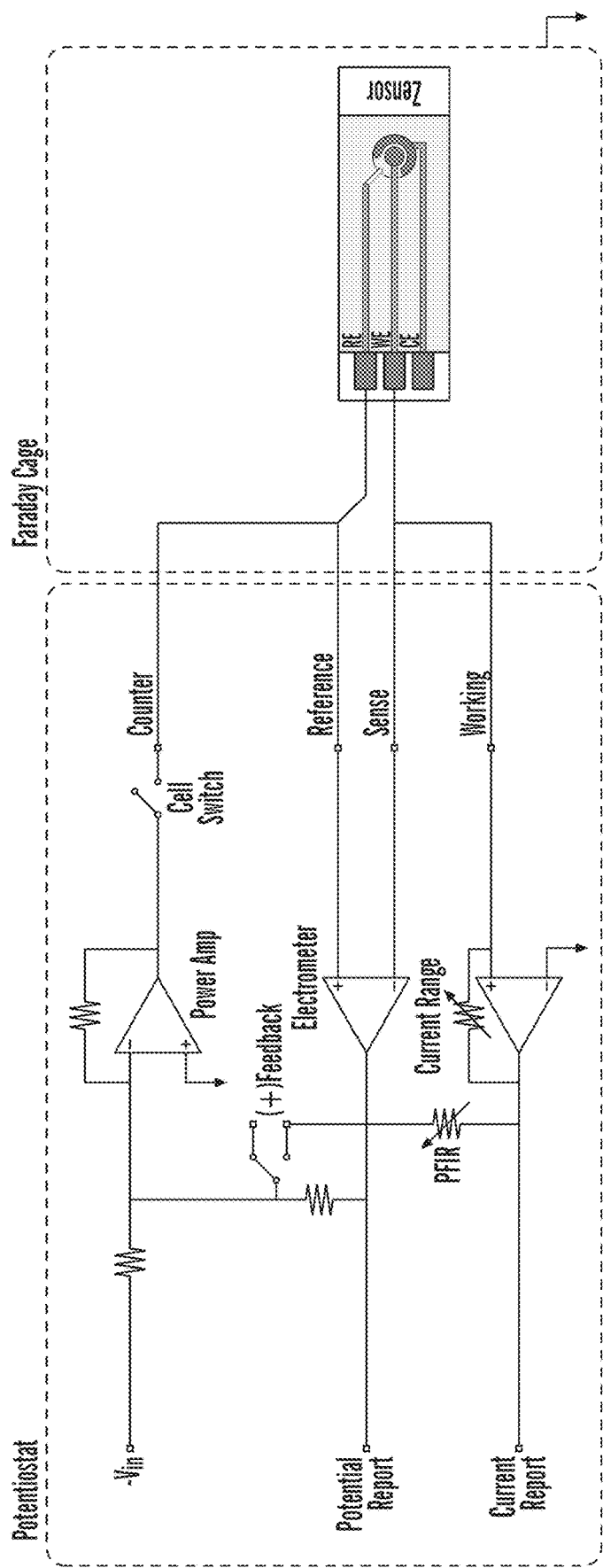
FIG. 5 shows a simplified representation of potentiostat circuitry which allows for the accurate measurement of a current response resulting from analyte addition to the electrochemical biosensor.

FIG. 5 shows an exemplary system comprising amperometric biosensor, e.g., a chronoamperometric biosensor that is electrically coupled to a potentiostat, for example through electrical leads to at least one electrode of the biosensor. In some embodiments of any of the aspects, the potentiostat is electrically coupled to the working electrode of the biosensor. In some embodiments of any of the aspects, the potentiostat is electrically coupled to the reference electrode of the biosensor. In some embodiments of any of the aspects, the potentiostat is electrically coupled to the counter electrode of the biosensor. In some embodiments of any of the aspects, the potentiostat is electrically coupled to the working electrode and the reference electrode of the biosensor. In some embodiments of any of the aspects, the potentiostat is electrically coupled to the working electrode, reference electrode, and counter electrode of the biosensor.

In some embodiments of any of the aspects, the amperometric biosensor, e.g., chronoamperometric biosensor is contained in a Faraday cage. A Faraday case is a grounded metal screen surrounding a piece of equipment to exclude electrostatic and electromagnetic influences.

In some embodiments of any of the aspects, the system comprises a portable device; as a non-limiting example, the biosensor and/or the potentiostat can be portable. In some embodiments of any of the aspects, the system comprises a wearable device; as a non-limiting example, the biosensor and/or the potentiostat can be wearable. See e.g., US patent publication 2015/0260674, Shiwaku et al., Scientific Report (2018) 8:6368; Steinberg et al., Talanta. 2015 Oct. 1; 143: 178-183; the contents of each of which are incorporated by reference herein in their entireties.

In some embodiments, a nicotine biosensor as disclosed herein can be fabricated by using screen-printing technology, or inkjet- or other 3D printing technology to print components of the biosensor, where the biosensor comprises a substrate, e.g., a backing layer, and at least one set of three electrodes. In some embodiments, the electrodes are printed from a conducting polymer onto the backing layer. An exemplary nicotine biosensor device useful herein includes a three-electrode geometry which include a reference electrode, a working electrode, which preferably includes a biofunctional polymeric coating, and a counter electrode. Typically, each electrode includes an active area, an electrical interconnect, and a contact area.

The electrodes may have a length between about 2 mm and about 20 mm, a width between about 0.1 mm and about 2 mm, and a height between about 0.1 mm and about 2 mm. The sensors may include an array of sets of three electrodes. The sensor may be connected to a data acquisition system, a display system, or both an acquisition and a display system, forming a sensor system.

In some embodiments, the working electrode includes a coating positioned over its active, and nicotine-catalyzing enzyme in or on the coating. The sensor typically includes a sensing area. The sensing area is usually formed of at least a portion of the active areas of the reference electrode, the working electrode, and the counter electrode. In some embodiments, the sensing areas is formed of all of the active area of the reference electrode, all of the active areas of the working electrode and all of the active areas of the counter electrode. In some embodiments, the sensing area may include a protective coating. The contact areas of the reference electrode, the working electrode, and the counter electrode connect the sensor to a data acquisition system, a display system, or both an acquisition and a display system, forming a sensor system. The electrical interconnects that connect the sensing area and the contact areas of the electrodes may include an insulation coating.

The electrodes of the biosensor may be printed from a conducting polymer. Suitable conducting polymers include poly(4,4-dioctylcyclopentadithiophene), poly(isothianapthene), poly (3,4-ethylenedioxythiophene), polyacetylene (PAC), polyaniline (PANI), polypyrrole (PPY) or polythiophenes (PT), poly(p-phenylene sulfide) (PPS), and poly (3,4 ethylenedioxythiophene) polystyrene sulfonate (PEDOT:PSS). The sensing area may include a protective coating. Typically, the protective coating is a polymer that reduces or prevents the non-specific interaction or interference of different molecules in the biological sample with the biofunctional coating of the sensor. The protective coating can be a cation exchange membrane containing a polymer that prevent negatively charged interferences from reaching the sensor surface. Exemplary polymers that may be used as or in a protective coating include polystyrene sulfonate, perfluorinated sulfonated ionomer such as Nafion® (E. I. Du Pont De Nemours And Company Corporation, Wilmington, Del.), AQUIVION® (Solvay SA Corporation, Brussels, Belgium), or a combination thereof.

Typically, the coating includes a mediator, such as a multivalent metal ion or an organometallic compound, and/or a polymer matrix formed of a positively charged polymer such as alginate amine, chitosan, dextran amine, heparin amine, and any combination thereof. The coating also includes a nicotine-catalyzing enzyme as described herein, which is capable of oxidizing nicotine in a test sample. The coating may also comprise other redox mediators (Med) as described herein, as well as intermediate redox enzymes as described herein having the capability of acting as both electron donors and electron acceptors. Additionally, the coating may also comprise multivalent metal ions such as copper, iron, magnesium, manganese, molybdenum, nickel and zinc, and co-factors such as nicotinamide adenine dinucleotide (NAD+), nicotinamide adenine dinucleotide phosphate (NADP+), ascorbic acid, flavin mononucleotide (FMN), flavin adenine dinucleotide (FAD), coenzyme F420, coenzyme B, Coenzyme Q, glutathione, heme, lipoamide, and pyrroloquinoline quinone. In some embodiments, the sensors may include either electrodes for amperometric tests or cyclovoltammetry.

Generally, the sensor is small enough to be applied onto a medical device or onto a subject. The surface of the biosensor, e.g., the substrate (e.g., backing layer) may be a planar surface, such as a paper, a tattoo, a tape, a textile, a wound dressing or bandage, a medical implant, a contact lens, or a pad. The sensor may be part of a catheter, a contact lens, or a medical implant. The sensor may be worn by a subject on a patch or a bandage, or may be provided in a kit, ready to be used as needed. In some embodiments, the sensor may be inserted in whole or in part into a biological sample such as blood, plasma, serum, urine, saliva, fecal matter, or cervicovaginal mucosa. In some embodiments, the sensor may be connected to a data or signal acquisition system, such as a potentiostat, and, optionally, to a display system. The display system may be a portable display system with a screen to display sensor reading. Portable display systems include smartphones, tablets, laptops, desktop, pagers, watches, and glasses.

Typically, the sensor permits non-invasive detection of a presence, absence, or a concentration of, nicotine in a biological sample. Exemplary biological samples include bodily fluids or mucus, such as saliva, sputum, tear, sweat, urine, exudate, blood, plasma, or vaginal discharge.

A nicotine biosensor comprising a nicotine-catalyzing enzyme can be configured according to a biosensor described in WO2019/224628, which is incorporated herein in its entirety by reference.

Printed nicotine-catalyzing enzymatic sensors and sensor systems as disclosed herein are capable of detecting nicotine concentrations in the relevant range from biological samples obtained non-invasively show long term stability use with accurate and reproducible measurement of nicotine levels.

The nicotine biosensor device system typically includes a sensor (also referred to as a biosensor), which may be attached to a reader containing an acquisition and/or a display component. The biosensor system is portable, and the acquisition and/or one or more display components may be attached or disconnected from the sensor as needed.

A. Nicotine BioSensor

The nicotine sensors typically include at least one backing layer, and at least one set of three electrodes printed from a conducting material onto the backing layer. Typically, the electrodes include an active area, an electrical interconnect, and a contact area. The electrodes can be formed from the same conducting material or different conducting materials. Typically, all electrodes are formed from the same conducting material, i.e. a conducting polymer. In some instances, all electrodes can be printed from the same conducting polymer on the backing layer in one step. The combination of the active areas of the reference electrode, the working electrode, and the counter electrode forms the sensing area. Each printed electrode may include 1, 2, 3, 4, 5, 6, 7, 8, 9, or 10 layers of a conducting polymer, for example, but not limited to, poly(3,4-ethylenedioxythiophene) doped with poly(styrene sulfonate) anions (PEDOT PSS), which is widely used in various organic optoelectronic devices. PEDOT: PSS is a blend of cationic polythiopene derivative, doped with a poly anion. In some embodiments, the working electrode with all layers (electrode, dielectric, nicotine catalyzing enzyme and redox mediator, and protective coating) can be printed successively.

An exemplary set includes a three electrode geometry with a reference electrode, a working electrode with a biofunctional coating, and a counter electrode. Typically, the electrodes have a length between about 2 mm and about 20 mm, a width between about 0.1 mm and about 2 mm, and a height between about 0.1 mm and about 2 mm.

The sensors may include an array of sets of three electrodes. The sensor may be connected to an acquisition system, a display system, or both an acquisition and a display system. The contact areas of the reference electrode, the working electrode, and the counter electrode may connect the sensor to a data acquisition system, a display system, or both an acquisition and a display system, forming a sensor system.

Generally, the sensors include a coating positioned over a surface of the working electrode, i.e. the active area of the working electrode, and an electron-generating nicotine-catalyzing enzyme in the biofunctional coating. The coating may further include a redox mediator and/or a polymer matrix. The sensor may include a sensing area, which is formed of active areas of the reference electrode, the working electrode, and the counter electrode. The sensing area typically includes a protective coating. Typically, the protective coating is a polymer that reduces or prevents the non-specific interaction or interference of different molecules in the biological sample with the biofunctional coating of the sensor. The protective coating may also stabilize the nicotine-catalyzing enzyme and/or the redox mediators in the coating. The protective coating can be a cation exchange membrane containing a polymer that prevent negatively charged interferences from reaching the sensor surface. The electrical interconnects that connect the sensing area and the contact areas of the electrodes may include an insulation coating, such as a dielectric coating. The dielectric coating can separate or insulate the sensing area from the contact areas. The sensor system can include a printed metabolite sensor on a backing layer, which can be as simple as a commercial disposable paper. The fabrication of a nicotine biosensor as described herein using ink-jet technology or other 3D printing technology enables the production of a highly sensitive, selective, portable, inexpensive, stable, and user-friendly nicotine sensing device. The printed nicotine biosensor can be tested over a period of one month and its long-term stability confirmed. This demonstrated that the nicotine biosensor may be used in real world applications with bodily fluids such as sweat, blood and saliva, enabling non-invasive monitoring. In some embodiments, the nicotine biosensor as described herein can be configured as an all-polymer "smart e-paper nicotine biosensor" providing the next generation of disposable low cost and eco-friendly high-performance nicotine biosensor devices.

1. Reference Electrode

The reference electrode is an electrode having a maintained potential, used as a reference for measurement of other electrodes. Exemplary reference electrodes are, but not limited to, silver, silver chloride, silver/silver chloride, gold, copper, carbon, and conducting polymer. The reference electrode may be screen-printed or inkjet-printed from the above-mentioned materials. Typically, the reference electrode is inkjet-printed from a conducting polymer. In some embodiments, the nicotine biosensor disclosed herein does not comprise a reference electrode.

2. Working Electrode

The working electrode typically includes a biofunctional coating. The biofunctional coating may contain the nicotine-catalyzing enzyme. The biofunctional coating may further include a redox mediator, and optionally an intermediate redox enzyme (IRE) and/or a polymer matrix.

The mechanism of the detection of nicotine is based on the specific nicotine-catalyzing enzyme and the cycle of electrochemical reactions, which alternatively oxidize/reduce the compounds immobilized at the surface of the sensor, i.e. at the surface of the working electrode. Typically, the electrons are transferred from nicotine (the analyte) to the conducting polymer through the cycle of electrochemical reactions, generating a current between the working and counter electrodes detected by the acquisition system. An exemplary cycle of reactions is depicted herein, where upon reacting with nicotine, the nicotine-catalyzing enzyme, i.e. NE gets reduced, and the reduced nicotine-catalyzing enzyme cycles back via the redox mediator, which mediated electron transfer from the nicotine-catalyzing enzyme to the conducting polymer, i.e. PEDOT:PSS.

As disclosed herein in the Examples, the inventors that the size of the working electrode influence the current produced from the NicA2 biosensor. Accordingly, in some embodiments, the working electrode has an area of >4π mm$^2$. In some embodiments, the size of the working electrode is in the range of 5-8 π mm$^2$, or 8-10π mm$^2$, or 10-12π mm$^2$, or 12-15π mm$^2$, or greater than 15π mm$^2$. In some embodiments, the shape of the working electrode is circular, and in some embodiments the shape is oval. In some embodiments, the counter electrode is a geometric shape which wraps or circles around the working electrode.

In some embodiments, the working electrode comprises NicA2 enzyme in a low- or medium molecular weight (MW) chitosan in 0.5% acetic acid layer. In some embodiments, the working electrode does not comprise Nafion.

Redox Mediators

Typically, a mediator is a small molecule compound participating in an electron donor/acceptance. Exemplary mediators include compounds containing multivalent metal ions such as copper, iron, magnesium, manganese, molybdenum, nickel and zinc, organometallic compounds, phenazine methosulfate, dichlorophenol indophenol, short chain ubiquinones, ferrocene complex, and co-factors such as nicotinamide adenine dinucleotide (NAD+), nicotinamide adenine dinucleotide phosphate (NADP+), ascorbic acid, flavin mononucleotide (FMN), flavin adenine dinucleotide (FAD), coenzyme F420, coenzyme B, Coenzyme Q, glutathione, heme, lipoamide, and pyrroloquinoline quinone. In some instances, the mediator is a ferrocene complex. In some embodiments, a FAD redox mediator is not used.

3. Counter Electrode

The counter electrode, often also called the auxiliary electrode, is an electrode used in a three electrode electrochemical cell for voltammetric analysis or other reactions in which an electric current is expected to flow. Exemplary counter electrodes are, but not limited to, gold, copper, carbon, and conducting polymer. The counter electrode may be screen-printed or inkjet-printed from the above-mentioned materials. Typically, the counter electrode is inkjet-printed from a conducting polymer.

4. Materials Forming the Electrodes

Generally, the sensor includes at least one set of three electrodes. Each electrode in the sensor may include one or more coatings. The electrode and the coatings can be inkjet-printed, in sequential manner, to obtain the arrangement described in section Sensors.

Materials forming the electrodes and its coatings include conductive polymers, dielectric inks, charged biocompatible polymers, and synthetic ionic polymers. Typically, the reference electrode, the working electrode, and the counter electrode are formed of conductive polymers. The reference electrode, the working electrode, and the counter electrode may also include a dielectric coating formed of dielectric ink. The working electrode typically includes a biofunctional coating containing a bifunctional molecule, a mediator, and polymer matrix formed of a charged biocompatible polymer. At least a portion, i.e., the active area of the reference electrode, the working electrode, and the counter electrode may be coated with a protective coating containing a synthetic ionic polymer.

a. Conducting Polymer

Conducting polymers which can be used to form the reference electrode, the working electrode, and the counter electrode. Exemplary conducting polymers include poly(3,4-ethylenedioxythiphene) (PEDOT), poly(hydrooxymethyl 3,4-ethylenedioxythiphene) (PEDOT-OH), polystyrene-sulfonate (PSS), F8BT, F8T2, J51, MDMO-PPV, MEH-PPV, PBDB-T, PBDTBO-TPD, PBDT(EH)-TPD, PBDTTT-C-T, PBDTTT-CF, PBTTPD, PBTTT-C14, PCDTBT, PCPDTBT, PDTSTPD, PffBT4T-20D, PffBT4T-C9C13, PFO-DBT, Poly([2,6'-4,8-di(5-ethylhexylthienyl)benzo[1,2-b;3,3-b]dithiophene] {3-fluoro-2[(2-ethylhexyl)carbonyl] thieno[3,4-b]thiophenediyl}), Poly(3-dodecylthiophene-2,5-diyl), Poly (3-hexyl thiophene-2,5-diyl), Poly(3-octylthiophene-2,5-diyl), PSiF-DBT, poly(triaryl amine) (PTAA), PTB7, TQ1, N2300, P(NDI-T2), poly(diketopyrrolopyrrole) (DPP), poly(benzimidazobenzophenanthroline), poly(2,5-di(3,7-dimethyloctyloxy)cyanoterephthalylidene), poly(2,5-di(hexyloxy)cyanoterephthalylidene), poly(5-(3,7-dimethyloctyloxy)-2-methoxy-cyanoterephthalylidene), poly(2,5-di(octyloxy)cyanoterephthalylidene), poly(5-(2-ethylhexyloxy)-2-methoxy-cyanoterephthalylidene), poly(4,4-dioctylcyclopentadithiophene), poly (isothianapthene), poly(3,4-ethylenedioxy thiophene), poly acetylene (PAC), polyaniline (PANI), polypyrrole (PPY) or polythiophenes (PT), and poly(p-phenylene sulfide) (PPS). In some instances, the conductive polymer is a combination of two or more conductive polymers described above. For example, the conductive polymer can be poly(3,4 ethylenedioxythiophene):polystyrene sulfonate (PEDOT:PSS).

b. Dielectric Coating

The dielectric coating may be a dielectric/insulator ink layer. The dielectric ink layer may be a dielectric polymer, copolymer, block polymer, or polymer-inorganic composite. The dielectric polymer may be polyimide, polyurethane, polysiloxane, polyacrylate, plyethylene, polystyrene, polyepoxide, polytetrafluoroethylene, polyarelene ether, methyl-silsesquioxone, fluorinated polyimide, or a combination thereof. Dielectric polymer-inorganic composite may include a polymer and an inorganic compound such as BaTi(¾, TiCb, Al2O3, Zr(¾. Exemplary dielectric polymer-inorganic composite may be polyimide-BaTi03.

Commercially available dielectric/insulator inks or pastes may be EMD 6200 (Sun Chemical Corporation, Parsippany, N.J.), KA 701 (DuPont), 125-17, 116-20, 113-48, 111-27, 118-02, 122-01, 119-07, 118-08, 118-12 (CREATIVE MATERIALS®), D2070423P5, D2071120P1, D2140114D5, D2020823P2, D50706P3, D2030210D1, D2070412P3, D2081009D6, D50706D2, D2130510D2 (Sun Chemical Corporation, Parsippany, N.J.), LOCTITE® EDAG 1020A E&C, LOCTITE® EDAG 452SS E&C, LOCTITE® EDAG PD 038 E&C, LOCTITE® EDAG PF 021 E&C, LOCTITE® EDAG PF 455B E&C, or LOCTITE® M 7000 A BLU E&C (Henkel Corporation).

c. Polymer Matrices Immobilizing Nicotine-Catalyzing Enzyme

In some instances, the biofunctional coating of the working electrode includes a redox mediator, a nicotine-catalyzing enzyme, and a polymer matrix for immobilizing the redox mediator and the nicotine-catalyzing enzyme. The polymer matrix can entrap the redox mediator and the nicotine-catalyzing enzyme within its matrix to prevent leaking and to improve the processability of the nicotine-catalyzing enzyme. The polymer matrix can be biocompatible.

The polymer matrices for immobilizing the mediator and the nicotine-catalyzing enzyme may be formed of positively charged polymers, such as alginate amine, chitosan, dextran amine, heparin amine, and any combination thereof.

d. Protective Coating

The protective coating is typically placed on top, e.g., inkjet-printed over, the electrodes, over a portion of the electrodes, and may be the outermost-layer of on the electrodes. The protective coating may be formed of synthetic ionic polymer, such as polystyrene sulfonate and perfluorinated sulfonated ionomers, such as NAFION®, AQUIVION® (Solvay Sa Corporation, Brussels Belgium), or a combination thereof. In some embodiments, NAFION® is not present.

5. Sensing Area

The sensing area (6) of the nicotine biosensor as disclosed herein typically includes a portion of the working, counter and reference electrodes, i.e. the active areas of the working, counter, and reference electrodes (FIG. 6B). Typically, the active area of the working electrode containing at least a portion of the biofunctional coating. The sensing area may include a polymer coating. The polymer coating typically reduces or prevents the non-specific interaction or interference of different molecules in the biological sample with the nicotine-catalyzing enzyme on the sensor. The polymer coating reduces or prevents any interaction or interference with the electron transport in the sensor from the different molecules in the biological sample.

6. Backing Layer or Substrate

In some embodiments, the surface of the biosensor is a substrate. In some embodiments, the surface of the sensor is a backing layer, and may be a planar surface such as paper, a tattoo, a tape, a textile, a wound dressing or bandage, a medical implant such as catheter, a contact lens, a patch, a pad, glass, or plastics. Typically, the backing layer is a paper. The paper may be disposable after one use or multiple uses, i.e. four times.

7. Wearable Nicotine Biosensor

Figure 29A:
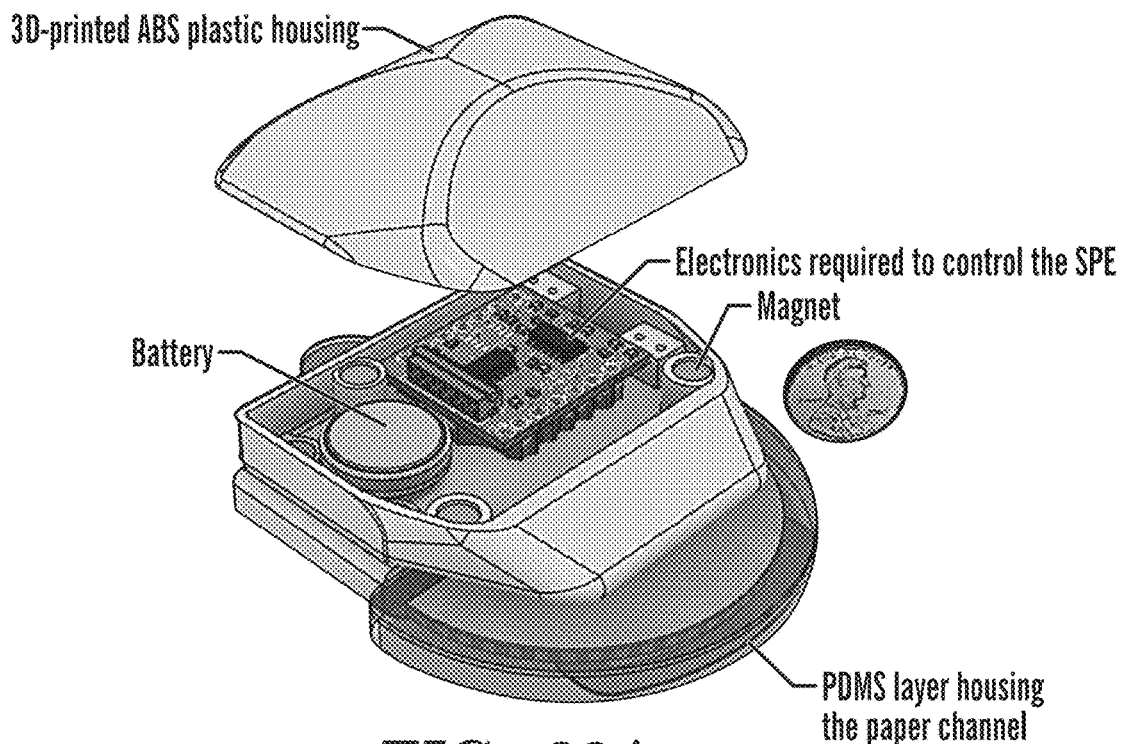
FIG. 29A-29E shows an embodiment of an exemplary wearable NicA2(N462H) biosensor device.
Figure 29B:
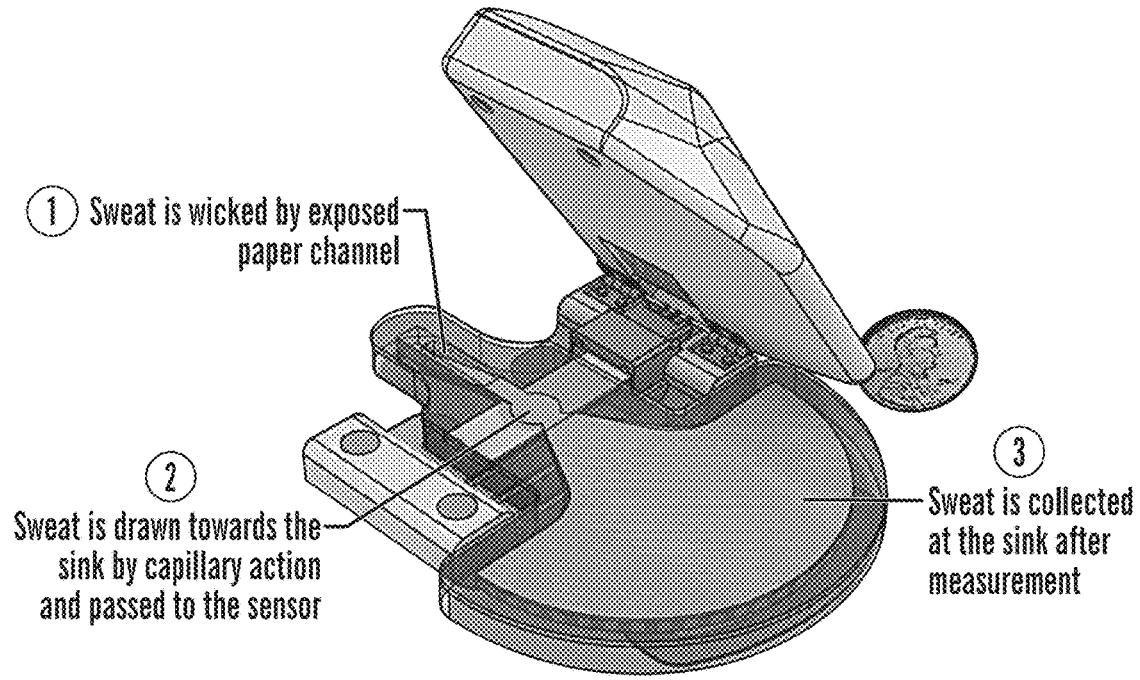

Another aspect of the technology described herein is a wearable nicotine biosensor device, for example, an exemplary wearable NicA2(N462H) biosensor device is shown in FIGS. 29A-29B herein. In some embodiments, a wearable NicA2 device comprises two parts, an electroconductive part comprising a housing with a removable lid, and within the housing an electric control circuit to control the screen printed electrode (SPE), a battery, and PDMS layer housing a paper channel to wick a subject's sweat from their skin into the SPE. Magnets or other means can be used to attach the removable lid to the housing. The housing is positioned above or adjacent to a two electrode-screen printed electrode (SPE), where at least one electrode has a NicA2 enzyme deposited on, where the NicA2 serves as the nicotine biorecognition element, and where the SPE is in fluid communication via the paper channel to a wicking apparatus, where the wicking apparatus contacts the skin of the wearer (i.e., the subject) and wicks sweat from the surface of a subject's skin. Accordingly, FIG. 29B shows an exemplary wearable nicotine electrochemical biosensor device that comprises a housing portion of the biosensor and underneath or adjacent to the housing is the placement of a 2-electrode SPE where one electrode is deposited with NicA2(N462H), and where the SPE is in fluid communication with a sweat sample. In particular, the SPE is in fluid communication via a paper channel with a wicking paper, where the wicking paper wicks sweat from the skin surface of a subject, and 1) the sweat is wicked onto the SPE by the paper channel, and then, 2) sweat is drawn towards the sink by capillary action and passed onto of the 2-electrode sensor comprising the NicA2 (N462H) biorecognition element, and 3) sweat is collected at the sink after measurement. The inventors demonstrate that such a wearable NicA2 biosensor has high sensitivity and can repeatedly measure nicotine in numerous samples, and has a sensitivity to be able to detect nicotine within a 2-50 µM and 50-1000 µM range.

In some embodiments, the wearable nicotine biosensor can be adapted by one of ordinary skill in the art, including using an adhesive sheet to attach the wicking apparatus to the surface of the wearers skin, as disclosed in U.S. Pat. No. 9,820,692, or use of sweat collection pads as disclosed in U.S. Pat. Nos. 10,182,795 and 10,646,142, each of which are incorporated herein their entirety by reference.

In some embodiment, a wearable nicotine biosensor disclosed herein will not necessarily include all obvious features needed for operation, examples being a battery or power source which is required to power electronics, or for example, a wax paper backing that is removed prior to applying an adhesive patch, or for example, a particular antenna design, that allows wireless communication with a particular external computing and information display device. Several specific, but non-limiting, examples can be provided as follows. In a particular embodiment, a wearable nicotine biosensor as disclosed herein is a type of sweat sensor device. In some embodiments, the wearable nicotine biosensor can take on forms including patches, bands, straps, portions of clothing, wearables, or any mechanism suitable to affordably, conveniently, effectively, intelligently, or reliably bring sweat stimulating, sweat collecting, and/or sweat sensing technology into intimate proximity with sweat as it is generated. In some embodiments of the wearable nicotine biosensor disclosed herein will require adhesives to the skin, but devices could also be held by other mechanisms that hold the device secure against the skin such as strap or embedding in a helmet. The wearable nicotine biosensor disclosed herein may benefit from chemicals, materials, sensors, electronics, microfluidics, algorithms, computing, software, systems, and other features or designs, as commonly known to those skilled in the art of electronics, biosensors, patches, diagnostics, clinical tools, wearable sensors, computing, and product design.

The wearable nicotine biosensor disclosed herein may include all known variations of the nicotine biosensors disclosed herein, and the description herein shows sensors as simple individual elements. It is understood that many sensors require two or more electrodes, reference electrodes, or additional supporting technology or features which are not captured in the description herein. The wearable nicotine biosensor disclosed herein are preferably electrical in nature such as ion-selective, potentiometric, amperometric, and impedance (faradaic and non-faradaic), but may also include optical, chemical, mechanical, or other known biosensing mechanisms. Sensors can allow for continuous monitoring of nicotine in the sweat of a subject. In some embodiments, a wearable nicotine biosensor disclosed herein can be in duplicate, triplicate, or more, to provide improved data and readings. Many of these auxiliary features of the device may, or may not, also require aspects of the present invention.

B. Reader

The biosensors as disclosed herein may be connected to a system, optionally including a display.

a. Acquisition System

In some embodiments, an acquisition system may be a potentiostat, a biosensor, or a galvanostat. In some embodiments, a potentiostat that has a current resolution of as low as 1 pA (100 nA range) is used, for example, a DropSens potentiostat. Typically, the acquisition system is connected to software that converts data into a graph, chart or table, for a compound or molecule such as a metabolite.

b. Display System

The display system may be a portable display system with a screen to display sensor reading. Portable display systems include smartphones, tablets, laptops, and monitors.

C. Packaging

The nicotine sensor as disclosed herein may be packaged to protect the electrodes prior to use. Examples of packaging are known in the art and include molded or sealed pouches with temperature and/or humidity control. The pouches may be foil pouches, paper pouches, cardboard boxes, polymeric pouches, or a combination thereof. In some embodiments, the nicotine biosensor as disclosed herein, and sensor systems may be packaged as one unit.

Alternatively, in some embodiments, the nicotine biosensors may be packaged separately, and used as needed with an acquisition and/or display system provided by the end user.

In some embodiments of any of the aspects, the system further comprises a computing device, a server, a network, a database and/or a server. As a non-limiting example, data output from the biosensor and potentiostat as described herein can be displayed on a computing device and/or input into a program that may be stored in a database. In some embodiments, the data is wirelessly transmitted from the biosensor and potentiostat to a computing device, such as but not limited to a mobile phone; see e.g., Ainla et al., April 2018Analytical Chemistry 90(10). The computing device and server may be connected by a network and the network may be connected to various other devices, servers, or network equipment for implementing the present disclosure. A computing device may be connected to a display. Computing device may be any suitable computing device, including a desktop computer, server (including remote servers), mobile device, or other suitable computing device. In some examples, algorithm(s) as described herein and other software may be stored in database and run on server. Additionally, data and data processed or produced by said algorithms or programs may be stored in a database.

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present technology as disclosed herein, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Aspects of the assay describe herein rely on catalyzing an electrochemical reaction (redox) of the redox-enzyme biosensor in the presence of nicotine. In use, nicotine is catalyzed, changing electron flow through the biosensor. In one non-limiting embodiment, the redox-enzyme (or a functional portion thereof) catalyzes a redox event in the presence of nicotine. In some embodiments, the redox-enzyme is a nicotine-catalyzing enzyme. The redox event can be coupled to a redox-mediator (referred to herein as a "Med") which acts as a conductor of electrons to permit detection of the redox event between nicotine and the redox-enzyme biosensor, thereby detecting the presence of the redox-enzyme biosensor. In some embodiments, the redox event between nicotine and redox-enzyme can be coupled to an intermediate redox enzyme (IRE), that acts as a conductor of electrons between the first redox event (between nicotine and the redox-enzyme biosensor) and the redox-mediator (Med) to permit detection of the activity of the redox-enzyme biosensor reacting with nicotine.

In some embodiments, the redox-mediator generates a signal detectable by optical methods, such as, without limitation, fluorescence, surface plasmon resonance, or piezoelectric methods.

Accordingly, described herein is a method of using an amperometric biosensor, e.g., chronoamperometric biosensor to measure the concentration of nicotine comprising: (a) assembling the amperometric biosensor, e.g., chronoamperometric biosensor (or system comprising said biosensor) as described herein; (b) providing a sample; and (c) measuring the current produced by the oxidation of any nicotine present in the sample.

The biosensor can be assembled as described herein. As a non-limiting example, described herein is a method of preparing amperometric biosensor, e.g., a chronoamperometric biosensor capable of measuring the concentration of nicotine comprising: (a) depositing an electronically active mediator on the electrode surface; (b) depositing a polymer on the electrode surface; and (c) depositing a nicotine-catalyzing enzyme on the electrode surface. These steps can occur in any order. In some embodiments of any of the aspects, an electrode is used that already comprises an electronically active mediator on the electrode surface. Accordingly, in another aspect the method of assembling or preparing the biosensor can comprise (a) depositing a polymer (e.g., chitosan) on the electrode surface and (b) depositing a nicotine-catalyzing enzyme on the electrode surface. In some embodiments of any of the aspects, the step of assembling the system can comprise electrically coupling the biosensor to a potentiostat and/or other devices such as a portable cellular device.

Variations to the nicotine biosensor described herein can include changes to the screen-printed electrodes (SPEs). Changes in size, shape, and material of the SPEs can be made to yield a similar result or improve the biosensor. Also, changes to the matrix which holds the nicotine-catalyzing enzyme can be made. Using a two or three electrode circuit with the potentiostat can affect the current response. Furthermore, the choice of a potentiostat for sensitivity to current can improve the biosensor. Mediators on the SPE can be changed or optimized by changing the ions concentrations that constitutive it to yield a higher current response and thus increase sensitivity of the biosensor.

D. Methods of Making the Sensors and the Sensor Systems

In some embodiments, inkjet technology may be used in all the steps for the fabrication of a nicotine biosensor as disclosed herein, according to the methods disclosed in international patent application WO2019/224628, which is disclosed herein in its entirety by reference. Other additive printing technologies, such as screen printing or inkjet printing can also be used and yields high performance nicotine biosensor devices.

For the deposition of the electronic components as well as the biological layers (such as nicotine-catalyzing enzyme for the detection of nicotine), inkjet technology not only allows for the controlled deposition of a variety of different materials but also constitutes a low temperature process which is a critical factor when it comes to the integration of biological molecules such as enzymes. Ink jetting enables the patterning of customizable geometries and can easily be integrated in roll-to-roll processes.

A general method of making the sensors include using a conducting polymer ink dedicated for inkjetting and adjusting the ink formulation to meet the substrate requirements for the formation of a uniform and conducting layer. For example, a cross linker, i.e. 3-glycidoxypropyltrimethoxysilane (GOPS) and/or a surfactant, i.e. dodecyl benzene sulfonic acid (DBSA) may be added to the conducting polymer ink to prevent delamination of the conducting pattern from the backing layer and to improve the wettability of the ink and film formation during printing, respectively. The cross linker can be added at a concentration between about 0.01 wt % and about 5 wt %, between about 0.1 wt % and about 5 wt %, between about 0.5 wt % and about 5 wt %, between about 0.5 wt % and about 4 wt %, between about 0.5 wt % and about 2 wt %, between about 1 wt % and about 5 wt %, and between about 0.1 wt % and about 1 wt %. In some instances, the cross linker can be added at a concentration of about 1 wt %. In some instances, the cross linker is absent. The surfactant can be added at a concentration of between about 0.01% (v/v) and about 1% (v/v), between about 0.05% (v/v) and about 1% (v/v), between about 0.1% (v/v) and about 1% (v/v), between about 0.1% (v/v) and about 0.5% (v/v), between about 0.1% (v/v) and about 0.4% (v/v), and between about 0.2% (v/v) and about 0.5% (v/v). In some instances, the surfactant can be added at a concentration of about 0.4% (v/v). The ink may be printed on most planar surface, including paper, such as a commercial glossy paper. The ink is printed on the planar surface to form all three electrodes (e.g. reference, working and counter electrodes) in the set. All electrodes in the set may be formed of the same material or different materials. Typically, all the electrodes in the set are formed of the same conducting polymer. All electrodes can be printed in a single step.

To insulate/separate the sensing area from the contact areas, one, two, three, or more layers of dielectric ink may be printed on top of the electrodes. In some instances, the dielectric ink is printed over a surface of at least one of the electrodes in a set of electrodes. In some instance, the dielectric ink is printed over a surface of all three electrodes in a set of electrodes. In some instances, the dielectric ink is printed over the electrical interconnects of the working, reference, and counter electrodes. Typically, the dielectric ink is UV-curable.

For the biofunctionalization of the sensor, a biological ink containing a mediator (e.g. ferrocene), a polymer matrix, (e.g., chitosan, a polymer for forming a biocompatible matrix and entrapping the mediator in a polymeric biocompatible matrix) and the nicotine-catalyzing enzyme, is printed on top of the working electrode to form a biofunctional coating. The nicotine-catalyzing enzyme may be immobilized on or in the polymer matrix via non-covalent or covalent bonding, such as via chemical conjugation, e.g., EDC-NHS coupling reaction where carboxyl groups of the enzyme may be conjugated to the amine groups of the polymeric matrix. In some instances, both the redox mediator and the nicotine-catalyzing enzyme are physically entrapped in the polymer matrix. In some instances, the nicotine-catalyzing enzyme are covalently immobilized on or in the polymer matrix and the mediator is physically entrapped in the polymer matrix. This typically forms the biofunctional coating of the working electrode.

A protective coating may be applied onto the electrodes, including onto the biofunctional coating, by printing a coating polymer on top of the electrodes. The protective coating may be printed on the entire surface of the electrodes, including on the biofunctional coating of the working electrode, or on a portion of the electrodes and on a portion of the biofunctional coating of the working electrode. In some instances, the protective coating is printed on the active areas of the working, reference, and counter electrode. In some instances, the protective coating is printed on the active area of the working electrode. In some instances, the protective coating is printed on the biofunctional coating of the working electrode.

For example, the coating polymer or a polymer mixture, such as a mixture containing Nafion® may be printed on top of the sensing area (comprising the active areas of the working, counter and reference electrodes) to block the interferences present in biologic milieu/media such as saliva or sweat.

An acquisition system, such as a potentiostat, is commercially available. It may be attached to the sensor by connecting each electrode to a lead in the acquisition system. The acquisition system may then be connected to a display system, such as a device with a display screen. Exemplary display systems include smartphones, tablets, laptops, desktops, and smartwatches, are commercially available. The display systems typically include electronic conversion means, such as software, to convert the signals received from the acquisition system to a concentration value or a graph, which is then displayed on the screen. Such conversion means are known in the art.

III. Uses and Applications of the Nicotine Biosensor Devices

In some embodiments of any of the aspects, the sample analyzed by the nicotine biosensor as described herein is preferably a fluid, which is contacted with the electrode surface. That is, a fluid sample contacts the NicA2 present on the substrate, and if nicotine is present in the fluid sample, it relays a redox event that is transmitted to the electrons as describe above. As a non-limiting example, a liquid sample can be applied to the area of the biosensor comprising at least one electrode. In some embodiments of any of the aspects, a non-liquid sample can be transformed into a liquid sample; as a non-limiting example a solid or gaseous sample can be dissolved in a liquid, such as an aqueous solvent that does not interfere with the redox reactions.

The term "sample" or "test sample" as used herein denotes a sample taken or isolated from a biological organism, e.g., a blood or plasma sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a biopsy, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject. In some embodiments of any of the aspects, the test sample can be sweat, gastric juice, urine, saliva, or blood (e.g., whole blood, plasma, or serum).

The test sample can be obtained by removing a sample from a subject, but can also be accomplished by using a previously isolated sample (e.g. isolated at a prior time point by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, homogenization, sonication, filtration, thawing, purification, and any combinations thereof. In some embodiments of any of the aspects, the test sample can be treated with a chemical and/or biological reagent. Chemical and/or biological reagents can be employed, for example, to protect and/or maintain the stability of the sample during processing. The skilled artisan is well aware of methods and processes appropriate for pre-processing of biological samples required for determination of the level of an analyte as described herein (e.g., nicotine).

In some embodiments of any of the aspects, the methods described herein can further comprise a step of obtaining or having obtained a test sample from a subject. In some embodiments of any of the aspects, the subject can be a human subject. In some embodiments of any of the aspects, the subject can be a subject in need of nicotine monitoring as described elsewhere herein.

In some embodiments of any of the aspects, measuring the current produced by the oxidation of any nicotine present in the sample allows for the determination of the concentration of nicotine. In some embodiments of any of the aspects, a known concentration of nicotine results in a predictable current, thus an unknown nicotine concentration can be determined using a known current and a standard curve of currents at known nicotine concentrations.

In some embodiments of any of the aspects, the nicotine concentration is measured in the range of 0.4 uM-100 uM. As a non-limiting example, the amperometric biosensor, e.g., chronoamperometric biosensor as described herein can detect nicotine in a sample at a concentration of at least 0.1 uM, at least 0.2 uM, at least 0.3 uM, at least 0.4 uM, at least 0.5 uM, at least 0.6 uM, at least 0.7 uM, at least 0.8 uM, at least 0.9 uM, at least 1.0 uM, at least 2.0 uM, at least 3.0 uM, at least 4.0 uM, at least 5.0 uM, at least 6.0 uM, at least 7.0 uM, at least 8.0 uM, at least 9.0 uM, at least 10 uM, at least 15 uM, at least 20 uM, at least 25 uM, at least 30 uM, at least 35 uM, at least 40 uM, at least 45 uM, at least 50 uM, at least 55 uM, at least 60 uM, at least 65 uM, at least 70 uM, at least 75 uM, at least 80 uM, at least 85 uM, at least 90 uM, at least 95 uM, at least 100 uM, at least 150 uM, at least 200 uM, at least 250 uM, at least 300 uM, at least 350 uM, at least 400 uM, at least 450 uM, at least 500 uM, at least 550 uM, at least 600 uM, at least 650 uM, at least 700 uM, at least 750 uM, at least 800 uM, at least 850 uM, at least 900 uM, at least 950 uM, or at least 100 uM. In some embodiments of any of the aspects, the amperometric biosensor, e.g., chronoamperometric biosensor as described herein can detect nicotine in a sample at a concentration between 0.4 uM-100 uM, 0.1 uM-100 uM, 0.1 uM-500 uM, or 0.1 uM-1000 uM.

As described herein, the current of the amperometric biosensor, e.g., chronoamperometric biosensor is not altered in the presence of an interferent. Such interferents can include but are not limited to L-(+)-lactic acid, ascorbic acid, uric acid, dopamine, (−)-epinephrine, creatinine, S-(+)-glucose, sodium, calcium, magnesium, potassium, phosphate, albumin, amino acids, and cotinine. The amperometric biosensor, e.g., chronoamperometric biosensor as described herein does not respond to the presence of cotinine, a metabolite of nicotine of which other nicotine biosensors are sensitive.

In some embodiments of any the aspects, the amperometric biosensor, e.g., chronoamperometric biosensor as described herein and the systems and methods comprising it can be used for any of the following applications: (a) preventing cigarette smoking in a restricted area; (b) reducing nicotine intake or cigarette smoking in a subject; (c) monitoring second-hand or environmental cigarette smoke; and/or (d) monitoring nicotine levels of a subject for a physician.

In some embodiments of any the aspects, the nicotine biosensor as described herein can be used to detect nicotine and thus the presence of nicotine containing devices and cigarette smoking in restricted areas such as hotels, hospitals, rental cars, or any area where smoking is strictly prohibited and can cause health or monetary detriment. In some embodiments of any the aspects, the biosensor can be used to monitor nicotine levels in a subject, such as for the reduction of nicotine intake. As such, the data obtained from the biosensor can be communicated to social applications, support groups, physicians, and/or insurance companies for the purpose of monitoring and/or reducing nicotine intake in a subject. In some embodiments of any the aspects, the biosensor can be used to detect nicotine in the environment and thus the presence of second-hand smoke exposure. In some embodiments of any the aspects, the biosensor can be used to monitor nicotine levels in the blood of a subject for a physician. As a non-limiting example, orthopedic surgeons have a need to monitor nicotine levels in a subject, as smoking is one of the strongest risk factors for failure of orthopedic bone fusions. One of ordinary skill in the art can use the biosensor as described herein for various other applications requiring nicotine monitoring.

A. Methods of Using the Sensors

The nicotine biosensor system described herein may be portable, wearable, or attachable to a subject. In some aspects, the sensor is small enough to be applied onto a medical device or onto a subject. In some embodiments, the nicotine biosensor has a backing layer which may be a planar surface, such as a paper, a tape, a bandage, a catheter, a lens, a patch, an implant, or a pad. The nicotine biosensor, therefore, may be part of a contact lens, or a medical implant or patch. In some embodiments, the nicotine biosensor as disclosed herein may be worn by a subject as a patch or on a bandage, or may be provided in a kit, ready to be used as needed.

The sensor may be connected to an acquisition system, such as a potentiostat, and, optionally, to a display system. The display system may be a portable display system with a screen to display sensor reading. Portable display systems include smartphones, tablets, laptops, desktop, pagers, watches, and glasses.

An exemplary method of use includes applying a test sample, e.g., a fluid biological sample onto the sensing area of the sensor, and obtaining a reading indicating that nicotine is detected. Optionally, a polymeric well is used on top of the sensing area of the nicotine biosensor to confine the test sample. Alternatively, if an acquisition system and/or a portable system is used, the method may include also obtaining a concentration of nicotine in the sample.

The information obtained from the sensors or sensor systems may be used to determine levels of nicotine in a subject, or metabolism of nicotine in a subject, or provide guidance on intake of nicotine, or appropriate treatment if surgery or anesthesia of the subject is needed.

There are numerous additional applications for a nicotine sensor. For example, a nicotine biosensor as described herein can be used to prevent, or deter, or detect use of nicotine containing devices, or detection of smoking in public spaces, for example, to prevent smoking in hotels, hospitals, rental cars, or any area where smoking is strictly prohibited and can cause health or monetary detriment. A nicotine sensor as disclosed herein can be used to detect use of a nicotine-containing device or smoking by a subject to provide feedback to the appropriate management in real time. The nicotine biosensor as disclosed herein can also be used as a personal health monitor which lets a wearer know how much nicotine they have been exposed to from any of: direct smoke, use of a nicotine containing device or supplement, or second-hand smoke. In some embodiments, the nicotine sensor can also be used by parents or guardians to monitor the nicotine exposure of a child or minor or child of the ward, or alternatively in the environments that are trafficked or frequented by their children, minors or persons of their guardianship. Without being limited to theory, a "nicotine containing device" includes vaporizers (e.g., vaping devices or e-cigarettes), e-vaporizers, electronic nicotine delivery systems, "smokeless cigarettes" as well as other nicotine dispensing-devices or nicotine applicators, which people use to inhale an aerosol containing nicotine. Nicotine containing devices can resemble traditional tobacco cigarettes (cig-a-likes), cigars, or pipes, or even everyday items like pens or USB memory sticks. Other devices, such as those with fillable tanks, may look different. Regardless of their design and appearance, these devices generally operate in a similar manner and are made of similar components. Some common nicknames for e-cigarettes are: e-cigs, e-hookahs, hookah pens, vapes, vape pens, mods (customizable, more powerful vaporizers). In some embodiments, the nicotine containing device can be a nicotine patch i.e. a nicotine administrating patch), or a nicotine medicament, e.g., a nicotine gum or lozenges.

A nicotine sensor as disclosed herein has several applications in the area of assisting with smoking cessation or reduction of nicotine intake. Smokers or persons using nicotine containing devices wishing to quit or reduce nicotine uptake could objectively monitor and track nicotine uptake and or intake. The nicotine sensor as disclosed herein can be connected to social applications to permit a support group to help track progress in smoking cessation. In some embodiments, the nicotine biosensor described herein can be used to monitor nicotine levels in patients and can be communicated to a physician, sometimes in real time, to assist the patient in the process of quitting smoking or intake using a nicotine containing device. In some embodiments, insurance companies can provide discounts to smokers or nicotine users seeking to quit or reduce input who monitor their progress with objective nicotine sensors.

Orthopedic surgeons also have an important interest in monitoring nicotine uptake by their patients. Smoking and nicotine intake is one of the strongest risk factors for failure of orthopedic bone fusions, and patients do not always accurately report smoking, use of nicotine containing devices or exposure to second hand smoke. Surgeons can use a nicotine biosensor as disclosed herein to accurately track nicotine exposure of a patient. Nicotine containing devices and nicotine administering patches and lozenges diffuse nicotine at an unknown rate, and therefore, in some embodiments, a nicotine biosensor disclosed herein can be coupled with a nicotine administration device, therefore enabling nicotine physiological levels to be controlled and be responsive, especially in the case of strong cravings. The growing use of e-cigarettes and vaping devices is another clear market for a nicotine sensor. Currently the levels of nicotine in these devices is unregulated. A nicotine sensor as disclosed herein could be coupled to such devices to help monitor safety for these devices.

In some embodiments, the nicotine biosensor described herein is an implantable device. More particularly, the nicotine biosensor described herein is designed to provide, and in conjunction with a suitable signal processing unit, a current which is proportional to the concentration of the analyte of interest, e.g., nicotine. In some embodiments, the nicotine biosensor described herein may be implanted in vivo, including intra-cerebral, sub-cutaneous, intra-muscular, inter-peritoneal oral, serum, and vascular implantation, for systemic monitoring and used to monitor nicotine levels in the subject in real-time. In some embodiments, the nicotine biosensor described herein can be joined, or electronically coupled with one or more other biosensors, to allow for the simultaneous recording of nicotine and one or more multiple analytes of interest. In addition to the in vivo applications, the nicotine biosensors described herein may also find use in medical monitoring, industrial processes, environmental monitoring, and waste water stream monitoring Definitions:

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

As used herein, the term "biological sample" refers to a sample obtained from a subject. The sample may be from a subject who has been treated with a drug, or may be from an untreated or drug naïve subject. Exemplary samples include, but are not limited to serum, plasma, cell lysate, milk, saliva, vitreous fluid, and other secretions, synovial fluid, peritoneal cavity fluid, lacrimal fluid, and tissue homogenate. In some embodiments, the sample is a bodily fluid, including sweat, blood, cerebrospinal fluid (CSF), plasma, whole blood, serum, semen, synovial fluid, saliva, vaginal lubrication, breast milk, amniotic fluid, urine, human feces, phlegm tears, saliva, lymph, peritoneal intracellular fluid, or an original tissue from fetuses, newborn babies, children, teenagers, adults or animals. Moreover, the sample can be in various forms including but not limited to a liquid, frozen, chilled, lyophilized sample. The sample may be subjected to additional purification or treatment steps prior to and/or following the affinity purification step herein.

As used herein, the term "analyte" refers to a substance which is catalyzed by the candidate redox-enzyme biosensor. In some embodiments, an analyte can be a "biological marker" or "biomarker", which is an analyte in a biological system and may be used as an indicator of the risk or progression of disease.

The term "redox" or "oxidation-reduction" or "oxidoreduction" reaction describes any reaction in which electrons are transferred from one molecule, compound, molecular group, etc. to another. The process of oxidation occurs in conjunction with (is coupled with) a reduction reaction, thus resulting in the transfer of electrons.

As used herein, a "redox enzyme" or "oxidoreductase" are used interchangeably herein and refer to an enzyme that catalyzes a reaction with one or more enzyme substrate(s), resulting in generation or utilization of electrons. The oxidoreductases (redox) enzyme reaction and the electrode coupling method has become attractive to develop biosensors. In particular, for a range of substrates, i.e., glucose (i.e., glucose oxidase and glucose dehydrogenase reaction, respectively), electrochemical detection reduced coenzyme nicotinamide adenine dinucleotide (NADH) or hydrogen peroxide has been used galvanometer biosensor. In some instances, redox enzymes employ no prosthetic group, such as those that use reversible formation of a disulfide bond between two cysteine residues, as in the case of thioredoxin. Other redox enzymes use prosthetic groups, such as flavins, NAD, transition metal ions or clusters of such metal ions, etc. The use of the transition metal ions in these enzymes is due to their ability to attain multiple oxidation and spin states.

As used herein, the term "oxidase" refers to an enzyme that catalyzes an oxidation-reduction reaction, especially one involving dioxygen ($O_2$) as the electron acceptor. In reactions involving donation of a hydrogen atom, oxygen is reduced to water ($H_2O$) or hydrogen peroxide ($H_2O_2$).

As used herein, the term "biosensor device" refers to an analytical device which integrates a biorecognition element (e.g., the nicotine-catalyzing enzyme) with a physical transducer to generate a measurable signal proportional to the concentration of an analyte (e.g., nicotine) recognized by the biorecognition element (e.g., the nicotine-catalyzing enzyme). In some embodiments, the biosensor is also referred to as a "sensor" and can be described as device containing elements required for generating an electrical current when a biological sample is applied to the sensor. The sensor may include additional elements, such as an acquisition system and/or a display system, forming a sensor system.

As used herein, the terms "redox molecule", "redox mediator" and "electroactive molecule" are used interchangeably herein and relate to any molecule that is able to undergo an electrochemical reaction. Upon which one or more electrons are either added to or removed from the molecule, converting it into a different oxidative state. For example, 1,4-Benzoquinone is an electroactive molecule that can be converted to hydroquinone upon the reduction of the molecule with an addition of two electrons and two protons according to a specific embodiment.

As used herein, the term "metabolite" refers to a small molecule formed during or after a metabolic reaction, or a metabolic pathway.

As used herein, the term "detection" or "detecting" in the context of detecting nicotine using a sensor, refers to an act of obtaining a value or a reading indicating the presence or absence of the nicotine in a sample. The detection may require a comparison of the obtained value or reading for a nicotine from a test sample to a value or reading obtained from a control sample for nicotine and tested in the same way as the test sample.

As used herein, the term "redox mediator" as refers to a molecule capable of participating in an electron exchange between nicotine, a nicotine-catalyzing enzyme, and/or the conducting polymer. As used herein, the term "biofunctional" in the context of a molecule or a coating refers to a property of the molecule or the coating capable of electron exchange.

As used herein, the term "planar surface" refers to a surface with a region that is sufficiently planar, i.e., sufficiently flat, over a surface area sufficient to accommodate an electrode. For example, if a planar surface is a contact lens, the contact lens has a sufficiently planar region to accommodate an electrode having a length of about 2 mm, and a width of about 2 mm.

As used herein, the term "ink" refers to a solution or suspension of a material to be deposited using inkjet printing onto a surface, such as a conducting polymer or metal, or a polymeric coating As used herein, the term "open reading frame" refers to a reading frame that has the ability to be translated. An ORF is a continuous stretch of codons that begins with a start codon (usually AUG) and ends at a stop codon (usually UAA, UAG or UGA). An ATG codon (AUG in terms of RNA) within the ORF (not necessarily the first) may indicate where translation starts. The transcription termination site is located after the ORF, beyond the translation stop codon. If transcription were to cease before the stop codon, an incomplete protein would be made during translation. In eukaryotic genes with multiple exons, introns are removed and exons are then joined together after transcription to yield the final mRNA for protein translation. In the context of gene finding, the start-stop definition of an ORF therefore only applies to spliced mRNAs, not genomic DNA, since introns may contain stop codons and/or cause shifts between reading frames. An alternative definition says that an ORF is a sequence that has a length divisible by three and is bounded by stop codons.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

As used herein, the term "affinity" refers to the strength of the binding interaction between a single biomolecule (e.g. a redox-enzyme) to it substrate or analyte.

As used herein, a "nucleoside" is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

As used herein, the term "small molecule" refers to low molecular weight molecules (<900 Daltons) that include lipids, monosaccharides, second messengers, other natural products and metabolites, as well as drugs and other xenobiotics. They are distinct from macromolecules such as proteins. A small molecule is able to enter cells easily because it has a low molecular weight. Once inside the cells, it can affect other molecules, such as proteins. This is different from drugs that have a large molecular weight, such as monoclonal antibodies, which are not able to get inside cells very easily.

As used herein, the term "conjugate" or "conjugation" refers to the attachment of two or more entities to form one entity. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art.

As used herein, the term "ligand" refers to a substance that forms a complex with a biomolecule to serve a biological purpose. In protein-ligand binding, the ligand is usually a molecule, which produces a signal by binding to a site on a target protein. The binding typically results in a change of conformational isomerism(conformation) of the target protein. In DNA-ligand binding studies, the ligand can be a small molecule, ion, or protein, which binds to the DNA double helix. The relationship between ligand and binding partner is a function of charge, hydrophobicity, and molecular structure. The instance of binding occurs over an infinitesimal range of time and space, so the rate constant is usually a very small number.

As used herein, the term "binding" refers to an association between proteins or nucleotides that occurs through intermolecular forces, such as ionic bonds, hydrogen bonds and Van der Waals forces. The association of docking is actually reversible through dissociation. Measurably irreversible covalent bonding between a ligand and target molecule is atypical in biological systems. Ligand binding to a receptor protein or to an allosteric transcription factor can alter the conformation by affecting the three-dimensional shape orientation. The conformation of a receptor protein or allosteric transcription factor composes the functional state. Ligands include small molecules, hormones, inhibitors, activators, and neurotransmitters.

As used herein, the term "fluorescent molecule" refers to a fluorescent chemical compound that can reemit light upon light excitation. Fluorescent molecules typically contain several combined aromatic groups, or planar or cyclic molecules with several π bonds. Current fluorescence imaging probes typically consist of single conventional fluorophore (e.g., organic dyes, fluorescent proteins), fluorescent proteins (e.g., GFP) and semiconductor quantum dots (Q-dots). Single fluorophores are usually not stable and have limited brightness for imaging. Similar to dyes, the fluorescent proteins tend to exhibit excited state interactions which can lead to stochastic blinking, quenching and photobleaching. Fluorescent molecules are known in the art and include florescent proteins (e.g. CAP, WFP, BFP, and other GFP derivatives). Other suitable fluorescent molecules are known in the art and commercially available from, for example, Molecular Probes (Eugene, Oreg.). These include, e.g., donor/acceptor (i.e., first and second signaling moieties) molecules such as: fluorescein isothiocyanate (FITC)/tetramethylrhodamine isothiocyanate (TRITC), FITC/Texas Red™ Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X (ROX), FITC/tetramethylrhodamine (TAMRA), and others. In addition to the organic fluorophores already mentioned, various types of nonorganic fluorescent labels are known in the art and are commercially available from, for example, Quantum Dot Corporation, Inc. Hayward Calif.). These include, e.g., donor/acceptor (i.e., first and second signaling moieties) semiconductor nanocrystals (i.e., 'quantum dots') whose absorption and emission spectra can be precisely controlled through the selection of nanoparticle material, size, and composition.

As used herein, the term "device" refers to an electrically addressable unit that performs some task, such as switching, storing a single bit of information, or sensing a particular molecule or class of molecules according to an embodiment of the present invention. Depending upon the embodiment, other examples of definitions also exist.

As used herein, the term "circuit" refers to a group of devices, each of which are designed to carry out similar tasks according to a specific embodiment. For example, a transistor is a switching device. A multiplier is a logic circuit constructed from many transistors, which is a circuit. As another example, a nanowire is a chemical sensing device. An array of nanowires each coated with a different molecular probe, constitutes a sensor circuit designed to sense many different molecular targets according to a specific embodiment. Depending upon the embodiment, other examples of definitions also exist.

The term "percent (%) amino acid sequence identity" or "% sequence identity to amino acids" with respect to a particular SEQ ID NO is defined as the percentage of amino acid residues in a candidate sequence that are identical with the amino acid residues in the comparative sequence identified by the SEQ ID NO, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., Methods in Enzymology 266, 460-480 (1996); available on the world wide web at blast.wustUedu/blast/README.html). WU-BLAST-2 uses several search parameters, most of which are set to the default values. The adjustable parameters are set with the following values; overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "integrated circuit" refers to a group of circuits, each design to carry out different specific tasks, but operating together to perform some larger function. For example, a multiplier circuit can retrieve two numbers from a memory circuit, multiply them together, and store them back into the memory circuit. Depending upon the embodiment, other examples of definitions also exist.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A biosensor for the measurement of the concentration of nicotine comprising:
   a. an electrode comprising a surface;
   b. optionally, an electronically active mediator (Med) deposited on the surface of the electrode; and
   c. a plurality of nicotine-catalyzing enzymes deposited on the surface of the electrode, wherein the nicotine-catalyzing enzyme catalyzes nicotine to produce hydrogen peroxide ($H_2O_2$).
2. The biosensor of paragraph 1, wherein the nicotine-catalyzing enzyme is *Pseudomonas putida* NicA2 or a functional variant or fragment thereof.
3. The biosensor of paragraph 2, wherein the nicotine-catalyzing enzyme, e.g., NicA2, is encoded by a nucleic acid comprising a sequence that is at least 90% identical to SEQ ID NO: 1 or SEQ ID NO: 5 or SEQ ID NO: 6.
4. The biosensor of paragraph 2, wherein the nicotine-catalyzing enzyme, e.g., NicA2, comprises an amino acid sequence that is at least 95% identical to SEQ ID NO: 2 or SEQ ID NO: 3 or SEQ ID NO: 4.
5. The biosensor of paragraph 2, wherein the NicA2 enzyme is a mutant NicA2 enzyme comprising at least one modification selected from any of: N462V, N462Y/W427Y, N462Y/W427Y N462H, A107R of SEQ ID NO: 2.
6. The biosensor of paragraph 2, wherein the NicA2 enzyme is selected from any of:
   a. a mutant NicA2(N462H) enzyme or a protein comprising at least 85% sequence identity to SEQ ID NO: 2 or SEQ ID NO: 3, and where amino acid 462 is changed from asparagine to a histidine (H) residue or a conservative amino acid of histidine (H), (e.g., any of Asn, Gln, Arg, Tyr, Glu);
   b. a mutant NicA2(N462Y/W427Y) enzyme or a protein comprising at least 85% sequence identity to SEQ ID NO: 2 or SEQ ID NO: 4 and where amino acid 462 is changed from asparagine (N) to a valine (V) residue or a conservative amino acid of valine (V) (e.g., any of Ile, Leu, Met, Ala, Thr), and amino acid residue 427 is changed from tryptophan (W) to tyrosine (Y), or a conservative amino acids of tyrosine (Y) (e.g., any of His, Phe, Trp).
7. The biosensor of any of paragraphs 1-6, wherein the nicotine-catalyzing enzyme, e.g., NicA2, is immobilized on the electrode with a polymer, and in some embodiments, the polymer contacts the surface of the working electrode, and in some embodiments, there is an optional top layer over (i.e., on top of) the polymer layer, where the top layer does not comprise Nifion, and in some embodiments, the top layer comprises Prussian-Blue (PB).
8. The biosensor of any of paragraphs 1-7, wherein the polymer comprises a low molecular weight (LMW) or medium molecular weight (MMW) chitosan in 0.5% acetic acid, or LMW or MMW chitosan in acetic acid at concentration between 0.1%-05% or 0.5%-1.5%, and optionally, the polymer also comprises Prussion Blue (PB).
9. The biosensor of any of paragraphs 1-9, wherein in the presence of nicotine, the NicA2(N462H) enzyme produces H2O2, wherein breakdown of $H_2O_2$ to $O_2$ and $H_2O$ releases electrons to produce an electrochemical signal, wherein the electrochemical signal is detected by current passed to the electrode.
10. The biosensor of any of claims 1-9, wherein the electronically active mediator (Med) can be oxidized from a reduced form ($Med_{re}a$) to an oxidized form ($Med_{ox}$), wherein the $Med_{ox}$ produces a detectable signal.
11. The biosensor of any of claims 1-7, wherein the detectable signal is produced when nicotine is catalyzed by the nicotine-catalyzing enzyme and transfers at least one electron from $Med_{re}a$ to hydrogen peroxide ($H_2O2$), resulting in its reduction to $Med_{ox}$.
12. The biosensor of any of claims 1-8, wherein the electronically active mediator $Med_{ox}$ is reduced by the electrode, producing a detectable signal.
13. The biosensor of any of claims 1-12, wherein the $Med_{ox}$ produces an electrochemical signal, wherein the electrochemical signal is detected by current passed to the electrode.
14. The biosensor of any of claims 1-13, wherein the detectable signal is electrochemical and/or colorimetric.
15. The biosensor of any of claims 1-14, wherein the biosensor is an amperometric biosensor and the detectable signal is electrochemical.
16. The biosensor of any of paragraphs 1-15, wherein the electrode is connected to a potentiostat having a current resolution to at least 1 pA (100 nA).
17. The biosensor of any of paragraphs 1-16, wherein the biosensor comprises a working electrode and a reference electrode.
18. The biosensor of any of paragraphs 1-17, wherein the biosensor does not comprise a counter electrode.
19. The biosensor of any of paragraphs 1-18, wherein the working electrode is $>10\pi$ mm$^2$.
20. The biosensor of any of paragraphs 1-19, wherein the electrode is either metallic or non-metallic.
21. The biosensor of any of paragraphs 1-20, wherein the metallic electrode is gold, silver, platinum, or palladium.
22. The biosensor of any of paragraphs 1-21, wherein the non-metallic electrode comprises carbon.
23. The biosensor of any of paragraphs 1-22, wherein the amperometric biosensor is a chronoamperometric biosensor.
24. The biosensor of any of claims 1-14, wherein the polymer further comprising a readout enzyme (ReadE), wherein the ReadE reduces the $Med_{red}$ to $Med_{ox}$ only in the presence of nicotine and/or hydrogen peroxide.
25. The biosensor of any of claims 1-10, wherein the readout enzyme (ReadE) is a peroxidase enzyme.
26. The biosensor of any of claims 1-14, wherein the biosensor is a colorimetric biosensor and the detectable signal is colorimetric.
27. The biosensor of any of paragraphs 1-26, wherein the electronically active mediator comprises a ferricyanide compound which is reducible in the presence of an electron from hydrogen peroxide ($H_2O_2$) to produce a ferrocyanide compound.
28. The biosensor of any of paragraphs 1-27, wherein the electronically active mediator comprises iron(II,III) hexacyanoferrate(II,III) (e.g., Prussian blue).
29. The biosensor of paragraph 24, wherein the readout enzyme (ReadE) converts a readout substrate (ReadS) to a readout product (ReadP) in the presence of hydrogen peroxide, wherein ReadP produces a detectable signal with is an optical signal.
30. The biosensor of paragraph 25, wherein the peroxidase is APEX2 or HRP.
31. The biosensor of any of paragraphs 1-22, wherein the optical signal is colorimetric, fluorescent, and/or bioluminescent.
32. The biosensor of any of paragraphs 24-31, wherein the Readout substrate (ReadS) is selected from any of: Amplex® UltraRed (AUR), PY1, PO1, Amplex® Red, Hamovanillic Acid (HVA), luminol, OPD, DCFH, ABST, K iodine, or ABST.
33. The biosensor of paragraph 24, wherein the Readout substrate (ReadS) is Amplex® Ultrared (AUR).
34. The biosensor of any of paragraphs 21-28, wherein the Readout Enzyme (ReadE) is APEX2 or a functional variant thereof, and the readout substrate (ReadS) is Amplex® Ultrared (AUR).
35. A system comprising:
    a. an biosensor of any of one of paragraphs 1-34; and
    b. a potentiostat.
36. The system of paragraph 35, wherein the biosensor is an amperometric biosensor which is contained in a Faraday cage.
37. The system of paragraph 35, wherein the potentiostat is linked to at least one electrode of the amperometric biosensor.
38. The system of paragraph 35, wherein the potentiostat is linked to a working electrode and a reference electrode of the amperometric biosensor.
39. The system of paragraph 38, wherein the potentiostat measures the current of the amperometric biosensor.
40. A wearable electrochemical nicotine biosensor device shown in FIGS. 29A and 29B.
41. The wearable nicotine biosensor device of paragraph 40, comprising the biosensor of any of paragraphs 1-24 electrically connected to a potentiostat, wherein the potentiostat is linked to at least the working electrode of the biosensor, and the working electrode is in fluid communication with a wicking paper that wicks sweat from the surface of a subjects' skin.
42. The wearable nicotine biosensor device of paragraph 40, wherein when attached to the skin of a subject, is operable to detect the amount of nicotine in the sweat of the subject, in a real time, quantitative and chronoamperometric manner.
43. A method of using an amperometric biosensor to measure the concentration of nicotine comprising:
    a. assembling the biosensor of any one of paragraphs 1-34, wherein the biosensor is a amperometric biosensor;
    b. providing a sample; and
    c. measuring the current produced by the oxidation of any nicotine present in the sample.
44. The method of paragraph 43, wherein the sample is selected from the group consisting of: sweat, gastric juice, urine, saliva, and blood.
45. The method of paragraph 43, wherein the sample is sweat.
46. The method of paragraph 43, wherein the method of using the amperometric biosensor is used to measure the physiological concentration of nicotine in the range of 0.4 µM-1000 µM range.
47. The method of any of paragraphs 43-46, wherein the nicotine concentration is measured in the range of 0.4 µM-1000 µM.
48. The method of any of claims 43-47, wherein the current of the amperometric biosensor is not altered in the presence of an interferent.

49. The method of any of claims 43-48, wherein the interferent is selected from the group consisting of: L-(+)-lactic acid, ascorbic acid, uric acid, dopamine, (−)-epinephrine, creatinine, S-(+)-glucose, sodium, calcium, magnesium, potassium, phosphate, albumin, amino acids, and cotinine.

50. The method of any of claims 43-49, wherein the interferent is cotinine.

51. Use of the amperometric biosensor of any one of paragraphs 1-34, the system of any one of paragraphs 35-39, the wearable electrochemical nicotine biosensor device of paragraphs 40-42, or the method of any one of paragraphs 43-50, in any one of:
   a. detecting a person smoking or using a nicotine containing device in a restricted area;
   b. reducing nicotine intake in a subject;
   c. reducing cigarette smoking or use of a nicotine containing device by a subject;
   d. monitoring exposure of a subject to second-hand or environmental cigarette smoke; or
   e. monitoring nicotine levels in a subject.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

Materials and Methods:
   Strain Selection: *Pseudomonas putida* (Trevisan) Migula (ATCC© BAA-2546™) was purchased from ATCC® (Manassas, Va.) and linked with a corresponding GenBank accession number (CP002870.1). The strain is aerobic and was propagated and grown in ATCC© Medium 18: Trypticase Soy Agar/Broth at 30° C. as recommended by ATCC®.

Strain Growth Curve: In order to determine the doubling time of the strain, growth curves were performed. All growth curves were done in 96 well flat clear bottom black polystyrene TC-treated microplates (Corning Inc.™, Corning, N.Y.). Measurements were taken with an Infinite M200 Pro™ (TECAN Group Ltd., Medford, Mass.) spectrophotometer at 30° C. Readings were performed over 96 cycles of 15 minutes each at 600 nm absorbance with 25 flashes in a 3×3 (XY-Line) type reads per well. In between reads there was orbital shaking at 150 rpm frequency for a total of 10 minutes. To first characterize the growth alone, a ½ serial dilution of 9 concentrations from 0.5-0.0020 $OD_{600}$ nm were prepared in M18 media. Then each concentration was measured as previously described by the TECAN microplate reader and normalized against a media background control in technical triplicate. Afterward, an appropriate starting concentration of cells was chosen which shows a substantially long lag-phase, linear log phase, and a plateau of stationary-phase.

Strain Solvent Growth Curve: Once an appropriate starting cell concentration was chosen, a secondary growth curve was performed to test the toxicity levels of the solvent used to dissolve nicotine. Since nicotine is readily soluble in water that was the solvent of choice. *P. putida* S16 was incubated under microplate reader conditions previously mentioned at a starting OD determined by the first growth curve with $H_2O$ at ½ serial dilutions for a total of eight concentrations (50-0.39%) tested in technical triplicate. Two controls were included per solvent; a positive control without solvent and a media control which allowed for appropriate normalization. Solvent exposure growth curves allowed for choosing the maximum amount of solvent concentration that *P. putida* S16 would sustain while maintaining relative viability in order to determine a range of nicotine concentrations which could be used.

Strain Nicotine Growth Curve: A tertiary growth curve was performed to test the toxicity levels of nicotine specific to *P. putida* S16. The strain was incubated under microplate reader conditions previously mentioned at a starting OD determined by the first growth curve and the highest solvent concentration with nicotine at ½ serial dilutions for a total of seven concentrations tested in singlet. Three controls were included; a positive control with the highest tolerable solvent concentration (%), a positive control with media, and a media control alone which allowed for normalization. Nicotine exposure growth curves allowed for choosing the maximum amount of nicotine concentration that *P. putida* S16 would sustain while maintaining relative phenotypic viability.

Strain RNA Extraction: Cells were grown in 5 mL M18 at a starting $OD_{600}$ of 0.005 with 21.6 µM nicotine in 14 mL polypropylene round-bottom tubes (Corning Inc.™, Corning, N.Y.) in singlet. The cells were incubated at 30° C. with continuous orbital shaking at 150 rpm until the end of lag-phase (3 hours) and mid-log phase (7.5 hours) from the start of inoculation. Controls were grown in the same conditions without nicotine. Afterward, samples were removed and a 1:1 ratio of RNAprotect Bacteria Reagent™ (Qiagen Inc.™, Germantown, Md.) was added followed by spinning down at 4° C. for 10 minutes at 4000×g. Supernatant was removed and the pellet re-suspended in 300 µL of RNAprotect™ and transferred into 2.0 mL Safe-Lock Tubes™ (Eppendorf™, Hauppauge, N.Y.). The samples were then spun down at 4° C. for 10 minutes at 10000×g. RNA extraction was done by Qiacube™ (Qiagen Inc.™ Germantown, Md.) set to the RNeasy Protect Bacteria Mini Kit™ protocol of bacterial cell pellet with enzymatic lysis.

Lysis buffer was prepared as described by the protocol with the exception of the addition of 150 mg/mL lysozyme (Sigma-Aldrich Corp.™, St. Louis, Mo.) and 20 mg/mL proteinase K (F. Hoffmann-La Roche Ltd™, Indianapolis, Ind.) all diluted in 1×TE buffer. RNA samples were subsequently quantified using Qubit RNA HS Assay Kit™ (Thermo Fisher Scientific Inc.™, Cambridge, Mass.) and analyzed using a RNA 6000 Pico Kit™ (Agilent Technologies Inc.™, Santa Clara, Calif.) in a 2100 Bioanalyzer™ (Agilent Technologies Inc.™, Santa Clara, Calif.). RNA samples were either immediately used for RNA-Seq library preparation or stored long-term at −80° C. after addition of 1 µL RNase Inhibitor, Murine (New England Biolabs™, MA).

RNA-Seq Library Preparation: After RNA samples have been quantified and analyzed they were DNase treated using TURBO™ DNase 2 U/µL (Thermo Fisher Scientific Inc™., Cambridge, Mass.) and cleaned using Agencourt RNAClean™ XP SPRI beads (Beckman Coulter, Inc™., Brea, Calif.). RNA-Seq libraries were then produced from these samples using a modified ScriptSeq v2 RNA-Seq Library Preparation Kit™ (Illumina Inc™, San Diego, Calif.) ensuring use of unique index primers through ScriptSeq™ Index PCR Primers (Sets 1-4) 48 rxns/set (Illumina Inc.™, San Diego, Calif.). Libraries were quantified by both a Qubit dsDNA HS Assay Kit™ (Thermo Fisher Scientific Inc.™, Cambridge, Mass.) and by Bioanalyzer™ with the High Sensitivity DNA Kit™ (Agilent Technologies Inc.™, Santa Clara, Calif.). The samples were then pooled to 2 nM and submitted to a sequencing core facility. Whole transcriptome RNA sequencing was performed by a NextSeq 500™ (Illumina Inc.™, San Diego, Calif.) at high output (400 µM reads) with 75 bp paired end sequencing read length. The data was then analyzed in-house through a proprietary lab computational pipeline.

Enzyme Expression and Purification: NicA2 was recombinantly produced with poly-histidine tags in *Escherichia coli*. Plasmids containing the gene for NicA2 were obtained through collaborative exchange (see e.g., Xue et al. 2015, supra). Plasmids were chemically transformed into *E. coli* BL21 (DE3) (New England Biolabs™, MA) with induction of lysogeny broth cultures at $OD_{600}$ 0.6 to 0.8 using 1 mL of 1M isopropyl b-D-1-thiogalactopyranoside (IPTG) before analysis by SDS-polysaccharide gel electrophoresis (SDS-PAGE). Confirmed expression prompted 1 L cultures for expression and protein purification through disruption of cells using lysozyme and by passing cell lysate over a HisPur™ Ni-NTA Resin-packed column (Fisher Scientific™, Pittsburgh, Pa.). Final protein products were quantified using the Pierce Micro BCA Protein Assay™ kit (Fisher Scientific™, Pittsburgh, Pa.).

In Vitro Enzyme Characterization: Amplex® UltraRed assays were performed per instruction of the manufacturer (Thermo Fisher Scientific, Cambridge, Mass.). Final concentrations of Amplex® UltraRed, 500 uM, and HRP, 1 U/mL, in a total volume of 20 µL were used. Nicotine and NicA2 concentrations varied with experiment. All measurements of fluorescence were done in a 384 well flat bottom black polystyrene microplate (Corning Inc.™, Corning, N.Y.) and read in an Infinite M200 Pro™ (TECAN Group Ltd.™, Medford, Mass.) spectrophotometer at room temperature with the excitation set to 490 nm and emission at 585 nm. Readings were done over 1 hour with each well read every 30 seconds.

Sensor Preparation: Electrochemical experiments were performed with VersaSTAT MC™ (Ametek Inc.™, Pennsylvania, Pa.). Sensors were prepared with Screen-Printed Prussian Blue/Carbon Electrode (Metrohm USA™, Riverview, Fla.). Equal volume of NicA2 (400 µM) and 1 wt % chitosan in 0.5 wt % acetic acid (Sigma-Aldrich Corp.™, St. Louis, Mo.) were mixed. NicA2 was immobilized onto the SPEs by drop-casting 10 µL of this mixture onto the working electrode. The sensors were allowed to dry overnight at 4° C. with no light prior to use.

Sensor Characterization: In order to quantify the current response of the nicotine biosensor, chronoamperometric experiments were performed where various concentrations of nicotine in PBS (0-1000 µM) were deposited onto SPEs with 2 nmol NicA2.

Chronoamperometric responses were recorded overtime, with a potential −0.2 V (versus Ag/AgCl). At the beginning of the experiment, 30 µL 1×DPBS was added to the biosensor, followed by an addition of 30 µL nicotine solution at predefined time point. To evaluate the selectivity of the sensor chronoamperometric responses to nicotine were measured in the presence of the common interferents at relevant physiological concentrations in sweat (see e.g., Table 4). Addition of 30 µL 200 µM nicotine solution to 30 µL mixture was performed at a predefined time point and the current was recorded over time. Similar experiments were performed to evaluate the selectivity of the sensor to cotinine. Current was recorded where 30 µL 200 µM nicotine solution was added to 30 µL cotinine solutions. Additionally, to confirm that the current response observed was due to NicA2, myosmine, an inhibitor of NicA2, was added in the middle of a chronoamperometric experiment.

Table 4 shows interferents and their estimated concentrations in human matrices. A sweat mixture was prepared based on the values in Table 4 and tested (see e.g., FIG. 3C).

| | Expected Concentrations (mM) | |
|---|---|---|
| Interferent | Sweat | Interstitial Fluid |
| L-(+)-Lactic acid | 5 | 0.8 |
| Ascorbic acid | 0.01 | 0.3 |
| Uric acid | 0.06 | 0.4 |
| Dopamine | 0.001 | <nmol |
| (−)-Epinephrine | 0.005 | 1.20E-01 |
| Creatinine | 84 | 0.13 |
| D-(+)-Glucose | 0.17 | 0.7 |
| Sodium | 36 | 136 |
| Calcium | 1.1 | 1.5 |
| Magnesium | 0.3 | 0.6 |
| Potassium | 11 | 3.2 |
| Phosphate | 40 mg/L | 0.6 |
| Albumin | ND | 0.18 |
| Amino acids | 6 | 2.6 |
| Cotinine | N/A | N/A |

Biosensor Preparation

All electrochemical experiments were performed by using a VersaSTAT MC (Ametek Inc., Pennsylvania, Pa.). Biosensors were prepared by using Zensor R&D TE100™ SPEs (CH Instruments Inc.™, Bee Cave, Tex.) and electrodepositing Prussian Blue (PB). PB solution was prepared by mixing equal volume of 10 mM $FeCl_3$, 400 mM KCl, 10 mM $K_3Fe(CN)_6$, and 400 mM HCl (Sigma-Aldrich Corp.™, St. Louis, Mo.). The electrodes were dipped into the PB solution and the potential was swept from 0 V to 0.5 V (versus Ag/AgCl) for 1 cycle at a scan rate of 0.02 V/s. NicA2 was then immobilized onto the SPEs by mixing an equal volume of NicA2 (2000 pmol) and 1 wt % chitosan in 0.5 wt % acetic acid (Sigma-Aldrich Corp.™, St. Louis, Mo.). 10 µL of this mixture was then cast onto the working electrode (WE) of the SPE and dried in fridge (4° C.) for 2 hours.

In Vitro Biosensor Characterization

The electrochemical performance of the nicotine biosensor was evaluated in vitro using 1× Dulbecco's Phosphate Buffered Saline (1×DPBS) (Life Technologies™, Grand Island, N.Y.). Chronoamperometric responses were recorded at −0.2 V vs. a Ag/AgCl reference electrode. The effect of interferents, such as lactic acid, creatinine, ascorbic acid, glucose, uric acid, dopamine, and epinephrine towards the nicotine biosensor were analyzed.

Example 1

Enzyme-Based Electrochemical Nicotine Biosensor

Physiologically relevant wearable sensors are in increasingly high demand, yet existing sensors are severely limited in the number and type of analyte they can detect. The lack of molecular sensing parts specifically is prohibiting the development of the next generation of biosensors. To overcome this challenge, RNA-Seq was used to identify enzymatic sensor parts from microbes for a virtually unlimited number of analytes. Described herein is the first electrochemical redox enzyme-based biosensor for nicotine. This nicotine biosensor has shown to have a detection range of 0.4-100 µM nicotine which is in the range of active smoke sweat, saliva, gastric juice, and urine.

Alternative terms for the nicotine biosensor described herein include but are not limited to the following: enzyme-based electrochemical nicotine biosensor monoamine oxidase biosensor for detection of nicotine; monoamine oxidase biosensors for electrochemical detection of nicotine; enzyme-based nicotine sensor, derived from microbial screening; electrochemical-enzymatic detection of nicotine; electrochemical nicotine sensing with an enzyme derived from microbial screening towards tobacco smoking monitoring.

Although it has been known since the 1950's that certain strains of bacteria degrade nicotine, the pathway by which this occurs has only recently been discovered. In *P. putida* S16, the nicotine sensitive gene cluster, nic1, includes nicotine oxidoreductase (NicA1) and HSP hydroxylase (HspA) while the nic2 cluster encodes another nicotine oxidoreductase NicA2, later identified as a monoamine oxidase (MAO) (see e.g., Tang et al. 2013, PloS Genetics 9(10) e1003923). Deleting the nicA2 gene produces a strain that no longer degrades nicotine, confirming the importance of NicA2 in the nicotine degradation pathway. To identify the nicotine specific redox enzymes, RNA-Seq was performed on *P. putida* S16 in the presence and absence of nicotine. The optimal RNA-Seq experimental conditions were selected by varying the bacterial inoculation, solvent, and nicotine concentrations used in the serial dilution growth assays so as to provide a distinct change in the transcriptome expression levels without drastically affecting bacterial physiological growth. Subsequent computational analyses revealed the key genomic island, nic2, and that the most highly differentially expressed enzyme encoding gene was nicA2, the target MAO (see e.g., FIG. 1). The nicA2 gene was cloned into a recombinant vector with a histidine tag and expressed (~10 mg/mL). The protein was purified via FPLC and SEC. NicA2 exhibited increased selectivity, but reduced catalytic activity compared to redox enzymes such as glucose oxidase ($GO_x$) and lactate oxidase ($LO_x$) (see e.g., Table 2; see e.g., Xue et al. 2015, J Am Chem Soc 137(32) 10136-9, the content of which is incorporated herein by reference in its entirety).

Figure 2A:
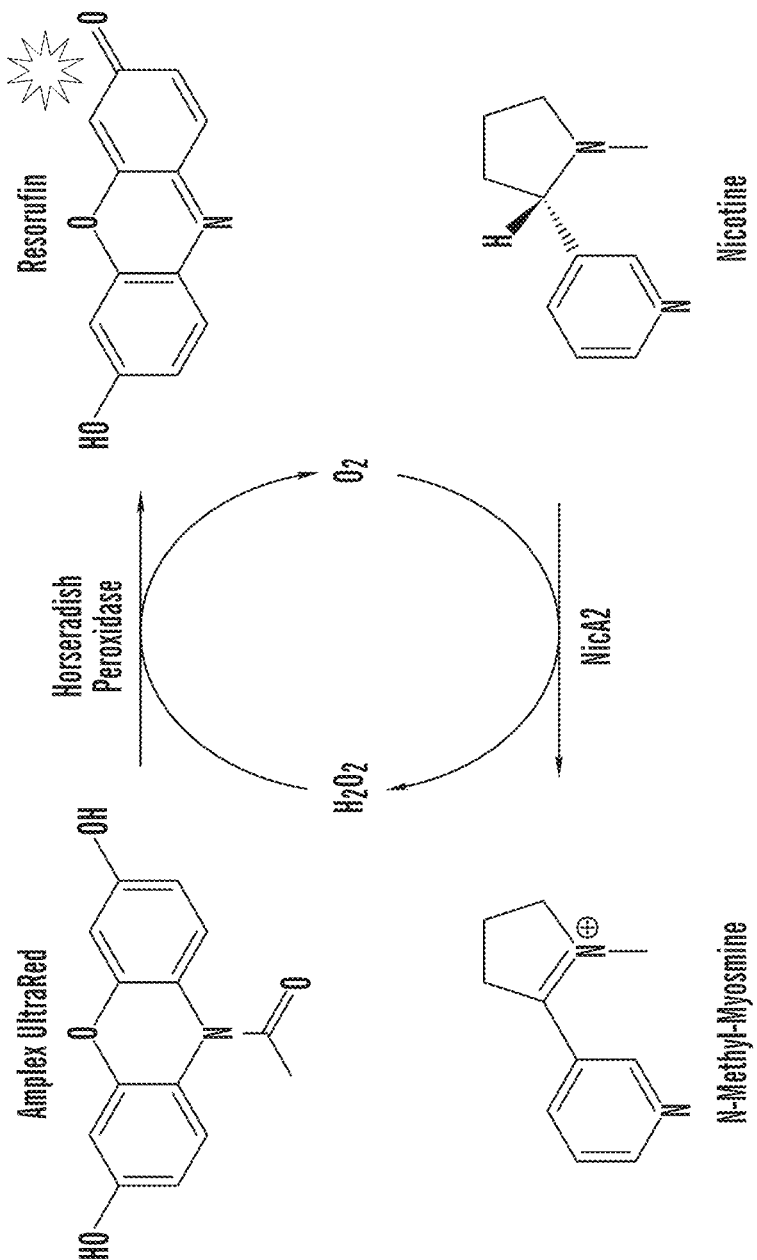
FIG. 2A-2E is a series of schematics and graphs. The Amplex® UltraRed Reagent assay showed that fluorescence is analyte limited, not enzyme limited, and that the signal has a 1:1 dependence on the concentration of analyte present.
Figure 2B:
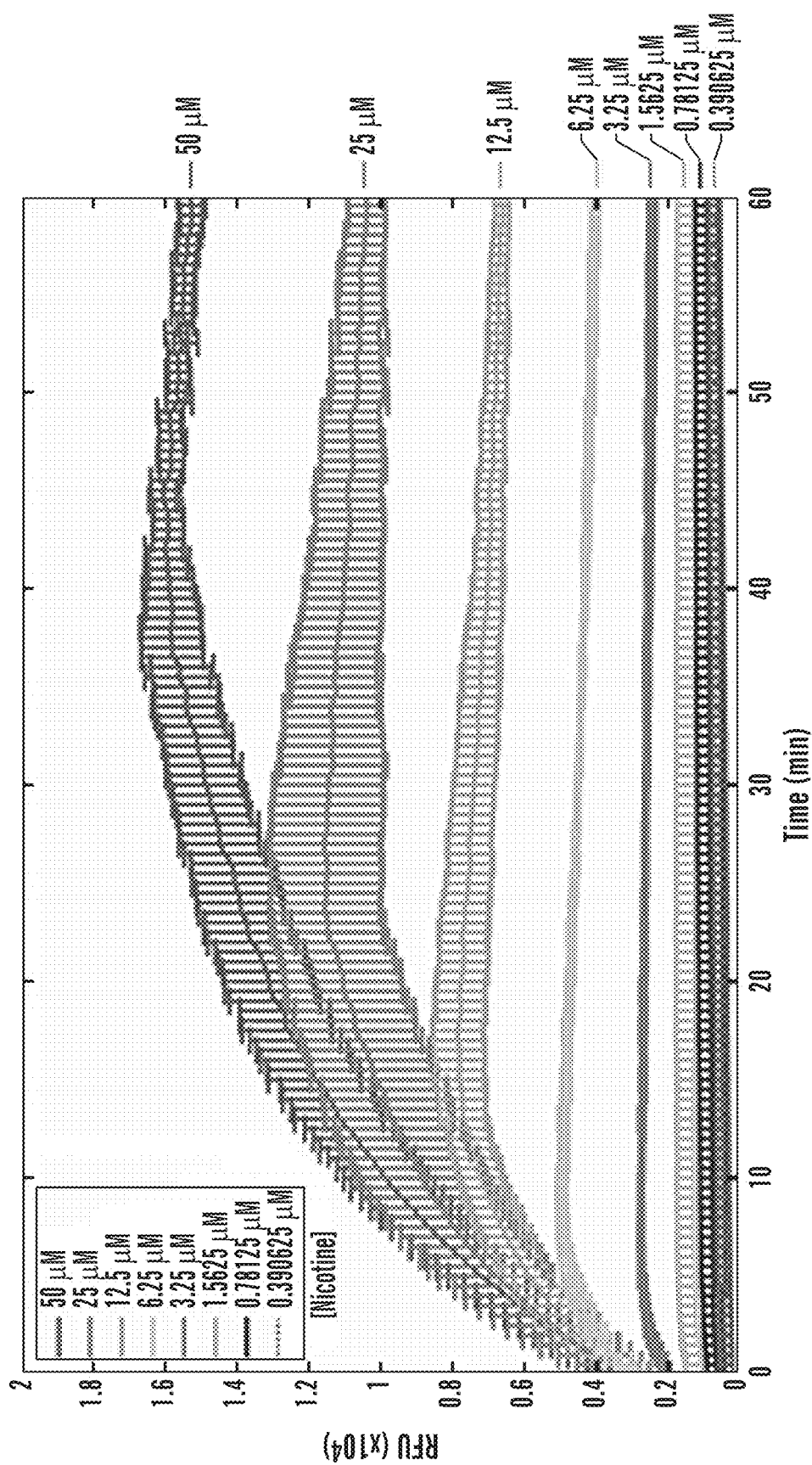
Figure 2C:
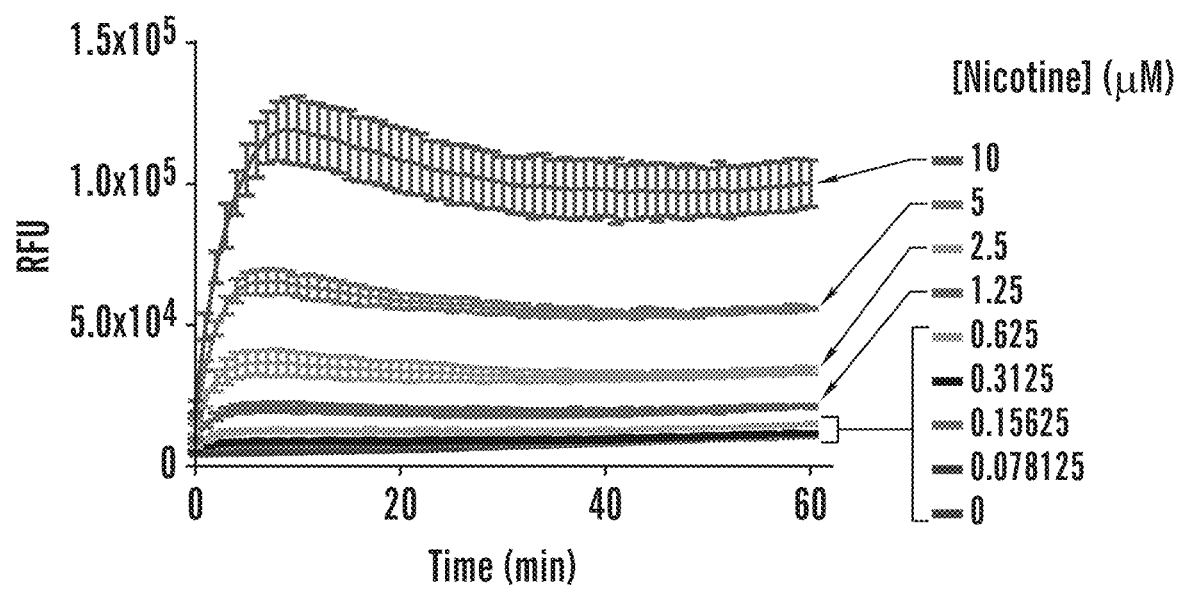
Figure 2D:
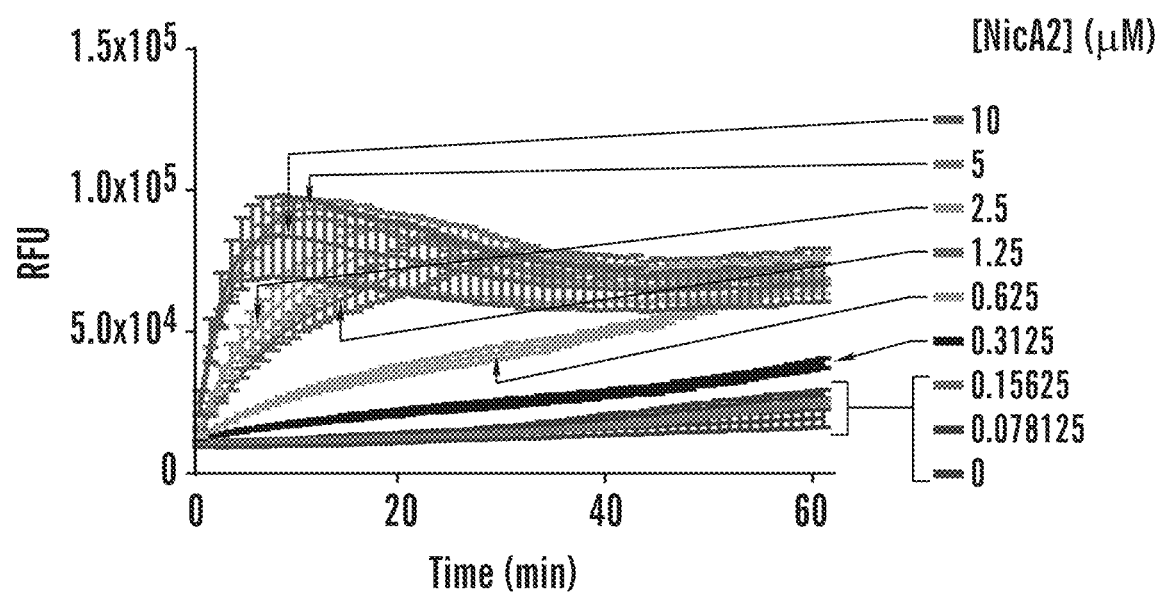

Herein, the inventors have used the FAD-binding nicotine oxidoreductase (NicA2) enzyme to develop and optimize a nicotine electrochemical biosensor. From an electrochemical biosensor perspective, NicA2 catalyzes nicotine and results in $H_2O_2$ production and n-methylomysomine, where the $H_2O_2$ can be used in redox reaction and detected electrochemically and enable quantitative detection of the amount of nicotine. The inventors assessed NicA2 using the Amplex® UltraRed Assay™ for $H_2O2$ detection by resorufin, serial dilutions of nicotine in the presence of NicA2 were associated with corresponding decreases in fluorescence (see e.g., FIG. 2B). In contrast, serial dilutions of NicA2 in the presence of a constant nicotine concentration increased the $H_2O_2$ production rate but not the total amount of $H_2O_2$ produced (see e.g., FIG. 2C). Together these data show that the reaction is substrate-limited but not enzyme-limited. Next, it was shown that NicA2 produces $H_2O_2$ from nicotine at a 1:1 ratio, as determined from a calibration curve obtained by adding increased known concentrations of $H_2O_2$ and monitoring the subsequent fluorescence output from the Amplex® UltraRed Assay™ (see e.g., FIG. 2D). These results demonstrate the use of NicA2 as a sensing element for nicotine in an electrochemical device via detection of $H_2O2$.

In order to develop a biosensor, NicA2 was immobilized onto a DS710 (DropSens™) Screen-Printed Prussian Blue/Carbon Electrode working electrode (WE) using a 0.5 wt % chitosan solution, and the electrode was connected to a VersaSTAT MC™ (Princeton Applied Research™) potentiostat with a Ag/AgCl reference electrode (RE) (see e.g., FIG. 5-6). Chronoamperometric responses, recorded over time with a potential −0.2 V versus the RE, quantified the current response as a function of added known nicotine concentration in PBS (e.g., 0-1000 µM; 2 nmol NicA2; see e.g., FIG. 3A). A significant correlation existed over the physiologically relevant urine nicotine concentration, 0-200 µM, with a coefficient of determination, $R^2$, of 0.98 (see e.g., FIG. 3B or Table 3). The insert in FIG. 3B shows a chronoamperometric response with the addition of 200 µM nicotine. Maximal current output (~250 nA) occurred after 4000 seconds with a return to baseline at 6000 seconds. The limit of detection (LOD), as defined as the nicotine concentration yielding a signal greater than 3 times the pool standard deviations above background, was 27 µM over the ranger of 0 µM-200 µM.

Table 2 below shows nicotine levels (nM) in physiologically relevant human matrices (e.g., industrial waste, drinking water, blood, saliva, gastric juice, urine, or sweat). The bolded concentrations are the concentrations that can be detected by the enzyme-based nicotine biosensor described herein.

TABLE 2

| Source | | |
|---|---|---|
| Industrial Waste | 200,000 tons of chemical waste | |
| Drinking Water (Global average) | 11.71 nM | |

| | Active Smoker (nM) | Passive Smoker (nM) |
|---|---|---|
| Human Blood | 25-444 | |
| Human Saliva | 561-1,418 | |
| Human Gastric Juice | 2,589-19,725 | |
| Human Urine | 15,866-80,984 | 0-302 |
| Human Sweat | 1,936-28,614 | 795-2,539 |

Figure 3A:
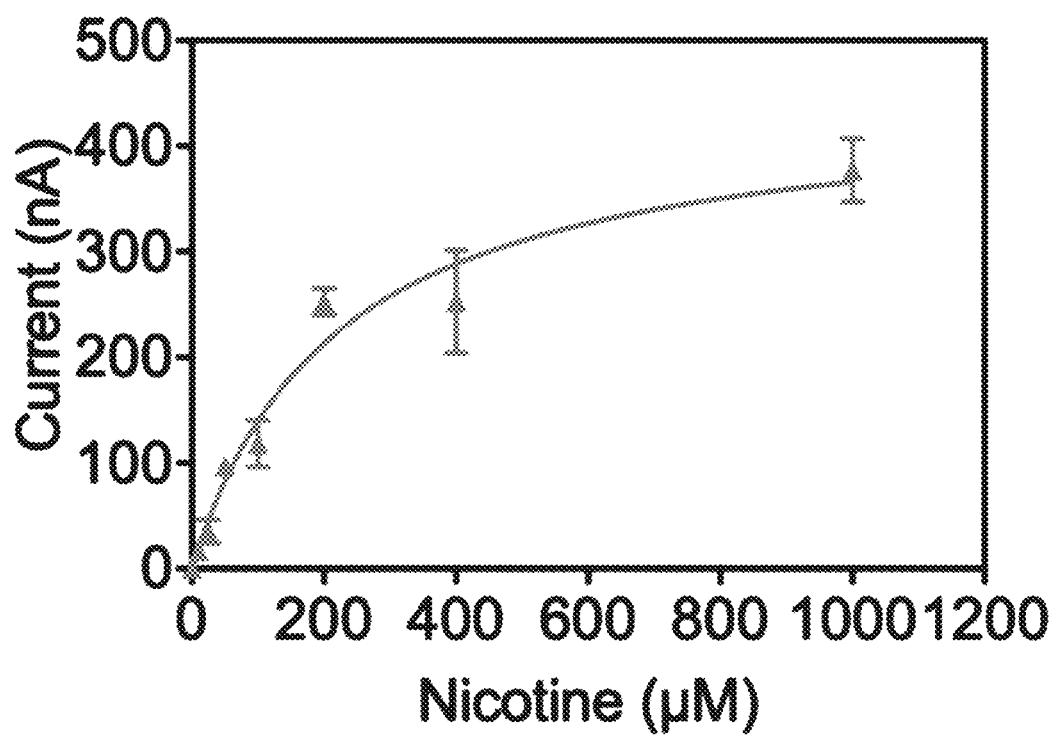
FIG. 3A-3E is a series of graphs showing that the nicotine biosensor is sensitive and accurate in PBS.
Figure 3B:
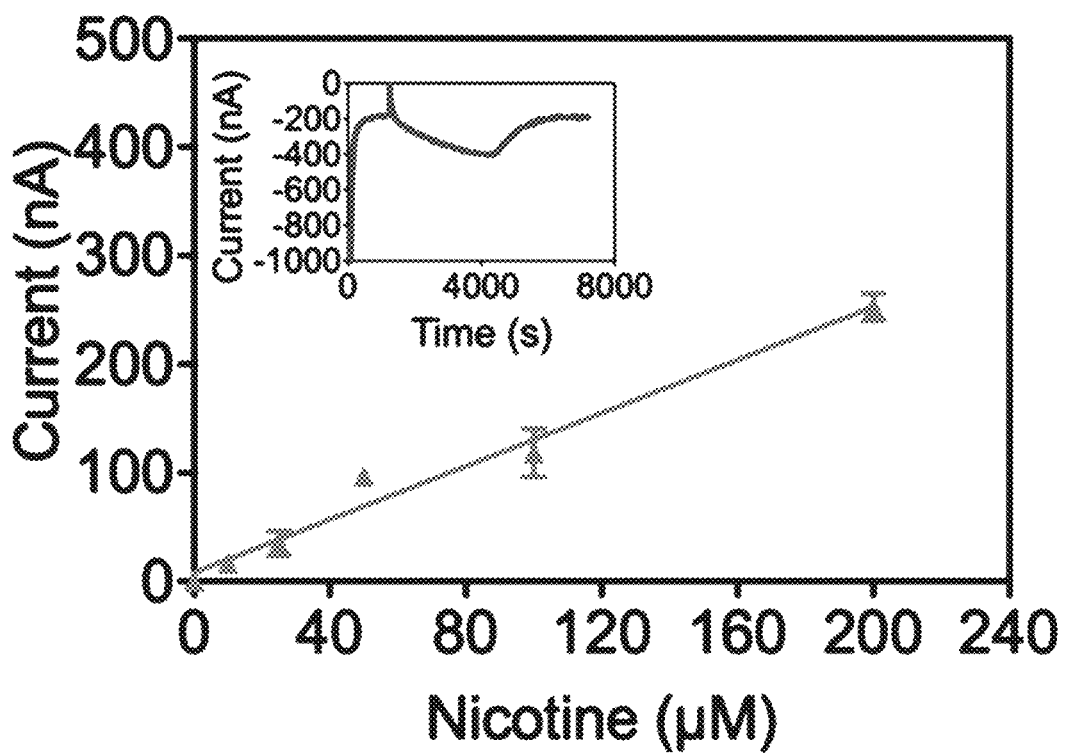
Figure 3C:
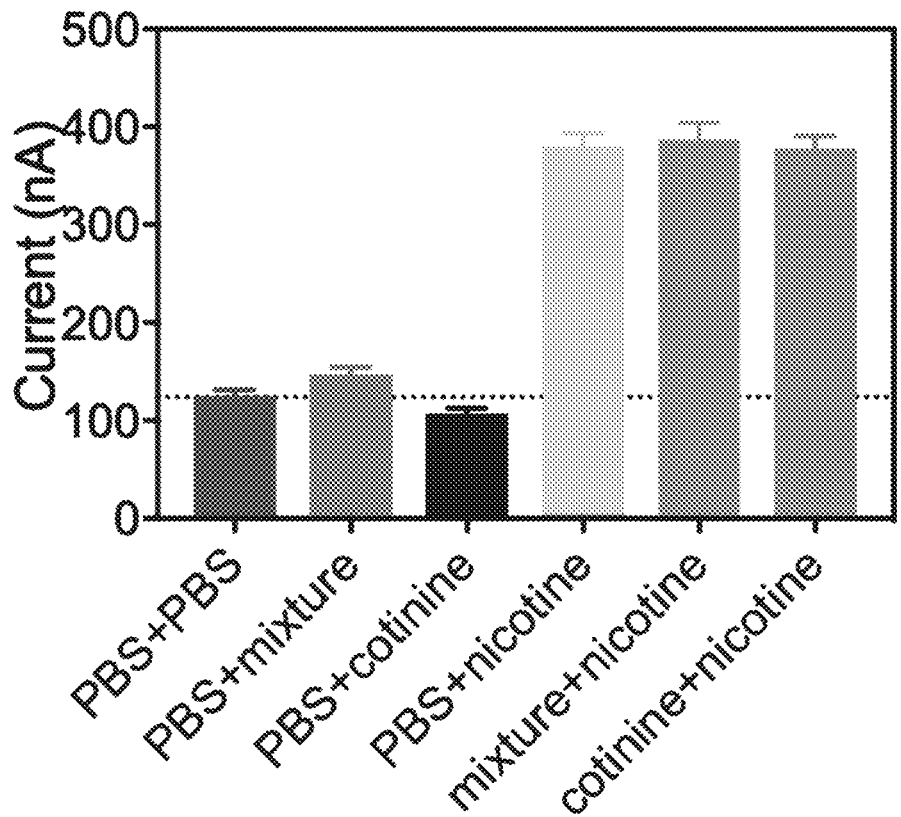
Figure 3D:
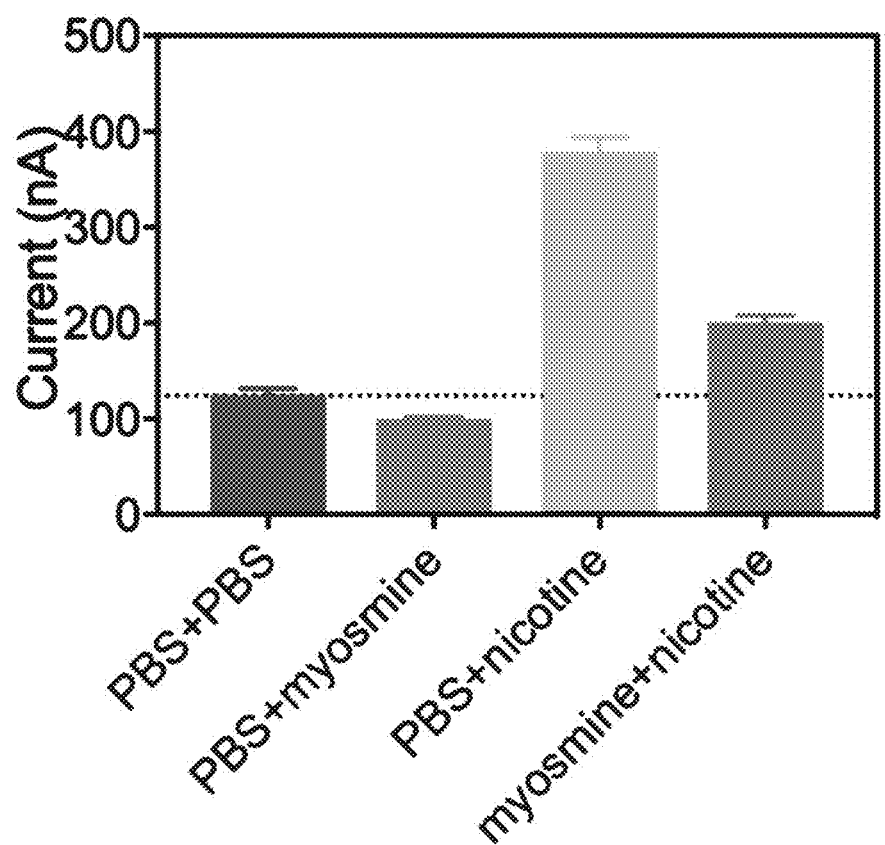
Figure 3E:
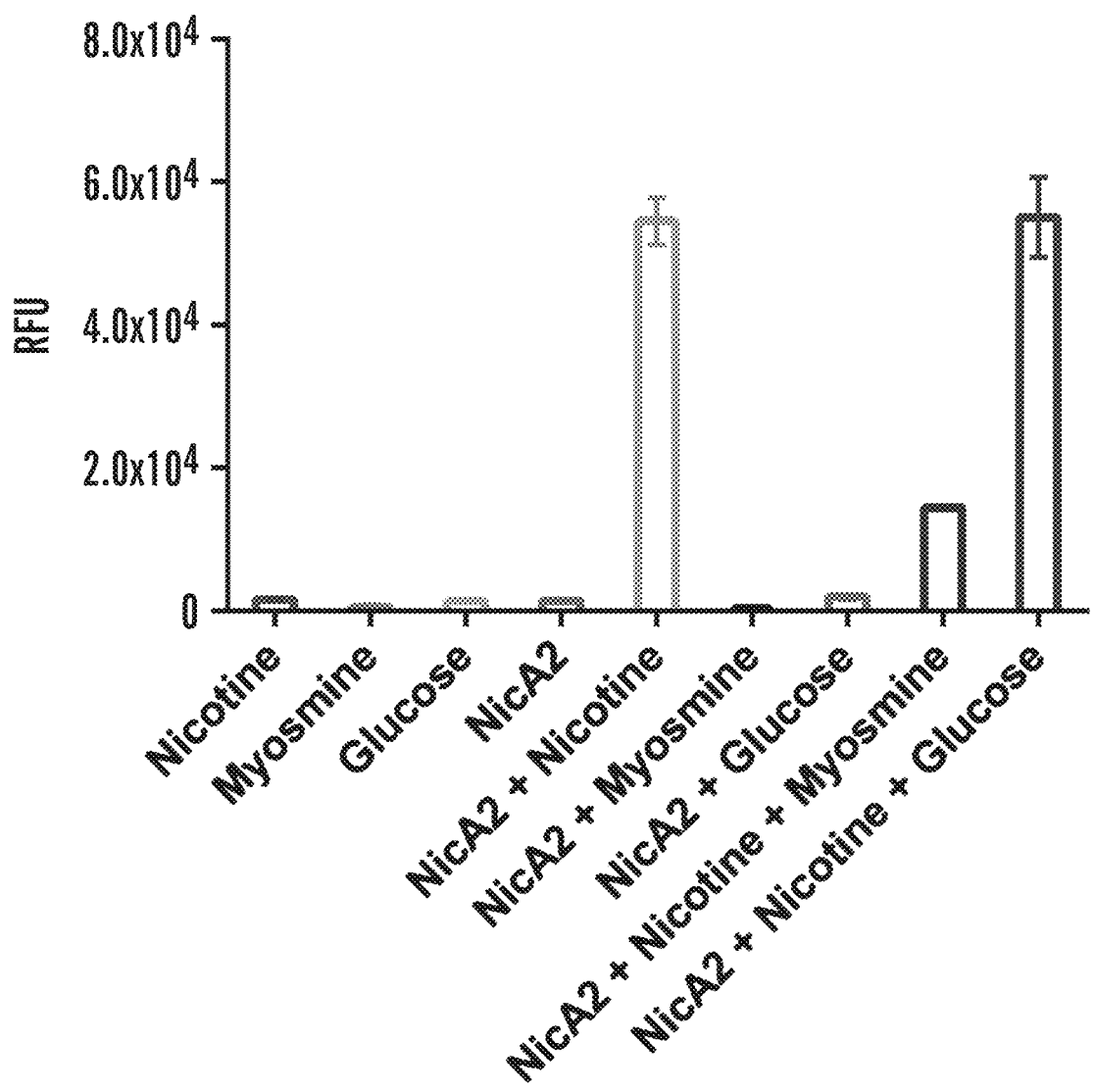
Figure 4:
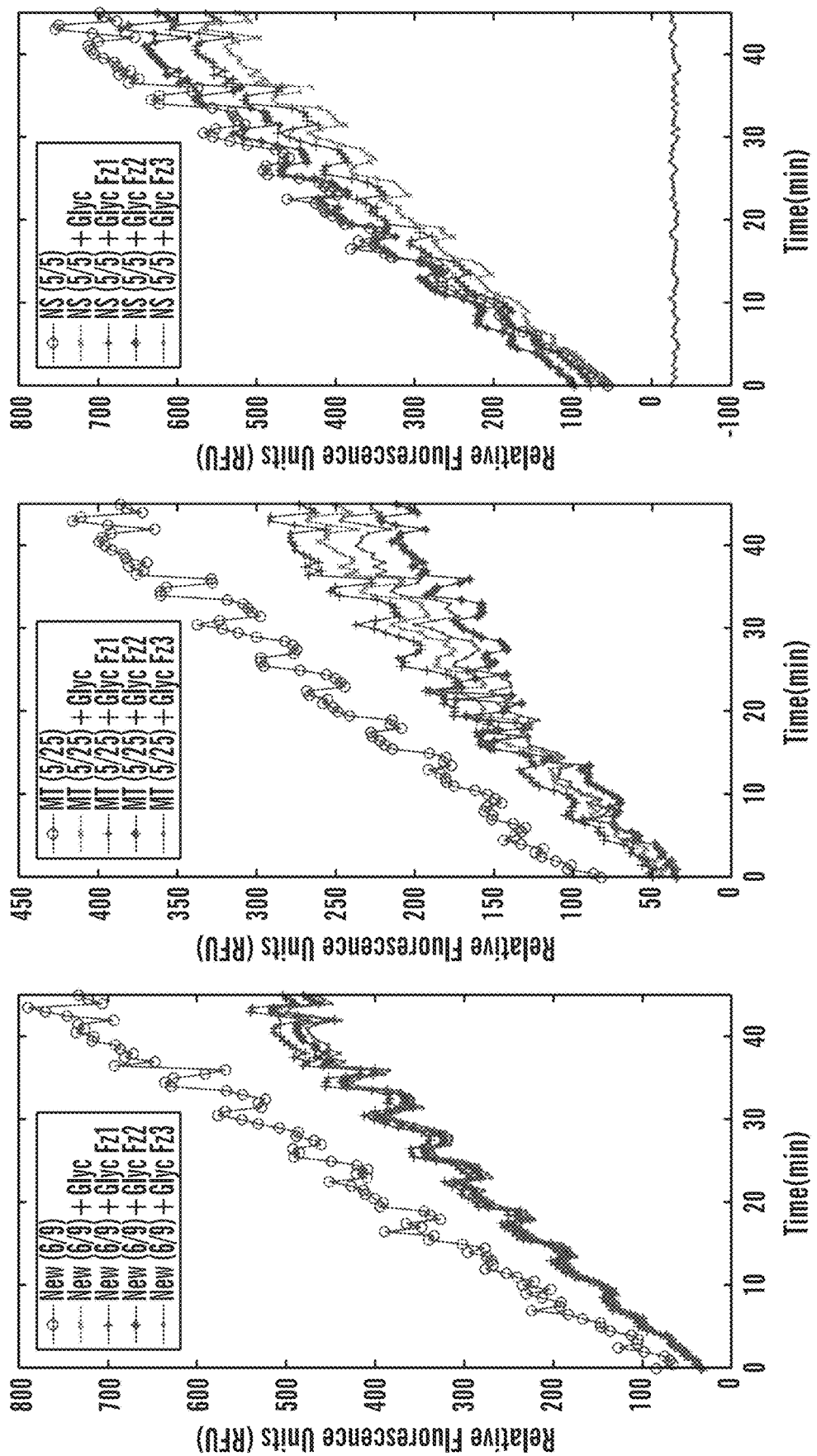
FIG. 4 is a series of graphs showing that NicA2 is resistant up to ~90% efficiency after 3 freeze/thaw cycles.

Given the intended clinical and at-home/personal use, the performance of the nicotine biosensor was determined in the presence of common interferents in urine or sweat (see e.g., FIG. 3C-3D). These co-existing compounds did not adversely affect the response to nicotine as the results were not statistically significant. Similarly, cotinine, the primary metabolite of nicotine in the human body, minimally affected the nicotine response, demonstrating the selectivity of the biosensor. Finally, to confirm the enzymatic role of NicA2 in electrochemical signal generation, myosmine, an inhibitor of NicA2, was added during a chronoamperometric experiment (see e.g., FIG. 3D). The addition of myosmine reduced the signal by approximately 50% with results similar to those obtained in the absence of nicotine.

To validate the point-of-care (POC) detection device, its performance was next evaluated with acquired human urine samples from smokers and nonsmokers (Lee Biosolutions™). Nonsmoker urine samples were first spiked with known concentrations of nicotine and a calibration curve was established. The results were comparable to that in PBS (LOD=34 µM, $R^2$=0.89 over the ranger of 0 µM-200 µM). Nicotine levels in smoker urine samples were then analyzed using chronoamperometric measurements as well as using an established mass spectrometry (MS) method. The chronoamperometric measurement results showed a strong significant correlation with the values measured in parallel by MS (data not shown). The nicotine sensors also demonstrated reproducibility. The performance of the nicotine sensor described herein was also compared with that of established techniques with regard to time and economics (data not shown). When measuring human urine samples, the device described herein requires simple filtration of the sample, whereas MS requires tedious and careful extraction of nicotine. Methods of detecting nicotine using the device as described herein thus allow all the steps, with the exception of the filtration step, to be performed on electrodes without the need for the technical expertise of running a MS instrument, thus further simplifying the procedure.

Several nicotine sensors are reported in literature. Current enzyme-based nicotine sensors rely on inhibition of choline oxidase by nicotine, of which selectivity against potential interferents in biological samples has not been thoroughly studied (see e.g., Campanella et al. Anal. Lett. 2001, 34 (6), 855-866; Yang et al. Anal. Chim. Acta 2004, 509 (2), 151-157; Mitsubayashi et al. Anal. Chim. Acta 2006, 573, 69-74). Molecularly imprinted polymers (MIP) can provide synthetic recognition sites for nicotine. Although functional, the use of a MIP-based sensor element requires additional transduction methods such as quartz crystal microbalance (see e.g., Tan et al. Bioelectrochemistry 2001, 53 (2), 141-148; Croux et al. Phys. Status Solidi A-Appl. Mat. 2012, 209 (5), 892-899; Alenus et al. Phys. Status Solidi A-Appl. Mat. 2012, 209 (5), 905-910; Alenus et al. Anal. Bioanal. Chem. 2013, 405 (20), 6479-6487), surface plasmon resonance (see e.g., Cennamo et al. Sens. Actuator B-Chem. 2014, 191, 529-536; Kamra et al. Anal. Chem. 2015, 87 (10), 5056-5061), or thermal read-out technique (see e.g., Peeters et al. Anal. Bioanal. Chem. 2013, 405 (20), 6453-6460; Geerets et al. Sensors 2013, 13 (7), 9148-9159; Wackers et al. Sensors 2014, 14 (6), 11016-11030). Nanoparticle-based biosensors utilize the electrocatalytic activity of nanoparticles on surface. Electrochemical oxidation of nicotine can also be developed as a means for detection using carbon nanotube infused electrodes and adsorptive stripping voltammetry, but specificity analysis and evaluation of clinical samples still need to be conducted (see e.g., Wang et al. Electrochemistry Communications 2009, 11 (4), 733-735; Sims et al. Sens. Actuator B-Chem. 2010, 144 (1), 153-158; Lo et al. Sens. Actuator B-Chem. 2012, 162 (1), 361-368). Graphene, nitrogen-doped graphene, and boron-doped diamond-based sensors require an extraction step for nicotine and have been validated with tobacco products and antismoking pharmaceuticals (see e.g., Svorc et al. Diam. Relat. Mat. 2014, 42, 1-7; Jing et al. Sci Rep-Uk 2016, 6, 8; Jing et al. RSC Adv. 2016, 6 (31), 26247-26253; Li et al. J. Electroanal. Chem. 2017, 784, 77-84).

In summary, described herein is an enzymatic biosensor for the detection and quantification of nicotine from samples such as human urine. The enzyme or sensing element comprises a MAO present in *Pseudomonas putida* (bacteria found in the soil around tobacco plants). RNA-Seq on *P. putida* in the presence and absence of nicotine identified NicA2 as a MAO enzyme. Experimental data with NicA2 demonstrated the conversion of nicotine to n-methylomysomine with production of hydrogen peroxide. Immobilization of MAO NicA2 on a screen-printed working electrode produced a device that linearly responded to nicotine with production of hydrogen peroxide for chronoamperometric measurement. The device quickly and accurately determined the concentration of nicotine in urine with the same precision and accuracy as linear ion trap mass spectrometer. This nicotine POC detection device can used in a clinical setting. Finally, the strategy of using metagenomic sequence mining can be used to further identify new redox enzymes for analytes of clinical relevance, especially given the diversity of microbes available for screening.

Example 2

Optimization of the Nicotine Biosensor

The inventors herein optimized multiple parameters of the NicA2 biosensor to enable it to be used for real-time measurements of nicotine, to enable it be sensitive to physiological levels of nicotine in sweat and other samples obtained from a smoker, as well as enabled repeated detection of nicotine in a variety of different samples.

Figures 10A, 10B:
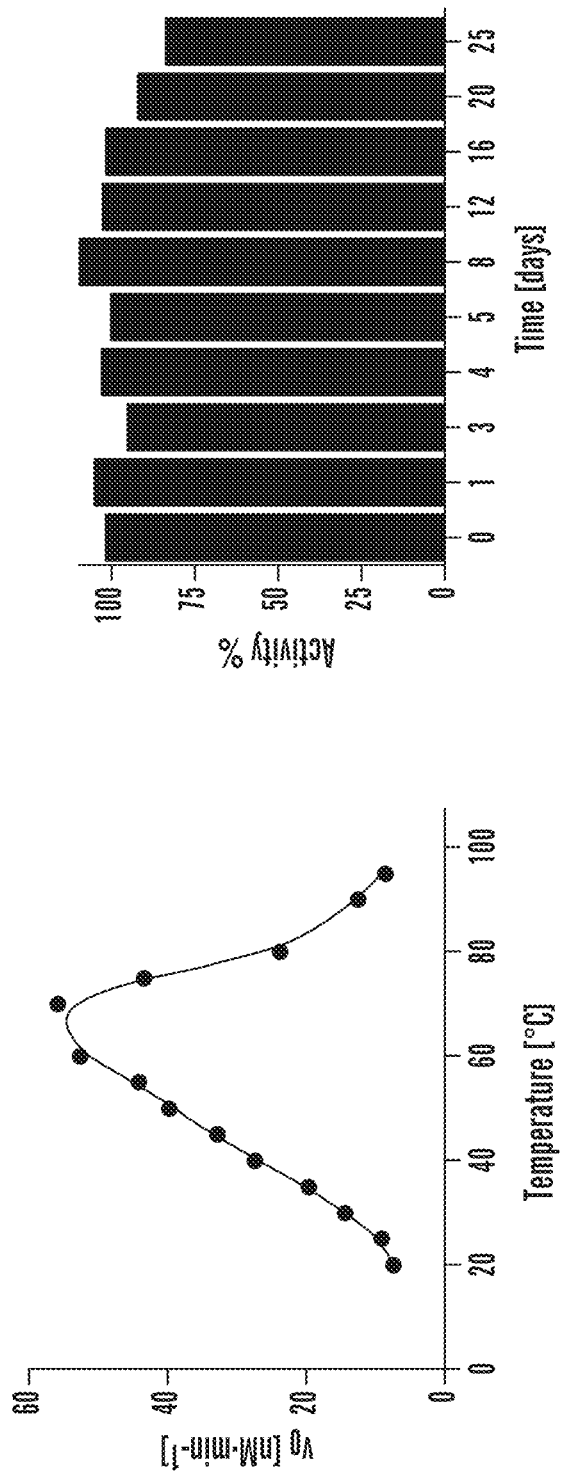

In particular, while NicA2 was determined to be specific for nicotine (see FIG. 10D), is stable for over 25 days (FIG. 10B), and has a high affinity for nicotine when maintained at between 37° C.-90° C. (FIG. 10A), the inventors assessed different NicA2 mutants to identify specific modifications that increase activity and oxidation of nicotine.

(i) NicA2 Mutants

Figure 11B:
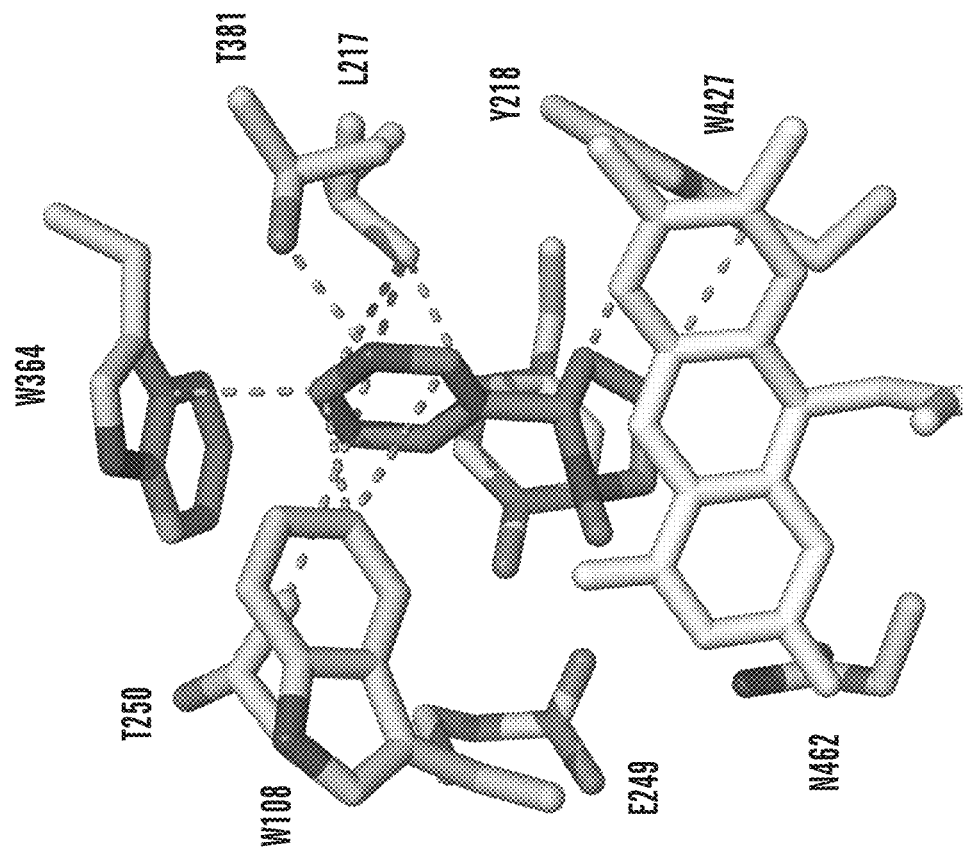
Figure 11A:
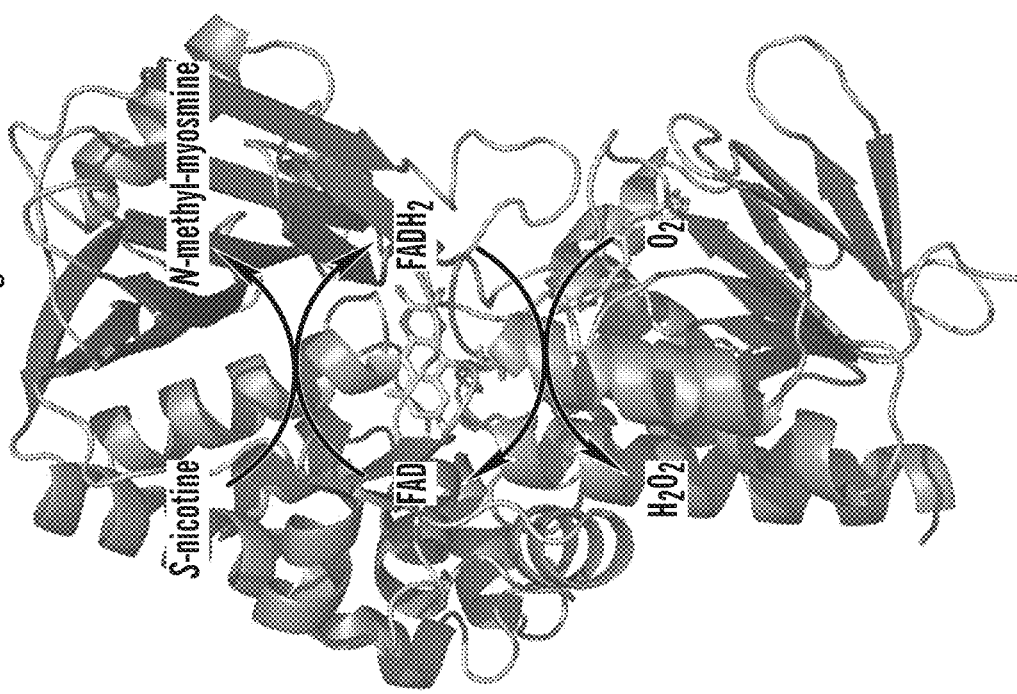
Figure 11C:
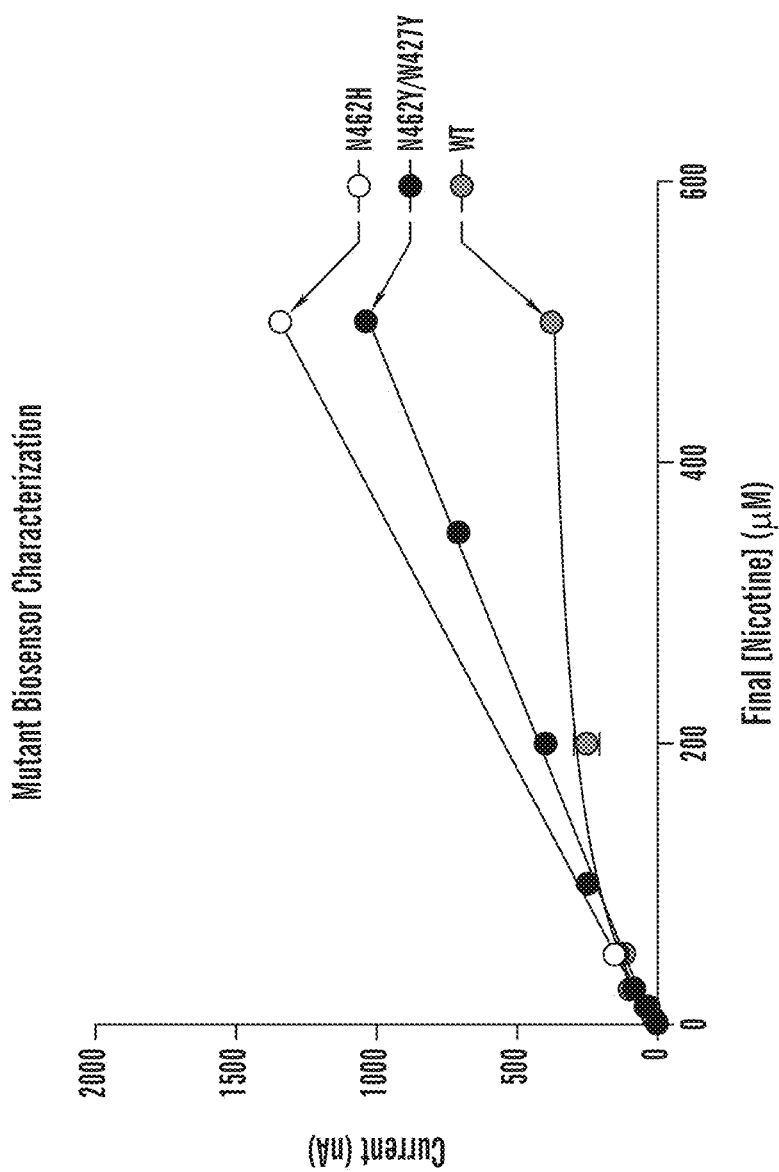

As shown in FIG. 11D, the inventors assessed NicA2 mutant enzymes comprising at least one mutation selected from any of: N462V, N462Y/W427Y, N462H, A107R of SEQ ID NO: 2 and determined that the NicA2 mutant N462H produced more current, was more sensitive to nicotine and thus can detect a lower concentration of nicotine (see, e.g., FIG. 11D). Accordingly, the rest of the experiments were done with this NicA2(N462H) mutant enzyme.

(ii) Working electrode optimization

Figure 12B:
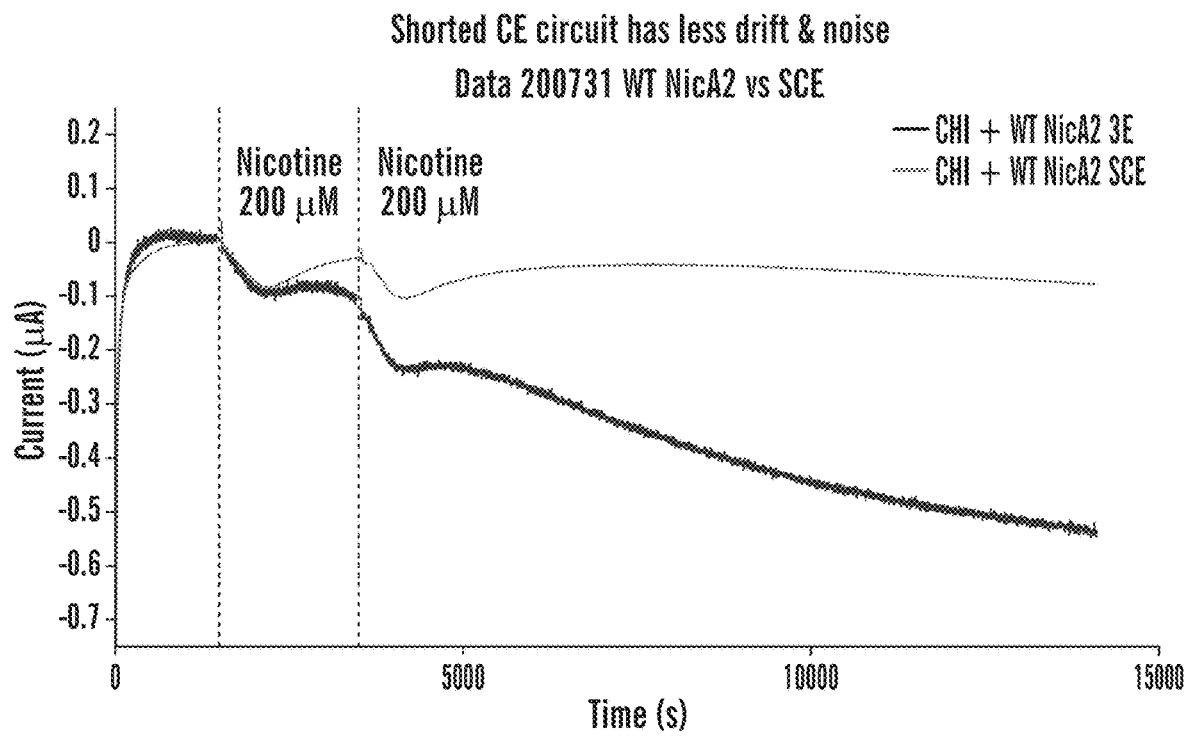

Interestingly, the inventor determined that the nicotine biosensor with three electrodes (a working electrode, a counter electrode and a reference electrode) resulted in sufficient decrease or shift in current over time (see, e.g., FIG. 12A), whereas a NicA2 biosensor with just two electrodes (2E), i.e., a working electrode and a reference electrode, eliminated the current shift (FIG. 12B). As such, unlike typical electrochemical sensors such as those for glucose oxidase that comprise three electrodes, the nicotine biosensor disclosed herein was optimized to comprise only two electrodes.

Figure 16:
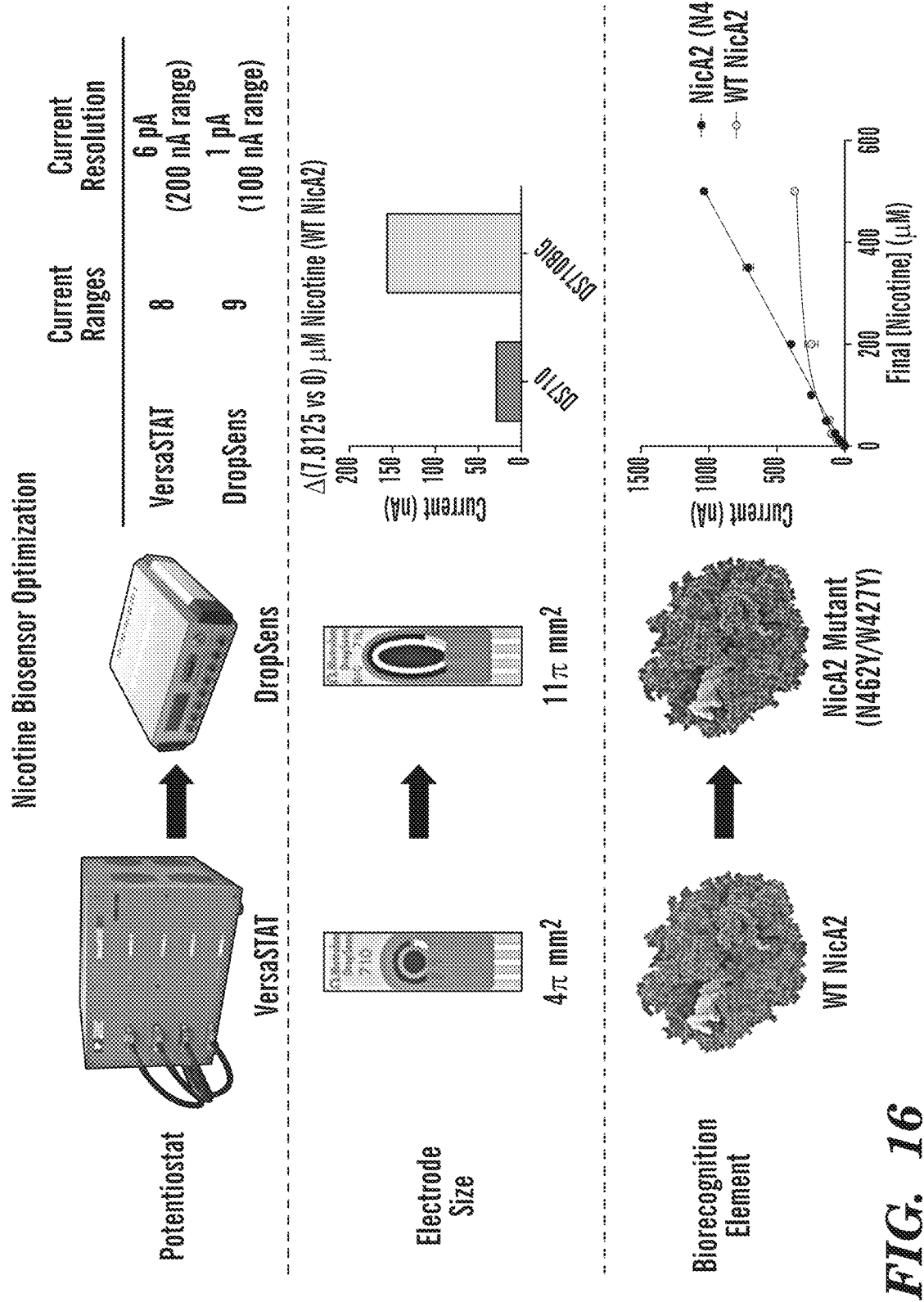
FIG. 16 shows a schematic of nicotine biosensor optimization. Potentiostat optimization was changed from a VeraSTAT™ to a DropSens™ machine, which could measure 9 current ranges, and 1 pA (100 nA range). Electrode size was optimized, where the electrode area was increased from $4\pi$ mm$^2$ (DS710) to $11\pi$ mm$^2$ (DS710BIG), with the graph showing the increased current with the larger $11\pi$ mm$^2$ electrode size. Optimization of the NicA2 biorecognition element was also performed, with NicA2 mutants, e.g., N462Y/W427Y or N462H, having increased oxidative activity compared to wildtype NicA2.

In addition to optimizing the number of electrodes, the inventors also determined that a larger surface area of the working electrode resulted in the greatest preservation in current. In particular, the inventors that the size of the working electrode influence the current produced from the NicA2 biosensor. Accordingly, the inventors determined that a working electrode that has an area of >11π mm² resulted in current preservation, and demonstrated efficient current detection with a working electrode of 11π mm² (FIG. 16). In some embodiments, the size of the working electrode is in the range of 5-8 π mm², or 8-10π mm², or 10-12π mm², or 12-15π mm², or greater than 15π mm². As shown in FIG. 16, the inventors assessed working electrode with different shapes, and determined that a circular or oval working electrode shape was sufficient for current preservation.

Figure 13A:
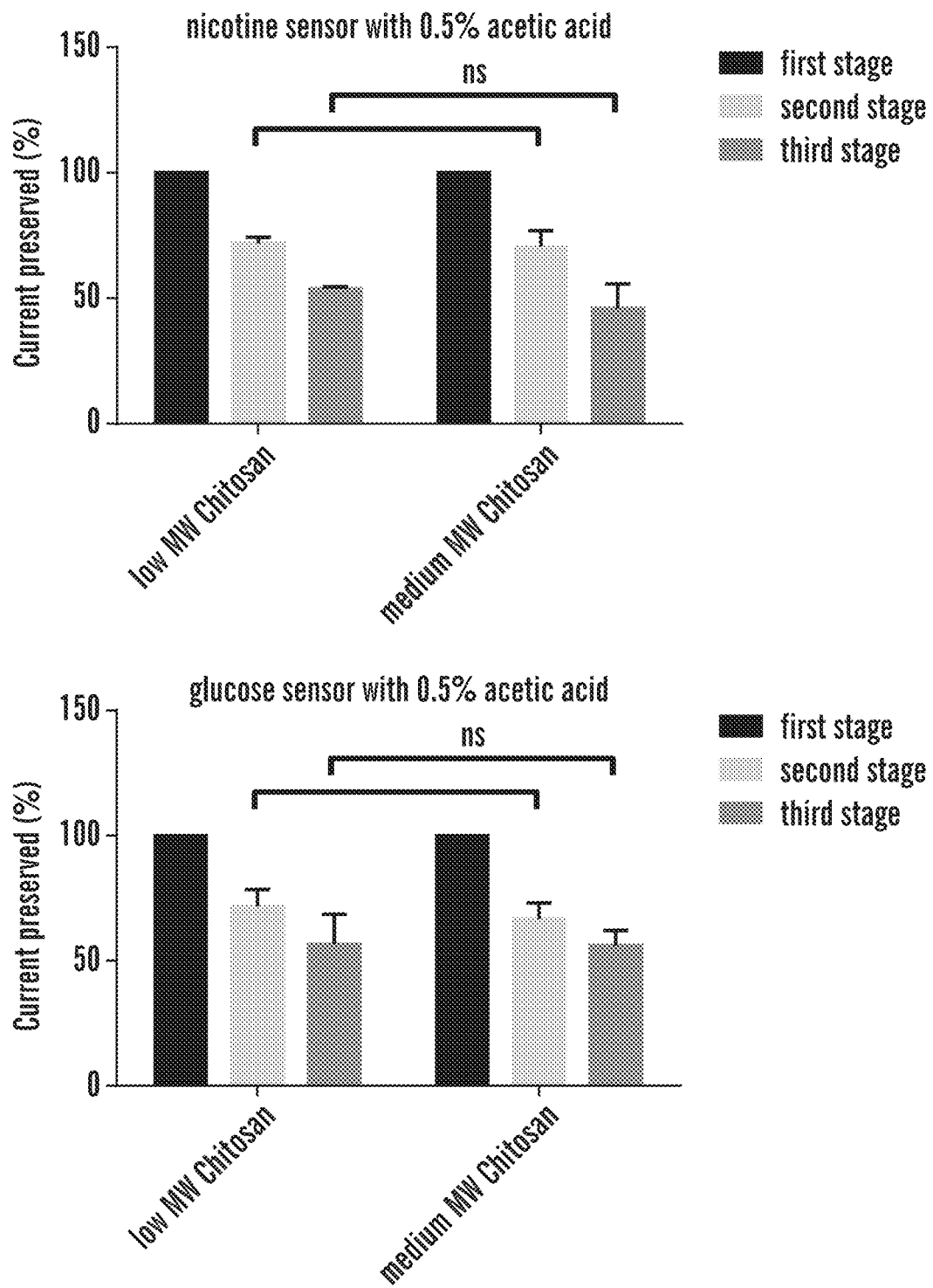
FIG. 13A-13B shows graphs of optimization of the electrode surface with chitosan and acetic acid concentrations when NicA2 is used as the biorecognition element as compared to glucose oxidase as the biorecognition element.
Figure 13B:
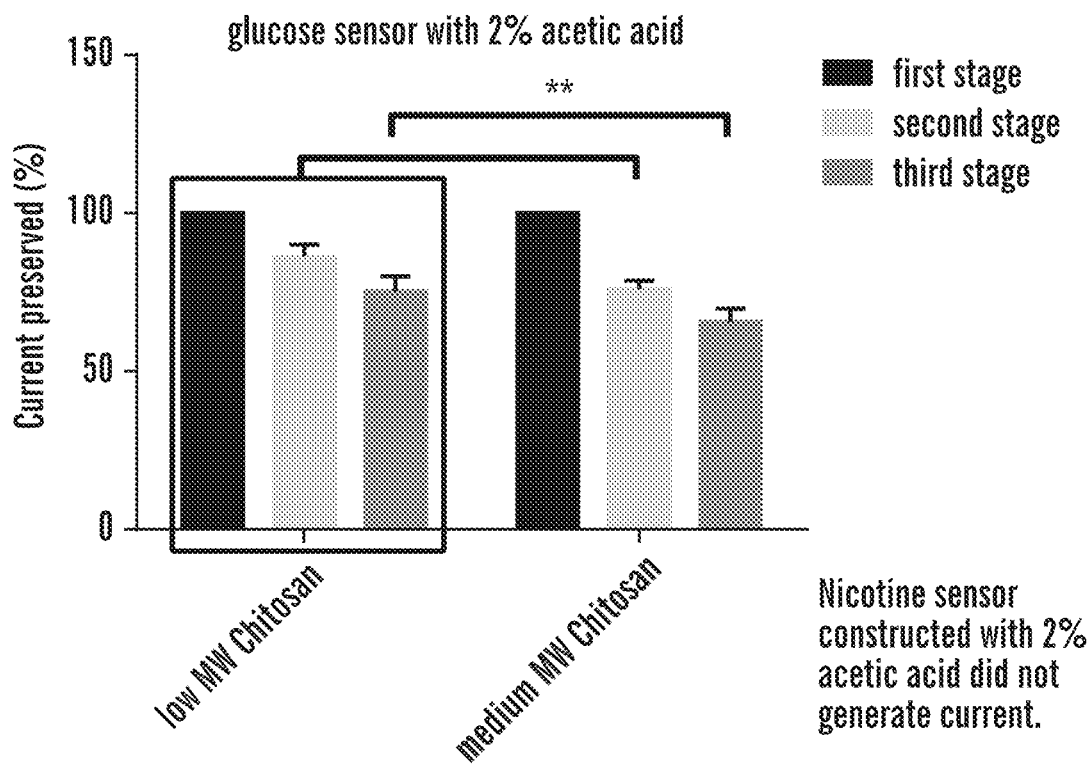
Figure 14A:
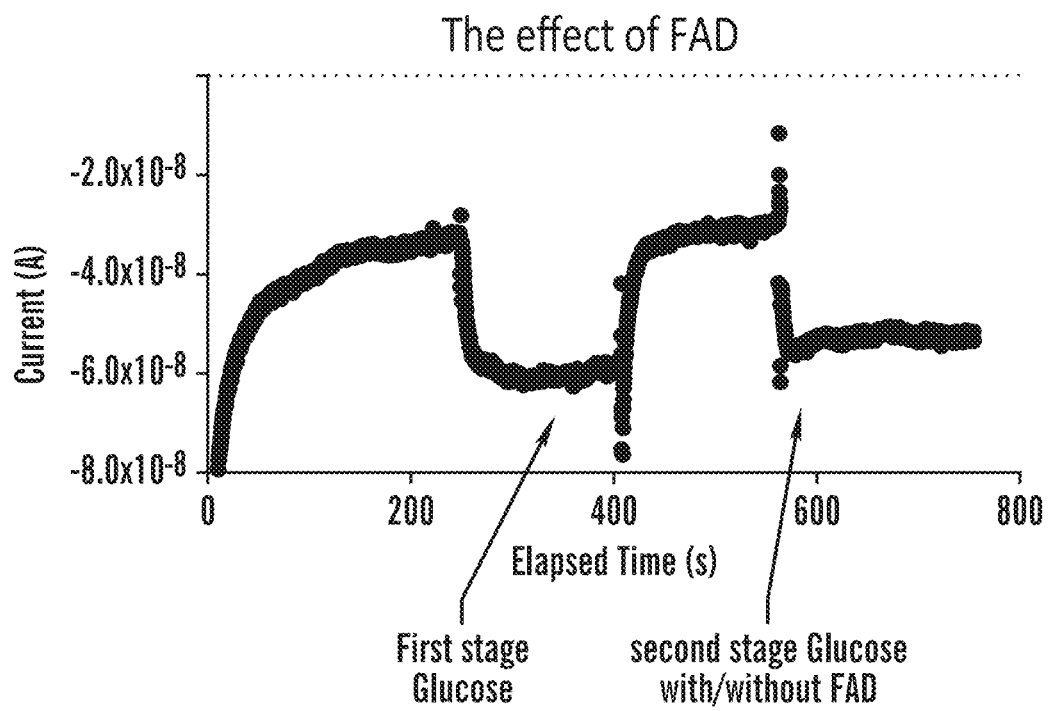
FIG. 14A-14B shows that FAD addition during a chronoamperometric experiment did not improve the current response of glucose oxidase.
Figure 14B:
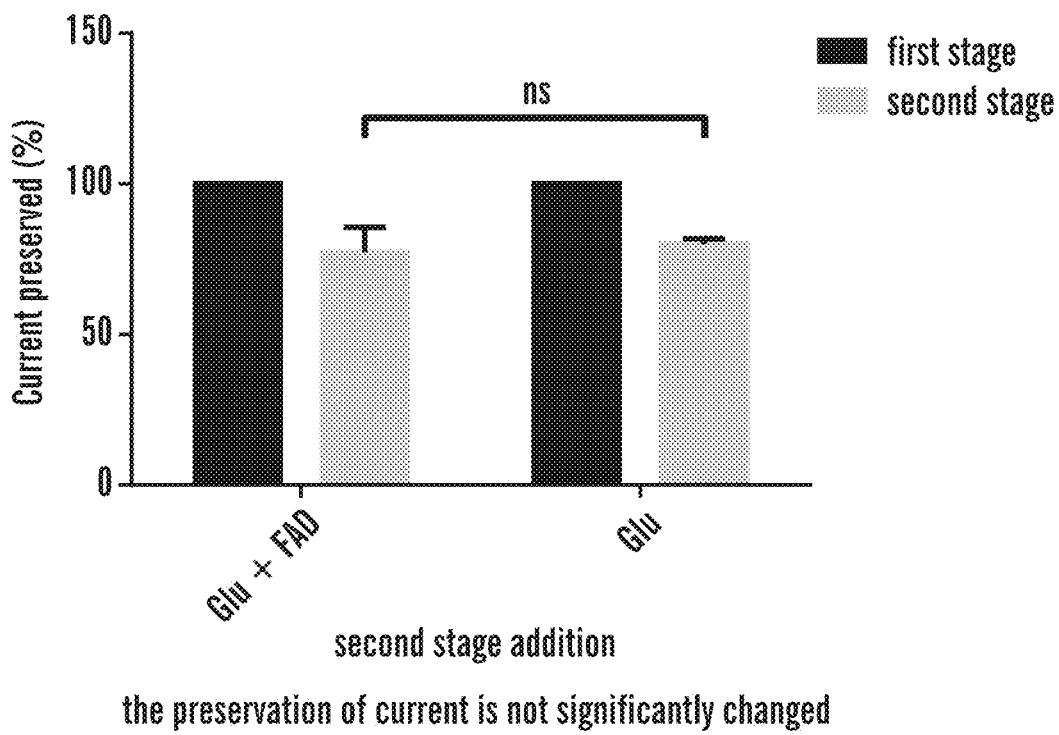
Figure 15A:
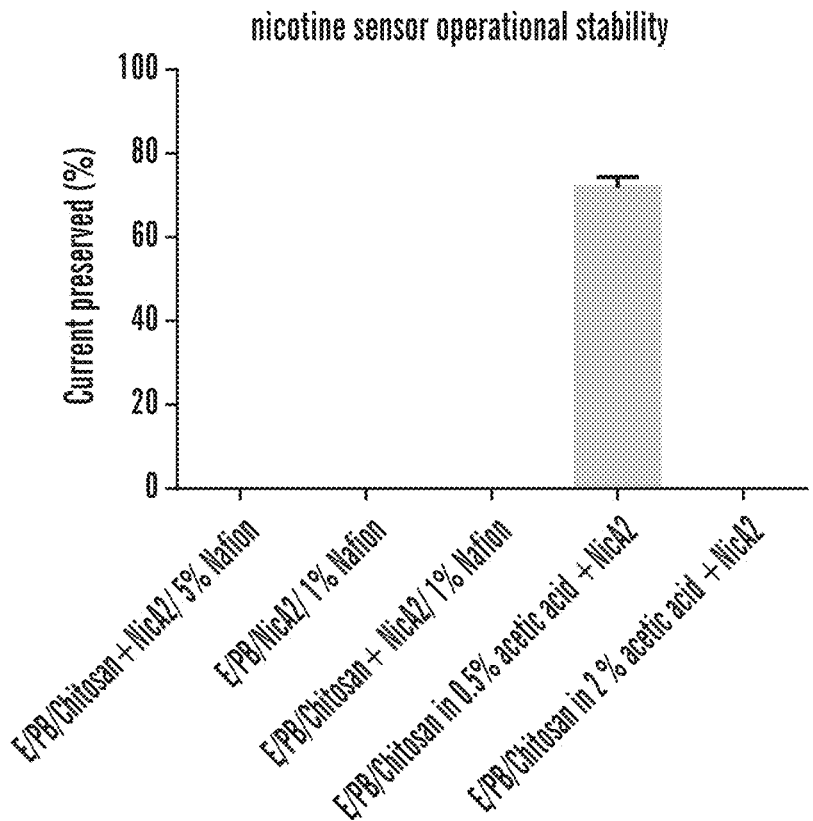
FIG. 15A-15C shows optimization of the surface of the electrode comprising the NicA2 biorecognition element.
Figure 15B:
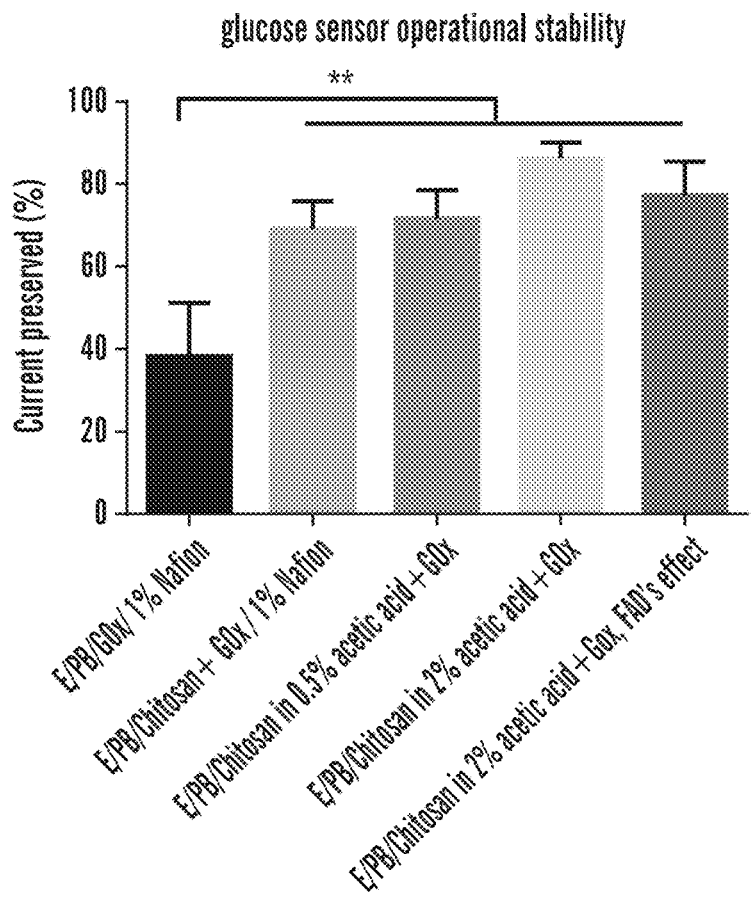
Figure 15C:
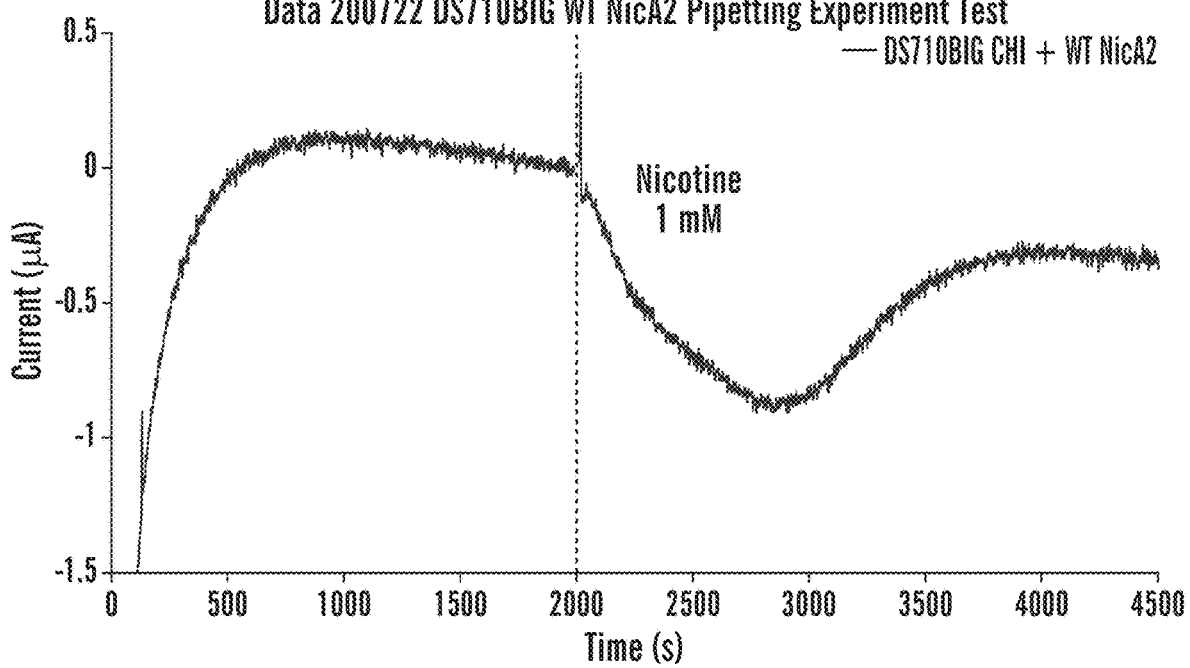

The inventors next assessed the effect of the surface optimization on current preservation. The inventors assessed different polymers, and determined that polymers comprising low- and medium molecular weight (MW) chitosan formulated in 0.5% acetic acid was optimal for maintaining current preservation (see, e.g., FIG. 13A). This was unexpected given that NicA2 appeared a robust enzyme stable for 25 days and could maintain current from 37° C.-90° C., and that glucose oxidase is stable in low MW chitosan in 2% acetic acid. The inventors also assessed and optimized the top layer of the working electrode, and the inventors determined that in contrast to glucose oxidase where Nafion preserved the current (FIG. 15B), the current was unexpectedly and completely inhibited when Nafion was placed on the top surface of a working electrode comprising NicA2 (FIG. 15A). Again, this demonstrated that while NicA2 is relatively robust and stable over time at different temperatures, it is highly susceptible to becoming non-functional when immobilized on a working electrode. For these reasons, the inventors' careful optimization of the parameters of the surface of the working electrode with NicA2 immobilized on was paramount to using NicA2 as functional nicotine biosensor that can be used to repeatedly measure nicotine at physiological levels in a variety of different samples. Accordingly, the NicA2 biosensor disclosed herein are very different from glucose oxidase biosensors.

(iii) Optimization of Detection of Nicotine from Different Physiologically Relevant Biological Samples.

Figure 17B:
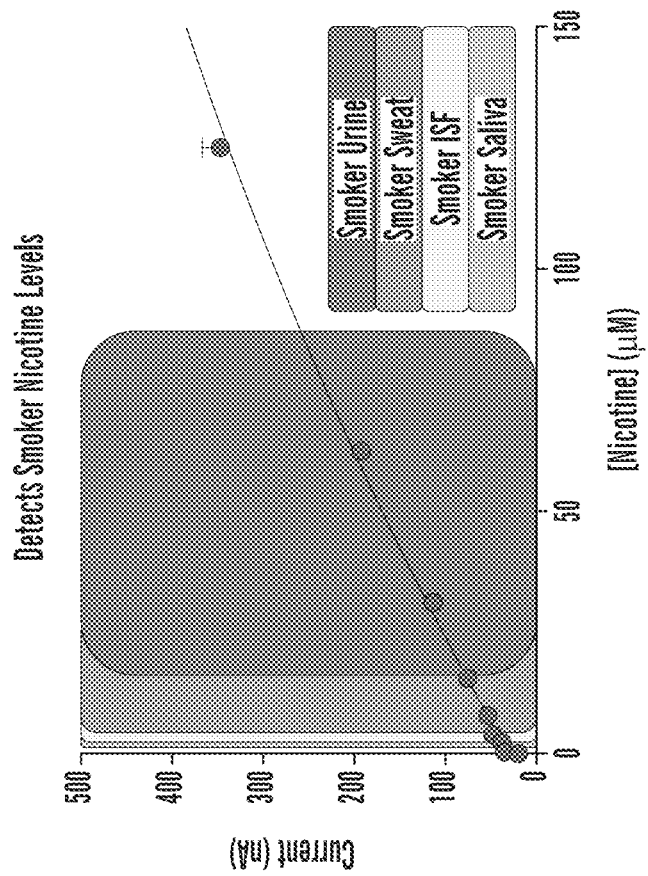
FIG. 17A-17H show optimization of the Nicotine biosensor.
Figure 17A:
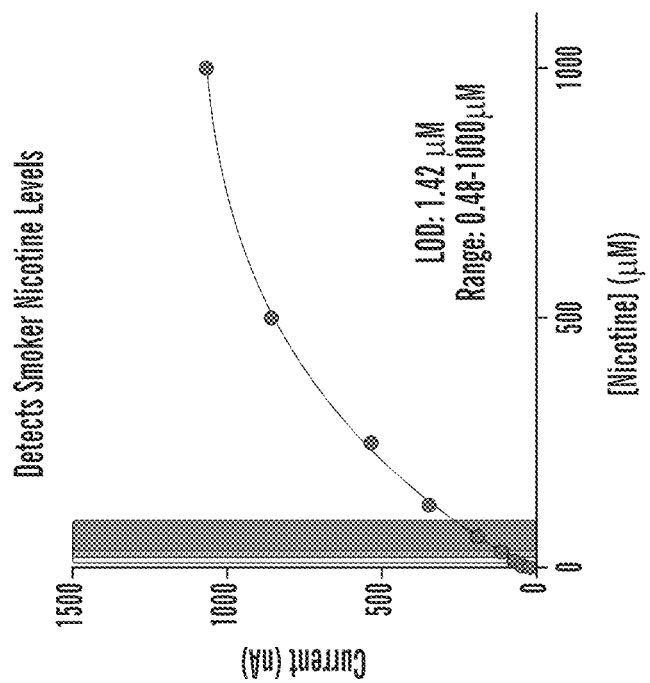
Figures 17C, 17D:
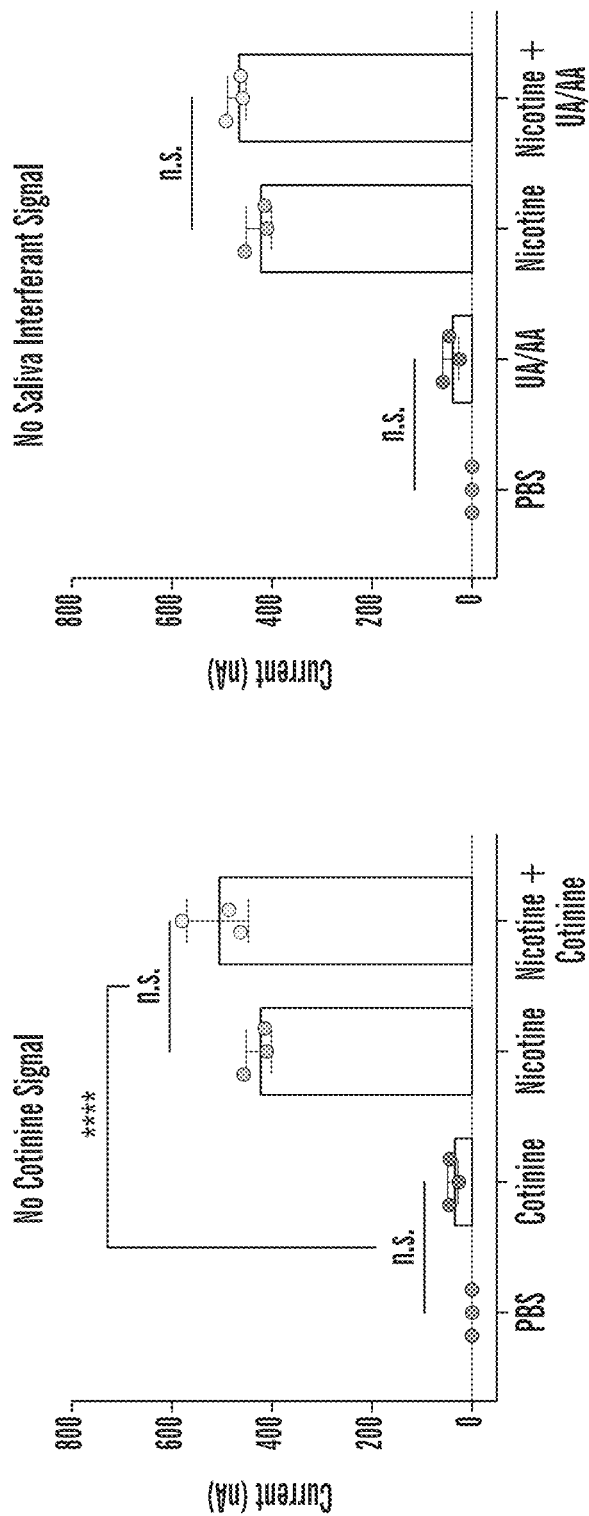
Figure 17F:
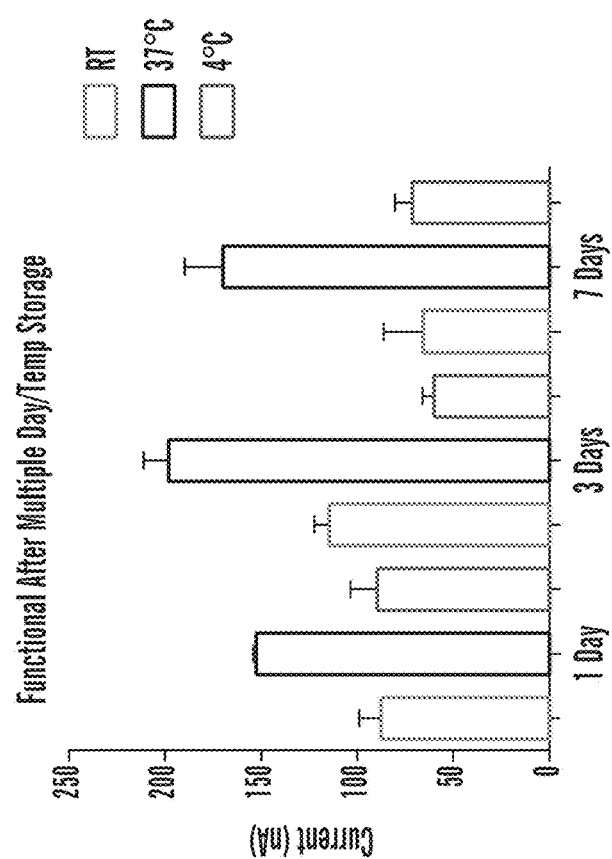
Figure 17E:
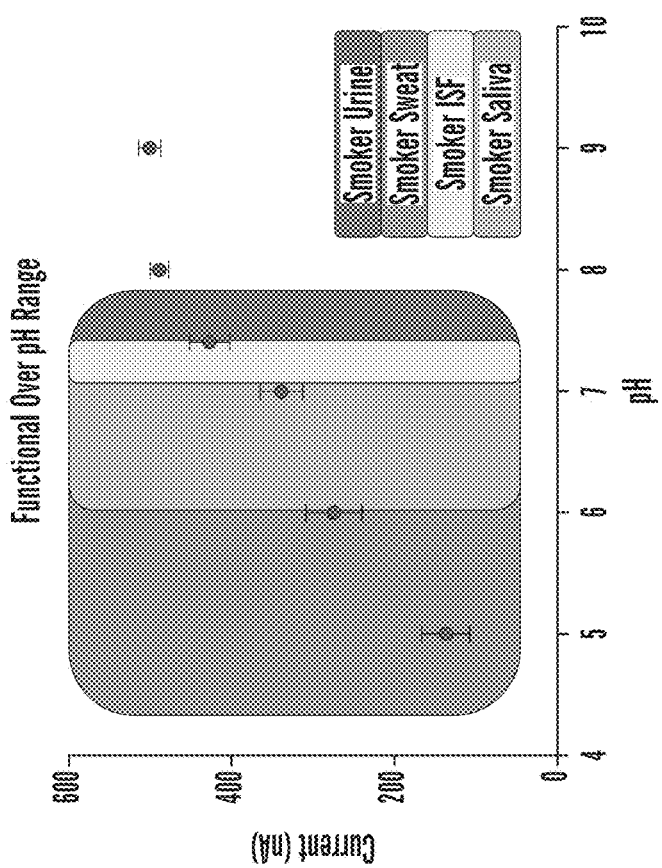
Figure 17G:
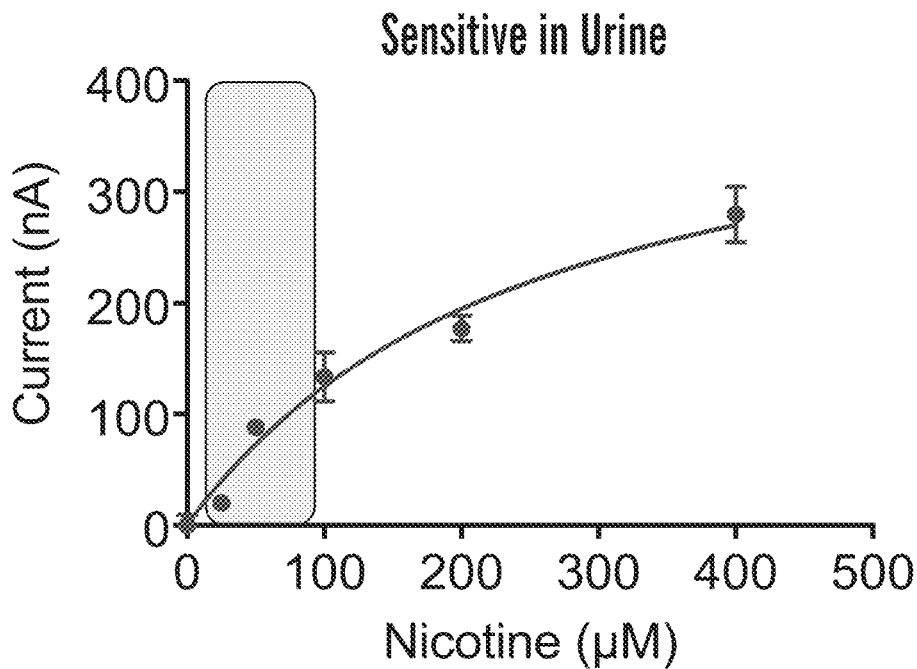
Figure 17H:
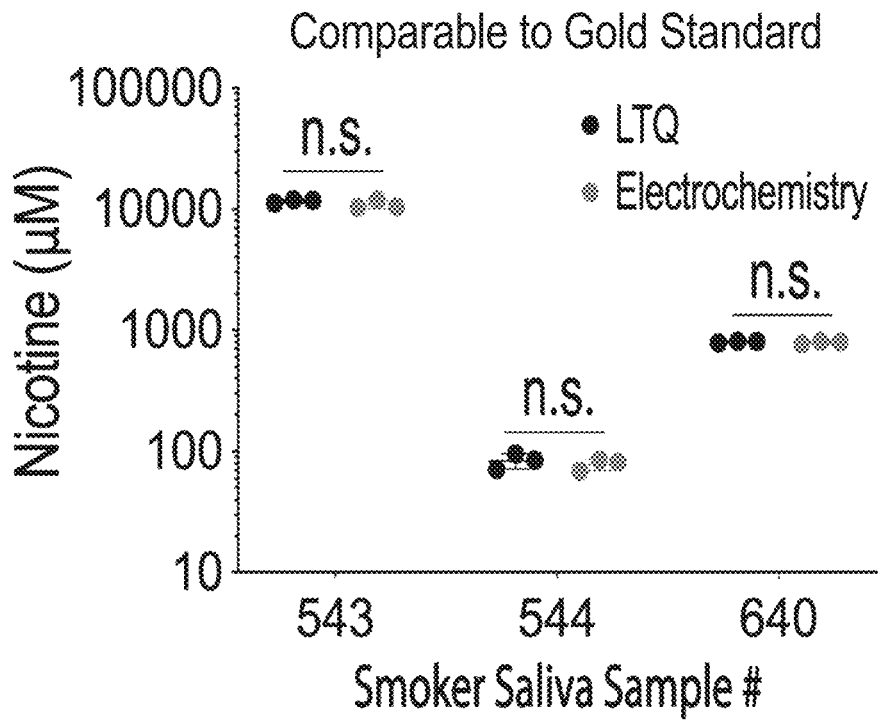

The inventors also assessed the ability of the NicA2 biosensor to repeatedly detect different amounts of nicotine in a range of different physiologically relevant samples. As shown in FIG. 17A, the NicA2 biosensor can detect nicotine in the range of 0.48-1000 μM, which is within the range of smoker nicotine levels, and can detect nicotine in a range of samples, including but not limited to smoker urine, smoker sweat, smoker ISF (FIG. 17B, and FIG. 17G). The NicA2 biosensor also produced a current at a range of pHs (FIG. 17E) and is also stable at 37° C. for as many of 7 days (FIG. 17E), demonstrating that the NicA2 biosensor would be suitable as a wearable nicotine biosensor. Importantly, NicA2 did not produce a current with cotinine (FIG. 17C), or other metabolites (FIG. 10D) and current was not affected by saliva interferrants (FIG. 17D). Importantly, as shown in FIG. 17H, the inventors demonstrated that the level of nicotine detected using the disclosed NicA2 biosensor was highly comparable to detection of nicotine of the same samples using mass spectrometry.

Figure 18A:
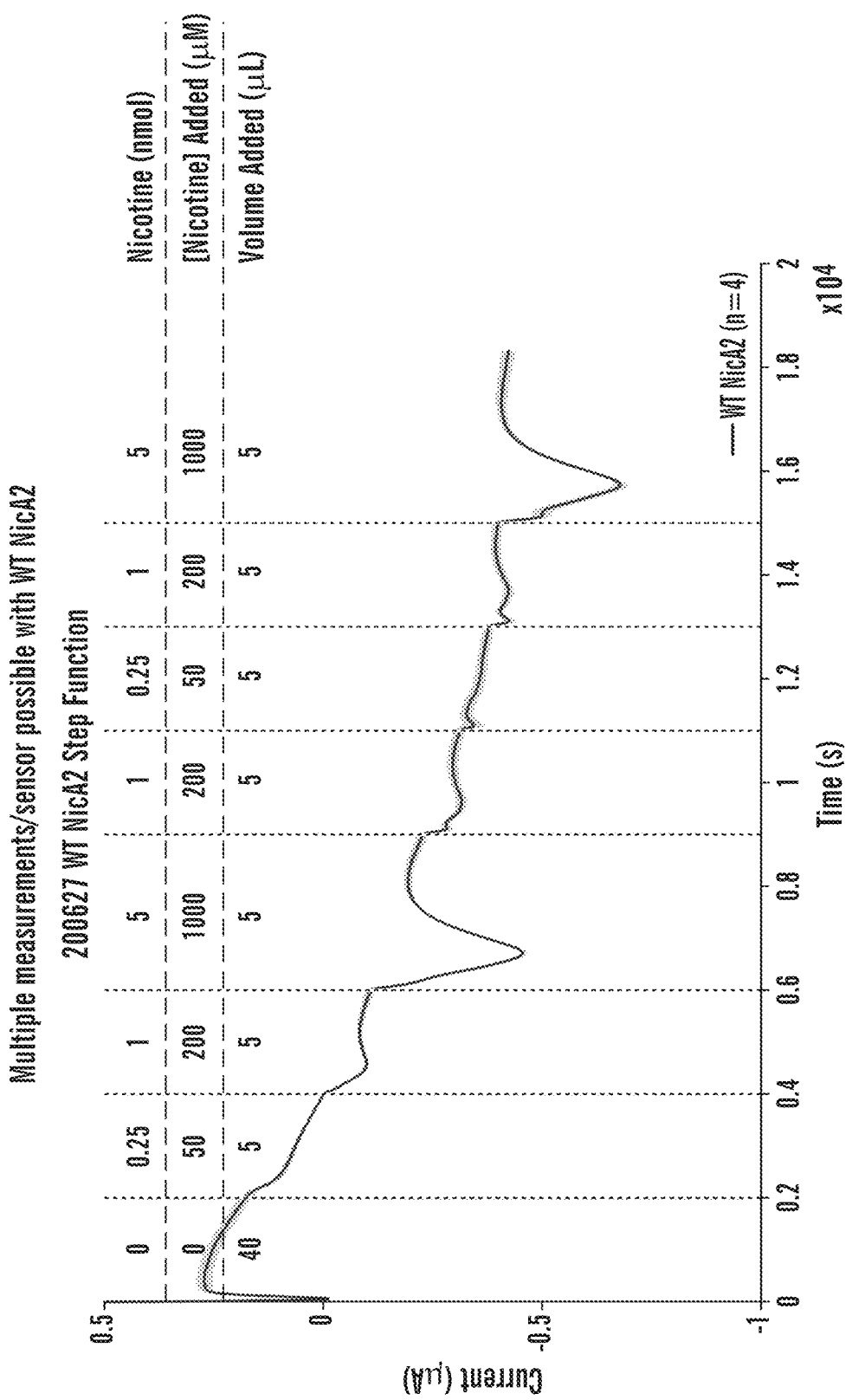
FIG. 18A-18C demonstrate that the NicA2 biosensor can be used for multiple measurements of nicotine.
Figure 18B:
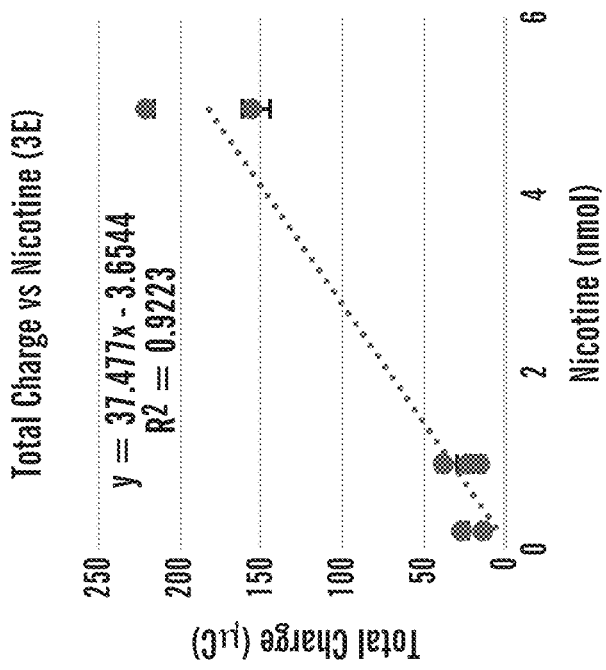
Figure 18C:
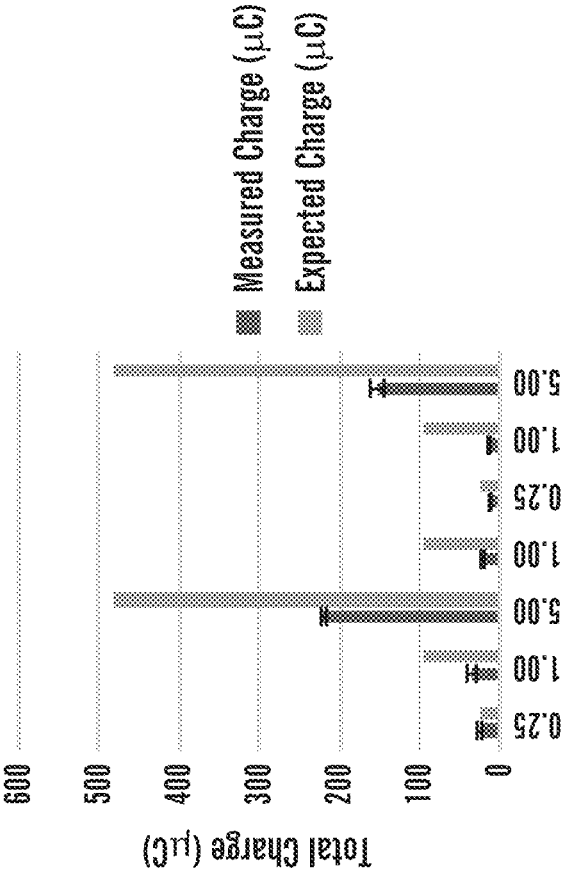
Figure 19A:
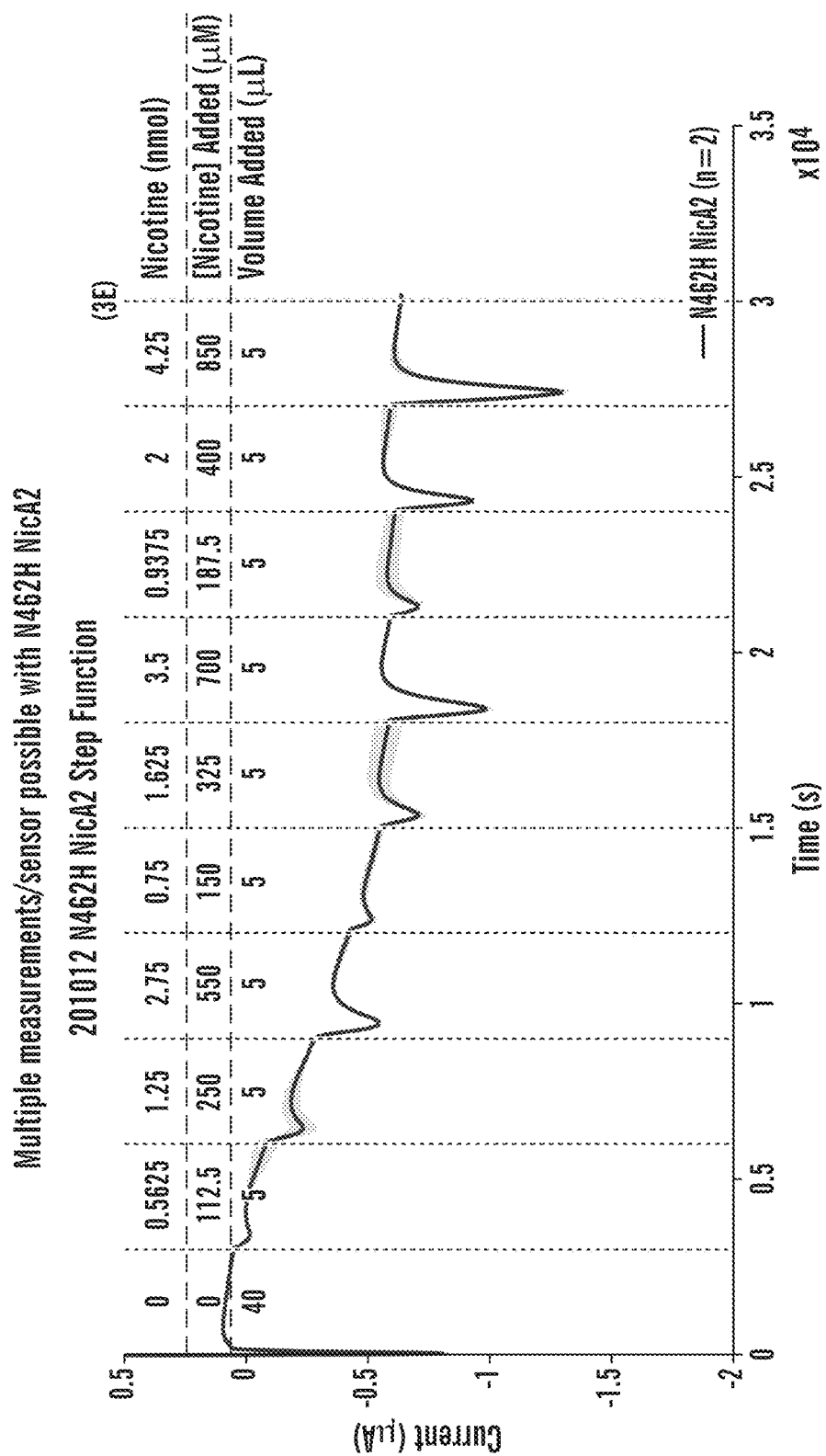
FIG. 19A-19C shows multiple measurements of nicotine using the NicA2(N462H) mutant.
Figure 19B:
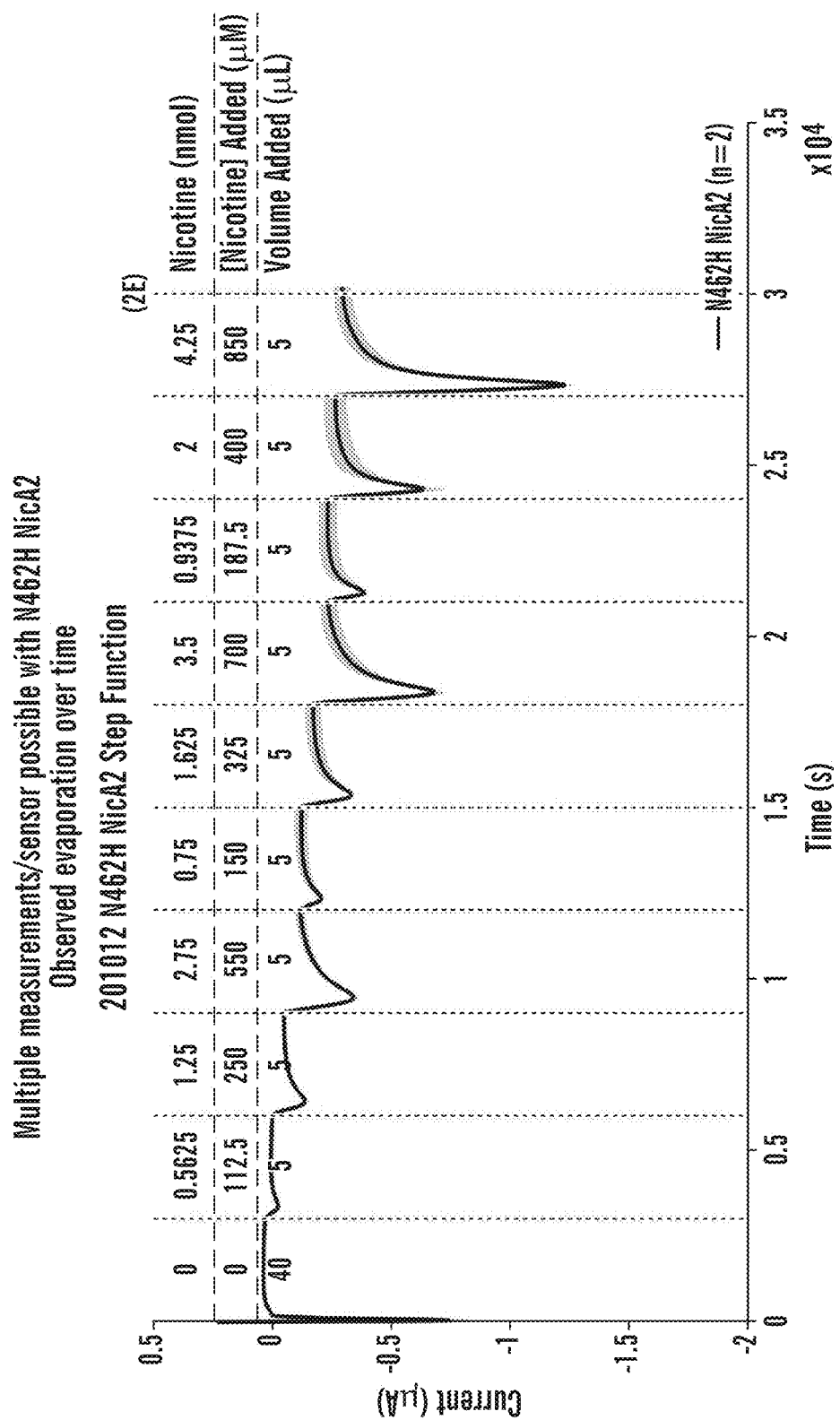
Figure 19C:
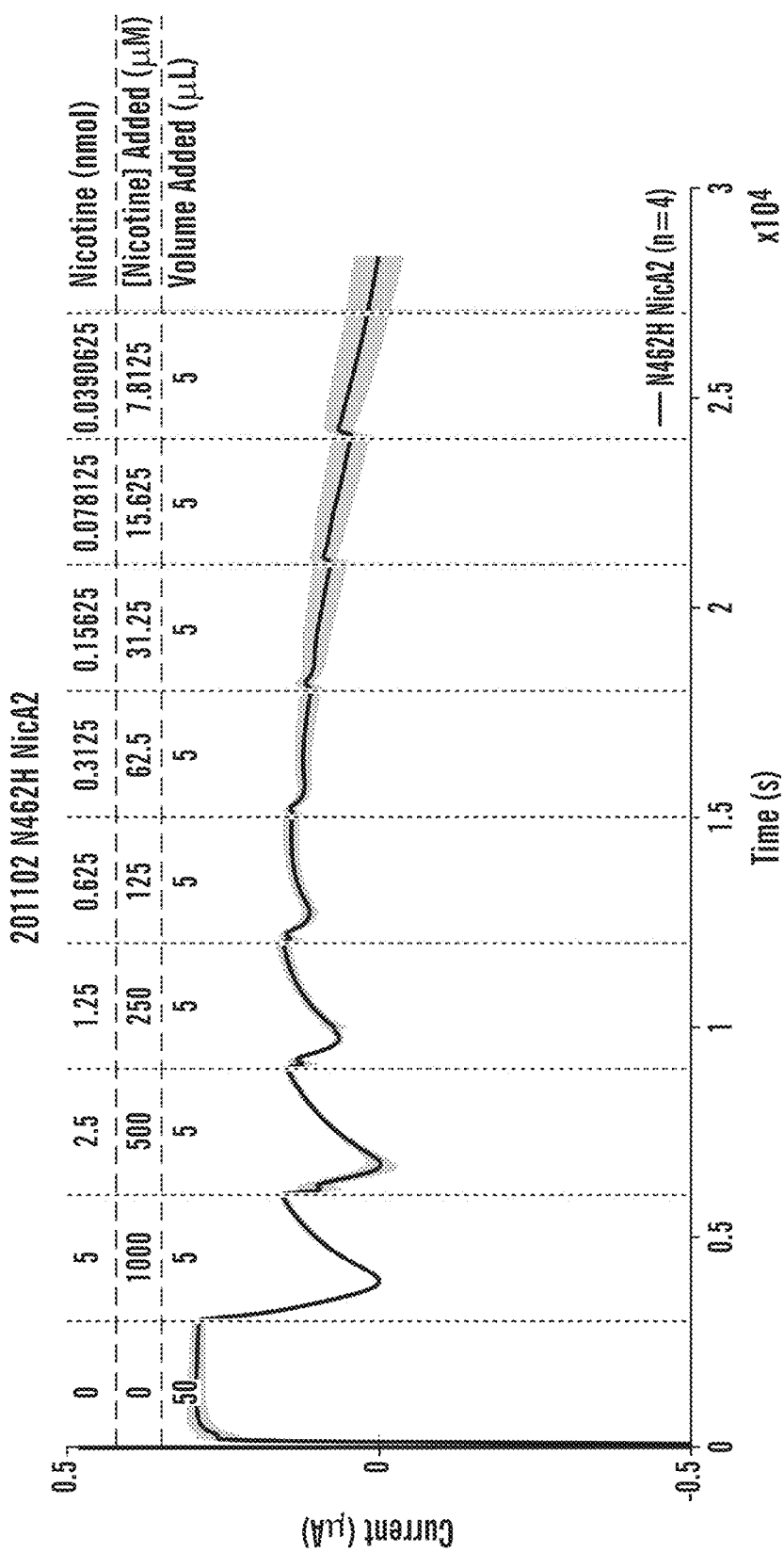
Figure 20B:
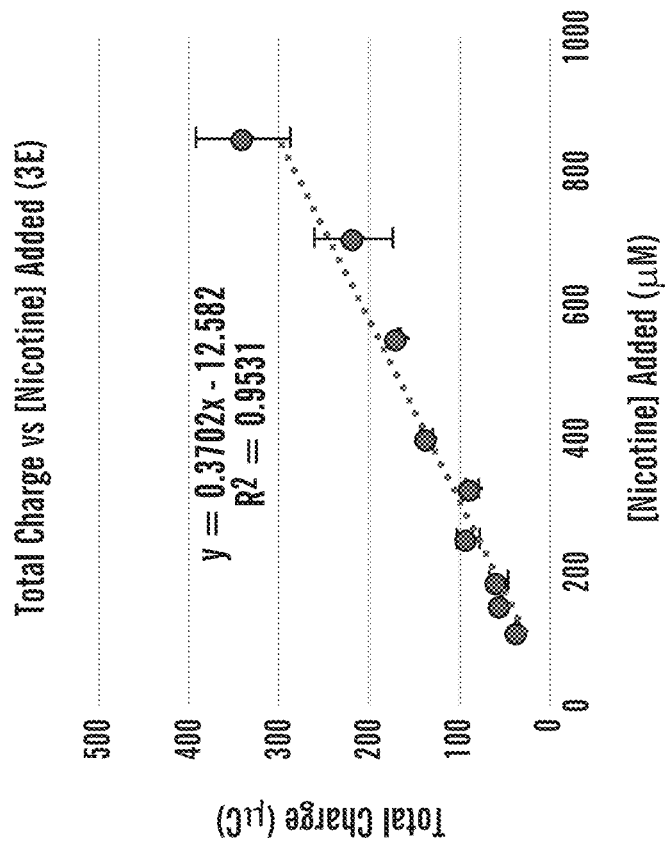
FIG. 20A-20D shows the 3 electron biosensor produced drift which is eliminated in the 2 electrode NicA2(N462H) biosensor.
Figure 20A:
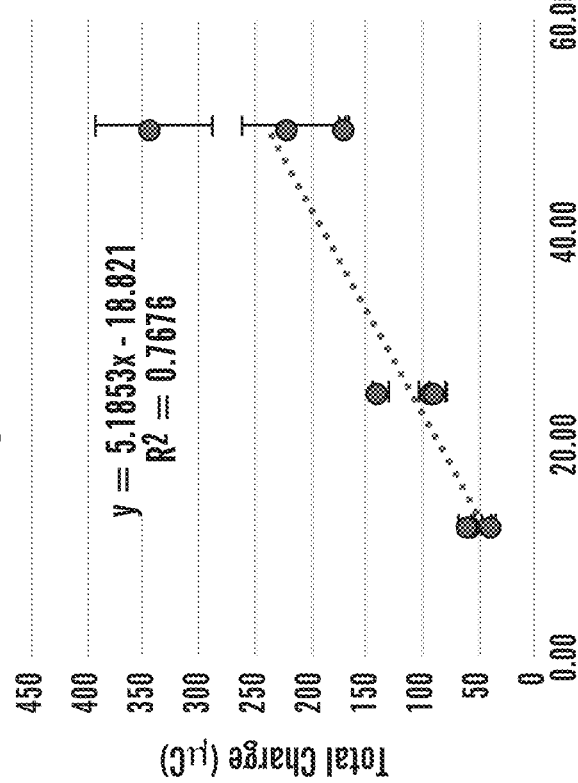
Figures 20C, 20D:
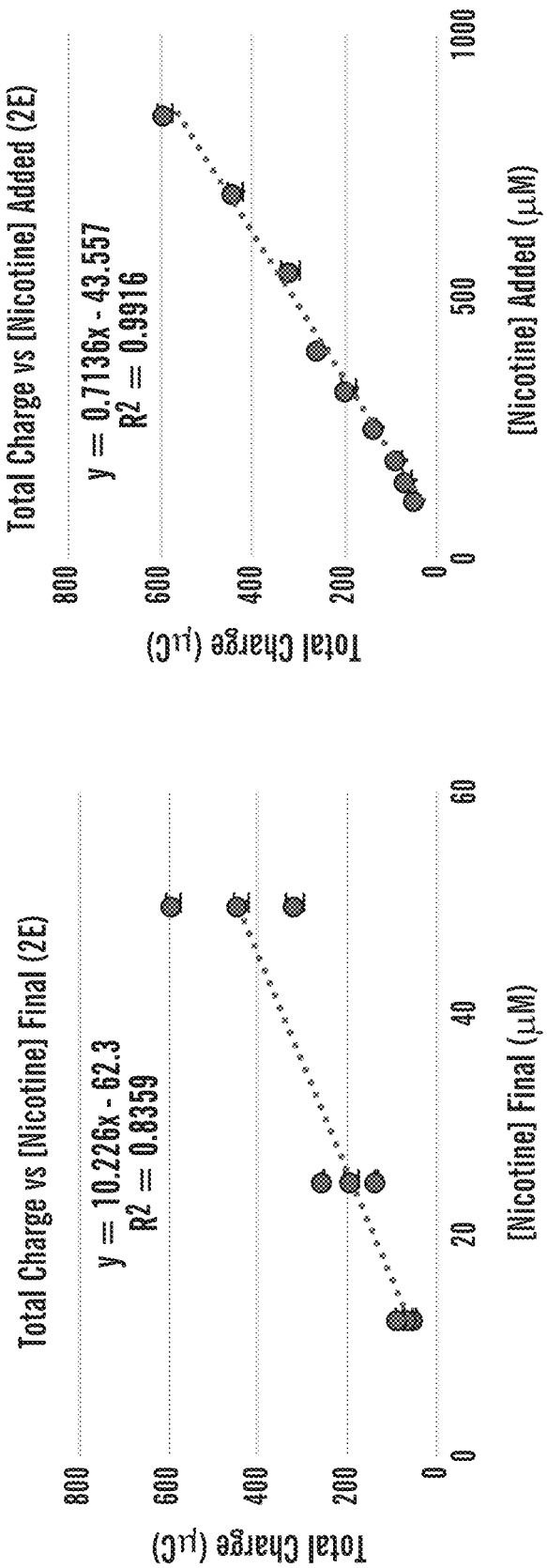

Next, the inventors assessed the reproducibly of the NicA2 biosensor with repeated nicotine measurements and also ability to predict nicotine amounts or levels in different biological samples. Using WT NicA2 in a 3 electrode biosensor, the current degenerated over time (FIGS. 18A and 18B), showing that the measured charge was significantly below the detected charge at different nicotine concentrations (0.25-5 nmol) (FIG. 18B). Next the inventors assessed the NicA2(N462H) mutant on a 3-electrode and 2-electrode biosensor, and determined that the 2-electrode biosensor had no drift and preserved the current over time with different concentrations of nicotine (FIG. 19B, 20C-20D) as compared to the 3-electrode biosensor (FIG. 19A, 20A-20B). Importantly, the 2-electrode NicA2(N462H) biosensor can detect nicotine at decreasing concentrations from 5-0.039 nmol, which demonstrated that the NicA2(N462H) biosensor has superior sensitivity to detect very low levels of nicotine (FIG. 19C), as well as demonstrating that the 2-electrode NicA2(N462H) biosensor is suitable for continuous detection of nicotine.

Figure 21A:
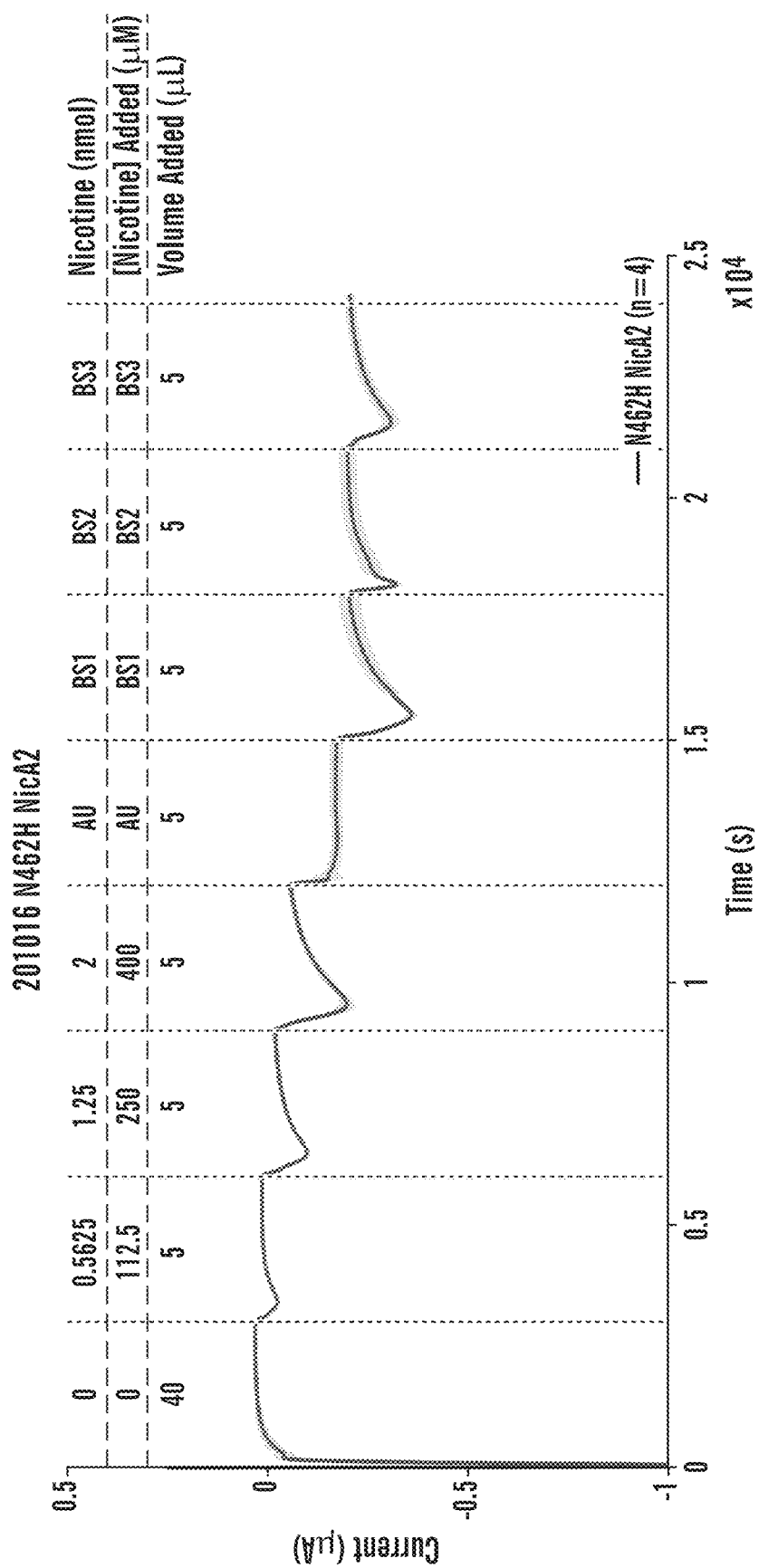
FIG. 21A-21B shows accurate detection of amounts of nicotine in artificial urine samples using the 2 electrode NicA2(N462H) biosensor.
Figure 21B:
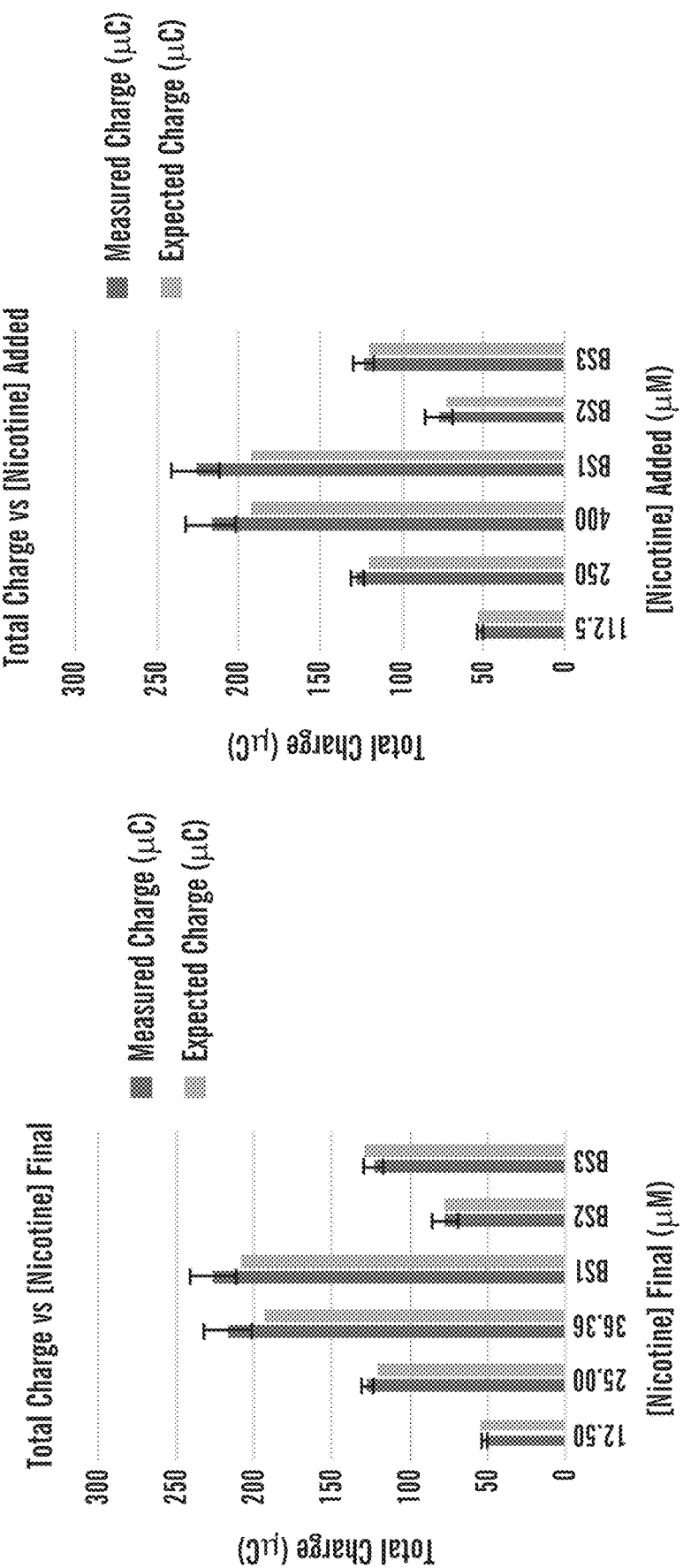
Figure 22B:
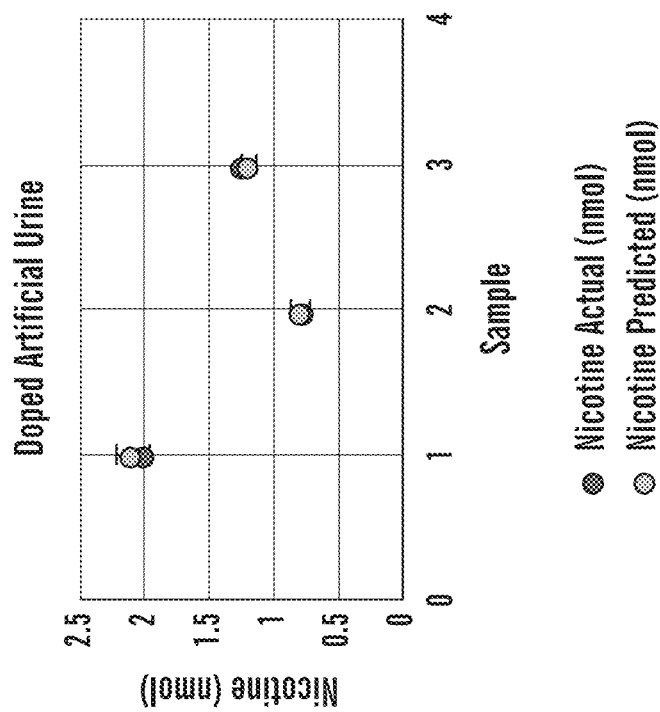
FIG. 22A-22B shows accurate detection of amounts of nicotine in blind doped artificial urine samples using the 2 electrode NicA2(N462H) biosensor.
Figure 22A:
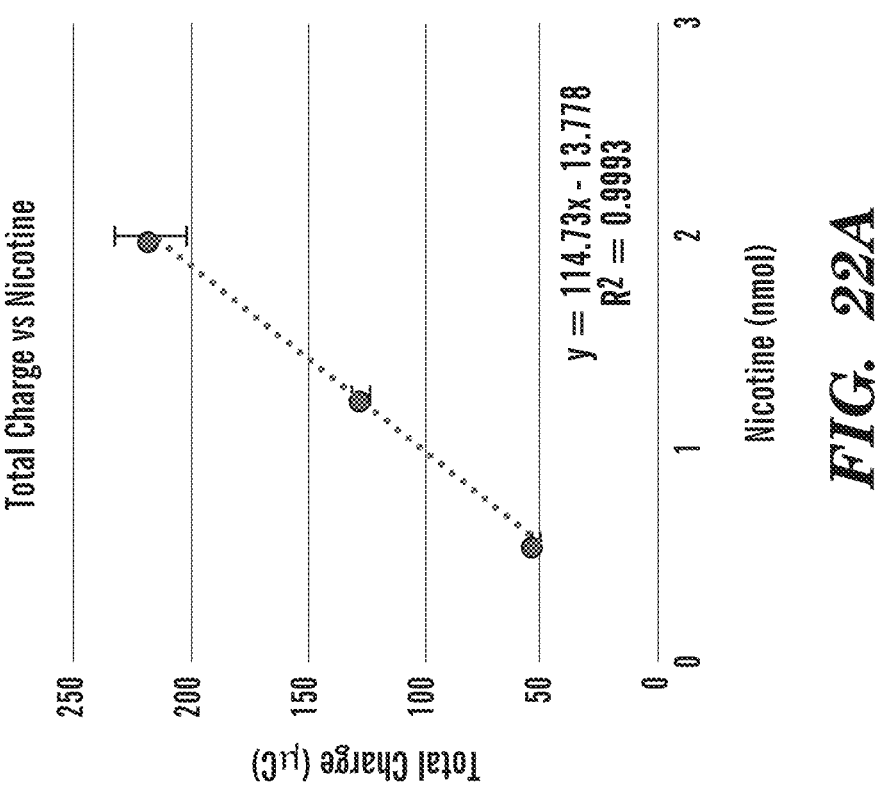
Figure 23A:
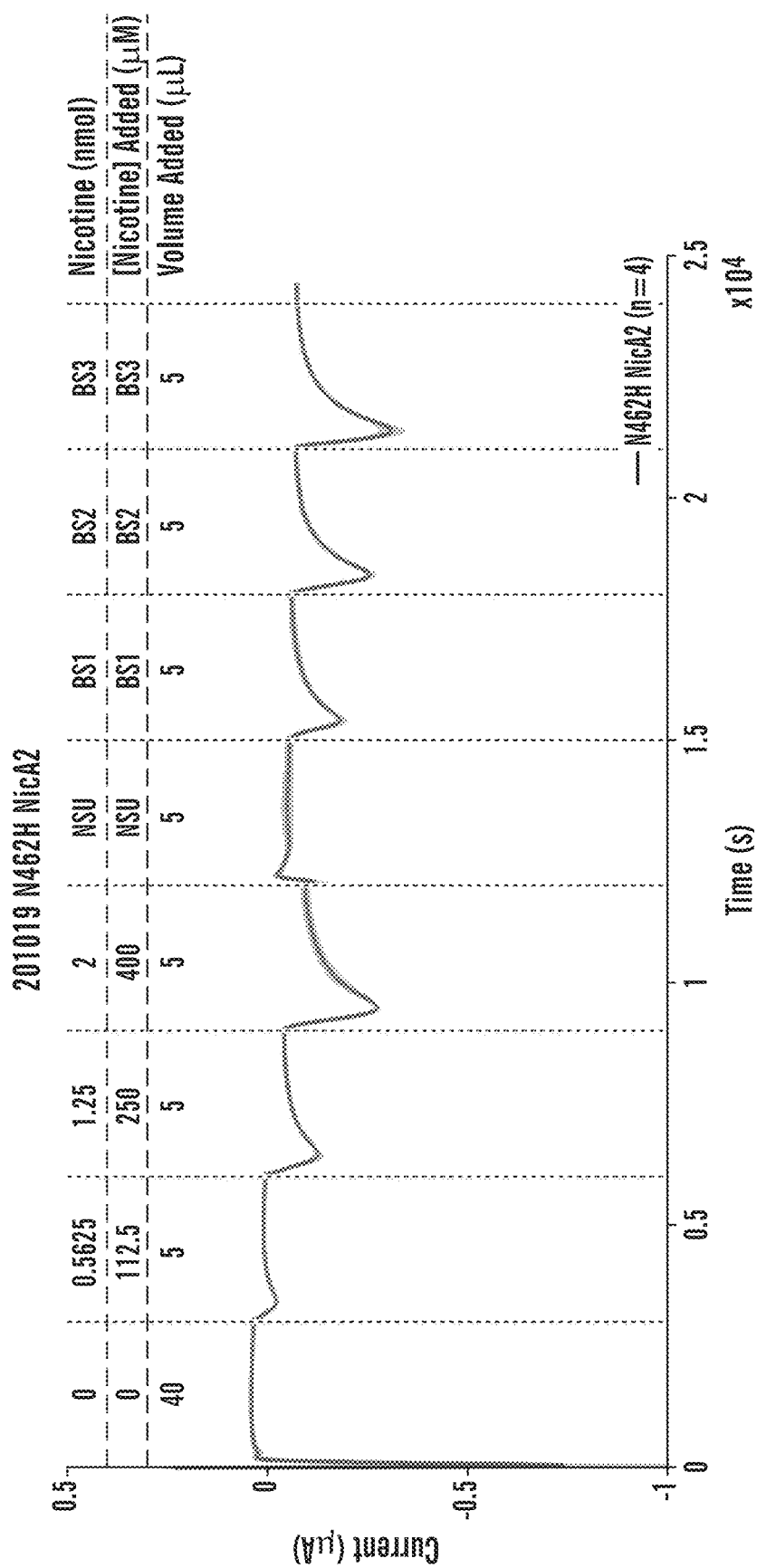
FIG. 23A-23B shows accurate detection of amounts of nicotine in non-smoker urine samples using the 2 electrode NicA2(N462H) biosensor.
Figure 23B:
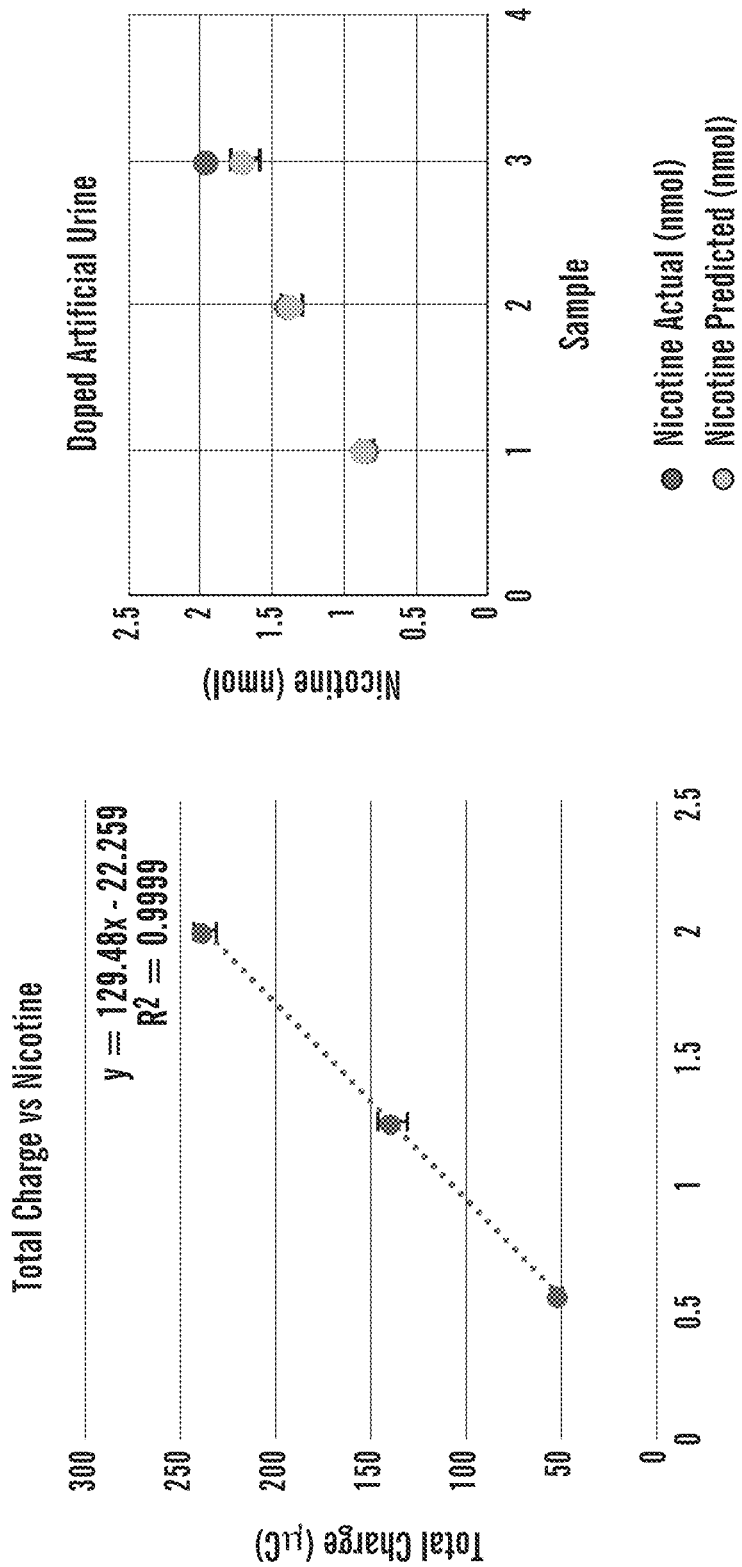
Figure 24A:
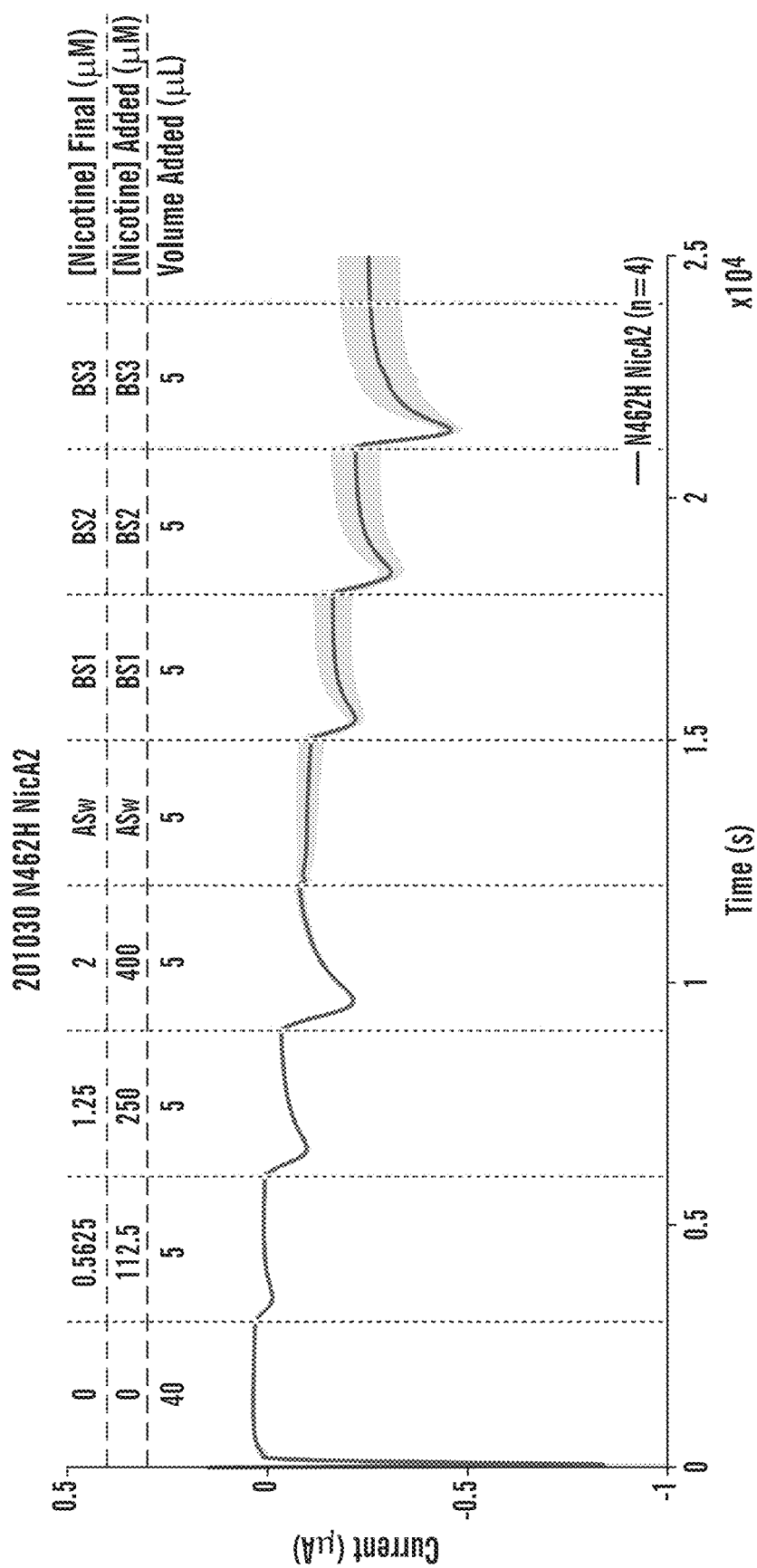
FIG. 24A-24B shows accurate detection of amounts of nicotine in artificial sweat samples using the 2 electrode NicA2(N462H) biosensor.
Figure 24B:
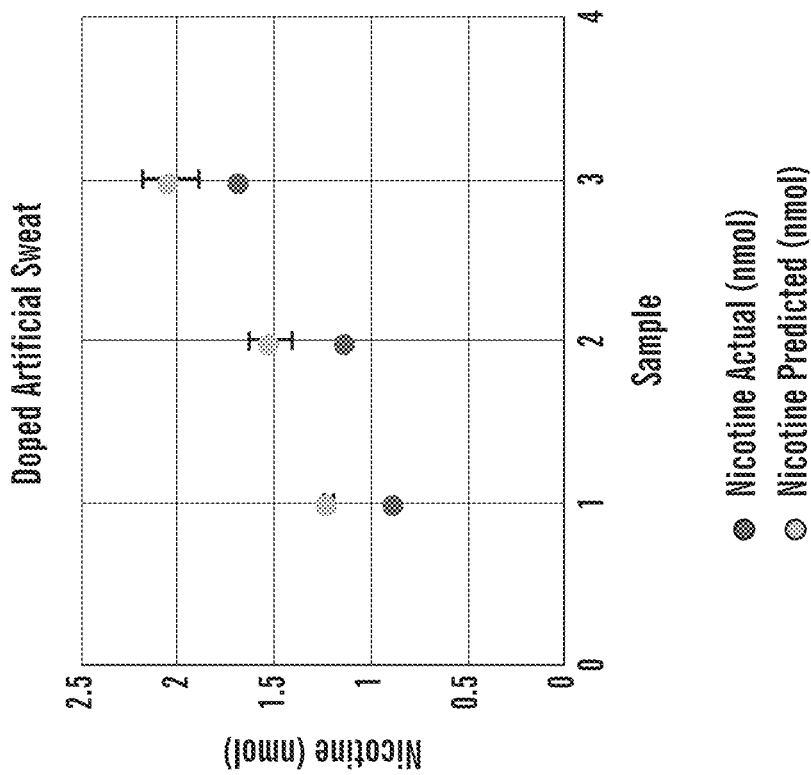
Figure 24B:
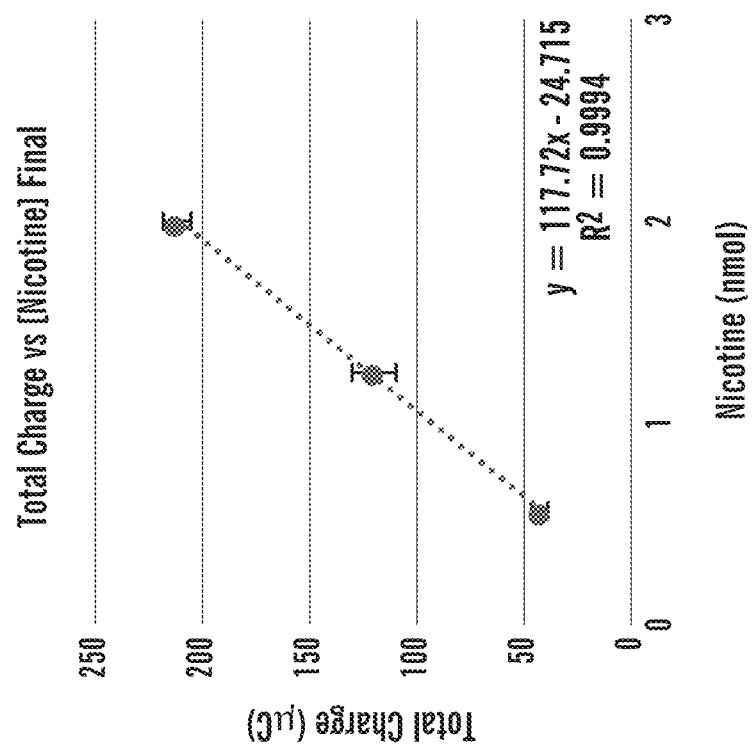
Figure 25:
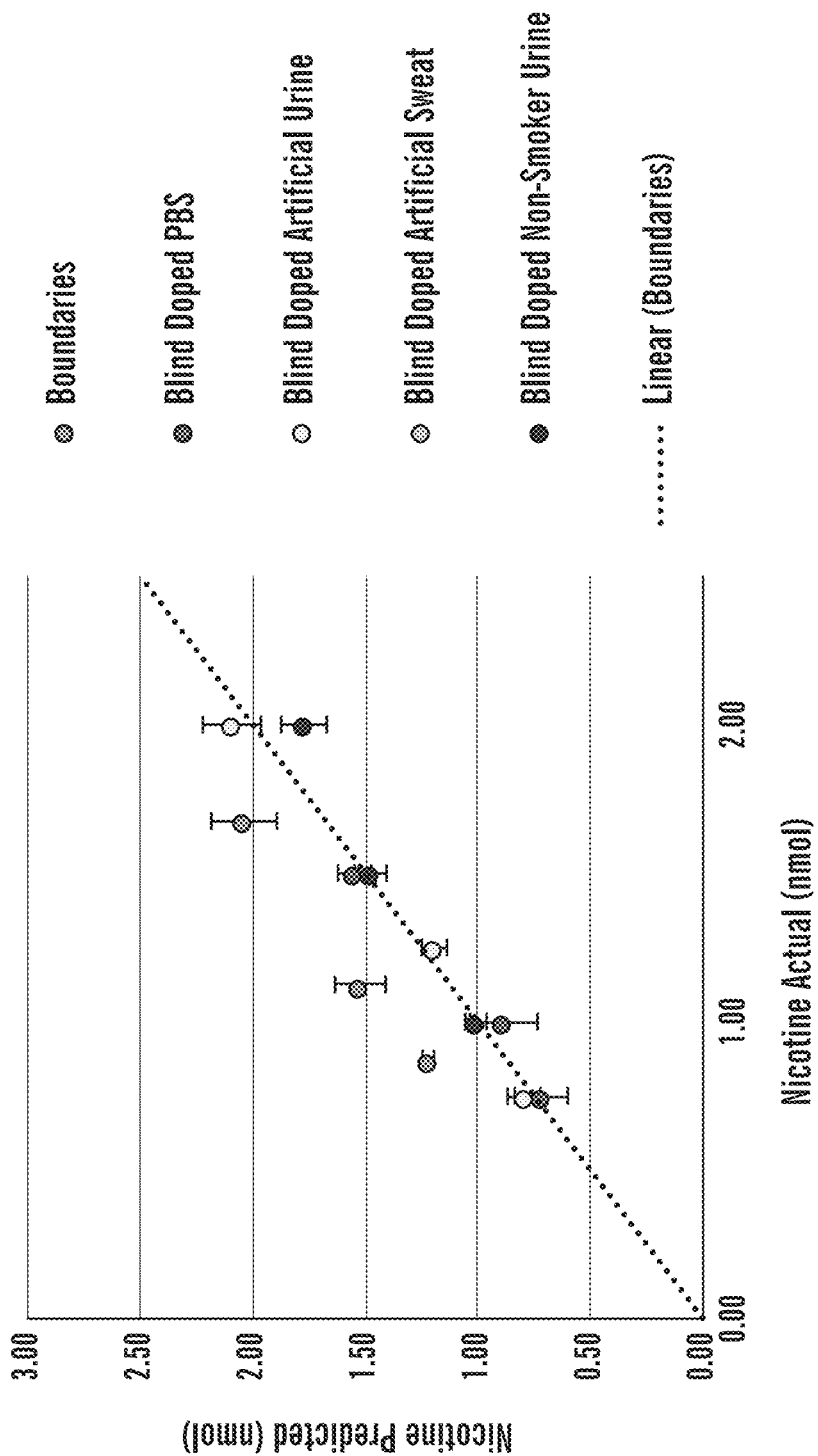
FIG. 25 shows the 2 electrode NicA2(N462H) biosensor can accurately predict the nicotine levels in blind nicotine-doped PBS, blind nicotine-doped artificial urine, blind nicotine-doped artificial sweat, or blind nicotine-doped non-smoker urine.
Figure 26:
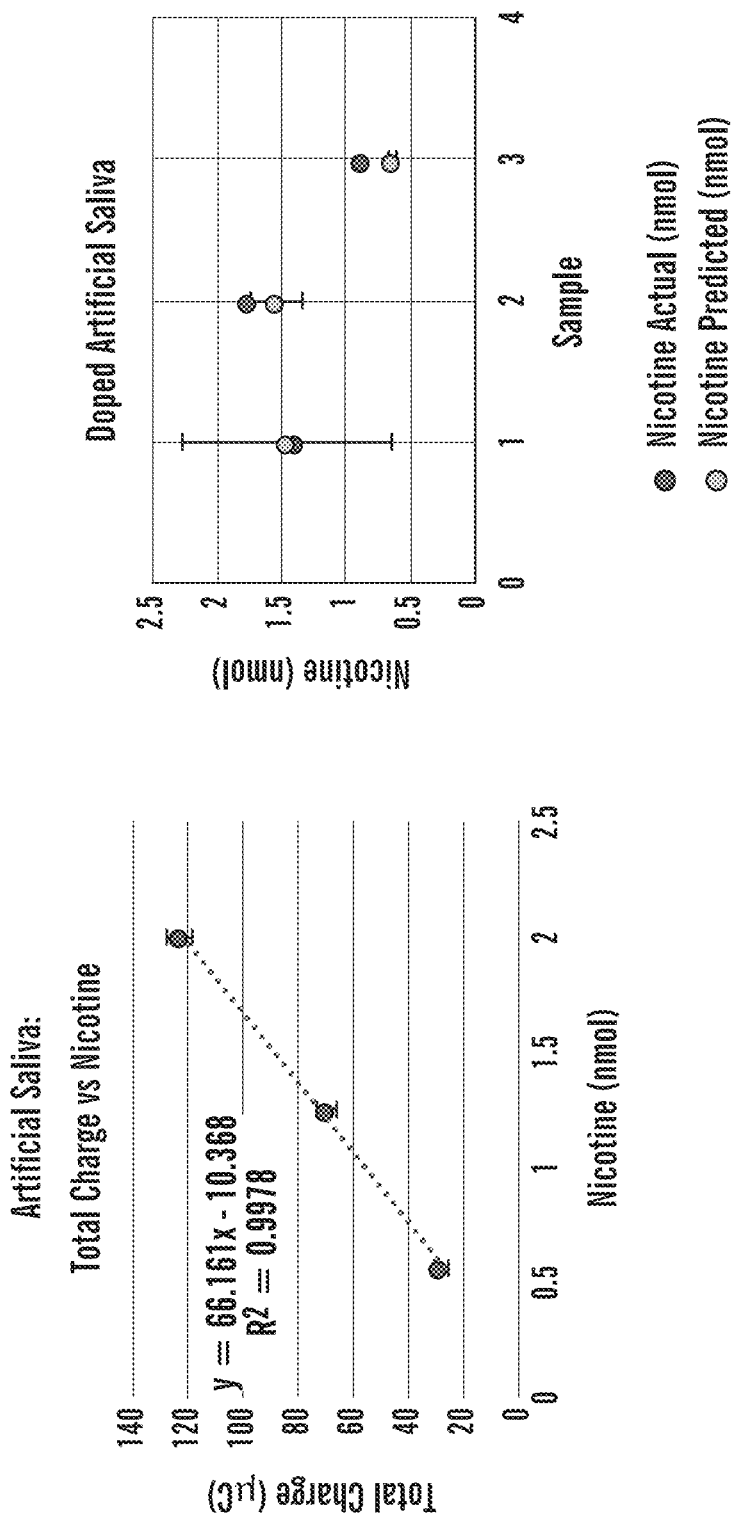
FIG. 26 shows accurate detection of amounts of nicotine in artificial saliva samples using the 2 electrode NicA2 (N462H) biosensor.

Using this optimized NicA2(N462H) nicotine biosensor, the inventors demonstrated the ability to accurately predict the amount of nicotine in a range of different biological samples (see, e.g., FIG. 25). In particular, accurate prediction of nicotine levels within the range of 0.5-2 nmol was performed in artificial urine (FIGS. 21A, 21B and 22B), doped non-smoker urine (FIGS. 23A-23B) and artificial sweat samples (FIGS. 24A-24B) and artificial saliva (FIG. 26).

Figure 27:
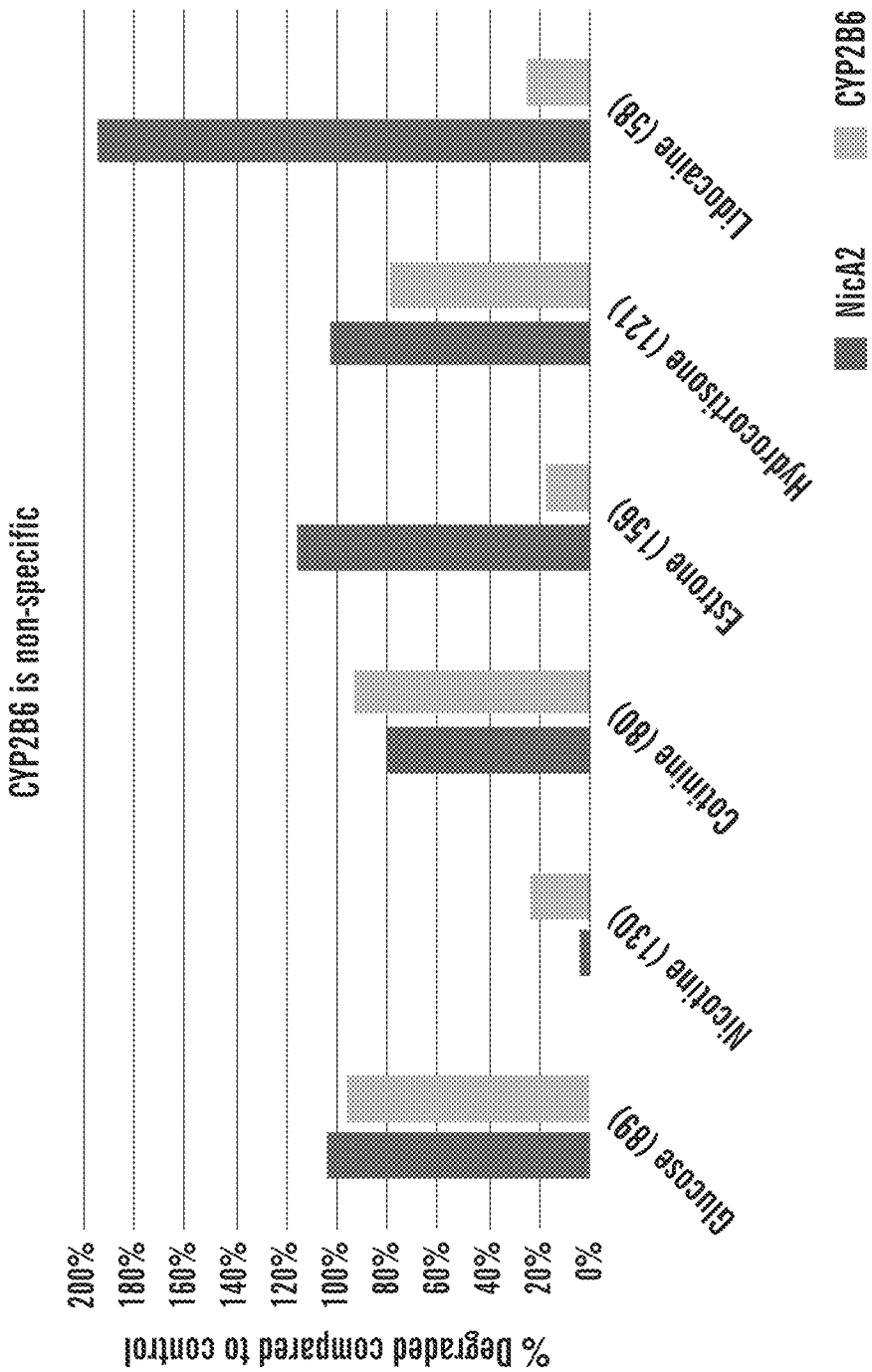
FIG. 27 shows the NicA2 biosensor disclosed herein is specific to nicotine, whereas another nicotine biosensor called CYP2B6 is non-specific and produces a current with glucose, cotinine, estrone, hydrocortisone, lidocaine. The results are normalized to 100% and y-axis is the percentage of molecule detected as compared to the control (no enzyme).

When the inventors assessed the specificity of NicA2 (N462H) compared to the CYP2B6 nicotine biosensor, NicA2(N462H) degraded only nicotine, whereas CYP2B6 degraded multiple different analytes in addition to nicotine, including glucose, cortinine, estrone, hydrocortisone and lidocane (FIG. 27) demonstrating that NicA2(N462H) is far superior as a biorecognition element specific for nicotine as compared to existing nicotine biosensors.

Example 3

Figure 28:
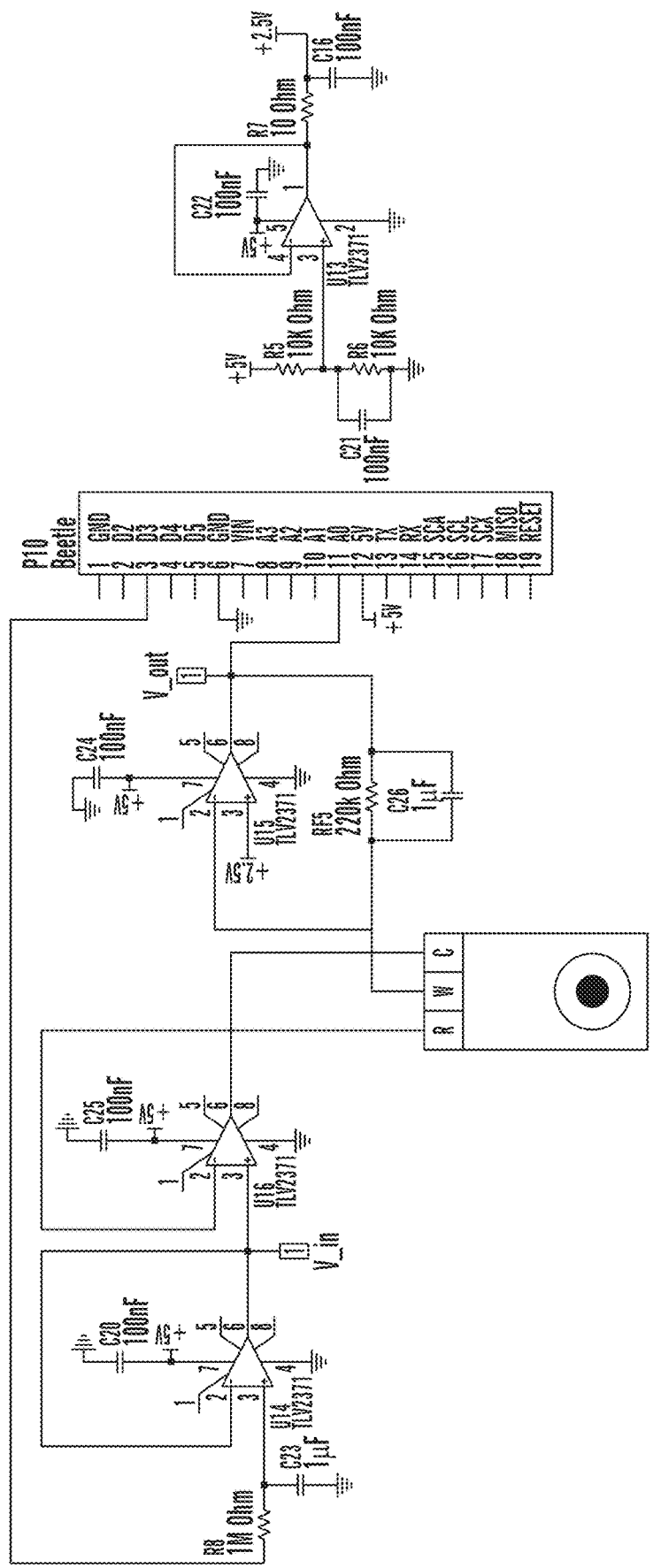
FIG. 28 shows an exemplary electronic circuit to control a 2- or 3-electrode SPE NicA2(N462H) biosensor.

Development of the NicA2(N462H) 2-Electrode Nicotine Biosensor into a Wearable Biosensor Accordingly, the inventors have optimized the nicotine biosensor herein into a wearable nicotine biosensor device, where the wearable nicotine biosensor comprises the NicA2 (N462H) enzyme immobilized on an optimized surface of a working electrode of a 2-electrode nicotine biosensor. Using an electrical circuit shown in FIG. 28, the inventors developed an exemplary wearable nicotine biosensor as shown in FIG. 29A-29B. One exemplary wearable biosensor can comprise an upper housing and a lower chamber, where the upper housing can comprise a removable lid and be configured to comprise the electrical circuit and other necessary components, e.g., battery etc. The electrical circuit can be configured to be in electronic communication with one of more of the electrodes on a screen printed electrode (SPE), which is located in the chamber below the upper housing. In one embodiment, the lower chamber comprises a sink for collecting sweat after it has passed over the working and/or reference electrode of the SPE by capillary action. For example, in one embodiment, the lower chamber comprises a SPE comprising a 2-electrode system, which is in fluid communication with a wick, where the wick can be a paper channel that, at the proximal end contacts the surface of a subjects' skin and at the distal end contacts the chamber sink, so that as sweat moves from the proximal to the distal end of the wick (or paper channel) by capillary action it passes over at least the working electrode of the SPE. The amount of nicotine in the sweat can be measured by the nicA2(N462H) enzyme on the working electrode in the SPE. The wick (or paper channel) can be readily replaced when saturated, and the SPE can be replaced after between 3-7 days. In some embodiments, the whole wearable nicotine biosensor device is affixed to the skin of a subject.

Figure 29C:
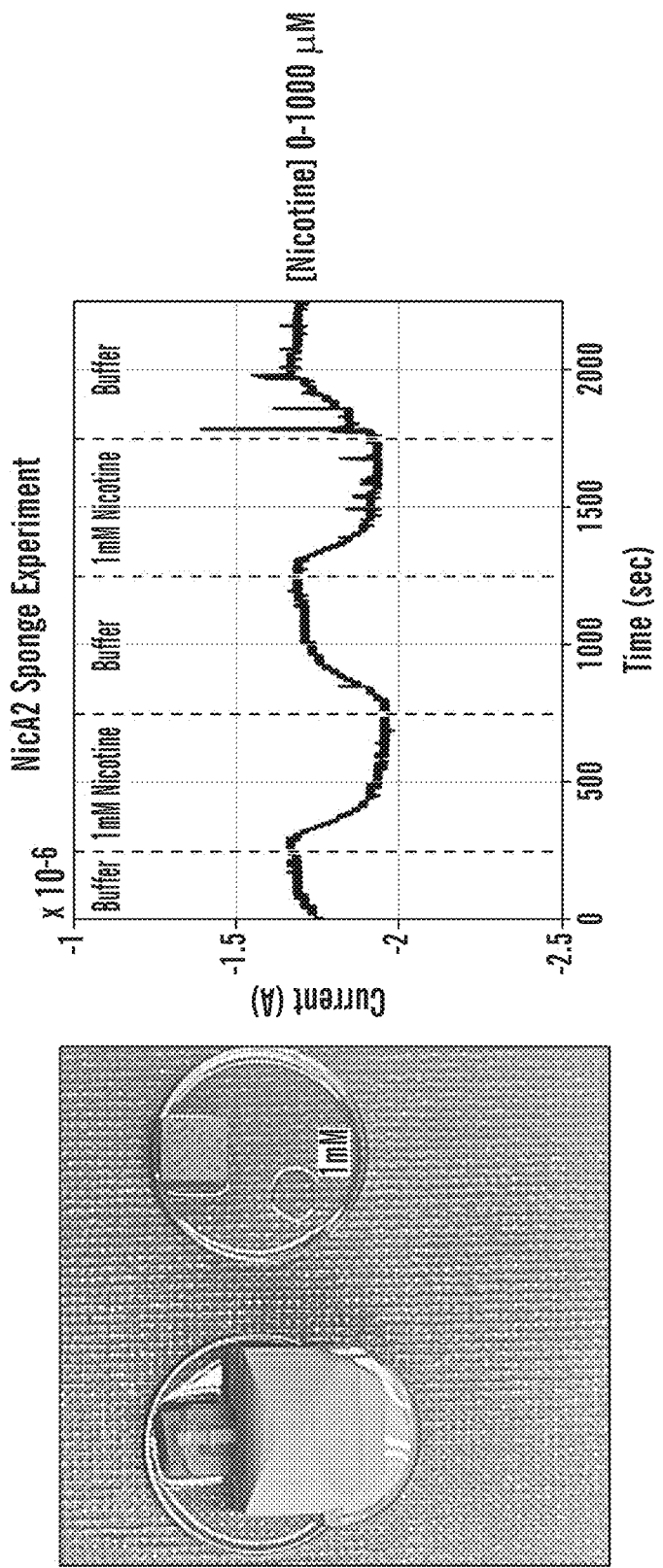
Figure 29D:
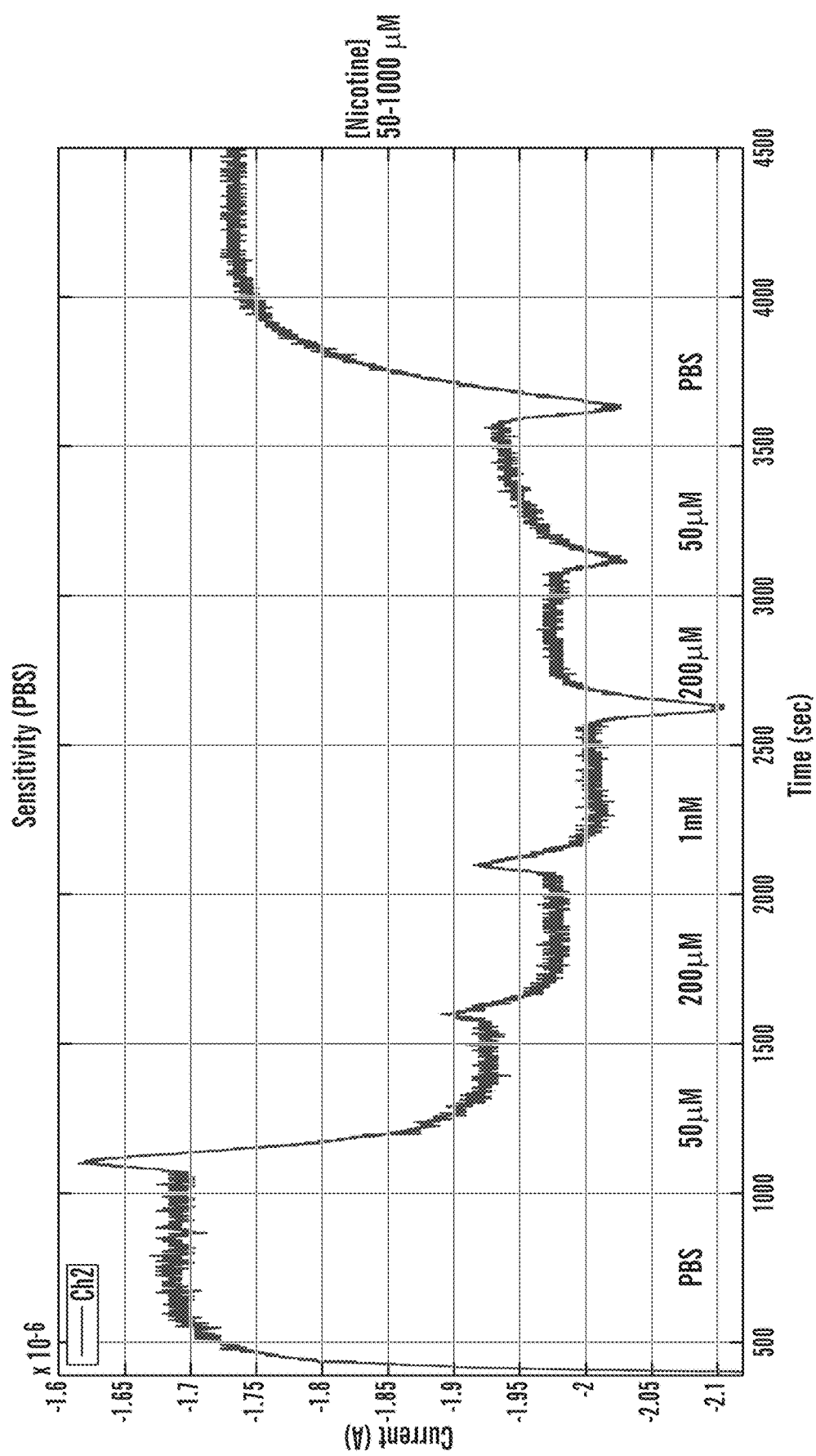
Figure 29D:
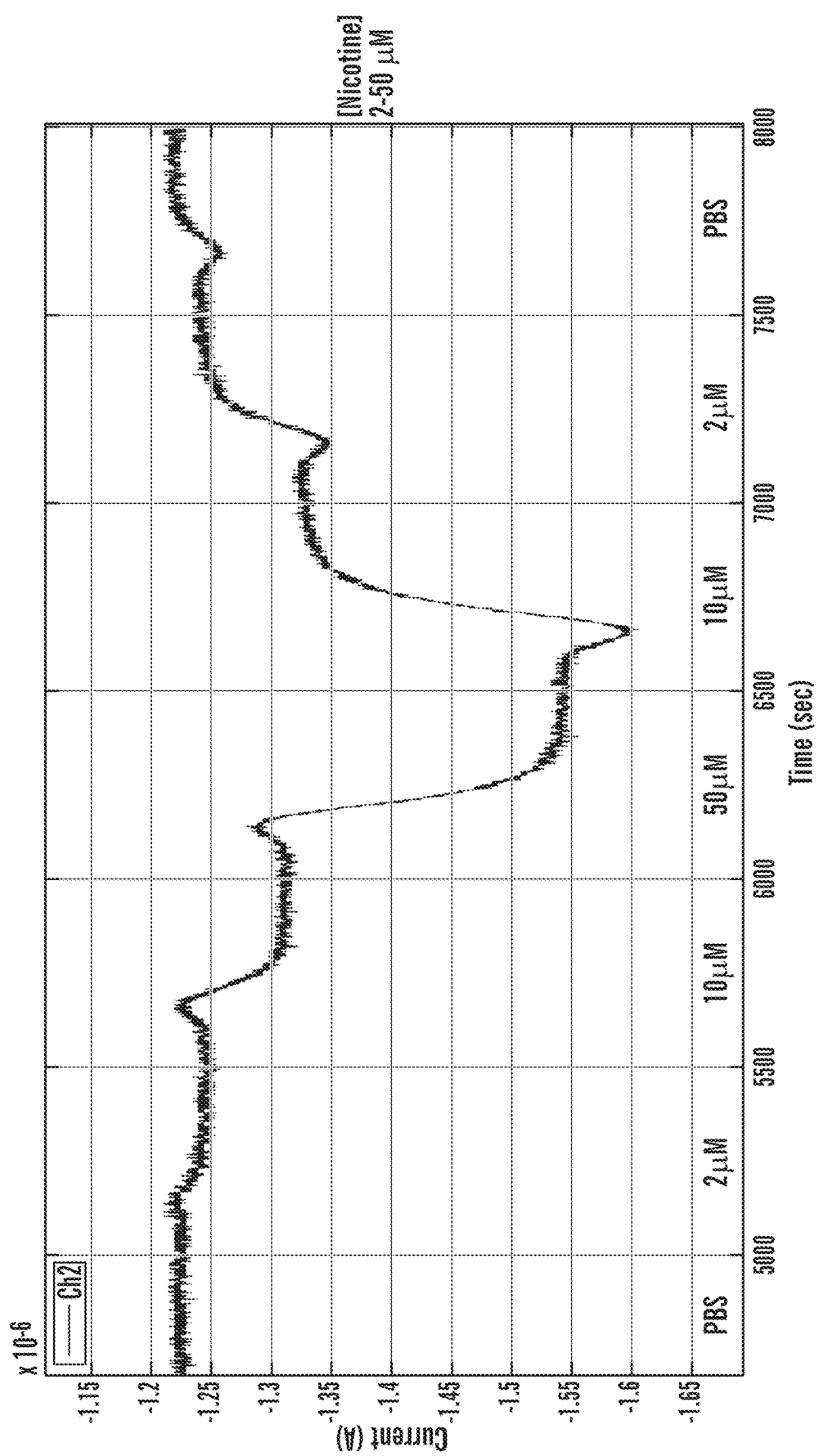
Figure 29E:
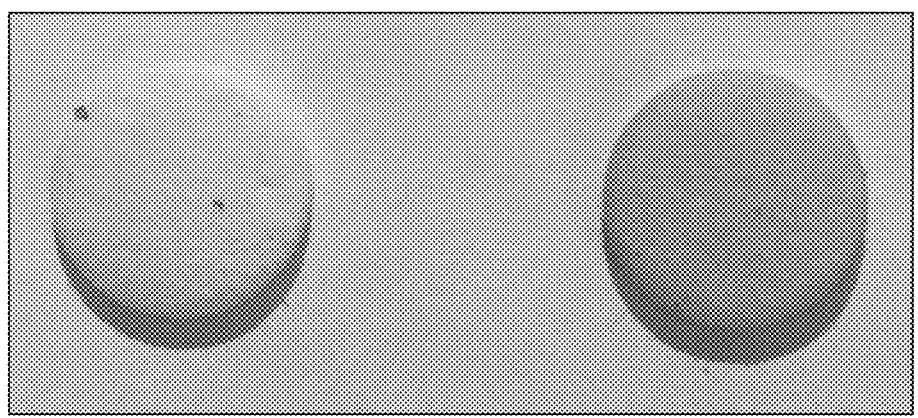

FIG. 29C demonstrates continuous, real-time, quantitative measurement of nicotine from artificial sweat using an exemplary wearable nicotine biosensor device disclosed herein, detecting nicotine between the range of 1-1000 µM, where the nicotine can be detected between the ranges 50-1000 µM and 2-50 µM (see. FIG. 29D). It is envisioned that the wearable nicotine biosensor comprising the NicA2 (N462H) enzyme exemplified herein can be readily adapted by one of ordinary skill in the art, including using an adhesive sheet to attach the wicking apparatus to the surface of the wearers skin, as disclosed in U.S. Pat. No. 9,820,692, or use of sweat collection pads as disclosed in U.S. Pat. Nos. 10,182,795 and 10,646,142, each of which are incorporated herein their entirety by reference.

Example 4

Current physiological sensors on the market such as the Fitbit™ and Apple Watch™ are limited to the detection of pH, hydration, temperature, heart rate, UX index, oxygen, sleep health, and energy expenditure with limited accuracy and reproducibility. Presently, the single best example of a commercially successful enzymatic biosensor is the glucose biosensor which has existed for approximately 50 years and has in the past two decades evolved into the continuous glucose monitor (CGM; see e.g., Olczuk et al. Diabetes Metab Syndr 2018, 12 (2), 181-187). By 2004, the glucose biosensor was responsible for about 85% of the world market for biosensors, estimated to be $5 billion USD at the time. By 2015, the market for glucose biosensors was valued at $15.3 billion USD and is expected to surpass $31 billion USD by 2024 per Hexa Research. The glucose monitor's functionality is based on the isolation and use of a glucose oxidase ($GO_X$) enzyme from *Aspergillus niger*, a fungus. Specifically, the ability of $GO_X$ to produce $H_2O_2$ from β-D-glucose and oxygen has been used to engineer the first glucose biosensor in an electrochemical fashion. With a mediator and a three-electrode system, $H_2O_2$ generated from $GO_X$ in response to β-D-glucose, along with a constant electrical potential, produces current which can be used as a readout for the amount of β-D-glucose present in solution.

Even with the immense commercial success of the glucose biosensor, comparable enzymatic biosensors have been limited. By 2007, commercially available enzyme based clinical tests could detect only glucose, lactate, choline, urea, uric acid, lysine, and oxygen. By 2008, amperometric based biosensors solely included those for glucose ($GO_X$), fructose (FDH), lactate ($LO_X$), glutamate ($LGO_X$), lysine (LDH), ethanol (ADH), and morphine (MDH) (see e.g., Dzyadevych et al. Irbm 2008, 29 (2-3), 171-180). The reason for the lack of a wide variety of biosensors is primarily due to two reasons. Of the seven biosensors listed, few have daily physiological relevance. The exception is the glucose biosensor due to diabetes affecting 382 million people and being the $8^{th}$ leading cause of death worldwide by 2013 which naturally created a large market and need for such a sensor. The second reason is that the current largest scientific vendors, such as Sigma-Aldrich™, have a limited inventory of enzymes such as $GO_X$, $LO_X$, FDH, $LGO_X$, and ADH with little intention of investing resources to provide new electrochemically relevant ones.

In response to the lack of electrochemical biosensors, the inventors have mined an unexplored reservoir of biorecognition elements in bacteria. Bacteria have evolved over 3 billion years to detect and respond to virtually all classes of stimuli relevant to human physiology, and thus contain molecular sensing enzymes of interest. Using a combination of whole transcriptome RNA sequencing (RNA-Seq) and a functional screen (Amplex® UltraRed Assay) the inventors have identified and isolated a number of biosensing oxidase enzymes, including NicA2. These redox enzymes can be used in biosensors, and the development of small, easy to use, and cheap electrochemical biosensors, which started from bacterial cultures for physiologically relevant analytes. These biosensors are typically composed of a screen-printed electrode (SPE), electron mediator (e.g. Prussian Blue), and a redox enzyme. This pipeline was used to build an enzyme-based electrochemical nicotine biosensor.

Out of all current preventable deaths nicotine is the leading cause. Approximately 6 million mortalities can be accounted for by nicotine use per year globally. Tobacco-related deaths cost the United States approximately $300 billion USD each year. Furthermore, nicotine is singularly responsible for the dependence-forming properties of tobacco smoking. Although most smokers are aware of the detrimental health consequences of smoking, the addictive properties of nicotine make it difficult to abstain in short periods of time or immediately. At the moment, leading pharmacological aids for quitting, which include the antidepressant drug bupropion and varenicline, show only a 15-30% abstinence rate after 1 year of treatment. Therefore, breaking nicotine addiction is challenging and relapse rates remain high. The extremely rapid timescale of nicotine action renders existing techniques for monitoring of nicotine levels ill-suited (see e.g., Benowitz et al. NIDA Res Monogr 1990, 99, 12-29). An alternative to pharmacological aids and their side effects is self-disciplined termination through the advent of a device which continuously measures internal nicotine levels. Such a biosensor offers smokers the ability to ease their dependency on nicotine addiction by incremental cessation. Another possibility is for a nicotine biosensor to monitor and regulate the amount of nicotine being administered to a patient, in concordance with a physician, or act as an acute-dosing product in times of particularly strong cravings (see e.g., Wadgave and Nagesh, L., Nicotine replacement therapy: An overview. International journal of health sciences 2016, 10 (3), 425).

Existing biosensor designs outside of electrochemical ones have noticeable limitations. The most common design utilizes a biorecognition element coupled to a physicochemical transduction mechanism (see e.g., Turner, A., Trends in Biotechnology 2013, 31 (3), 119-120; Mary et al., Measurement Science and Technology 2014, 25 (3), 032001; Evtugyn, G., Biosensors: Essentials. Springer: 2014; Vol. 84). The gold standard for clinical relevant analytes use antibodies as this biorecognition element. However, antibodies suffer from several important shortcomings: 1) Traditionally, antibody production requires animal immunization followed by monoclonal isolation and is expensive, highly variable, time consuming, and challenging with small molecule analytes (see e.g., Mary et al. 2014, supra). More recent recombinant techniques simplify this process and improve reproducibility, but the process remains expensive due to the use of mammalian cell lines or heterologous hosts (see e.g., Frenzel, et al. Frontiers in immunology 2013, 4, 217; Hornsby et al. Molecular & cellular proteomics: MCP 2015, 14 (10), 2833-47). 2) Binding of the analyte to the antibody leads to only a small physicochemical change, requiring the use of a secondary assay to detect the binding event (see e.g., Mary et al. 2014, supra; az-Gonzale et al. Electroanalysis 2005, 17 (21)). Enzyme-linked immunosorbent assays (ELISAs) are the most common transduction approach and are multistep, labor-intensive, time-consuming, and not well-suited for integration into wearable technology (see e.g., az-Gonzale et al. 2005, supra). More recently, aptamers have been studied as an alternative to antibodies, but also lack an intrinsic transduction mechanism (see e.g., Mary et al. 2014, supra; Marrazza, G., Aptamer Sensors. Biosensors (Basel) 2017, 7 (1)). Due to these limitations, non-electrochemical biosensors often are suboptimal design choices for physiological monitoring.

Numerous non-enzymatic nicotine sensors have been reported in literature. These include electrochemical biosensors which function by electropolymerization of o-aminophenol (see e.g., Wu et al. Frontiers of Chemistry in China 2006, 1 (2), 183-187), alumina-coated silica nanocomposites (see e.g., Wang et al. Electrochemistry Communications 2009, 11 (4), 733-735), pyrolytic graphite (see e.g., Sims et al. Sensors and Actuators B: Chemical 2010, 144 (1), 153-158), cerium nanoparticles (see e.g., Fekry et al. RSC Advances 2015, 5 (64), 51662-51671), carbon nanotubes (see e.g., Goodarzi et al. Journal of Nanostructure in Chemistry 2015, 5 (3), 237-242), carboxylated graphene (see e.g., Xiao et al. Analytical Methods 2015, 7 (3), 1147-1153), polydopamine functionalized nanoparticles (see e.g., Jing et al. Sci Rep 2016, 6, 29230), and nitrogen-doped graphene sheets (see e.g., Li et al. J. Electroanal. Chem. 2017, 784, 77-84). The lowest limit of detection was reported by the polydopamine functionalized nanoparticles at 15 nM and a detection range of 0.05-500 µM (see e.g., Jing et al 2016, supra), and it is the only nicotine sensor thus far to prove unresponsiveness to cotinine, the primary metabolite of nicotine in the human body. Furthermore, the same biosensor was reported to have 92.8% activity after storage at 4° C. for four weeks (see e.g., Jing et al 2016, supra). Although the reported biosensors have demonstrated sensitivity and stability, they require optimization and designing de novo for the particular analyte of interest. In contrast, evolution of bacterial enzymes for the recognition and metabolism of a multitude of physiologically relevant analytes has already been performed by nature. A pipeline to identify them in a timely fashion has not been described. Once identified, if the enzymes are not selective, sensitive, fast, or stable as desired, directed evolution, which has been well documented, can be used to improve them (see e.g., Lutz, S.; Iamurri, S. M., Protein Engineering: Past, Present, and Future. In Protein Engineering, Springer: 2018; pp 1-12).

Therefore, redox enzymes are the detection and transducing element, analogous to the glucose biosensor, but with the use of new enzymes identified from microbes. Described herein is the generation of the first enzyme-based electrochemical nicotine biosensor using nicotine oxidoreductase (NicA2). The example shown here offers a platform for designing future biosensors for physiological monitoring.

Genomic Mining

It has been known since the 1950s that there are nicotine degrading bacteria (see e.g., Liu et al. Applied microbiology and biotechnology 2015, 99 (9), 3775-3785). Certain bacterial strains, such as *Pseudomonas putida* S16 first isolated from a tobacco field in Shandong, People's Republic of China, are reported to be able to grow on nicotine as its sole carbon source (see e.g., Tang et al. PLoS Genet 2013, 9 (10), e1003923). Since *P. putida* S16 is known to metabolize nicotine into fumaric acid through the pyrrolidine pathway *P. putida* S16 was chosen as a screening proof of concept to mine for the reported nicotine degrading enzyme, NicA2, to build a novel enzyme based biosensor (see e.g., Tang et al. 2013, supra; Yu et al. J Bacteriol 2011, 193 (19), 5541-2). The first nicotine sensitive cluster, nic1, in *P. putida* S16 included nicotine oxidoreductase (NicA1) and HSP hydroxylase (HspA) and then further expanded to become nic2 (see e.g., Tang et al. Appl Environ Microbiol 2008, 74 (5), 1567-74; Tang et al., Appl Environ Microbiol 2009, 75 (3), 772-8; Tang et al. Sci Rep 2012, 2, 377). In an update of the nic2 cluster, nicA2, encoding another nicotine oxidoreductase, was identified and subsequently characterized where it was shown that NicA2 had only 10.9% amino acid identity to NicA1 (see e.g., Tang et al. 2013, supra). Once the nicA2 gene was knocked out the strain could no longer degrade nicotine (see e.g., Tang et al. 2013, supra). This detail proved that the NicA2 enzyme was the first enzyme in the pathway responsible for metabolizing nicotine and so it was the main target to see if a RNA-Seq based approach could identify redox enzymes to build enzyme-based biosensors.

To identify redox enzymes specific to nicotine, RNA-Seq with was performed and without nicotine in *P. putida* S16. In order to see a distinct change in the transcriptome expression levels without drastically affecting bacterial physiological growth, serial dilution growth curves were performed the key genomic island, nic2 was identified as responsive to nicotine using computational analyses (see e.g., FIG. 1). In the nic2 genomic island, the most highly differentially expressed enzyme encoding gene was nicA2, the target oxidoreductase enzyme. These results validated the screening pipeline and showcased the ability to isolate biosensing parts from microbes which can be used for device fabrication.

NicA2 Enzyme Characterization

The FAD-binding nicotine oxidoreductase, NicA2, is an essential enzyme of the pyrrolidine pathway which converts nicotine to n-methylomysomine (see e.g., Tararina et al. Biochemistry 2016, 55 (48), 6595-6598, the content of which is incorporated herein by reference in its entirety). The nicA2 gene was cloned into a recombinant vector, expressed, purified, and characterized. Kinetic values of NicA2 showed increased selectivity, but reduced catalytic activity compared to well-studied redox enzymes such as glucose oxidase ($GO_x$) and lactate oxidase ($LO_x$) (see e.g., Table 2 above; see e.g., Xue et al. 2015, supra). The NicA2 enzyme was also reported to have impressive stability as it was able to retain activity over 3 weeks at 37° C. in HEPES buffer at pH 7.4 (see e.g., Xue et al. 2015, supra).

Figure 2E:
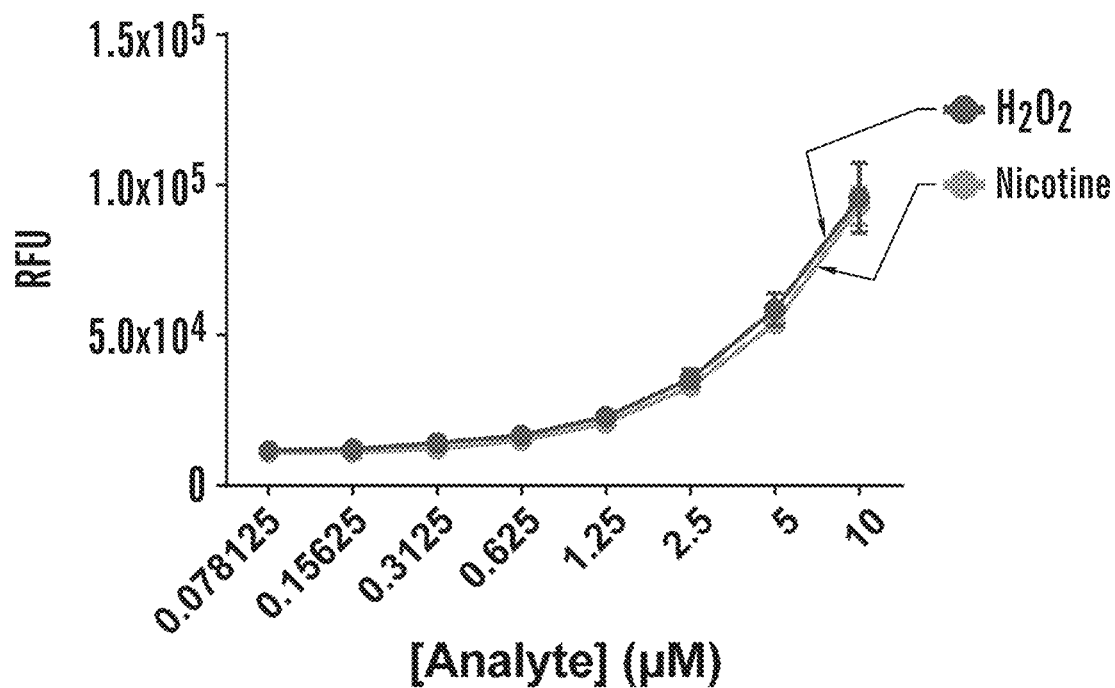

It is known that NicA2 is an oxidoreductase but its mechanism of $H_2O_2$ production from nicotine was not yet characterized. This information was critical for engineering an electrochemical biosensor because the ratio of $H_2O_2$ produced from a single nicotine molecule directly affects the current response in an electrochemical setup and therefore the final determined analyte concentration in a solution. NicA2 $H_2O_2$ production was characterized through the Amplex® UltraRed Assay (see e.g., FIG. 2A). In the presence of nicotine, NicA2 converts the analyte to n-methylmyosmine and $H_2O_2$. In the presence of $H_2O_2$, horseradish peroxidase (HRP) converts $H_2O_2$ and Amplex® UltraRed into oxygen and resorufin, a fluorescent molecule. The fluorescent readout of resorufin was therefore used to assess $H_2O_2$ production. Under a serial dilution of nicotine and the same amount of NicA2 there were corresponding levels of fluorescence decrease (see e.g., FIG. 2B-C). With a consistent amount of nicotine in solution and a serial dilution of NicA2, there was no change in fluorescence, but only in the rate of $H_2O_2$ production (see e.g., FIG. 2D). This indicated that $H_2O_2$ production was not enzyme limited, but substrate limited. The final crucial assessment was to know the ratio of $H_2O_2$ production compared to analyte addition. In order to determine this a calibration curve of $H_2O_2$ was performed and the fluorescence levels were compared to that of nicotine addition at the same concentrations (see e.g., FIG. 2E). It was found that NicA2 produces $H_2O_2$ from nicotine at a 1:1 ratio. Therefore, NicA2 produces equivalent fluorescence with the Amplex® UltraRed Assay™ and current electrochemically with nicotine and $H_2O_2$.

Electrochemical Biosensor Characterization

The electrochemical biosensors were assembled and connected to a potentiostat (see e.g., FIG. 5-6). The electrochemical biosensor was composed of a Screen-Printed Prussian Blue/Carbon Electrode with a Ag/AgCl reference electrode (RE). To immobilize NicA2 onto the SPE working electrode (WE) chitosan polymer was used. Chronoamperometric responses were recorded over time with a potential −0.2 V versus the RE.

To quantify the current response, chronoamperometric experiments were performed whereby various concentrations of nicotine in PBS (0-1000 μM) were added to the biosensor with 2 nmol NicA2 (see e.g., FIG. 3A). A calibration curve of current to nicotine concentrations was produced from a range of 0-200 μM (see e.g., FIG. 3B) and the coefficient of determination, $R^2$, was found to be 0.9768. A chronoamperometric assay with 200 μM nicotine is shown (see e.g., FIG. 3B inset). Maximal current (~250 nA) was reached after 4000 seconds with a return to baseline after 6000 seconds. The level of nicotine in active smokers' urine (see e.g., Table 3) falls into this range.

The selectivity of the biosensor was evaluated by measuring the chronoamperometric response in the presence of common interferents at relevant physiological concentrations in sweat (see e.g., FIG. 3C). These co-existing compounds had a minimal effect upon the response to nicotine. Similar experiments were performed to evaluate the selectivity of the sensor to cotinine. Cotinine, the primary metabolite of nicotine in the human body, had a minimal effect upon the nicotine response (see e.g., FIG. 3C). Finally, to evaluate NicA2 dependence of the nicotine sensor's mechanism of action, myosmine, an inhibitor of NicA2, was added in the middle of a chronoamperometric experiment (see e.g., FIG. 3D). Minimal responses were observed from myosmine alone (red bar) or nicotine addition after NicA2 was inhibited by myosmine (purple bar).

The inventors have developed a system and platform for identifying enzymatic sensor parts for virtually an unlimited number of analytes. Furthermore, the sensor can be brought to a closed-loop continuous measurement system similar to the glucose biosensor. This approach thus allows capitalization on the enormous and untapped reservoir of microbes to identify biosensing elements for any analyte of interest including, but not limited to, hormones, pharmaceutical agents, pesticides, toxins, neurotransmitters, immunomodulators, metabolites, and carcinogens.

Example 5

Prior art Nicotine Biosensors

The most accurate methods for currently measuring nicotine require sample collection followed by mass spectroscopy analysis. These methods are not practical for portable or point-of-need applications. Most nicotine detecting kits use antibodies to give a positive or negative result with a certain cutoff (e.g. NicAlert™, NicoTests™, and One Step™). These kits lack a continuous measurement and cannot specify how much nicotine is present in a solution. Furthermore, these kits lack a digital interface which could communicate information with a physician or one's phone or computer. Although these kits are fairly cheap, the cost effectiveness of one-time use does not compare to continuous monitoring. If one were to receive quantitative results, expensive and time consuming analytical techniques such as gas or liquid chromatography-mass spectrometry (GCMS or LCMS) would have to be used which are not accessible to a majority of users.

Nicotine Sensors

For nicotine sensing in second-hand smoke, there is only one known commercial competitor (FreshAir™); see e.g., See e.g., Richter and BelBruno (2012) Journal of Applied Polymer Science 124(4): 2798-2806; Liu et al. (2013) Nicotine Tob Res 15(9): 1511-1518; Antwi-Boampong et al. (2014) IEEE Sensors Journal 14(5): 1490-1498; Antwi-Boampong and BelBruno (2013) Sensors and Actuators B: Chemical 182: 300-306; U.S. Pat. Nos. 9,429,536, 9,228, 988, 9,034,262, 10,451,598, 10,024,814; US patent publications US 2016/0370310, US 2015/0132857, US 2018/0292341; and international PCT publication WO 2012/034115; the contents of each of which are incorporated herein by reference in their entireties.

The FreshAir™ technology which detects nicotine present in air has several disadvantages compared to the nicotine biosensor described herein. First, the technology used by FreshAir™ molecularly imprinted polymers (MIP), is notorious for its non-specificity. It is noteworthy that no specificity data is presented in any publications of this technology. The nicotine biosensor described herein is highly specific. Second, MIPs are not catalytic. The enzyme based approach described herein is catalytic and thus allows for much higher signals for a given nicotine concentration. Third, the FreshAir™ sensor does not permit itself to be wearable technology as it is limited to being plugged into a wall outlet. Although there is published work showing the ability to quantify nicotine concentrations in air in real time, the commercial FreshAir™ device at its current state does not report the weight or concentration of nicotine present in the air, but only if a cigarette has been smoked or not. Moreover, the current FreshAir™ implementation can require data processing at a remote location. Finally, the nicotine biosensor described herein is a cheaper device than FreshAir™ ($120 USD) and is a portable device which can be worn and linked to a smart phone.

Several other non-enzymatic nicotine biosensors have been reported. These include biosensors which function by electropolymerization of o-aminophenol (see e.g., Wu et al. 2006, supra), alumina-coated silica nanocomposites (see e.g. Wang et al. 2009, supra), pyrolytic graphite (see e.g., Sims et al., 2010, supra), cerium nanoparticles (see e.g., Fekry et al., 2015, supra), carbon nanotubes (see e.g., Goodarzi et al. 2015, supra), carboxylated graphene (see e.g., Xiao et al. 2015, supra), polydopamine functionalized nanoparticles (see e.g., Jing et al. 2016, supra), and nitrogen-doped graphene sheets (see e.g., Li et al. 2017, supra). The lowest limit of detection was reported by the polydopamine functionalized nanoparticles at 15 nM and a detection range of 0.05-500 μM (see e.g., Jing et al. 2016, supra), and it was the only nicotine device proven unresponsiveness to cotinine, the primary metabolite of nicotine in the human body.

While numerous non-enzymatic nicotine sensors have been reported in literature, including electrochemical biosensors which function by electropolymerization of o-aminophenol[157], alumina-coated silica nanocomposites[158], pyrolytic graphite[159], cerium nanoparticles[160], carbon nanotubes[161], carboxylated graphene[162], polydopamine functionalized nanoparticles[163], and nitrogen-doped graphene sheets[164], their utility for real-time detection of nicotine, and their level detection of nicotine at physiologically low nicotine levels is limited. The lowest limit of detection was reported by the polydopamine functionalized nanoparticles at 15 nM at a detection range of 0.05-500 μM[163]. The same publication from the list referenced was the only one to prove unresponsiveness to cotinine, the primary metabolite of nicotine in the human body[165]. Furthermore, the same biosensor was reported to have 92.8% activity after storage at 4° C. for four weeks[163]. Existing nicotine sensors and their detection limits are reported (Table 4).

TABLE 1

Table of existing nicotine sensors and their linear ranges and limits of detection[163].

| Electrode | Linear range (µM) | LOD (µM) | Reference |
|---|---|---|---|
| MWCNT | 31-220 | 7.6 | 166 |
| Carbon paste | 50-500 | 6.1 | 167 |
| Boron-doped diamond electrode | 9.9-170 | 6.1 | 168 |
| Pencil graphite electrode | 7-107.5 | 2 | 169 |
| Electrochemically activated GCE | 1-200 | 0.7 | 170 |
| Molecularly imprinted TiO$_2$-modified electrodes | 0-5000 | 4.9 | 171 |
| CuNPs | 1-90 | 0.164 | 161 |
| Poly(4-Amino-3-Hydroxynaphthalene Sulfonic Acid) | 1-200 | 0.866 | 172 |
| MWCNT-alumina-coated silica | 5-400 | 1.42 | 158 |
| PDA-RGO/Au | 0.05-500 | 0.015 | 163 |

Although the reported biosensors have shown impressive sensitivity and stability, they require optimization and designing de novo for the particular analyte of interest. It happens to be that nicotine is electroactive, but other analytes of interest might not be or the electroactivity coincides with other interferents in solution reducing selectivity. In contrast, the evolution of bacterial enzymes for the recognition and metabolism of a multitude of physiologically relevant analytes has already been performed by nature. An imperfect example of an enzymatic electrochemical biosensor which can successfully detect nicotine in sweat was recently published[173]. The group used the human cytochrome P450 2B6 enzyme, a known nicotine degrader[174,175] which contains a heme group in the catalytic core as the central biorecognition element. In order to covalently link the enzyme to the electrode surface and facilitate electron transfer from the oxidation of nicotine to the electrode, the group used a monolayer of 11-mercaptoundecanoic acid (MUA) coated on top of gold nanodendrites. They reported a limit of detection of 1.6 µM. Although the group was able to demonstrate detection of nicotine in smoker sweat in real time for the first time, the P450 2B6 enzyme has been reported to sense more than 60 currently used clinical drugs along with various procarcinogens, toxins, and hormones[176]. Even though directed evolution techniques have been able to hone the specificity of enzymes to specific substrates[177], more optimal biorecognition elements which have evolved to sense nicotine specifically exist.

SEQUENCES:

SEQ ID NO: 5 (nucleic acid of NicA2 N462H)
ATGAGTGATAAAACAAAAACAAATGAAGGCTTTAGCCGCAGGTCTTTT
ATCGGAAGCGCGGCAGTCGTAACAGCAGGTGTTGCGGGATTGGGAGCT
ATTGATGCGGCTTCGGCTACGCAAAAAACGAACCGAGCAAGCACCGTC
AAAGGTGGCTTCGATTACGATGTGGTAGTAGTTGGTGGAGGGTTTGCT
GGCGCGACAGCCGCCCGTGAATGTGGTTTGCAGGGTTATCGAACGCTT
TTATTGGAAGCGAGGTCCCGCCTAGGTGGTCGTACGTTTACCTCGCGC
TTTGCAGGTCAAGAAATTGAATTTGGCGGGCATGGGTGCACTGGCTG
CAGCCGCATGTTTGGGCAGAAATGCAGCGTTACGGTCTGGGTGTAGTG
GAAGATCCACTTACTAATTTAGATAAAACCTTAATCATGTATAACGAC
GGAAGCGTCGAAAGTATTTCGCCCGATGAATTTGGCAAAAACATTCGA

SEQUENCES:

ATAGCTTTTGAAAAGCTTTGTCACGATGCCTGGGAAGTATTTCCTCGT
CCGCATGAGCCGATGTTTACTGAGCGCGCTCGGGAATTGGATAAATCT
TCTGTTCTTGATCGCATCAAAACTTTGGGCTTAAGTCGGCTGCAACAG
GCTCAAATCAATAGTTACATGGCCTTGTATGCAGGTGAGACAACTGAC
AAATTTGGCCTGCCTGGTGTACTTAAGTTGTTTGCATGCGGCGGTTGG
AACTATGACGCCTTCATGGACACTGAAACTCATTATAGAATTCAAGGG
GGCACGATAGGCCTCATTAATGCAATGTTGACCGATAGCGGTGCCGAG
GTCCGCATGTCTGTGCCCGTCACTGCTGTTGAGCAAGTCAATGGTGGC
GTCAAAATCAAGACCGACGACGACGAAATTATTACCGCCGGAGTGGTC
GTAATGACAGTTCCACTCAATACGTATAAACATATCGGTTTTACGCCT
GCCCTTTCTAAAGGTAAACAACGATTCATCAAAGAGGGGCAGCTTAGC
AAAGGTGCTAAGCTTTATGTTCATGTTAAGCAGAATCTCGGACGGGTT
TTTGCGTTTGCGGATGAACAGCAACCTTTAAACTGGGTCCAGACGCAC
GATTACAGCGACGAGTTGGGGACAATACTGTCGATCACCATCGCTCGC
AAAGAAACAATTGATGTGAATGACCGAGATGCTGTAACTCGCGAAGTT
CAAAAAATGTTTCCGGGTGTTGAGGTTCTTGGTACAGCGGCTTACGAC
TGGACAGCTGATCCATTTTCCTTGGGGGCATGGGCGGCTTATGGAGTA
GGTCAACTAAGTCGTCTCAAAGATCTACAGGCGGCTGAAGGACGTATT
TTATTTGCAGGAGCTGAAACCAGTAACGGTTGGCACGCGCATATCGAT
GGTGCTGTTGAAAGTGGACTACGTGCCGGTAGGGAGGTTAAGCAGCTC
TTAAGCCTAGAGCACCACCACCACCACCACTAG

SEQ ID NO: 6 (nucleic acid of NicA2 N462Y/W427Y)
ATGAGTGATAAAACAAAAACAAATGAAGGCTTTAGCCGCAGGTCTTTT
ATCGGAAGCGCGGCAGTCGTAACAGCAGGTGTTGCGGGATTGGGAGCT
ATTGATGCGGCTTCGGCTACGCAAAAAACGAACCGAGCAAGCACCGTC
AAAGGTGGCTTCGATTACGATGTGGTAGTAGTTGGTGGAGGGTTTGCT
GGCGCGACAGCCGCCCGTGAATGTGGTTTGCAGGGTTATCGAACGCTT
TTATTGGAAGCGAGGTCCCGCCTAGGTGGTCGTACGTTTACCTCGCGC
TTTGCAGGTCAAGAAATTGAATTTGGCGGGCATGGGTGCACTGGCTG
CAGCCGCATGTTTGGGCAGAAATGCAGCGTTACGGTCTGGGTGTAGTG
GAAGATCCACTTACTAATTTAGATAAAACCTTAATCATGTATAACGAC
GGAAGCGTCGAAAGTATTTCGCCCGATGAATTTGGCAAAAACATTCGA
ATAGCTTTTGAAAAGCTTTGTCACGATGCCTGGGAAGTATTTCCTCGT
CCGCATGAGCCGATGTTTACTGAGCGCGCTCGGGAATTGGATAAATCT
TCTGTTCTTGATCGCATCAAAACTTTGGGCTTAAGTCGGCTGCAACAG
GCTCAAATCAATAGTTACATGGCCTTGTATGCAGGTGAGACAACTGAC
AAATTTGGCCTGCCTGGTGTACTTAAGTTGTTTGCATGCGGCGGTTGG
AACTATGACGCCTTCATGGACACTGAAACTCATTATAGAATTCAAGGG
GGCACGATAGGCCTCATTAATGCAATGTTGACCGATAGCGGTGCCGAG
GTCCGCATGTCTGTGCCCGTCACTGCTGTTGAGCAAGTCAATGGTGGC
GTCAAAATCAAGACCGACGACGACGAAATTATTACCGCCGGAGTGGTC
GTAATGACAGTTCCACTCAATACGTATAAACATATCGGTTTTACGCCT
GCCCTTTCTAAAGGTAAACAACGATTCATCAAAGAGGGGCAGCTTAGC
AAAGGTGCTAAGCTTTATGTTCATGTTAAGCAGAATCTCGGACGGGTT
TTTGCGTTTGCGGATGAACAGCAACCTTTAAACTGGGTCCAGACGCAC
GATTACAGCGACGAGTTGGGGACAATACTGTCGATCACCATCGCTCGC
AAAGAAACAATTGATGTGAATGACCGAGATGCTGTAACTCGCGAAGTT
CAAAAAATGTTTCCGGGTGTTGAGGTTCTTGGTACAGCGGCTTACGAC
TGGACAGCTGATCCATTTTCCTTGGGGGCATACGCGGCTTATGGAGTA
GGTCAACTAAGTCGTCTCAAAGATCTACAGGCGGCTGAAGGACGTATT
TTATTTGCAGGAGCTGAAACCAGTAACGGTTGGCACGCGTACATCGAT
GGTGCTGTTGAAAGTGGACTACGTGCCGGTAGGGAGGTTAAGCAGCTC
TTAAGCCTAGAGCACCACCACCACCACCACTAG

REFERENCES

All references and publication cited in the specification and Examples are incorporated herein in their entirety by reference.

1. Organization, W. H., WHO report on the global tobacco epidemic 2017: Monitoring tobacco use and prevention policies. 2017.
2. Xu, X.; Bishop, E. E.; Kennedy, S. M.; Simpson, S. A.; Pechacek, T. F., Annual healthcare spending attributable to cigarette smoking: an update. *Am J Prev Med* 2015, 48 (3), 326-33.
3. McGinnis, J. M.; Foege, W. H., Actual causes of death in the United States. *Jama* 1993, 270 (18), 2207-2212.
4. Rice, V. H.; Stead, L. F., Nursing interventions for smoking cessation. *Cochrane Database Syst Rev* 2008, 1.

5. Benowitz, N. L., Clinical pharmacology of inhaled drugs of abuse: implications in understanding nicotine dependence. *NIDA Res Monogr* 1990, 99, 12-29.
6. Wadgave, U.; Nagesh, L., Nicotine replacement therapy: An overview. *International journal of health sciences* 2016, 10 (3), 425.
7. Tang, H.; Wang, L.; Wang, W.; Yu, H.; Zhang, K.; Yao, Y.; Xu, P., Systematic unraveling of the unsolved pathway of nicotine degradation in Pseudomonas. *PLoS Genet* 2013, 9 (10), e1003923.
8. Xue, S.; Schlosburg, J. E.; Janda, K. D., A New Strategy for Smoking Cessation: Characterization of a Bacterial Enzyme for the Degradation of Nicotine. *J Am Chem Soc* 2015, 137 (32), 10136-9.
9. Benowitz, N. L., Cotinine as a biomarker of environmental tobacco smoke exposure. *Epidemiologic reviews* 1996, 18 (2), 188-204.
10. Campanella, L.; Favero, G.; Tomassetti, M., Direct determination of nicotine in antismoking pharmaceutical products and in tobacco using an inhibition biosensor. *Anal. Lett.* 2001, 34 (6), 855-866.
11. Yang, Y. H.; Yang, M. H.; Wang, H.; Tang, L.; Shen, G. L.; Yu, R. Q., Inhibition biosensor for determination of nicotine. *Anal. Chim. Acta* 2004, 509 (2), 151-157.
12. Mitsubayashi, K.; Nakayama, K.; Taniguchi, M.; Saito, H.; Otsuka, K.; Kudo, H., Bioelectronic sniffer for nicotine using enzyme inhibition. *Anal. Chim. Acta* 2006, 573, 69-74.
13. Tan, Y. G.; Yin, J.; Liang, C. D.; Peng, H.; Nie, L. H.; Yao, S. Z., A study of a new TSM bio-mimetic sensor using a molecularly imprinted polymer coating and its application for the determination of nicotine in human serum and urine. *Bioelectrochemistry* 2001, 53 (2), 141-148.
14. Croux, D.; Weustenraed, A.; Pobedinskas, P.; Horemans, F.; Dilien, H.; Haenen, K.; Cleij, T.; Wagner, P.; Thoelen, R.; De Ceuninck, W., Development of multichannel quartz crystal microbalances for MIP-based biosensing. *Phys. Status Solidi A-Appl. Mat.* 2012, 209 (5), 892-899.
15. Alenus, J.; Galar, P.; Ethirajan, A.; Horemans, F.; Weustenraed, A.; Cleij, T. J.; Wagner, P., Detection of L-nicotine with dissipation mode quartz crystal microbalance using molecular imprinted polymers. *Phys. Status Solidi A-Appl. Mat.* 2012, 209 (5), 905-910.
16. Alenus, J.; Ethirajan, A.; Horemans, F.; Weustenraed, A.; Csipai, P.; Gruber, J.; Peeters, M.; Cleij, T. J.; Wagner, P., Molecularly imprinted polymers as synthetic receptors for the QCM-D-based detection of L-nicotine in diluted saliva and urine samples. *Anal. Bioanal. Chem.* 2013, 405 (20), 6479-6487.
17. Cennamo, N.; D'Agostino, G.; Pesavento, M.; Zeni, L., High selectivity and sensitivity sensor based on MIP and SPR in tapered plastic optical fibers for the detection of L-nicotine. *Sens. Actuator B-Chem.* 2014, 191, 529-536.
18. Kamra, T.; Zhou, T. C.; Montelius, L.; Schnadt, J.; Ye, L., Implementation of Molecularly Imprinted Polymer Beads for Surface Enhanced Raman Detection. *Anal. Chem.* 2015, 87 (10), 5056-5061.
19. Peeters, M.; Csipai, P.; Geerets, B.; Weustenraed, A.; van Grinsven, B.; Thoelen, R.; Gruber, J.; De Ceuninck, W.; Cleij, T. J.; Troost, F. J.; Wagner, P., Heat-transfer-based detection of L-nicotine, histamine, and serotonin using molecularly imprinted polymers as biomimetic receptors. *Anal. Bioanal. Chem.* 2013, 405 (20), 6453-6460.
20. Geerets, B.; Peeters, M.; van Grinsven, B.; Bers, K.; de Ceuninck, W.; Wagner, P., Optimizing the Thermal Read-Out Technique for MIP-Based Biomimetic Sensors: Towards Nanomolar Detection Limits. *Sensors* 2013, 13 (7), 9148-9159.
21. Wackers, G.; Vandenryt, T.; Cornelis, P.; Kellens, E.; Thoelen, R.; De Ceuninck, W.; Losada-Perez, P.; van Grinsven, B.; Peeters, M.; Wagner, P., Array Formatting of the Heat-Transfer Method (HTM) for the Detection of Small Organic Molecules by Molecularly Imprinted Polymers. *Sensors* 2014, 14 (6), 11016-11030.
22. Wang, S. J.; Liaw, H. W.; Tsai, Y. C., Low potential detection of nicotine at multiwalled carbon nanotube-alumina-coated silica nanocomposite. *Electrochemistry Communications* 2009, 11 (4), 733-735.
23. Sims, M. J.; Rees, N. V.; Dickinson, E. J. F.; Compton, R. G., Effects of thin-layer diffusion in the electrochemical detection of nicotine on basal plane pyrolytic graphite (BPPG) electrodes modified with layers of multi-walled carbon nanotubes (MWCNT-BPPG). *Sens. Actuator B-Chem.* 2010, 144 (1), 153-158.
24. Lo, T. W. B.; Aldous, L.; Compton, R. G., The use of nano-carbon as an alternative to multi-walled carbon nanotubes in modified electrodes for adsorptive stripping voltammetry. *Sens. Actuator B-Chem.* 2012, 162 (1), 361-368.
25. Svorc, L.; Stankovic, D. M.; Kalcher, K., Boron-doped diamond electrochemical sensor for sensitive determination of nicotine in tobacco products and anti-smoking pharmaceuticals. *Diam. Relat. Mat.* 2014, 42, 1-7.
26. Jing, Y. Q.; Yuan, X. X.; Yuan, Q.; He, K. X.; Liu, Y. J.; Lu, P.; Li, H. Q.; Li, B.; Zhan, H.; Li, G. L., Determination of nicotine in tobacco products based on mussel-inspired reduced graphene oxide-supported gold nanoparticles. *Sci Rep-Uk* 2016, 6, 8.
27. Jing, Y. Q.; Lin, E. G.; Su, X. H.; Liu, Y. J.; Li, H. Q.; Yuan, X. X.; Ping, L.; Fan, Y. K., Electrodeposition of Au nanoparticles on poly(diallyldimethylammonium chloride) functionalized reduced graphene oxide sheets for voltammetric determination of nicotine in tobacco products and anti-smoking pharmaceuticals. *RSC Adv.* 2016, 6 (31), 26247-26253.
28. Li, X. Q.; Zhao, H. L.; Shi, L. B.; Zhu, X.; Lan, M. B.; Zhang, Q.; Fan, Z. H., Electrochemical sensing of nicotine using screen-printed carbon electrodes modified with nitrogen-doped graphene sheets. *J. Electroanal. Chem.* 2017, 784, 77-84.
29. Wang, R.; Blackburn, G.; Desai, M.; Phelan, D.; Gillinov, L.; Houghtaling, P.; Gillinov, M., Accuracy of wrist-worn heart rate monitors. *Jama cardiology* 2017, 2 (1), 104-106.
30. Wallen, M. P.; Gomersall, S. R.; Keating, S. E.; Wisloff, U.; Coombes, J. S., Accuracy of heart rate watches: implications for weight management. *PLoS One* 2016, 11 (5), e0154420.
31. Sanders, J. P.; Loveday, A.; Pearson, N.; Edwardson, C.; Yates, T.; Biddle, S. J.; Esliger, D. W., Devices for self-monitoring sedentary time or physical activity: a scoping review. *Journal of medical Internet research* 2016, 18 (5).
32. Harrison, D.; Marshall, P.; Bianchi-Berthouze, N.; Bird, J. In *Activity tracking: barriers, workarounds and customisation*, Proceedings of the 2015 ACM International Joint Conference on Pervasive and Ubiquitous Computing, ACM: 2015; pp 617-621.
33. El-Amrawy, F.; Nounou, M. I., Are currently available wearable devices for activity tracking and heart rate monitoring accurate, precise, and medically beneficial? *Healthcare informatics research* 2015, 21 (4), 315-320.

34. Ko, P.-R. T.; Kientz, J. A.; Choe, E. K.; Kay, M.; Landis, C. A.; Watson, N. F., Consumer sleep technologies: a review of the landscape. *Journal of clinical sleep medicine: JCSM: official publication of the American Academy of Sleep Medicine* 2015, 11 (12), 1455.
35. Olczuk, D.; Priefer, R., A history of continuous glucose monitors (CGMs) in self-monitoring of diabetes mellitus. *Diabetes Metab Syndr* 2018, 12 (2), 181-187.
36. Newman, J.; Tigwell, L.; Turner, A.; Warner, P., Biosensors: a clearer view. *Biosensors* 2004.
37. Turner, A., Biosensors: then and now. *Trends in Biotechnology* 2013, 31 (3), 119-120.
38. Dzyadevych, S. V.; Arkhypova, V. N.; Soldatkin, A. P.; El'skaya, A. V.; Martelet, C.; Jaffrezic-Renault, N., Amperometric enzyme biosensors: Past, present and future. *Irbm* 2008, 29 (2-3), 171-180.
39. Tao, Z.; Shi, A.; Zhao, J., Epidemiological Perspectives of Diabetes. *Cell Biochem Biophys* 2015, 73 (1), 181-5.
40. Mary, A. A.; Aleksandr, S., Novel trends in affinity biosensors: current challenges and perspectives. *Measurement Science and Technology* 2014, 25 (3), 032001.
41. Evtugyn, G., *Biosensors: Essentials*. Springer: 2014; Vol. 84.
42. Frenzel, A.; Hust, M.; Schirrmann, T., Expression of recombinant antibodies. *Frontiers in immunology* 2013, 4, 217.
43. Hornsby, M.; Paduch, M.; Miersch, S.; Saaf, A.; Matsuguchi, T.; Lee, B.; Wypisniak, K.; Doak, A.; King, D.; Usatyuk, S.; Perry, K.; Lu, V.; Thomas, W.; Luke, J.; Goodman, J.; Hoey, R. J.; Lai, D.; Griffin, C.; Li, Z.; Vizeacoumar, F. J.; Dong, D.; Campbell, E.; Anderson, S.; Zhong, N.; Graslund, S.; Koide, S.; Moffat, J.; Sidhu, S.; Kossiakoff, A.; Wells, J., A High Through-put Platform for Recombinant Antibodies to Folded Proteins. *Molecular &cellular proteomics: MCP* 2015, 14 (10), 2833-47.
44. az-Gonzalez, M. i. D.; a, M. a. B. G.-G.; ia, A. n. C.-G., Recent Advances in Electrochemical Enzyme Immunoassays. *Electroanalysis* 2005, 17 (21).
45. Marrazza, G., Aptamer Sensors. *Biosensors (Basel)* 2017, 7 (1).
46. Wu, Z.; Zhang, X.; Yang, Y.; Shen, G.; Yu, R., A sensitive nicotine sensor based on molecularly imprinted electropolymer of o-aminophenol. *Frontiers of Chemistry in China* 2006, 1 (2), 183-187.
47. Wang, S.-J.; Liaw, H.-W.; Tsai, Y.-C., Low potential detection of nicotine at multiwalled carbon nanotube-alumina-coated silica nanocomposite. *Electrochemistry Communications* 2009, 11 (4), 733-735.
48. Sims, M. J.; Rees, N. V.; Dickinson, E. J.; Compton, R. G., Effects of thin-layer diffusion in the electrochemical detection of nicotine on basal plane pyrolytic graphite (BPPG) electrodes modified with layers of multi-walled carbon nanotubes (MWCNT-BPPG). *Sensors and Actuators B: Chemical* 2010, 144 (1), 153-158.
49. Fekry, A.; Azab, S.; Shehata, M.; Ameer, M., A novel electrochemical nicotine sensor based on cerium nanoparticles with anionic surfactant. *RSC Advances* 2015, 5 (64), 51662-51671.
50. Goodarzi, Z.; Maghrebi, M.; Zavareh, A. F.; Mokhtari-Hosseini, Z. B.; Ebrahimi-Hoseinzadeh, B.; Zarmi, A. H.; Barshan-Tashnizi, M., Evaluation of nicotine sensor based on copper nanoparticles and carbon nanotubes. *Journal of Nanostructure in Chemistry* 2015, 5 (3), 237-242.
51. Xiao, H.; Sun, L.; Yan, H.; Wang, W.; Liu, J.; Yan, Q.; Chao, L.; Chen, C.; Xie, Q.; Wen, J., Electroanalysis of nicotine at an electroreduced carboxylated graphene modified glassy carbon electrode. *Analytical Methods* 2015, 7 (3), 1147-1153.
52. Jing, Y.; Yuan, X.; Yuan, Q.; He, K.; Liu, Y.; Lu, P.; Li, H.; Li, B.; Zhan, H.; Li, G., Determination of nicotine in tobacco products based on mussel-inspired reduced graphene oxide-supported gold nanoparticles. *Sci Rep* 2016, 6, 29230.
53. Lutz, S.; Iamurri, S. M., Protein Engineering: Past, Present, and Future. In *Protein Engineering*, Springer: 2018; pp 1-12.
54. Liu, J.; Ma, G.; Chen, T.; Hou, Y.; Yang, S.; Zhang, K.-Q.; Yang, J., Nicotine-degrading microorganisms and their potential applications. *Applied microbiology and biotechnology* 2015, 99 (9), 3775-3785.
55. Yu, H.; Tang, H.; Wang, L.; Yao, Y.; Wu, G.; Xu, P., Complete genome sequence of the nicotine-degrading *Pseudomonas putida* strain S16. *J Bacteriol* 2011, 193 (19), 5541-2.
56. Tang, H.; Wang, S.; Ma, L.; Meng, X.; Deng, Z.; Zhang, D.; Ma, C.; Xu, P., A novel gene, encoding 6-hydroxy-3-succinoylpyridine hydroxylase, involved in nicotine degradation by *Pseudomonas putida* strain S16. *Appl Environ Microbiol* 2008, 74 (5), 1567-74.
57. Tang, H.; Wang, L.; Meng, X.; Ma, L.; Wang, S.; He, X.; Wu, G.; Xu, P., Novel nicotine oxidoreductase-encoding gene involved in nicotine degradation by *Pseudomonas putida* strain S16. *Appl Environ Microbiol* 2009, 75 (3), 772-8.
58. Tang, H.; Yao, Y.; Wang, L.; Yu, H.; Ren, Y.; Wu, G.; Xu, P., Genomic analysis of *Pseudomonas putida*: genes in a genome island are crucial for nicotine degradation. *Sci Rep* 2012, 2, 377.
59. Tararina, M. A.; Janda, K. D.; Allen, K. N., Structural Analysis Provides Mechanistic Insight into Nicotine Oxidoreductase from *Pseudomonas putida*. *Biochemistry* 2016, 55 (48), 6595-6598.
60. Russell, M. A.; Jarvis, M.; Iyer, R.; Feyerabend, C., Relation of nicotine yield of cigarettes to blood nicotine concentrations in smokers. *Br Med J* 1980, 280 (6219), 972-6.
61. Moyer, T. P.; Charlson, J. R.; Enger, R. J.; Dale, L. C.; Ebbert, J. O.; Schroeder, D. R.; Hurt, R. D., Simultaneous analysis of nicotine, nicotine metabolites, and tobacco alkaloids in serum or urine by tandem mass spectrometry, with clinically relevant metabolic profiles. *Clin Chem* 2002, 48 (9), 1460-71.
62. Lindell, G.; Lunell, E.; Graffner, H., Transdermally administered nicotine accumulates in gastric juice. *Eur J Clin Pharmacol* 1996, 51 (3-4), 315-8.
63. Henningfield, J. E.; London, E.; Pogun, S., *Nicotine psychopharmacology*. Springer Science & Business Media: 2009; Vol. 192.
64. Etter, J. F.; Vu Duc, T.; Perneger, T. V., Saliva cotinine levels in smokers and nonsmokers. *Am J Epidemiol* 2000, 151 (3), 251-8.
65. Balabanova, S.; Buhler, G.; Schneider, E.; Boschek, H. J.; Schneitler, H., [Nicotine excretion by the apocrine and eccrne sweat in smokers and passive smokers]. *Hautarzt* 1992, 43 (2), 73-6.
66. Tararina et al., Crystallography Coupled with Kinetic Analysis Provide Mechanistic Underpinnings of a Nicotine-Degrading Enzyme. Biochemistry. 2018 Jul. 3; 57(26): 3741-3751.
67. Xue et al., An Enzymatic Advance in Nicotine Cessation Therapy, Chem Commun (Camb). 2018 Feb. 13; 54(14): 1686-1689.
68. Thisted et al., Optimization of a nicotine degrading enzyme for potential use in treatment of nicotine addiction, BMC Biotechnology (2019) 19:56.

The invention claimed is:

1. A biosensor for the measurement of the concentration of nicotine comprising:
   a. an electrode comprising a surface;
   b. an electronically active mediator (Med) deposited on the surface of the electrode; and
   c. a mutant nicotine-catalyzing enzyme deposited on the surface of the electrode, wherein the mutant nicotine-catalyzing enzyme is selected from any of:
      (i) a mutant NicA2 enzyme comprising at least one modification selected from any of: N462V, N462Y/W427Y, or N462H of SEQ ID NO: 2;
      (ii) a mutant NicA2(N462H) enzyme;
      (iii) a protein comprising at least 85% sequence identity to SEQ ID NO: 2 or SEQ ID NO: 3, and where amino acid 462 is changed from asparagine (N) to histidine (H);
      (iv) a mutant NicA2(N462Y/W427Y) enzyme; or
      (v) a protein comprising at least 85% sequence identity to SEQ ID NO: 2 or SEQ ID NO: 4, and where amino acid 462 is changed from asparagine (N) to valine (V), and amino acid residue 427 is changed from tryptophan (W) to tyrosine (Y).

2. The biosensor of claim 1, wherein the nicotine-catalyzing enzyme is immobilized on the surface of the electrode with a polymer, and optionally, a top layer above the polymer, wherein the top layer comprises Prussian-Blue (PB).

3. The biosensor of claim 2, wherein the polymer comprises low molecular weight (LMW) or a medium molecular weight (MMW) chitosan in 0.5% acetic acid, and optionally Prussian-Blue (PB).

4. The biosensor of claim 1, wherein in the presence of nicotine, the nicotine-catalyzing enzyme produces $H_2O_2$, wherein breakdown of $H_2O_2$ to $O_2$ and $H_2O$ releases electrons to produce an electrochemical signal, wherein the electrochemical signal is detected by current passed to the electrode.

5. The biosensor of claim 1, wherein a detectable signal is produced when nicotine is catalyzed by the nicotine-catalyzing enzyme and transfers at least one electron from $Med_{red}$ to hydrogen peroxide ($H_2O_2$), resulting in its reduction to $Med_{ox}$, wherein $Med_{ox}$ is reduced by the electrode producing a detectable signal.

6. The biosensor of claim 5, wherein the biosensor is an amperometric biosensor and the detectable signal is electrochemical.

7. The biosensor of claim 6, wherein the amperometric biosensor is a chronoamperometric biosensor.

8. The biosensor of claim 1, wherein the $Med_{ox}$ produces an electrochemical signal, wherein the electrochemical signal is detected by current passed to the electrode.

9. The biosensor of claim 1, wherein the electrode is connected to a potentiostat having a current resolution to at least 1pA (100 nA).

10. The biosensor of claim 1, wherein the biosensor comprises a working electrode and a reference electrode.

11. The biosensor of claim 10, wherein the working electrode surface area is $>10\pi$ mm$^2$.

12. The biosensor of claim 1, wherein the biosensor does not comprise a counter electrode.

13. The biosensor of claim 1, wherein the electrode is either metallic or non-metallic.

14. The biosensor of claim 13, wherein the metallic electrode is gold, silver, platinum, or palladium.

15. The biosensor of claim 13, wherein the non-metallic electrode comprises carbon.

16. A wearable electrochemical nicotine biosensor device comprising:
    an electroconductive part comprising a housing containing an electric control circuit;
    a working electrode comprising a surface; and
    a mutant nicotine-catalyzing enzyme according to claim 1 deposited on the surface of a working electrode.

17. The wearable nicotine biosensor device of claim 16, wherein the biosensor is electrically connected to a potentiostat, wherein the potentiostat is linked to at least the working electrode of the biosensor, and the working electrode is in fluid communication with a wicking paper that wicks sweat from the surface of a subjects' skin.

18. The wearable nicotine biosensor device of claim 16, wherein when attached to the skin of a subject, is operable to detect the amount of nicotine in the sweat of the subject, in a real time, quantitative and chronoamperometric manner.

19. A method of using an amperometric biosensor to measure the concentration of nicotine comprising:
    a. providing the biosensor of claim 1, wherein the biosensor is an amperometric biosensor;
    b. providing a sample; and
    c. measuring the current produced by the oxidation of any nicotine present in the sample.

20. The method of claim 19, wherein the sample is selected from the group consisting of: sweat, gastric juice, urine, saliva, and blood.

21. The method of claim 19, wherein the sample is sweat.

22. The method of claim 19, wherein the method of using the amperometric biosensor is used to measure the physiological concentration of nicotine in the range of 0.4 µM-1000 µM range.

23. The method of claim 19, wherein the nicotine concentration is measured in the range of 0.4 µM-1000 µM.

24. The method of claim 19, wherein the current of the amperometric biosensor is not altered in the presence of an interferent.

25. The method of claim 24, wherein the interferent is selected from the group consisting of: L-(+)-lactic acid, ascorbic acid, uric acid, dopamine, (−)-epinephrine, creatinine, S-(+)-glucose, sodium, calcium, magnesium, potassium, phosphate, albumin, amino acids, and cotinine.

* * * * *

UNITED STATES PATENT AND TRADEMARK OFFICE
CERTIFICATE OF CORRECTION

| | | |
|---|---|---|
| PATENT NO. | : 11,331,020 B2 | Page 1 of 1 |
| APPLICATION NO. | : 17/169193 | |
| DATED | : May 17, 2022 | |
| INVENTOR(S) | : James Galagan et al. | |

It is certified that error appears in the above-identified patent and that said Letters Patent is hereby corrected as shown below:

On the Title Page

At Item (72) List of Inventors, please add the name of the following inventor:
Abdurrahman Addokhi, Cambridge, MA (US)

Signed and Sealed this
First Day of November, 2022

Katherine Kelly Vidal
Director of the United States Patent and Trademark Office